(12) United States Patent
Delbeck et al.

(10) Patent No.: US 11,208,422 B2
(45) Date of Patent: Dec. 28, 2021

(54) SUBSTITUTED BRIDGED DIAZEPANE DERIVATIVES AND USE THEREOF AS TASK-1 AND TASK-3 INHIBITORS

(71) Applicants: Bayer Pharma Aktiengesellschaft, Berlin (DE); Bayer Aktiengesellschaft, Leverkusen (DE)

(72) Inventors: Martina Delbeck, Heiligenhaus (DE); Michael Hahn, Langenfeld (DE); Thomas Müller, Langenfeld (DE); Klemens Lustig, Wuppertal (DE); Johanna Anlahr, Dortmund (DE); Karl Collins, Düsseldorf (DE); Janine Nicolai, Essen (DE); Moritz Beck-Broichsitter, Darmstadt (DE); Udo Albus, Florstadt (DE); Doris Gehring, Kelkheim (DE); Björn Rosenstein, Bad Soden-Salmünster (DE); Hongkai Dang, Xi'an (CN); Dehe Duan, Xi'an (CN); Jianfei Yang, Xi'an (CN); Denghui Chen, Wuhan (CN)

(73) Assignees: Bayer Pharma Aktiengesellschaft, Berlin (DE); Bayer Aktiengesellschaft, Leverkusen (DE)

( * ) Notice: Subject to any disclaimer, the term of this patent is extended or adjusted under 35 U.S.C. 154(b) by 24 days.

(21) Appl. No.: 16/622,779

(22) PCT Filed: Jun. 7, 2018

(86) PCT No.: PCT/EP2018/064980
§ 371 (c)(1),
(2) Date: Dec. 13, 2019

(87) PCT Pub. No.: WO2018/228909
PCT Pub. Date: Dec. 20, 2018

(65) Prior Publication Data
US 2020/0140461 A1 May 7, 2020

(30) Foreign Application Priority Data
Jun. 14, 2017 (WO) ................ PCT/CN2017/088237

(51) Int. Cl.
| C07D 519/00 | (2006.01) |
| A61P 11/00 | (2006.01) |
| A61K 45/06 | (2006.01) |
| A61K 31/5513 | (2006.01) |
| A61P 25/00 | (2006.01) |

(52) U.S. Cl.
CPC ............ *C07D 519/00* (2013.01); *A61P 11/00* (2018.01); *A61K 45/06* (2013.01)

(58) Field of Classification Search
CPC ........ C07D 519/00; A61P 11/00; A61P 25/00; A61K 45/06; A61K 31/5513
See application file for complete search history.

(56) References Cited

U.S. PATENT DOCUMENTS

| 10,414,765 | B2 | 9/2019 | Delbeck |
| 10,759,794 | B2 | 9/2020 | Delbeck |
| 2018/0370965 | A1 | 12/2018 | Delbeck |
| 2019/0062326 | A1 | 2/2019 | Delbeck |
| 2020/0085734 | A1 | 3/2020 | Anlahr |

(Continued)

FOREIGN PATENT DOCUMENTS

| WO | 2017097671 A1 | 6/2017 |
| WO | 2017097792 A1 | 6/2017 |

(Continued)

OTHER PUBLICATIONS

Bittner, S., "TASK1 modulates inflammation and neurodegeneration in autoimmune inflammation of the central nervous system." Brain 132.9 (2009): 2501-2516.*

(Continued)

*Primary Examiner* — John M Mauro
(74) *Attorney, Agent, or Firm* — Morrison & Foerster LLP

(57) ABSTRACT

The present application relates to novel imidazopyridinyl- or imidazopyrimidinyl-substituted, bridged 1,4-diazepane derivatives of formula (I), to processes for their preparation, to their use alone or in combinations for the treatment and/or prevention of diseases, and to their use for preparing medicaments for the treatment and/or prevention of diseases, in particular for treatment and/or prevention of respiratory disorders including, sleep-related respiratory disorders such as obstructive sleep apnoeas and central sleep apnoeas and snoring. Formula (I) in which the ring Q represents a bridged 1,4-diazepane cycle.

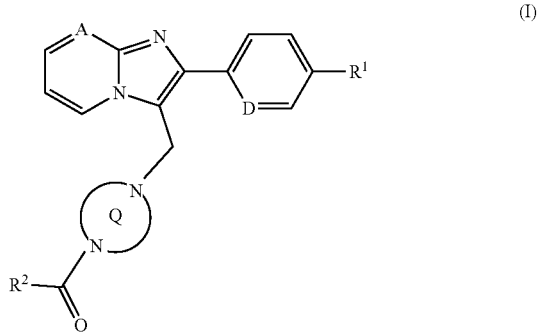

19 Claims, No Drawings

(56) References Cited

U.S. PATENT DOCUMENTS

2020/0109155 A1 4/2020 Delbeck
2021/0024545 A1 1/2021 Delbeck

FOREIGN PATENT DOCUMENTS

| WO | WO-2018015196 A1 * | 1/2018 | ................ A61P 9/06 |
| WO | 2018114503 A1 | 6/2018 | |
| WO | 2018228907 A1 | 12/2018 | |

OTHER PUBLICATIONS

Bittner, S., "From the background to the spotlight: TASK channels in pathological conditions." Brain Pathology 20.6 (2010): 999-1009.*

Verweij, M. F., Preventive medicine between obligation and aspiration. vol. 4. Springer Science & Business Media, 2000, p. 1-31.*

Bittner, S. et al. (2012). "The TASK1 channel inhibitor A293 shows efficacy in a mouse model of multiple sclerosis," Experimental Neurology, 238:149-155.

Bittner, S. et al. (2013). "Endothelial TWIK-related potassium channel-1 (TREK1) regulates immune-cell trafficking into the CNS," Nature Medicine, 19(9):1161-1169.

Bobak, N. et al. (2011). "Volume regulation of murine T lymphocytes relies on voltage-dependent and two-pore domain potassium channels," Biochimica et Biophysica Acta, 1808:2036 2044.

Decher et al. (2011). "Knock-Out of the Potassium Channel TASK-1 Leads to a Prolonged QT Interval and a Disturbed QRS Complex," Cell Physiol Biochem 28:77-86.

Limberg et al., (Oct. 28, 2011). "TASK-1 Channels May Modulate Action Potential Duration of Human Atrial Cardiomyocytes," Cell Physiol Biochem 25:613-624.

Meuth et al., (May 23, 2008). "TWIK-related Acid-sensitive K+ Channel 1 (TASK1) and TASK3 Critically Influence T Lymphocyte Effector Functions," The Journal of Biological Chemistry 283(21):14559-14579.

Schmidt, C. et al. (2015). "Upregulation of K2p3.1 K+ Current Causes Action Potential Shortening in Patients with Chronic Atrial Fibrillation," Circulation, 132:82-92.

Schmidt, C. et al. (2019). "Genetic Ablation of TASK-1 (Tandem of P Domains in a Weak Inward Rectifying K+ Channel-Related Acid-Sensititve K+ Channel-1) (K2p3.1) K+ Channels Suppresses Atrial Fibrillation and Prevents Electrical Remodeling," Circ Arrhythm Electrophysiol, 12:1-10.

Wiedmann, F. et al. (2020). "Pharmacologic TWIK-Related Acid-Sensitive K+ Channel (TASK-1) Potassium Channel Inhibitor A293 Facilitates Acute Cardioversion of Paroxysmal Atrial Fibrillation in a Porcine Large Animal Model," J Am Heart Assoc. 9:1-16.

* cited by examiner

SUBSTITUTED BRIDGED DIAZEPANE DERIVATIVES AND USE THEREOF AS TASK-1 AND TASK-3 INHIBITORS

CROSS REFERENCE TO RELATED APPLICATIONS

This application is a national stage application under 35 U.S.C. § 371 of International Application No. PCT/EP2018/064980, filed internationally on Jun. 7, 2018, which claims the benefit of International Application No. PCT/CN2017/088237, filed Jun. 14, 2017.

The present application relates to novel imidazopyridinyl- or imidazopyrimidinyl-substituted, bridged 1,4-diazepane derivatives, to processes for their preparation, to their use alone or in combinations for the treatment and/or prevention of diseases, and to their use for preparing medicaments for the treatment and/or prevention of diseases, in particular for treatment and/or prevention of respiratory disorders including, sleep-related respiratory disorders such as obstructive sleep apnoeas and central sleep apnoeas and snoring.

Potassium channels are virtually ubiquitous membrane proteins which are involved in a large number of different physiological processes. This also includes the regulation of the membrane potential and the electric excitability of neurons and muscle cells. Potassium channels are divided into three major groups which differ in the number of transmembrane domains (2, 4 or 6). The group of potassium channels where two pore-forming domains are flanked by four transmembrane domains is referred to as K2P channels. Functionally, the K2P channels mediate, substantially time- and voltage-independently, $K^+$ background currents, and their contribution to the maintenance of the resting membrane potential is crucial. The family of the K2P channels includes 15 members which are divided into six subfamilies, based on similarities in sequence, structure and function: TWIK, TREK, TASK, TALK, THIK and TRESK.

Of particular interest are TASK-1 (KCNK3 or K2P3.1) and TASK-3 (KCNK9 or K2P9.1) of the TASK (TWIK-related acid-sensitive $K^+$ channel) subfamily. Functionally, these channels are characterized in that, during maintenance of voltage-independent kinetics, they have "leak" or "background" streams flowing through them, and they respond to numerous physiological and pathological influences by increasing or decreasing their activity. A characteristic feature of TASK channels is the sensitive reaction to a change of the extracellular pH: at acidic pH the channels are inhibited, and at alkaline pH they are activated.

TASK-1 is expressed mainly in the central nervous system and in the cardiovascular system. Relevant expression of TASK-1 was demonstrated in the brain, in spinal ganglia, in motoneurons of the Nervus hypoglossus and Nervus trigeminus, in the heart, Glomus caroticum, the pulmonary artery, aorta, lung, pancreas, placenta, uterus, kidney, adrenal gland, small intestine and stomach, and also on T lymphocytes. TASK-3 is expressed mainly in the central nervous system. Relevant expression of TASK-3 was demonstrated in the brain, in motoneurons of the Nervus hypoglossus and Nervus trigeminus and in neuroepithelial cells of the Glomus caroticum and the lung, and also on T lymphocytes. A lower expression is found in the heart, stomach, testicular tissue and adrenal gland.

TASK-1 and TASK-3 channels play a role in respiratory regulation. Both channels are expressed in the respiratory neurons of the respiratory centre in the brain stem, inter alia in neurons which generate the respiratory rhythm (ventral respiratory group with pre-Botzinger complex), and in the noradrenergic Locus caeruleus, and also in serotonergic neurons of the raphe nuclei. Owing to the pH dependency, here the TASK channels have the function of a sensor which translates changes in extracellular pH into corresponding cellular signals [Bayliss et al., *Pflugers Arch.* 467, 917-929 (2015)]. TASK-1 and TASK-3 are also expressed in the Glomus caroticum, a peripheral chemoreceptor which measures pH, $O_2$ and $CO_2$ content of the blood and transmits signals to the respiratory centre in the brain stem to regulate respiration. It was shown that TASK-1 knock-out mice have a reduced ventilatory response (increase of respiratory rate and tidal volume) to hypoxia and normoxic hypercapnia [Trapp et al., *J. Neurosci.* 28, 8844-8850 (2008)]. Furthermore, TASK-1 and TASK-3 channels were demonstrated in motoneurons of the Nervus hypoglossus, the XIIth cranial nerve, which has an important role in keeping the upper airways open [Berg et al., *J. Neurosci.* 24, 6693-6702 (2004)].

In a sleep apnoea model in the anaesthetized pig, intranasal administration of a potassium channel blocker which blocks the TASK-1 channel in the nanomolar range led to inhibition of collapsization of the pharyngeal respiratory musculature and sensitization of the negative pressure reflex of the upper airways. It is assumed that intranasal administration of the potassium channel blocker depolarizes mechanoreceptors in the upper airways and, via activation of the negative pressure reflex, leads to increased activity of the musculature of the upper airways, thus stabilizing the upper airways and preventing collapse. By virtue of this stabilization of the upper airways, the TASK channel blockade may be of great importance for obstructive sleep apnoea and also for snoring [Wirth et al., *Sleep* 36, 699-708 (2013); Kiper et al., *Pflugers Arch.* 467, 1081-1090 (2015)].

Obstructive sleep apnoea (OSA) is a sleep-related respiratory disorder which is characterized by repeat episodes of obstruction of the upper airways. When breathing in, the patency of the upper airways is ensured by the interaction of two opposite forces. The dilative effects of the musculature of the upper airways counteract the negative intraluminal pressure, which constricts the lumen. The active contraction of the diaphragm and the other auxiliary respiratory muscles generates a negative pressure in the airways, thus constituting the driving force for breathing. The stability of the upper respiratory tract is substantially determined by the coordination and contraction property of the dilating muscles of the upper airways.

The Musculus genioglossus plays a decisive role in the pathogenesis of obstructive sleep apnoea. The activity of the Musculus genioglossus increases with decreasing pressure in the pharynx in the sense of a dilative compensation mechanism. Innervated by the Nervus hypoglossus, it drives the tongue forward and downward, thus widening the pharyngeal airway [Verse et al., *Somnologie* 3, 14-20 (1999)]. Tensioning of the dilating muscles of the upper airways is modulated inter alia via mechanoreceptors/stretch receptors in the nasal cavity/pharynx [Bouillette et al., *J. Appl. Physiol. Respir. Environ. Exerc. Physiol.* 46, 772-779 (1979)]. In sleeping patients suffering from serious sleep apnoea, under local anaesthesia an additional reduction of the activity of the Musculus genioglossus can be observed [Berry et al., *Am. J. Respir. Crit. Care Med.* 156, 127-132 (1997)]. Patients suffering from obstructive sleep apnoea have high mortality and morbidity as a result of cardiovascular disorders such as hypertension, myocardial infarction and stroke [Vrints et al., *Acta Clin. Belg.* 68, 169-178 (2013)].

In the case of central sleep apnoea, owing to impaired brain function and impaired respiratory regulation there are episodic inhibitions of the respiratory drive. Central respiratory disorders result in mechanical respiratory arrests, i.e. during these episodes there is no breathing activity; temporarily, all respiratory muscles including the diaphragm are at rest. In the case of central sleep apnoea, there is no obstruction of the upper airways.

In the case of primary snoring, there is likewise no obstruction of the upper airways. However, owing to the constriction of the upper airways, the flow rate of the air that is inhaled and exhaled increases. This, combined with the relaxed musculature, causes the soft tissues of the oral cavity and the pharynx to flutter in the stream of air. This gentle vibration then generates the typical snoring noises.

Obstructive snoring (upper airway resistance syndrome, heavy snoring, hypopnoea syndrome) is caused by repeat partial obstruction of the upper airways during sleep. This results in an increased respiratory resistance and thus in an increase in work of breathing with considerable fluctuations in intrathoracic pressure. During inspiration, the negative intrathoracic pressure may reach values similar to those that are encountered as a result of complete airway obstruction during obstructive sleep apnoea. The pathophysiological consequences for heart, circulation and sleep quality correspond to those of obstructive sleep apnoea. As in obstructive sleep apnoea, the pathogenesis is assumed to be an impaired reflex mechanism of the pharynx-dilating muscles during inspiration when sleeping. Frequently, obstructive snoring is the preliminary stage of obstructive sleep apnoea [Hollandt et al., *HNO* 48, 628-634 (2000)].

In addition, TASK channels also appear to play a role in the apoptosis of neurons. In the animal model of myelin oligodendrocyte glycoprotein (MOG)-induced autoimmune encephalomyelitis, an animal model of multiple sclerosis, TASK-1 knock-out mice showed reduced neuronal degeneration. By preventing neuronal apoptosis, inhibition of TASK channels appears to act neuroprotectively, and may thus be of interest for the treatment of neurodegenerative disorders [Bittner et al., *Brain* 132, 2501-2516 (2009)].

Furthermore, it has been described that T lymphocytes express TASK-1 and TASK-3 channels and that inhibition of these channels leads to reduced cytokine production and proliferation after stimulation of T lymphocytes. The selective inhibition of TASK channels on T lymphocytes improved the course of the disease in an animal model of multiple sclerosis. The blockade of TASK channels may therefore also be of importance for treatment of autoimmune disorders [Meuth et al., *J. Biol. Chem.* 283, 14559-14579 (2008)].

TASK-1 and TASK-3 are also expressed in the heart [Rinné et al., *J. Mol. Cell. Cardiol.* 81, 71-80 (2015)]. Since TASK-1 is expressed particularly strongly in the nervous stimuli conduction system and in the atrium, this channel may have a role in disrupting stimuli conduction or triggering supraventricular arrhythmias. In the heart, TASK-1 appears to contribute to a background current which for its part contributes to maintenance of the resting potential, to action potential duration and to repolarization [Kim et al., *Am. J. Physiol.* 277, H1669-1678 (1999)]. Using human heart muscle cells, it was shown that blockade of the TASK-1 ion current results in a longer action potential [Limberg et al., *Cell. Physiol. Biochem.* 28, 613-624 (2011)]. Furthermore, for TASK-1 knock-out mice a prolonged QT time was demonstrated [Decher et al., *Cell. Physiol. Biochem.* 28, 77-86 (2011)]. Inhibition of TASK channels may therefore be of importance for the treatment of cardiac arrythmias, in particular atrial fibrillation.

In certain vessels, TASK channels also appear to play a role in the regulation of the vascular tone. A relevant expression of TASK-1 was noticed in smooth muscles of pulmonary and mesenteric arteries. In studies on smooth muscle cells of human pulmonary arteries, it was shown that TASK-1 plays a role in the regulation of the pulmonary vascular tone. TASK-1 may be involved in hypoxic and acidosis-induced pulmonary vasoconstriction [Tang et al., *Am. J. Respir. Cell. Mol. Biol.* 41, 476-483 (2009)].

In glomerulosa cells of the adrenal cortex, TASK-1 plays a role in potassium conductivity [Czirjak et al., *Mol. Endocrinol.* 14, 863-874 (2000)].

Possibly, TASK channels also play an important role in apoptosis and tumorigenesis. In breast cancer, colon cancer and lung cancer biopsies and also in metastasizing prostate cancer and in melanoma cells, TASK-3 has been found to be strongly overexpressed [Mu et al., *Cancer Cell* 3, 297-302 (2003); Kim et al., *APMIS* 112, 588-594 (2004); Pocsai et al., *Cell. Mol. Life Sci.* 63, 2364-2376 (2006)]. A point mutation at the TASK-3 channel, which switches off the channel function, simultaneously cancels the tumour-forming action (proliferation, tumour growth, apoptosis resistance) [Mu et al., *Cancer Cell* 3, 297-302 (2003)]. Overexpression of TASK-3 and TASK-1 in a murine fibroblast cell line (C8 cells) inhibits intracellular apoptosis routes [Liu et al., *Brain Res.* 1031, 164-173 (2005)]. Accordingly, the blockade of TASK channels may also be relevant for the treatment of various neoplastic disorders.

Therefore, it is an object of the present invention to provide novel substances which act as potent and selective blockers of TASK-1 and TASK-3 channels and, as such, are suitable in particular for the treatment and/or prevention of respiratory disorders including sleep-related respiratory disorders such as obstructive and central sleep apnoea and snoring, and also other disorders.

US 2002/0022624-A1 describes various azaindole derivatives including imidazo[1,2-a]pyridines as substance P antagonists for the treatment of CNS disorders. WO 2009/143156-A2 discloses 2-phenylimidazo[1,2-a]pyridine derivatives which, as modulators of GABA$_A$ receptors, are likewise suitable for treating CNS disorders. WO 2011/113606-A1 and WO 2012/143796-A2 disclose bicyclic imidazole derivatives suitable for the treatment of bacterial infections and inflammatory disorders. EP 2 671 582-A1 discloses further bicyclic imidazole derivatives and options for their therapeutic use as inhibitors of T type calcium channels. WO 2012/130322-A1 claims 2,6-diaryl-3-(1,4-diazepanylmethyl)imidazo[1,2-a]pyridines which, by virtue of their HIF-1 inhibiting activity, are suitable in particular for the treatment of inflammatory and hyperproliferative disorders. WO 2014/187922-A1 discloses various 2-phenyl-3-(heterocyclomethyl)imidazo[1,2-a]pyridine and -imidazo[1,2-a]pyrazine derivatives as inhibitors of glucose transporters (GLUT) which can be employed for treating inflammatory, proliferative, metabolic, neurological and/or autoimmune disorders. WO 2015/144605-A1 and WO 2017/050732-A1, inter alia, describe acylated bicyclic amine compounds suitable as inhibitors of autotaxin and of lysophosphatidic acid production for the treatment of various disorders. WO 2016/084866-A1 and WO 2016/088813-A1 disclose acylated bridged piperazine derivatives and WO 2016/085783-A1 and WO 2016/085784-A1 acylated 1,4-diazepane derivatives as orexin receptor antagonists which can be used for treating neurodegenerative, neurological and psychiatric disorders, mental disorders and eating and sleep disorders, in particular insomnia.

Furthermore, the compounds
(2-chlorophenyl) {4-[(2-phenylimidazo[1,2-a]pyridin-3-yl)methyl]-1,4-diazepan-1-yl}methanone [CAS Registry No. 1299434-44-8]
and
{4-[(2-phenylimidazo[1,2-a]pyridin-3-yl)methyl]-1,4-diazepan-1-yl}(pyridin-2-yl)methanone [CAS Registry No. 12888 72-88-7]
are indexed by Chemical Abstracts as "Chemical Library" substances without literature reference; a medicinal-therapeutic application of these compounds has hitherto not been described.

The present invention provides compounds of the general formula (I)

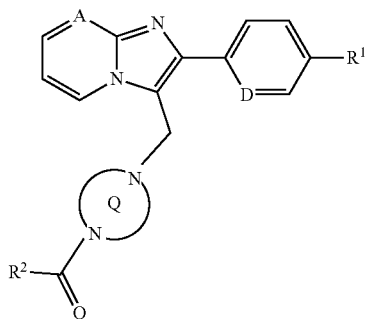

in which
the ring Q represents a bridged 1,4-diazepane cycle of the formula

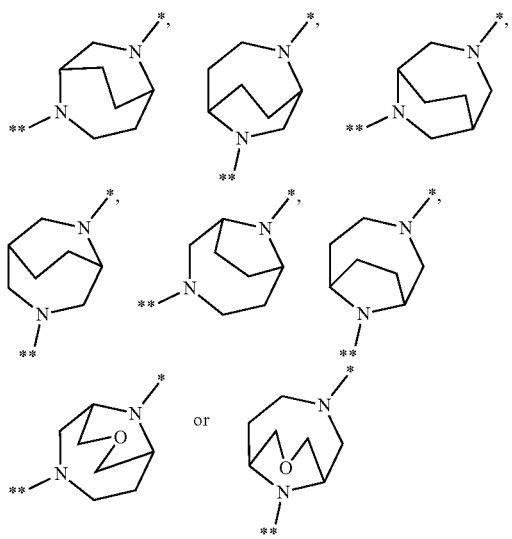

in which * denotes the bond to the adjacent methylene group and ** the bond to the carbonyl group,
A represents CH or N,
D represents CH or N,
$R^1$ represents halogen, cyano, $(C_1-C_4)$-alkyl, cyclopropyl or cyclobutyl
where $(C_1-C_4)$-alkyl may be up to trisubstituted by fluorine and cyclopropyl and cyclobutyl may be up to disubstituted by fluorine, and
$R^2$ represents $(C_4-C_6)$-cycloalkyl in which a ring $CH_2$ group may be replaced by —O—,
or
$R^2$ represents a phenyl group of the formula (a), a pyridyl group of the formula (b) or (c) or an azole group of the formula (d), (e), (f) or (g),

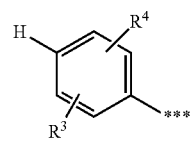

(a)

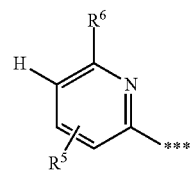

(b)

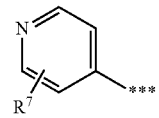

(c)

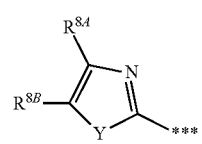

(d)

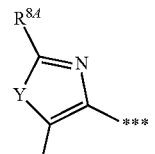

(e)

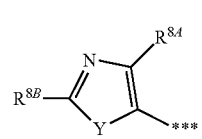

(f)

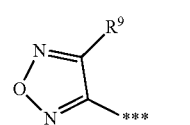

(g)

in which *** marks the bond to the adjacent carbonyl group and
$R^3$ represents hydrogen, fluorine, chlorine, bromine or methyl,
$R^4$ represents hydrogen, fluorine, chlorine, bromine, cyano, $(C_1-C_3)$-alkyl or $(C_1-C_3)$-alkoxy,
where $(C_1-C_3)$-alkyl and $(C_1-C_3)$-alkoxy may each be up to trisubstituted by fluorine,
$R^5$ represents hydrogen, fluorine, chlorine, bromine or methyl,
$R^6$ represents hydrogen, $(C_1-C_3)$-alkoxy, cyclobutyloxy, oxetan-3-yloxy, tetrahydrofuran-3-yloxy, tetrahydro-2H-pyran-4-yloxy, mono-$(C_1-C_3)$-alkylamino, di-$(C_1-C_3)$-alkylamino or $(C_1-C_3)$-alkylsulfanyl, where $(C_1-C_3)$-alkoxy may be up to trisubstituted by fluorine, $R^7$ represents hydrogen, fluorine, chlorine, bromine, $(C_1-C_3)$-alkyl or $(C_1-C_3)$-alkoxy, $R^{8A}$ and $R^{8B}$ are identical or different and independently of one another represent hydrogen, fluorine, chlorine, bromine, $(C_1-C_3)$-alkyl, cyclopropyl or $(C_1-C_3)$-alkoxy, where $(C_1-C_3)$-alkyl and $(C_1-C_3)$-alkoxy may each be up to trisubstituted by fluorine, $R^9$ represents hydrogen, $(C_1-C_3)$-alkyl or amino and Y represents O or S, or $R^2$ represents an —$OR^{10}$ or —$NR^{11}R^{12}$ group in which $R^{10}$ represents $(C_1-C_6)$-alkyl, $(C_4-C_6)$-cycloalkyl or $[(C_3-C_6)$-cycloalkyl]methyl, $R^{11}$ represents hydrogen or $(C_1-C_3)$-alkyl and $R^{12}$ represents $(C_1-C_6)$-alkyl, $(C_3-C_6)$-cycloalkyl, phenyl or benzyl, where $(C_1-C_6)$-alkyl may be up to trisubstituted by fluorine, and where phenyl and the phenyl group in benzyl may be up to trisubstituted by identical or different radicals selected from the group consisting of fluorine, chlorine, methyl, ethyl, trifluoromethyl, methoxy, ethoxy and trifluoromethoxy, or $R^{11}$ and $R^{12}$ are attached to one another and, together with the nitrogen atom to which they are bonded, form a pyrrolidine, piperidine, morpholine or thiomorpholine ring, and the salts, solvates and solvates of the salts thereof.

Inventive compounds are the compounds of the formula (I) and the salts, solvates and solvates of the salts thereof, the compounds of the formulae (I-A), (I-B), (I-C) and (I-D) below that are encompassed by formula (I) and the salts, solvates and solvates of the salts thereof, and the compounds cited hereinafter as working examples that are encompassed by formula (I) and the salts, solvates and solvates of the salts thereof, if the compounds cited hereinafter that are encompassed by formula (I) are not already salts, solvates and solvates of the salts.

Preferred salts in the context of the present invention are physiologically acceptable salts of the compounds of the invention. Also encompassed are salts which are not themselves suitable for pharmaceutical applications but can be used, for example, for the isolation, purification or storage of the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably employed for the purpose, especially HPLC chromatography on chiral or achiral separation phases. In the case of chiral amines as intermediates or end products, separation is alternatively also possible via diastereomeric salts using enantiomerically pure carboxylic acids.

If the compounds of the invention can occur in tautomeric forms, the present invention encompasses all the tautomeric forms.

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulfur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labeled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds of the invention. The term "prodrugs" refers here to compounds which may themselves be biologically active or inactive, but are converted while present in the body, for example by a metabolic or hydrolytic route, to compounds of the invention.

In the context of the present invention, unless specified otherwise, the substituents and radicals are defined as follows:

In the context of the invention, $(C_1-C_6$-alkyl is a straight-chain or branched alkyl radical having 1 to 6 carbon atoms. Examples include: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

In the context of the invention, $(C_1-C_4)$-alkyl is a straight-chain or branched alkyl radical having 1 to 4 carbon atoms. Examples include: methyl, ethyl, n-propyl, isopropyl, n-butyl, isobutyl, sec-butyl and tert-butyl.

In the context of the invention, $(C_1-C_3)$-alkyl is a straight-chain or branched alkyl radical having 1 to 3 carbon atoms. Examples include: methyl, ethyl, n-propyl and isopropyl.

$(C_1-C_3)$-Alkoxy in the context of the invention is a straight-chain or branched alkoxy radical having 1 to 3 carbon atoms. Examples include: methoxy, ethoxy, n-propoxy and isopropoxy.

Mono-$(C_1-C_3)$-alkylamino in the context of the invention is an amino group having a straight-chain or branched alkyl substituent having 1 to 3 carbon atoms. Examples include: methylamino, ethylamino, n-propylamino and isopropylamino.

Di-$C_1-C_3$-alkylamino in the context of the invention is an amino group having two identical or different straight-chain or branched alkyl substituents each having 1 to 3 carbon atoms. Examples include: N,N-dimethylamino, N,N-diethylamino, N-ethyl-N-methylamino, N-methyl-N-n-propylamino, N-isopropyl-N-methylamino, N,N-di-n-propylamino, N-isopropyl-N-n-propylamino and N,N-diisopropylamino.

$(C_1-C_3)$-Alkylsulfanyl [also referred to as $(C_1-C_3)$-alkylthio] in the context of the invention is a straight-chain or branched alkyl radical having 1 to 3 carbon atoms which is attached to the remainder of the molecule via a sulfur atom. Examples include: methylsulfanyl, ethylsulfanyl, n-propylsulfanyl and isopropylsulfanyl.

$(C_3-C_6)$-Cycloalkyl in the context of the invention is a monocyclic saturated cycloalkyl group having 3 to 6 ring carbon atoms. Examples include: cyclopropyl, cyclobutyl, cyclopentyl and cyclohexyl.

$(C_4-C_6)$-Cycloalkyl in the context of the invention is a monocyclic saturated cycloalkyl group having 4 to 6 carbon atoms. Examples include: cyclobutyl, cyclopentyl and cyclohexyl.

Halogen in the context of the invention includes fluorine, chlorine, bromine and iodine. Preference is given to fluorine, chlorine or bromine.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

Preference is given in the context of the present invention to compounds of the formula (I) in which
the ring Q represents a bridged 1,4-diazepane cycle of the formula in which * denotes the bond to the adjacent methylene group and  the bond to the carbonyl group, A represents CH or N, D represents CH or N, $R^1$ represents fluorine, chlorine, bromine, methyl, isopropyl, tert-butyl, cyclopropyl or cyclobutyl and $R^2$ represents cyclobutyl, cyclopentyl or cyclohexyl or $R^2$ represents a phenyl group of the formula (a), a pyridyl group of the formula (b) or an azole group of the formula (d), (e), (f) or (g), in which * marks the bond to the adjacent carbonyl group and $R^3$ represents hydrogen, fluorine or chlorine, $R^4$ represents fluorine, chlorine, cyano, $(C_1-C_3)$-alkyl, $(C_1-C_3)$-alkoxy or trifluoromethoxy, R⁵ represents hydrogen, fluorine, chlorine, bromine or methyl, R⁶ represents $(C_1-C_3)$-alkoxy, cyclobutyloxy or $(C_1-C_3)$-alkylsulfanyl,
  where $(C_1-C_3)$-alkoxy may be up to trisubstituted by fluorine, $R^{8A}$ and $R^{8B}$ are identical or different and independently of one another represent hydrogen, chlorine, bromine, $(C_1-C_3)$-alkyl or cyclopropyl,
  where $(C_1-C_3)$-alkyl may be up to trisubstituted by fluorine, R⁹ represents methyl or amino
and
Y represents O or S,
and the salts, solvates and solvates of the salts thereof.

A particular embodiment of the present invention relates to compounds of the formula (I) in which
the ring Q represents a bridged 1,4-diazepane cycle of the formula

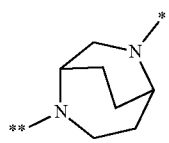

in which * denotes the bond to the adjacent methylene group and ** the bond to the carbonyl group,
and the salts, solvates and solvates of the salts thereof.

A further particular embodiment of the present invention relates to compounds of the formula (I) in which
the ring Q represents a bridged 1,4-diazepane cycle of the formula

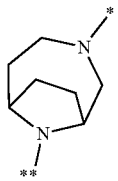

in which * denotes the bond to the adjacent methylene group and ** the bond to the carbonyl group, and the salts, solvates and solvates of the salts thereof.

A further particular embodiment of the present invention relates to compounds of the formula (I) in which
the ring Q represents a bridged 1,4-diazepane cycle of the formula

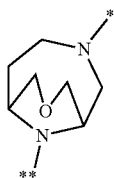

in which * denotes the bond to the adjacent methylene group and ** the bond to the carbonyl group,
and the salts, solvates and solvates of the salts thereof.

A further particular embodiment of the present invention relates to compounds of the formula (I) in which
A is CH and D is N,
and the salts, solvates and solvates of the salts thereof.

A further particular embodiment of the present invention relates to compounds of the formula (I) in which
A is N and D is CH,
and the salts, solvates and solvates of the salts thereof.

A further particular embodiment of the present invention relates to compounds of the formula (I) in which
R¹ is chlorine, bromine or isopropyl,
and the salts, solvates and solvates of the salts thereof.

A further particular embodiment of the present invention relates to compounds of the formula (I) in which
R² represents cyclopentyl or cyclohexyl,
and the salts, solvates and solvates of the salts thereof.

A further particular embodiment of the present invention relates to compounds of the formula (I) in which
R² is a phenyl group of the formula (a)

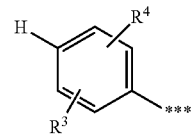

in which ** marks the bond to the adjacent carbonyl group,
R³ is hydrogen, fluorine or chlorine
and
R⁴ is fluorine, chlorine, $(C_1-C_3)$-alkyl or $(C_1-C_3)$-alkoxy,
and the salts, solvates and solvates of the salts thereof.

A further particular embodiment of the present invention relates to compounds of the formula (I) in which
R² is a pyridyl group of the formula (b)

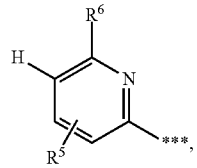

in which ** marks the bond to the adjacent carbonyl group,
R⁵ is hydrogen, fluorine, chlorine, bromine or methyl
and
R⁶ represents $(C_1-C_3)$-alkoxy, cyclobutyloxy or $(C_1-C_3)$-alkylsulfanyl,
  where $(C_1-C_3)$-alkoxy may be up to trisubstituted by fluorine,
and the salts, solvates and solvates of the salts thereof.

A further particular embodiment of the present invention relates to compounds of the formula (I) in which
R² represents an azole group of the formula (d), (e) or (f)

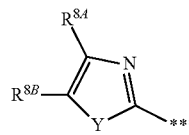

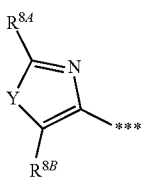
(e)

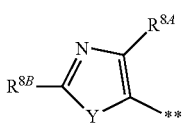
(f)

in which ** marks the bond to the adjacent carbonyl group, $R^{8A}$ and $R^{8B}$ are identical or different and independently of one another represent hydrogen, chlorine, bromine, $(C_1-C_3)$-alkyl or cyclopropyl,
where $(C_1-C_3)$-alkyl may be up to trisubstituted by fluorine,
and
Y represents O or S,
and the salts, solvates and solvates of the salts thereof.

A further particular embodiment of the present invention relates to compounds of the formula (I) in which $R^2$ represents an azole group of the formula (g)

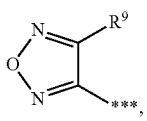
(g)

in which *** marks the bond to the adjacent carbonyl group
and
$R^9$ represents $(C_1-C_3)$-alkyl or amino,
and the salts, solvates and solvates of the salts thereof.

In the context of the present invention, particular preference is given to compounds of the formula (I) in which the ring Q represents a bridged 1,4-diazepane cycle of the formula

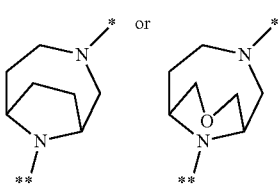

in which * denotes the bond to the adjacent methylene group and ** the bond to the carbonyl group,
A represents CH or N,
D represents CH or N,
$R^1$ represents chlorine, bromine, isopropyl or cyclopropyl and
$R^2$ represents cyclopentyl or cyclohexyl,
or
$R^2$ represents a phenyl group of the formula (a), a pyridyl group of the formula (b) or an azole group of the formula (g),

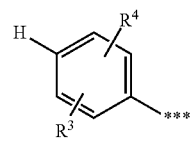
(a)

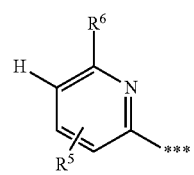
(b)

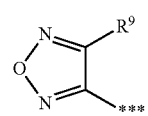
(c)

in which *** marks the bond to the adjacent carbonyl group and $R^3$ represents hydrogen, fluorine or chlorine, $R^4$ represents fluorine, chlorine, methyl, isopropyl, methoxy or ethoxy, $R^5$ represents hydrogen, fluorine, chlorine, bromine or methyl, $R^6$ represents methoxy, difluoromethoxy, trifluoromethoxy, isopropoxy, cyclobutyloxy or methylsulfanyl
and $R^9$ represents methyl or amino, and the salts, solvates and solvates of the salts thereof.

The individual radical definitions specified in the respective combinations or preferred combinations of radicals are, independently of the respective combinations of the radicals specified, also replaced as desired by radical definitions of other combinations. Particular preference is given to combinations of two or more of the abovementioned preferred ranges.

The invention furthermore provides a process for preparing the compounds of the formula (I) according to the invention, characterized in that a compound of the formula (II)

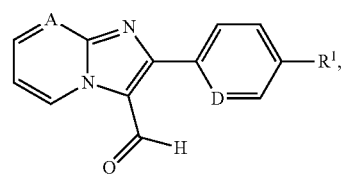
(II)

in which A, D and $R^1$ have the meanings given above is reacted in the presence of a suitable reducing agent either

[A] with a compound of the formula (III)

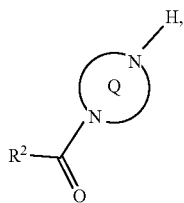
(III)

in which $R^2$ and the ring Q have the meanings above to give a compound of the formula (I)

or

[B] with a protected diazabicyclic system of the formula (IV)

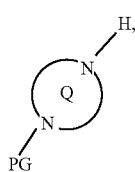
(IV)

in which the ring Q has the meaning given above and

PG represents a suitable amino protecting group, for example tert-butoxycarbonyl, benzyloxycarbonyl or (9H-fluoren-9-ylmethoxy)carbonyl at first to give a compound of the formula (V)

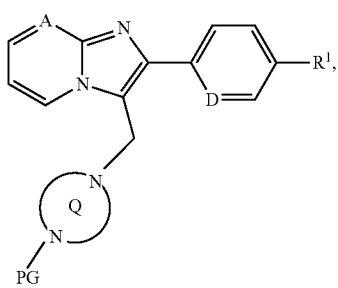
(V)

in which A, D, PG, $R^1$ and the ring Q have the meanings given above, then the protecting group PG is removed and the resulting compound of the formula (VI)

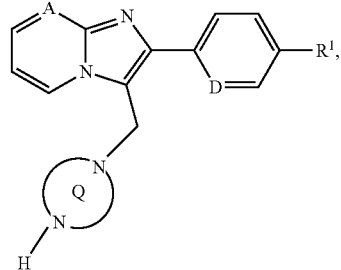
(VI)

in which A, D, $R^1$ and the ring Q have the meanings given above is then reacted, depending on the specific meaning of the $R^2$ radical,

[B-1] with a carboxylic acid of the formula (VII)

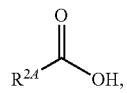
(VII)

in which $R^{2A}$ represents $(C_4\text{-}C_6)$-cycloalkyl in which a ring $CH_2$ group may be replaced by —O—, or is a phenyl group of the formula (a), a pyridyl group of the formula (b) or (c) or an azole group of the formula (d), (e), (f) or (g), as described above, with activation of the carboxylic acid function in (VII), or is reacted with the corresponding acid chloride of the formula (VIII)

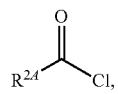
(VIII)

in which $R^{2A}$ has the meaning given above to give a compound of the formula (I-A)

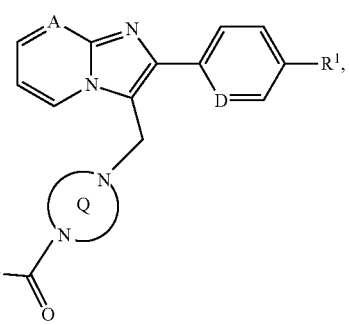
(I-A)

in which A, D, $R^1$, $R^{2A}$ and the ring Q have the meanings given above or

[B-2] with a chloroformate or carbamoyl chloride of the formula (IX)

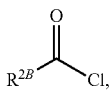 (IX)

in which
R²ᴮ is the —OR¹⁰ or —NR¹¹ᴬR¹² group in which
R¹⁰ and R¹² have the meanings given above
and
R¹¹ᴬ has the definition of R¹¹ given above, but is not hydrogen,
to give a compound of the formula (I-B)

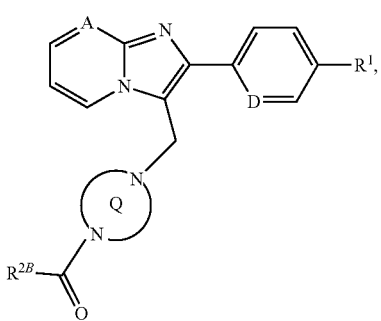 (I-B)

in which A, D, R¹, R²ᴮ and the ring Q have the meanings given above
or
[B-3] with an isocyanate of the formula (X)

 (X),

R¹²—N═C═O in which R¹² has the meaning given above,
to give a compound of the formula (I-C)

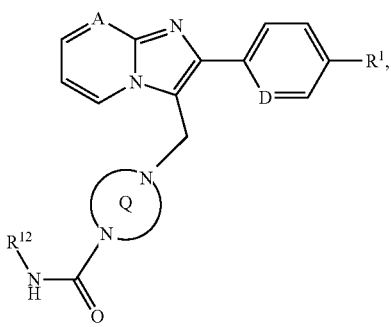 (I-C)

in which A, D, R¹, R¹² and the ring Q have the meanings given above
and the compounds of the formulae (I), (I-A), (I-B) or (I-C) thus obtained are optionally separated into their enantiomers and/or diastereomers and/or optionally converted with the appropriate (i) solvents and/or (ii) acids to the solvates, salts and/or solvates of the salts thereof.

Suitable reducing agents for the process steps [A] (II)+(III)→(I) and [B] (II)+(IV)→(V) [reductive aminations] for such purposes are customary alkali metal borohydrides such as sodium borohydride, sodium cyanoborohydride or sodium triacetoxyborohydride; preference is given to using sodium triacetoxyborohydride. The addition of an acid, such as acetic acid in particular, and/or of a dehydrating agent, for example molecular sieve or trimethyl orthoformate or triethyl orthoformate, may be advantageous in these reactions.

Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran. The reactions are generally effected within a temperature range of 0° C. to +50° C.

The protecting group PG used in compound (IV) may be a standard amino protecting group, for example tert-butoxycarbonyl (Boc), benzyloxycarbonyl (Z) or (9H-fluoren-9-ylmethoxy)carbonyl (Fmoc); preference is given to using tert-butoxycarbonyl (Boc). The detachment of the protecting group in process step [B] (V)→(VI) is effected by known methods. Thus, the tert-butoxycarbonyl group is typically detached by treatment with a strong acid such as hydrogen chloride, hydrogen bromide or trifluoroacetic acid, in an inert solvent such as diethyl ether, 1,4-dioxane, dichloromethane or acetic acid. In the case of benzyloxycarbonyl as protecting group, this is preferably removed by hydrogenolysis in the presence of a suitable palladium catalyst such as palladium on activated carbon. The (9H-fluoren-9-ylmethoxy)carbonyl group is generally detached with the aid of a secondary amine base such as diethylamine or piperidine [see, for example, T. W. Greene and P. G. M. Wuts, *Protective Groups in Organic Synthesis*, Wiley, New York, 1999; P. J. Kocienski, *Protecting Groups*, 3ʳᵈ edition, Thieme, 2005].

Certain compounds of the formula (V), especially those in which PG is tert-butoxycarbonyl, likewise have significant inhibitory activity with respect to TASK-1 and/or TASK-3, and in this respect are also encompassed by the scope of definition of the present invention, i.e. the compounds of the formula (I).

The process step [B-1] (VI)+(VII)→(I-A) [amide formation] is conducted by known methods with the aid of a condensing or activating agent. Suitable agents of this kind are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chlorenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(1H-1-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also as base an alkali metal carbonate, for example sodium carbonate or potassium carbonate, or a tertiary amine base such as triethylamine, N,N-diisopropylethylamine, N-methylmorpholine (NMM), N-methylpiperidine (NMP), pyridine or 4-N,N-dimethylaminopyridine (DMAP). The condensing agent or activating agent used with preference is O-(7-azabenzotriazol-1-yl)-N,N,N',N'-tetramethyluronium hexafluorophosphate (HATU) in combination with N,N-diisopropylethylamine as base.

The alternative process via the carbonyl chloride (VIII) [(VI)+(VIII)→(I-A)] is generally effected in the presence of a base such as sodium carbonate, potassium carbonate, triethylamine, N,N-diisopropylethylamine, N-methylmorpholine (NMM), N-methylpiperidine (NMP), pyridine, 2,6-dimethylpyridine, 4-N,N-dimethylaminopyridine (DMAP), 1,5-diazabicyclo[4.3.0]non-5-ene (DBN) or 1,8-diazabicyclo[5.4.0]undec-7-ene (DBU); preference is given to using triethylamine or N,N-diisopropylethylamine.

Suitable inert solvents for these amide-forming reactions are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP); it is also possible to use mixtures of such solvents. Preference is given to using dichloromethane, 1,2-dichloroethane, tetrahydrofuran, N,N-dimethylformamide or mixtures of these solvents. The reactions are generally conducted within a temperature range of from −20° C. to +60° C., preferably at from 0° C. to +40° C.

The process [B-2] (VI)+(IX)→(I-B) [formation of urethanes or substituted ureas] is conducted under similar reaction conditions with regard to solvent, addition of base and temperature as described above for the amide formation [B-1] (VI)+(VIII)→(I-A).

The reaction [B-3] (VI)+(X)→(I-C) is likewise effected in one of the above-listed inert solvents or solvent mixtures at a temperature in the range from 0° C. to +60° C.; the addition of a base in this reaction can optionally be dispensed with.

The amine compound (VI) can also be also be used in the process steps [B-1] (VI)+(VII) or (VIII)→(I-A), [B-2] (VI)+(IX)→(I-B) and [B-3] (VI)+(X)→(I-C) in the form of a salt, for example as hydrochloride or trifluoroacetate. In such a case, the conversion is effected in the presence of an appropriately increased amount of the respective auxiliary base used.

Compounds of the formula (I) according to the invention may also be obtained by initially reducing the above-mentioned carbaldehyde of the formula (II)

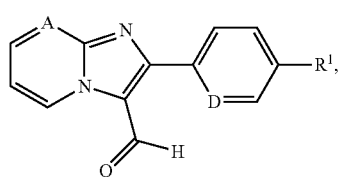

(II)

in which A, D and R$^1$ have the meanings given above, with the aid of sodium borohydride to give an alcohol of the formula (XI)

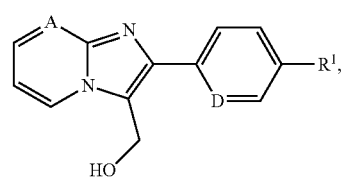

(XI)

in which A, D and R$^1$ have the meanings given above, subsequently converting this by treatment with methanesulfonyl chloride in the presence of a base into the corresponding mesylate of the formula (XII)

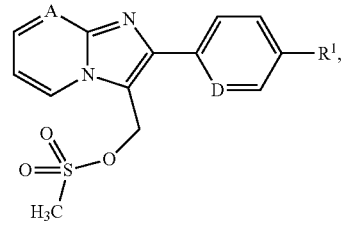

(XII)

in which A, D and R$^1$ have the meanings given above, and then reacting the latter in the presence of a base with a compound of the formula (III)

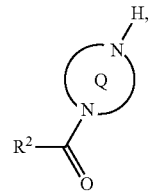

(III)

in which R$^2$ and the ring Q have the meanings given above, to give a compound of the formula (I).

The reduction (II)→(XI) is carried out by known methods using sodium borohydride in an alcoholic solvent such as ethanol in a temperature range from 0° C. to +30° C. Subsequent conversion into the mesylate (XII) is carried out in a customary manner by treating the alcohol (XI) with methanesulfonyl chloride in the presence of a tertiary amine base such as, for example, triethylamine, N,N-diisopropylethylamine, N-methylmorpholine or else pyridine; the reaction is typically carried out in a chlorinated hydrocarbon such as dichloromethane or 1,2-dichloroethane as inert solvent in a temperature range from −20° C. to +20° C. For the subsequent reaction with the compound (III), the mesylate (XII) is preferably not isolated beforehand but employed directly as crude product in a one-pot process with addition of a dipolar-aprotic solvent. As such, preference is given to using acetonitrile or N,N-dimethylformamide, and the reaction is generally carried out in a temperature range from 0° C. to +60° C. The reaction (XII)+(III)→(I) is likewise carried out in the presence of a base; expediently—in the case of the configuration mentioned as a one-pot reaction—, an appropriate excess of the amine base used beforehand for the preparation of the mesylate may be used for this purpose.

The compounds of the formula (II) can be prepared by a process known from the literature by condensing a compound of the formula (XIII) (XIII)

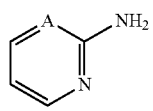

(XIII)

in which A has the meaning given above,
under the influence of a base with a compound of the formula (XIV)

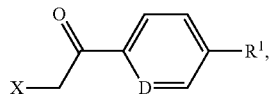

(XIV)

in which D and $R^1$ have the meanings given above
and
X represents a suitable leaving group, for example chlorine, bromine or iodine,
to give a bicyclic system of the formula (XV)

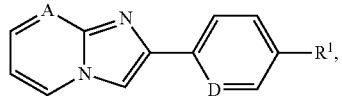

(XV)

in which A, D and $R^1$ have the meanings given above
and then formylating this with a mixture of N,N-dimethylformamide and phosphorus oxychloride to give (II).

The condensation reaction (XIII)+(XIV)→(XV) is usually conducted in an alcoholic solvent such as methanol, ethanol, n-propanol, isopropanol or n-butanol, in an ether such as diethyl ether, diisopropyl ether, methyl tert-butyl ether, tetrahydrofuran, 1,4-dioxane, 1,2-dimethoxyethane or bis(2-methoxyethyl) ether, in a dipolar aprotic solvent such as N,N-dimethylformamide (DMF), N,N'-dimethylpropyleneurea (DMPU) or N-methylpyrrolidinone (NMP), or else in water, at a temperature in the range from +50° C. to +150° C.; preference is given to using ethanol or water as solvent.

Bases suitable for this reaction are in particular alkali metal bicarbonates or carbonates such as sodium bicarbonate or potassium bicarbonate or lithium carbonate, sodium carbonate, potassium carbonate or caesium carbonate, alkali metal hydroxides such as sodium hydroxide or potassium hydroxide, or else alumina; preference is given to using sodium bicarbonate or sodium hydroxide. Optionally—if the reaction temperature is increased appropriately—the reaction can also be carried out without addition of a base.

The regioselective formylation (XV)→(II) is carried out under the customary conditions of a Vilsmaier-Haack reaction by treating (XV) with a pre-formed mixture of N,N-dimethylformamide and phosphorus oxychloride which is employed in a large excess and simultaneously also serves as solvent. The reaction is generally carried out within a temperature range of from 0° C. to +100° C.

The processes described above can be conducted at atmospheric, elevated or reduced pressure (for example in the range from 0.5 to 5 bar); in general, the reactions are each carried out at atmospheric pressure.

Separation of the compounds of the invention into the corresponding enantiomers and/or diastereomers can, as appropriate, optionally also be carried out at the early stage of the compounds (III), (IV), (V) or (VI), which are then converted further in separated form in accordance with the process steps described above. Such a separation of stereoisomers can be conducted by customary methods known to the person skilled in the art. In the context of the present invention, preference is given to using chromatographic methods on chiral or achiral separation phases; in the case of chiral amines as intermediates or end products, separation can alternatively be effected via diastereomeric salts with the aid of enantiomerically pure carboxylic acids.

Some of the compounds of the formula (IV) are commercially available, or they are described as such in the literature, or they can be prepared from other commercially available compounds analogously to methods known from the literature. One such preparation is shown in an exemplary manner in Reaction Schemes 1-3 below and then in each case explained in greater detail:

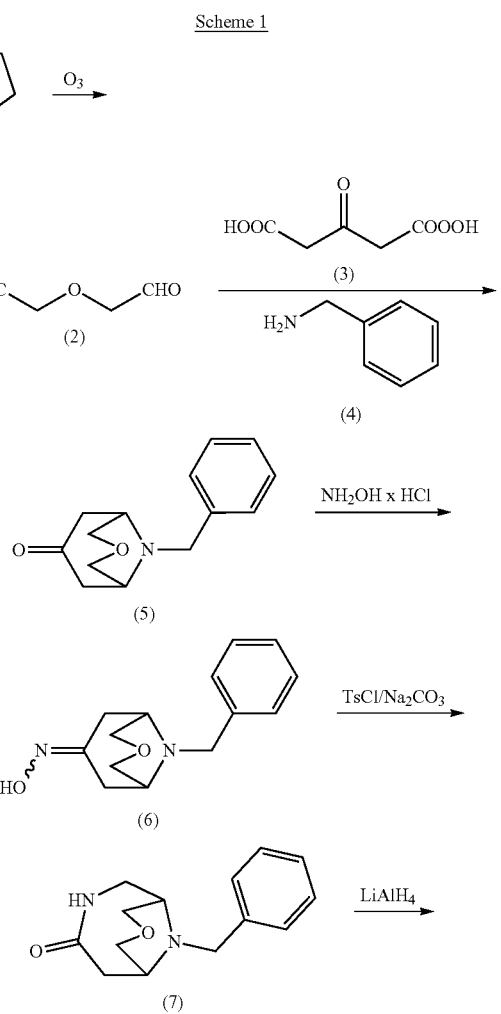

Scheme 1

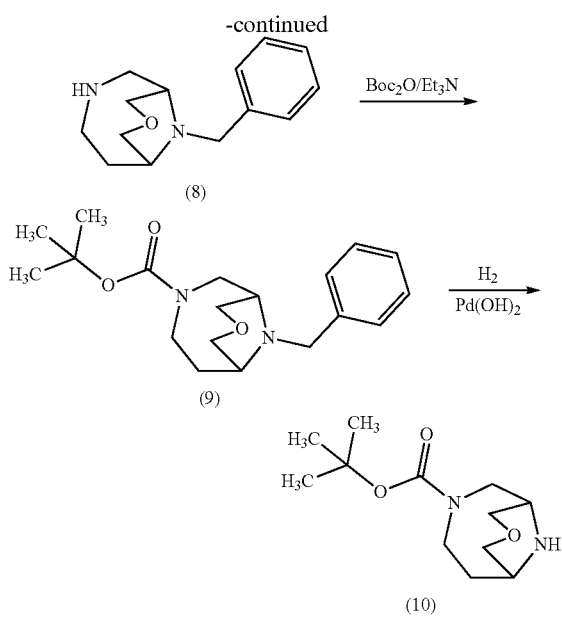

Here, starting with 2,5-dihydrofuran (1), initially dialdehyde (2) was obtained by ozonolysis at −78° C. in dichloromethane as solvent, which was directly, as crude product without any further purification, taken up in water and treated with dicarboxylic acid (3) and sodium acetate. After subsequent addition of benzylamine (4) in 3 N hydrochloric acid, the resulting mixture was stirred at room temperature for 16 h, and the bicyclic aminoketone (5) was then isolated in a yield of 16%. In an ethanol/water mixture, ketone (5) was then converted in a yield of 87% into the oxime (6) as an E/Z mixture, by reacting with hydroxylamine hydrochloride and sodium acetate at 70°-80° C. for three hours. Reaction with sodium carbonate and tosyl chloride in an acetonitrile/water mixture at a temperature of 70°-80° C. over 15 h gave the ring-extended product, the seven-membered lactam (7), in a yield of 71%. This lactam (7) was then, by reduction with lithium aluminium hydride in THF at a temperature of 20°-30° C. and a reaction time of 16 h, converted into the bridged diamine (8), which was reacted as a crude product with di-tert-butyl dicarbonate and triethylamine in dichloromethane over 5 h at 20°-30° C. The resulting doubly protected diamine (9) was, after work-up and chromatographic purification, obtained in a yield of 82%. The final hydrogenation with palladium hydroxide as catalyst in methanol at a temperature of 20°-30° C. and a hydrogen pressure of 50 Psi (about 3.45 bar) over 4 h then gave the desired target compound, the monoprotected diamine (10), in a yield of 69% after chromatographic purification.

Scheme 2

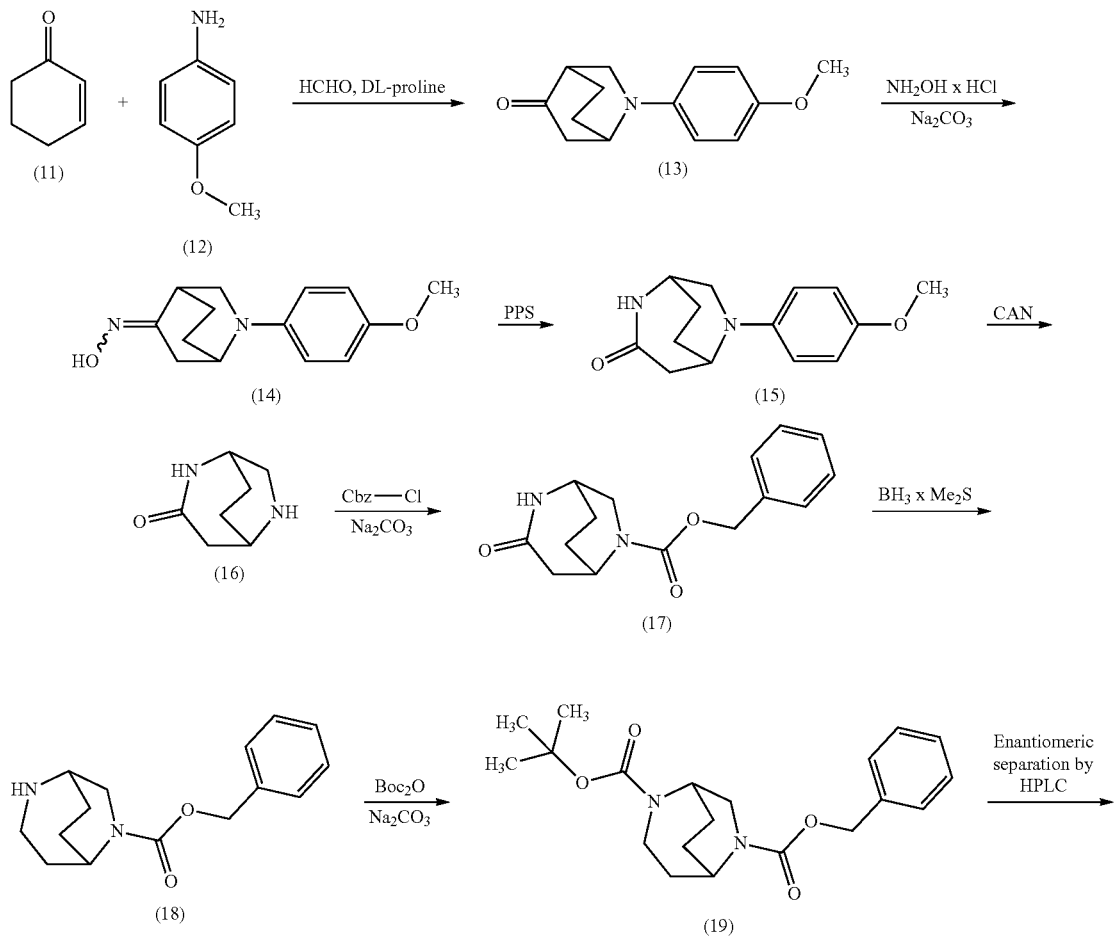

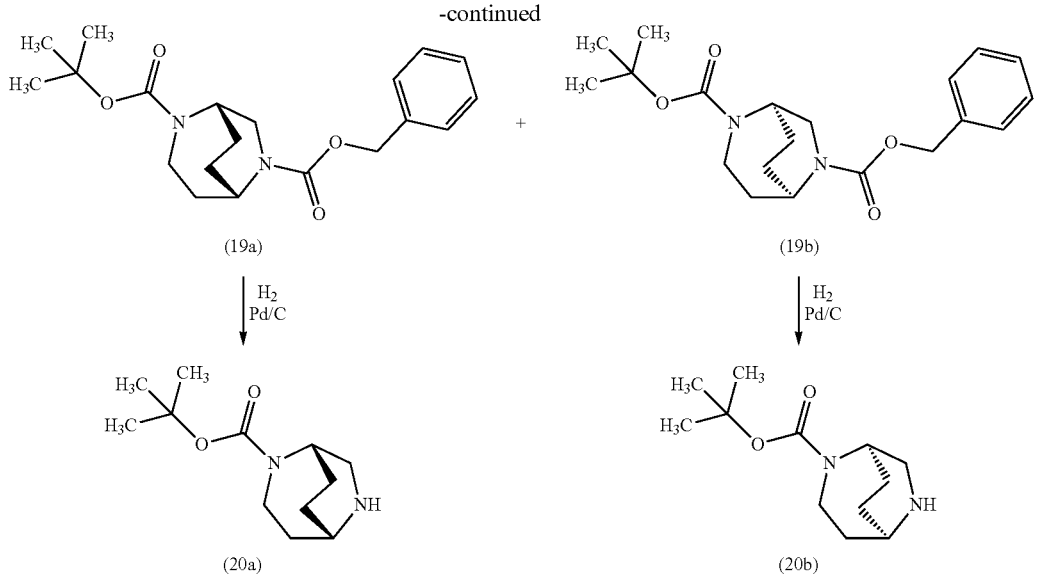

Here, initially cyclohex-2-en-1-one (11), 4-methoxyaniline (12) and formaldehyd were reacted with one another in the presence of DL-proline in a 3-component reaction. After a reaction time of 30 h at 50° C. in DMSO as solvent, the bicyclic aminoketone (13) was obtained in racemic form with a yield of 18% [cf. L. Eriksson et al., *Angew. Chem. Int. Ed.* 44, 4877 (2005)]. By reaction with hydroxylamine hydrochloride and sodium carbonate in THF at room temperature, ketone (13) was then converted into the E/Z oxime (14), which was subsequently treated with polyphosphoric acid in toluene at 100° C. for 5 h. After work-up of the reaction, the ring-extended product, i.e. the bicyclic lactam (15), was isolated in a yield of 39%. Subsequent oxidative removal of the anisole group with the aid of cerium(IV) ammonium nitrate in an acetonitrile/water mixture at room temperature afforded the aminolactam (16), which was directly, as an aqueous crude product solution, reacted further with benzyloxycarbonyl chloride (benzyl carbonochloridate) in the presence of sodium carbonate (pH 10). Chromatographic purification gave the Cbz protected derivative (17) in a total yield of 48% over the last two steps. Via reduction of the lactam (17) using borane/dimethyl sulfide complex in THF at 65° C., it was possible to obtain the amine (18), which for its part was directly reacted further as an aqueous crude product solution in the presence of sodium carbonate (pH 10) with di-tert-butyl dicarbonate, giving, in a total yield of 63% over the last two steps, the doubly protected diamine (19). The racemic compound obtained in this manner was then separated into the enantiomers (19a) and (19b) (in each case with >98% ee) by SFC-HPLC on a chiral phase. Removal of the Cbz protective group by hydrogenolysis (1 bar of hydrogen, 10% palladium on carbon as catalyst) in methanol finally gave the desired target compounds, i.e. the monoprotected diamines (20a) and (20b), in enantiomerically pure form.

Scheme 3

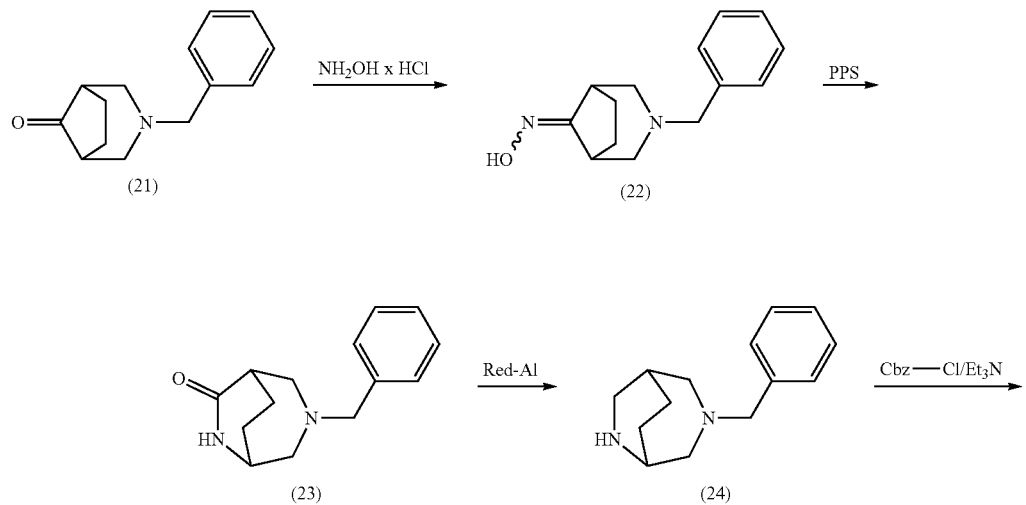

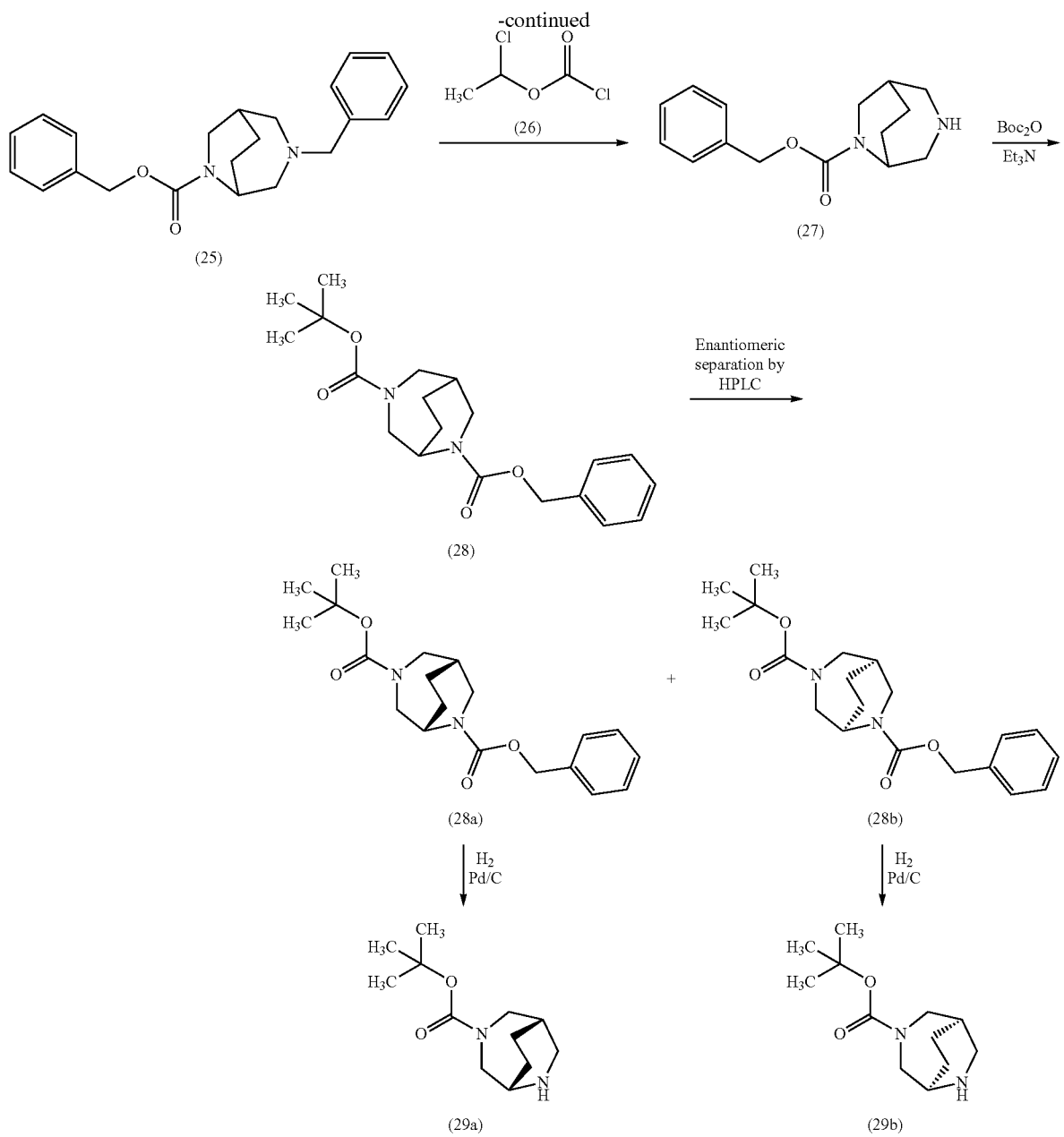

Here, initially the bicyclic aminoketone (21) was converted by reaction with hydroxylamine hydrochloride and diisopropylethylamine in ethanol at a temperature of 35° C. over 2 h into the E/Z oxime (22) (yield 84%). Oxime (22) was then treated with polyphosphoric acid in toluene at 110°-120° C. for 2 h. After work-up of the reaction, the ring-extended product, i.e. the bicyclic lactam (23), was isolated in a yield of 49%. Subsequent reduction with sodium bis(2-methoxyethoxy)aluminiumhydride (Red-Al®) in THF at a temperature of 50° C. for 3 h gave the diamine (24), which was subsequently converted by reaction with benzyloxycarbonyl chloride (benzyl carbonochloridate) and triethylamine in dichloromethane at 0°-10° C. into the Cbz-protected derivative (25). Reaction of compound (25) with 1-chloroethyl carbonochloridate (26) in 1,2-dichloroethane at 85° C. for 5 h, addition of methanol and further heating at 85° C. for 1 h gave the N-debenzylated compound (27). This was subsequently reacted in dichloromethane with di-tert-butyl dicarbonate in the presence of triethylamine and 4-N,N-dimethylaminopyridine; after a reaction time of 2 h at 10° C., the doubly protected diamine (28) was isolated in a yield of 69%. The racemic compound obtained in this manner was then separated into the enantiomers (28a) and (28b) (in each case with >95.5% ee) by SFC-HPLC on a chiral phase. Removal of the Cbz protective group by hydrogenolysis (1 atm of hydrogen, 10% palladium on carbon as catalyst) in methanol finally gave the desired target compounds, i.e. the monoprotected diamines (29a) and (29b), in enantiomerically pure form.

The compounds of the formulae (III), (VII), (VIII), (IX), (X), (XIII) and (XIV) are either commercially available or described as such in the literature, or they can be prepared in a simple manner from other commercially available compounds by methods familiar to the person skilled in the art and known from the literature. Numerous detailed procedures and further literature references can also be found in the experimental section, in the section on the preparation of the starting compounds and intermediates.

The preparation of the compounds according to the invention can be illustrated further in an exemplary manner by the Reaction Schemes 4-7 below:

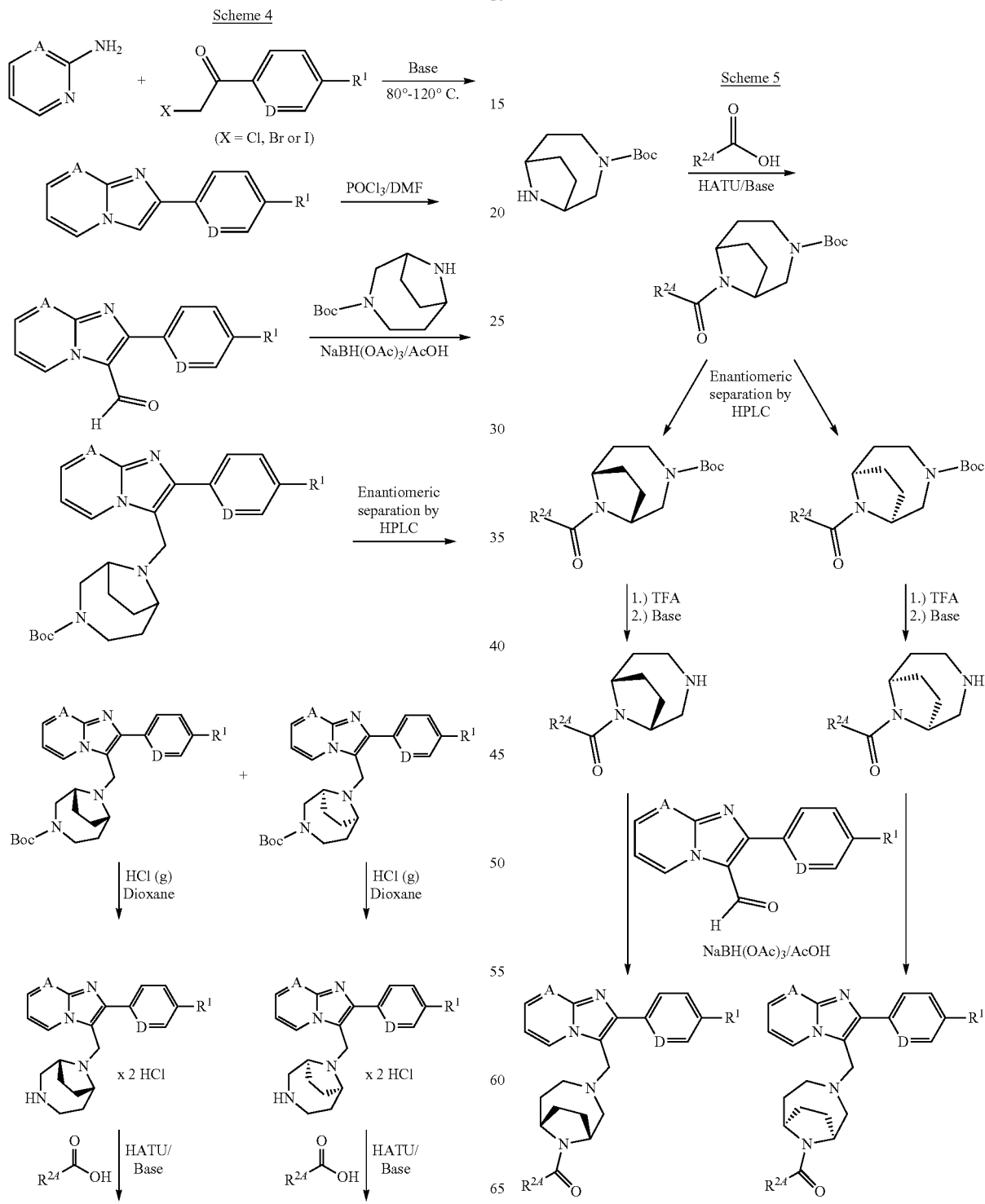

Scheme 6

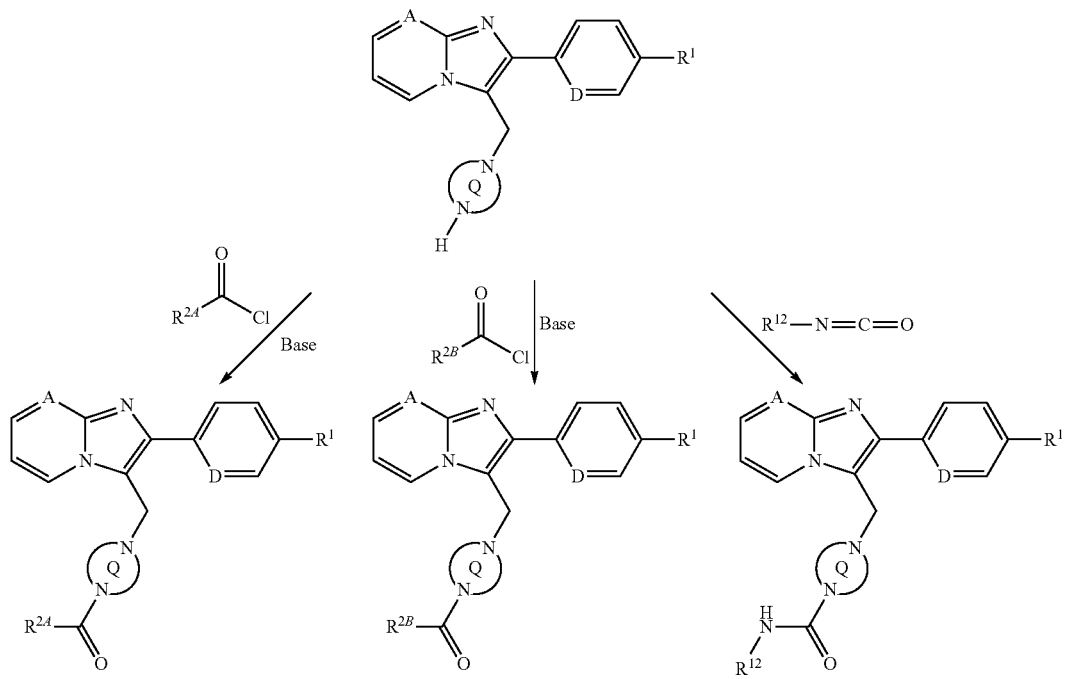

Scheme 7

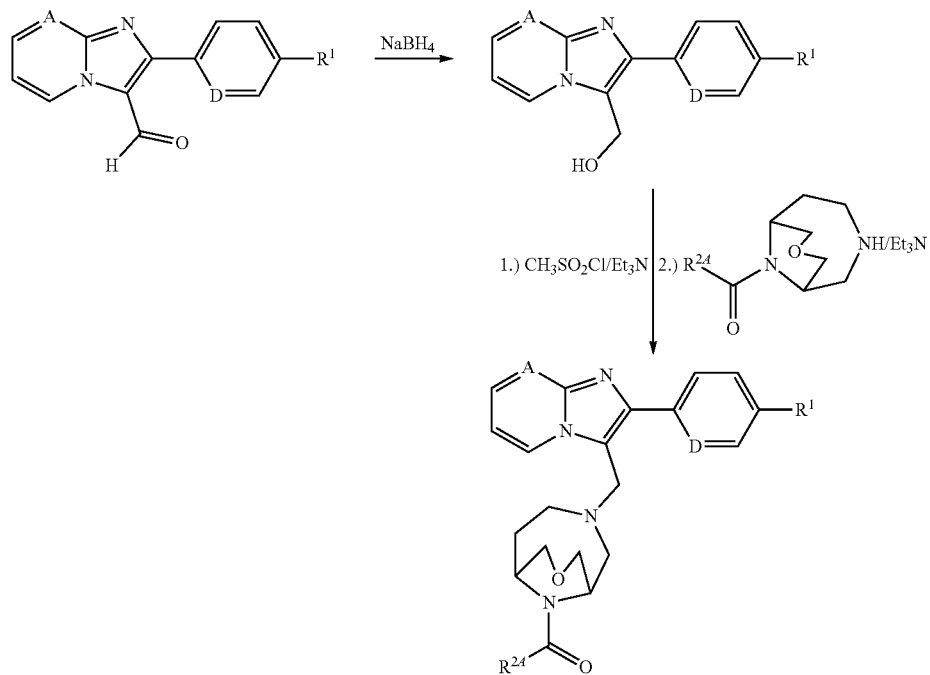

The compounds of the invention have valuable pharmacological properties and can be used for prevention and treatment of diseases in humans and animals.

The compounds of the invention are potent and selective blockers of TASK-1 and in particular TASK-3 channels and are therefore suitable for the treatment and/or prevention of disorders and pathological processes, in particular those caused by activation of TASK-1 and/or TASK-3 or by activated TASK-1 and/or TASK-3, and of disorders secondary to damage caused by TASK-1 and/or TASK-3.

For the purposes of the present invention, this includes in particular disorders from the group of the respiratory disorders and sleep-related respiratory disorders, such as obstructive sleep apnoea (in adults and children), primary snoring, obstructive snoring (upper airway resistance syndrome, heavy snoring, hypopnoea syndrome), central sleep apnoea, mixed sleep apnoea, Cheyne-Stokes respiration, primary sleep apnoea of infancy, apparent life-threatening event, central sleep apnoea as a result of the use of medicaments or the use of other substances, obesity hypoventilation syndrome, disrupted central respiratory drive, sudden infant death, primary alveolar hypoventilation syndrome, postoperative hypoxia and apnoea, muscular respiratory disorders, respiratory disorders following long-term ventilation, respiratory disorders during adaptation in high mountains, acute and chronic pulmonary diseases with hypoxia and hypercapnia, sleep-related non-obstructive alveolar hypoventilation and the congenital central alveolar hypoventilation syndrome.

The compounds of the invention can additionally be used for treatment and/or prevention of neurodegenerative disorders such as dementia, dementia with Lewy bodies, Alzheimer's disease, Parkinson's disease, Huntington's disease, Pick's disease, Wilson's disease, progressive supranuclear paresis, corticobasal degeneration, tauopathy, frontotemporal dementia and parkinsonism linked to chromosome 17, multisystem atrophy, spinocerebellar ataxias, spinobulbar muscular atrophy of the Kennedy type, Friedreich's ataxia, dentatorubral-pallidoluysian atrophy, amyotrophic lateral sclerosis, primary lateral sclerosis, spinal muscular atrophy, Creutzfeldt-Jakob disease and variants of Creutzfeldt-Jakob disease, infantile neuroaxonal dystrophy, neurodegeneration with brain iron accumulation, frontotemporal lobar degeneration with ubiquitin proteasome system and familial encephalopathy with neuroserpin inclusions.

In addition, the compounds of the invention can be used for treatment and/or prevention of neuroinflammatory and neuroimmunological disorders of the central nervous system (CNS), for example multiple sclerosis (Encephalomyelitis disseminata), transverse myelitis, Neuromyelitis optica, acute disseminated encephalomyelitis, optic neuritis, meningitis, encephalitis, demyelinating diseases and also inflammatory vascular changes in the central nervous system.

Moreover, the compounds of the invention are suitable for the treatment and/or prevention of neoplastic disorders such as, for example, skin cancer, breast cancer, lung cancer, colon cancer and prostate cancer.

The compounds of the invention are also suitable for treatment and/or prevention of cardiac arrhythmias, for example atrial and ventricular arrhythmias, conduction defects such as first- to third-degree atrio-ventricular blocks, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes and AV nodal re-entrant tachycardia.

Further cardiovascular disorders where the compounds of the invention can be employed for treatment and/or prevention are, for example, heart failure, coronary heart disease, stable and unstable angina pectoris, high blood pressure (hypertension), pulmonary-arterial hypertension (PAH) and other forms of pulmonary hypertension (PH), renal hypertension, peripheral and cardial vascular disorders, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention are further suitable for treatment and/or prevention of inflammatory disorders and autoimmune disorders such as, for example, rheumatoid disorders, inflammatory eye disorders, chronic obstructive pulmonary disease (COPD), acute respiratory distress syndrome (ARDS), acute lung injury (ALI), alpha-1-antitrypsin deficiency (AATD), pulmonary emphysema (e.g. pulmonary emphysema induced by cigarette smoke), cystic fibrosis (CF), sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis and vulvovaginitis, and also for the treatment and/or prevention of fibrotic disorders of internal organs such as, for example, the lung, the heart, the kidney, the bone marrow and especially the liver, of dermatological fibroses and of fibrotic disorders of the eye. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphea, keloids, hypertrophic scarring, nevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for ageing or keratinized skin.

In addition, the compounds of the invention can be used for treatment and/or prevention of arteriosclerosis, impaired lipid metabolism and dyslipidemias (hypolipoproteinaemia, hypertriglyceridaemias, hyperlipidaemia, combined hyperlipidaemias, hypercholesterolaemia, abetalipoproteinaemia, sitosterolaemia), xanthomatosis, Tangier disease, adiposity, obesity, metabolic disorders (metabolic syndrome, hyperglycaemia, insulin-dependent diabetes, non-insulin-dependent diabetes, gestation diabetes, hyperinsulinaemia, insulin resistance, glucose intolerance and diabetic sequelae, such as retinopathy, nephropathy and neuropathy), of anaemias such as hemolytic anaemias, in particular haemoglobinopathies such as sickle cell anaemia and thalassaemias, megaloblastic anaemias, iron deficiency anaemias, anaemias owing to acute blood loss, displacement anaemias and aplastic anaemias, of disorders of the gastrointestinal tract and the abdomen (glossitis, gingivitis, periodontitis, esophagitis, eosinophilic gastroenteritis, mastocytosis, Crohn's disease, colitis, proctitis, anus pruritis, diarrhea, coeliac disease, hepatitis, hepatic fibrosis, cirrhosis of the liver, pancreatitis and cholecystitis), of disorders of the central nervous system (stroke, epilepsy, depression), immune disorders, thyroid disorders (hyperthyreosis), skin disorders (psoriasis, acne, eczema, neurodermatitis, various forms of dermatitis, keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), of viral diseases (caused by influenza, adeno and corona viruses, for example HPV, HCMV, HIV, SARS), of disorders of the skeletal bone and the joints and also the skeletal muscle (various forms of arthritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, leprosy, Sezary syndrome and paraneoplastic syndrome, in the event of rejection reactions after organ transplants and for wound healing and angiogenesis particularly in the case of chronic wounds.

By virtue of their property profile, the compounds of the invention are preferably suitable for treatment and/or prevention of respiratory disorders, in particular of sleep-related respiratory disorders such as obstructive and central sleep apnoea and also primary and obstructive snoring, for treatment and/or prevention of cardiac arrhythmias and also for treatment and/or prevention of neurodegenerative, neuroinflammatory and neuroimmunological disorders.

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

- respiratory stimulants, by way of example and with preference theophylline, doxapram, nikethamide or caffeine;
- psychostimulants, by way of example and with preference modafinil or armodafinil;
- amphetamines and amphetamine derivatives, by way of example and with preference amphetamine, metamphetamine or methylphenidate;
- serotonin reuptake inhibitors, by way of example and with preference fluoxetine, paroxetine, citalopram, escitalopram, sertraline, fluvoxamine or trazodone;
- serotonin precursors, by way of example and with preference L-tryptophan;
- selective serotonin noradrenaline reuptake inhibitors, by way of example and with preference venlafaxine or duloxetine;
- noradrenergic and specific serotonergic antidepressants, by way of example and with preference mirtazapine;
- selective noradrenaline reuptake inhibitors, by way of example and with preference reboxetine;
- tricyclic antidepressants, by way of example and with preference amitriptyline, protriptyline, doxepine, trimipramine, imipramine, clomipramine or desipramine;
- alpha2-adrenergic agonists, by way of example and with preference clonidine;
- GABA agonists, by way of example and with preference baclofen;
- alpha sympathomimetics, by way of example and with preference xylometazoline, oxymetazoline, phenylephrine, naphazoline, tetryzoline or tramazoline;
- glucocorticoids, by way of example and with preference fluticasone, budesonide, beclometasone, mometasone, tixocortol or triamcinolone;
- cannabinoid receptor agonists;
- carboanhydrase inhibitors, by way of example and with preference acetazolamide, methazolamide or diclofenamide;
- opioid and benzodiazepine receptor antagonists, by way of example and with preference flumazenil, naloxone or naltrexone;
- cholinesterase inhibitors, by way of example and with preference neostigmine, pyridostigmine, physostigmine, donepezil, galantamine or rivastigmine;
- N-methyl-D-aspartate and glutamate antagonists, by way of example and with preference amantadine, memantine or sabeluzole;
- nicotine receptor agonists;
- leukotriene receptor antagonists, by way of example and with preference montelukast or tipelukast;
- dopamine receptor antagonists, by way of example and with preference dromperidone, metoclopramide or benzamide, butyrophenone or phenothiazine derivatives;
- appetite suppressants, by way of example and with preference sibutramine, topiramate, phentermine, lipase inhibitors or cannabinoid receptor antagonists;
- proton pump inhibitors, by way of example and with preference pantoprazole, omeprazole, esomeprazole, lansoprazole or rabeprazole;
- organic nitrates and NO donors, for example sodium nitroprusside, nitroglycerin, isosorbide mononitrate, isosorbide dinitrate, molsidomine or SIN-1, and inhaled NO;
- compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;
- NO- and heme-independent activators of soluble guanylate cyclase (sGC), such as in particular the compounds described in WO 01/19355, WO 01/19776, WO 01/19778, WO 01/19780, WO 02/070462 and WO 02/070510;
- NO-independent but haem-dependent stimulators of soluble guanylate cyclase (sGC), such as in particular riociguat, vericiguat and the compounds described in WO 00/06568, WO 00/06569, WO 02/42301, WO 03/095451, WO 2011/147809, WO 2012/004258, WO 2012/028647 and WO 2012/059549;
- prostacyclin analogs and IP receptor agonists, by way of example and with preference iloprost, beraprost, treprostinil, epoprostenol or selexipag;
- edothelin receptor antagonists, by way of example and with preference bosentan, darusentan, ambrisentan or sitaxsentan;
- compounds which inhibit human neutrophile elastase (HNE), by way of example and with preference sivelestat or DX-890 (reltran);
- compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);
- compounds which block the binding of serotonin to its receptors, by way of example and with preference antagonists of the 5-HT$_{2B}$ receptor such as PRX-08066;
- antagonists of growth factors, cytokines and chemokines, by way of example and with preference antagonists of TGF-β, CTGF, IL-1, IL-4, IL-5, IL-6, IL-8, IL-13 and integrins;
- Rho kinase-inhibiting compounds, by way of example and with preference fasudil, Y-27632, SLx-2119, BF-66851, BF-66852, BF-66853, KI-23095 or BA-1049;
- compounds which influence the energy metabolism of the heart, by way of example and with preference etomoxir, dichloroacetate, ranolazine or trimetazidine;
- compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

anti-obstructive agents as used, for example, for treatment of chronic obstructive pulmonary disease (COPD) or bronchial asthma, by way of example and with preference from the group of the inhalatively or systemically administered agonists of the beta-adrenergic receptor (beta-mimetics) and the inhalatively administered antimuscarinergic substances;

antiinflammatory, immunomodulating, immunosuppressive and/or cytotoxic agents, by way of example and with preference from the group of the systemically or inhalatively administered corticosteroids and also dimethyl fumarate, fingolimod, glatiramer acetate, β-interferons, natalizumab, teriflunomide, mitoxantrone, immunoglobulins, acetylcysteine, montelukast, tipelukast, azathioprine, cyclophosphamide, hydroxycarbamide, azithromycin, interferon-γ, pirfenidone or etanercept;

antifibrotic agents, by way of example and with preference lysophosphatidic acid receptor 1 (LPA-1) antagonists, CTGF inhibitors, IL-4 antagonists, IL-13 antagonists, TGF-β antagonists or pirfenidone;

antithrombotic agents, by way of example and with preference from the group of platelet aggregation inhibitors, the anticoagulants and the profibrinolytic substances;

hypotensive active ingredients, by way of example and with preference from the group of the calcium antagonists, angiotensin AII antagonists, ACE inhibitors, vasopeptidase inhibitors, endothelin antagonists, renin inhibitors, alpha receptor blockers, beta receptor blockers, mineralocorticoid receptor antagonists and also the diuretics; and/or active ingredients altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

In a preferred embodiment of the invention, the compounds of the invention are administered in combination with a beta-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, betamethasone, beclomethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, preferred examples being losartan, candesartan, valsartan, telmisartan or embusartan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of respiratory stimulants, psychostimulants, serotonin reuptake inhibitors, noradrenergic, serotonergic and tricyclic antidepressants, sGC stimulators, mineralocorticoid receptor antagonists, antiinflammatory drugs, immunomodulators, immunosuppressives and cytotoxic drugs.

If required, the substances of the invention can also be employed in conjunction with the use of one or more medical technical devices or auxiliaries, provided that this does not lead to unwanted and unacceptable side-effects. Medical devices and auxiliaries suitable for such a combined application are, by way of example and with preference:

devices for positive airway pressure ventilation, by way of example and with preference CPAP (continuous positive airway pressure) devices, BiPAP (bilevel positive airway pressure) devices and IPPV (intermittent positive pressure ventilation) devices;
neurostimulators of the Nervus hypoglossus;
intraoral auxiliaries, by way of example and with preference protrusion braces;
nasal disposable valves;
nasal stents.

The present invention further provides medicaments which comprise at least one compound of the invention, typically together with one or more inert, non-toxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, intrapulmonal (inhalative), nasal, intranasal, pharyngeal, lingual, sublingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

Suitable for the other administration routes are, for example, pharmaceutical forms for inhalation (including powder inhalers, nebulizers, metered aerosols), nasal drops, solutions or sprays, throat sprays, tablets for lingual, sublingual or buccal administration, films/wafers or capsules, suppositories, eye drops, eye ointments or eyewashes, ocular inserts, ear drops, sprays, powders, washes or tampons, vaginal capsules, aqueous suspensions (lotions, shaking mixtures), lipophilic suspensions, emulsions, microemulsions, ointments, creams, transdermal therapeutic systems (e.g. patches), milk, pastes, foams, dusting powders, implants or stents.

Preference is given to oral, intravenous, intranasal and pharyngeal administration.

In one embodiment, administration is by the intranasal route. In one embodiment, intranasal administration is effected with the eye of eye drops or a nasal spray. In one embodiment, intranasal administration is effected with the eye of a nasal spray.

The compounds of the invention can be converted to the administration forms mentioned. This can be done in a manner known per se, by mixing with inert, nontoxic, pharmaceutically suitable excipients. These excipients include

- fillers and carriers (for example cellulose, microcrystalline cellulose, for example Avicel®, lactose, mannitol, starch, calcium phosphates, for example Di-Cafos®),
- ointment bases (for example vaseline, paraffins, triglycerides, waxes, wool wax, wool wax alcohols, lanolin, hydrophilic ointment, polyethylene glycols),
- suppository bases (for example polyethylene glycols, cocoa butter, hard fat),
- solvents (e.g. water, ethanol, isopropanol, glycerol, propylene glycol, mid-chain triglycerides fatty oils, liquid polyethylene glycols, paraffins),
- surfactants, emulsifiers, dispersants or wetting agents (for example sodium dodecylsulfate, lecithin, phospholipids, fatty alcohols, for example Lanette®, sorbitan fatty acid esters, for example Span®, polyoxyethylene sorbitan fatty acid esters, for example Tween®, polyoxyethylene fatty acid glycerides, for example Cremophor®, polyoxyethylene fatty acid esters, polyoxyethylene fatty alcohol ethers, glycerol fatty acid esters, poloxamers, for example Pluronic®),
- buffer substances, and also acids and bases (for example phosphates, carbonates, citric acid, acetic acid, hydrochloric acid, sodium hydroxide, ammonium carbonate, trometamol, triethanolamine),
- isotonizing agents (for example glucose, sodium chloride),
- adsorbents (for example finely divided silicas),
- viscosity-increasing agents, gel formers, thickeners or binders (for example polyvinylpyrrolidone, methyl cellulose, hydroxypropyl cellulose, hydroxypropyl methylcellulose, carboxymethyl cellulose-sodium, starch, carbomers, polyacrylic acids, for example Carbopol®, alginates, gelatins),
- disintegrants (for example modified starch, carboxymethyl cellulose-sodium, sodium starch glycolate, for example Explotab®, crosslinked polyvinylpyrrolidone, croscarmellose-sodium, for example AcDiSol®),
- flow regulators, lubricants, glidants and mould release agents (for example magnesium stearate, stearic acid, talc, finely divided silicas, for example Aerosil®),
- coating agents (for example sugar, shellac) and film formers for films or diffusion membranes with fast or modified dissolution (for example polyvinylpyrrolidones, for example Kollidon®, polyvinyl alcohol, ethyl cellulose, hydroxypropyl cellulose, hydroxypropy methyl cellulose, hydroxypropyl methyl cellulose phthalate, cellulose acetate, cellulose acetate phthalate, polyacrylates, polymethacrylates, for example Eudragit®),
- capsule materials (e.g. gelatins, hydroxypropyl methyl cellulose),
- natural polymers (for example albumins);
- synthetic polymers (for example polylactides, polyglycolides, polyacrylates, polymethacrylates, for example Eudragit®, polyvinylpyrrolidones, for example Kollidon®, polyvinyl alcohols, polyvinyl acetates, polyethylene oxides, polyethylene glycols and the copolymers and block copolymers thereof),
- plasticizers (for example polyethylene glycols, propylene glycol, glycerol, triacetin, triacetyl citrate, dibutyl phthalate),
- penetrants;
- stabilizers (e.g. antioxidants, for example ascorbic acid, sodium ascorbate, ascorbyl palmitate, butylhydroxyanisole, butylhydroxytoluene, propyl gallate),
- preservatives (for example parabens, sorbic acid, sodium benzoate, thiomersal, benzalkonium chloride, chlorhexidine acetate);
- dyes (e.g. inorganic pigments, for example iron oxides, titanium dioxide),
- aromas, sweeteners, flavour and/or odour correctors.

In general, it has been found to be advantageous in the case of parenteral administration to administer amounts of active compound of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight. In the case of intrapulmonary administration, the amount of active compound is generally about 0.1 to 50 mg per inhalation.

In one embodiment, the dosage in the case of intranasal administration is about 0.1 µg to 500 µg per day. In a further embodiment, the dosage in the case of intranasal administration is about 1 µg to 250 µg per day. In a further embodiment, the dosage in the case of intranasal administration is about 1 µg to 120 µg per day. In a further embodiment, the dose of about 0.1 µg to 500 µg per day, or of about 1 µg to 250 µg per day, or of about 1 µg to 120 µg per day, is administered once daily by the intranasal route before sleeping. In one embodiment, the dose of about 0.1 µg to 500 µg per day, or of about 1 µg to 250 µg per day, or of about 1 µg to 120 µg per day, is administered once daily with half to each nostril. In one embodiment, the dose of about 0.1 µg to 500 µg per day, or of about 1 µg to 250 µg per day, or of about 1 μg to 120 μg per day, is administered once daily with half to each nostril before sleeping.

It may nevertheless be necessary in some cases to deviate from the stated amounts of active compounds, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms abs. absolute
Ac acetyl
aq. aqueous, aqueous solution
Boc tert-butoxycarbonyl
br. broad (in NMR signal)
Ex. Example
Bu butyl
c Concentration
CAN cerium(IV) ammonium nitrate
cat. catalytic
Cbz benzyloxycarbonyl
CI chemical ionization (in MS)
d doublet (in NMR)
d day(s)
TLC thin layer chromatography
DCI direct chemical ionization (in MS)
dd doublet of doublets (in NMR)
DMF N,N-dimethylformamide
DMSO dimethyl sulfoxide
dq doublet of quartets (in NMR)
dt doublet of triplets (in NMR)
EI electron impact ionization (in MS)
eq. equivalent(s)
ESI electrospray ionization (in MS)
Et ethyl
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure, high-performance liquid chromatography
iPr isopropyl
conc. concentrated (in the case of a solution)
LC liquid chromatography
LC-MS liquid chromatography-coupled mass spectrometry
lit. literature (reference)
m multiplet (in NMR)
Me methyl
min minute(s)
MS mass spectrometry
NMR nuclear magnetic resonance spectrometry
Pd/C palladium on activated charcoal
Ph phenyl
PPS Polyphosphoric acid
Pr propyl
q quartet (in NMR)
quant. quantitative (in chemical yield)
Red-Al® sodium bis(2-methoxyethoxy)aluminiumhydride
$R_f$ retention index (in TLC)
RP reverse phase (in HPLC)
$R_t$ retention time (in HPLC, LC-MS)
RT room temperature
s singlet (in NMR)
SFC supercritical liquid chromatography
t triplet (in NMR)
tBu tert-butyl
TFA trifluoroacetic acid
THF tetrahydrofuran
Ts tosyl (p-toluenesulfonyl)
UV ultraviolet spectrometry
v/v volume to volume ratio (of a solution)
LC-MS and HPLC Methods:

Method 1 (LC-MS):
Instrument: Waters Acquity SQD UPLC System; column: Waters Acquity UPLC HSS T3 1.8 μm, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; temperature: 50° C.; flow rate: 0.40 ml/min; UV detection: 208-400 nm.

Method 2 (LC-MS):
MS instrument: Thermo Scientific FT-MS; instrument type UHPLC: Thermo Scientific UltiMate 3000; column: Waters HSS T3 C18 1.8 μm, 75 mm×2.1 mm; mobile phase A: 1 l of water+0.01% formic acid, mobile phase B: 1 l of acetonitrile+0.01% formic acid; gradient: 0.0 min 10% B→2.5 min 95% B→3.5 min 95% B; temperature: 50° C.; flow rate: 0.90 ml/min; UV detection: 210 nm/optimum integration path 210-300 nm.

Method 3 (LC-MS):
MS instrument: Waters Micromass QM; HPLC instrument: Agilent 1100 series; column: Agilent ZORBAX Extend-C18 3.5 μm, 50 mm×3.0 mm; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; temperature: 40° C.; flow rate: 1.75 ml/min; UV detection: 210 nm.

Method 4 (LC-MS):
MS instrument: Waters Micromass Quattro Micro; HPLC instrument: Waters UPLC Acquity; column: Waters BEH C18 1.7 μm, 50 mm×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; temperature: 40° C.; flow rate: 0.5 ml/min; UV detection: 210 nm.

Method 5 (LC-MS):
Instrument: Agilent MS Quad 6150 with HPLC Agilent 1290; column: Waters Acquity UPLC HSS T3 1.8 μm, 50 mm×2.1 mm; mobile phase A: 1 l of water+0.25 ml of 99% strength formic acid, mobile phase B: 1 l of acetonitrile+ 0.25 ml of 99% strength formic acid; gradient: 0.0 min 90% A→0.3 min 90% A→1.7 min 5% A→3.0 min 5% A; flow rate 1.20 ml/min; temperature: 50° C.; UV detection: 205-305 nm.

Method 6 (LC-MS):
MS instrument: Waters Single Quad MS-System; HPLC instrument: Waters UPLC Acquity; column: Waters BEH C18 1.7 μm, 50 mm×2.1 mm; mobile phase A: 1 l of water+1.0 ml of 25% strength ammonia; mobile phase B: 1 l of acetonitrile; gradient: 0.0 min 92% A→0.1 min 92% A→1.8 min 5% A→3.5 min 5% A; temperature: 50° C.; flow rate: 0.45 ml/min; UV detection: 210 nm (208-400 nm).

Method 7 (LC-MS):
MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile+0.025% formic acid; gradient: 0.0 min 98% A→0.9 min 25% A→1.0 min 5% A→1.4 min 5% A→1.41 min 98% A→1.5 min 98% A; temperature: 40° C.; flow rate: 0.60 ml/min; UV detection: DAD, 210 nm.

Method 8 (preparative HPLC):
Instrument: Abimed Gilson 305; column: Reprosil C18 10 μm, 250 mm×30 mm; mobile phase A: water, eluent B: acetonitrile; gradient: 0-3 min 10% B, 3-27 min 10% B→95% B, 27-34.5 min 95% B, 34.5-35.5 min 95% B→10% B, 35.5-36.5 min 10% B; flow rate: 50 ml/min; room temperature; UV detection: 210 nm.

Method 9 (preparative HPLC):
Instrument: Knauer P 2.1 L-Azura; column: Chromatorex C18 10 μm, 125 mm×40 mm; mobile phase A: water, eluent B: acetonitrile; gradient: 0-3 min 20% B, 3-21 min 20% B→95% B, 21-24 min 95% B, 24-25 min 95% B→20% B, 25-27.5 min 20% B; flow rate: 100 ml/min; room temperature; UV detection: 210 nm.

Method 10 (preparative HPLC):
Instrument: Knauer P 2.1 L-Azura; column: Reprosil C18 10 μm, 250 mm×30 mm; mobile phase A: water, eluent B: acetonitrile; gradient: 0-5 min 10% B, 5-19 min 10% B→50% B, 19-20 min 50% B→95% B, 20-25 min 95% B, 25-26 min 95% B→10% B, 26-28.5 min 10% B; flow rate: 100 ml/min; room temperature; UV detection: 210 nm.

Method 11 (LC-MS):
Instrument: Shimadzu LCMS-2020; column Kinetex 2.6 μm XB-C18 H16-198547, 50 mm×3.0 mm; mobile phase A: water with 0.05% trifluoroacetic acid, mobile phase B: acetonitrile; gradient: 0.0 min 5% B→1.2 min 100% B→1.8 min 100% B→1.9 min 5% B→2.0 min 5% B; flow rate: 1.50 ml/min; UV detection: 190-400 nm; temperature: 40° C.

Method 12 (LC-MS):
Instrument: Shimadzu MS 2020 with LC Shimadzu 20ADxr; column: Kinetex 2.6 μm XB-C18, 50 mm×3.0 mm; mobile phase A: water with 0.05% trifluoroacetic acid, mobile phase B: acetonitrile; gradient: 0.0 min 5% B→2.0 min 80% B→1.8 min 80% B→2.9 min 5% B→3.0 min 5% B; flow rate: 1.50 ml/min; UV detection: 190-400 nm; temperature: 40° C.

Method 13 (LC-MS):
Instrument: Shimadzu shim-pack XR-ODS; column: Kinetex 2.6 μm XB-C18 40332846, 50 mm×3.0 mm; mobile phase A: water with 0.05% trifluoroacetic acid, mobile phase B: acetonitrile; gradient: 0.0 min 5% B→1.2 min 100% B→2.2 min 100% B→2.25 min 5% B→2.6 min 5% B; flow rate: 1.50 ml/min; UV detection: 190-400 nm; temperature: 40° C.

Method 14 (LC-MS):
Instrument: Shimadzu LCMS-2020; column Kinetex 2.6 μm XB-C18 H15-179292, 50 mm×3.0 mm; mobile phase A: water with 0.05% trifluoroacetic acid, mobile phase B: acetonitrile; gradient: 0.0 min 5% B→1.2 min 100% B→1.8 min 100% B→1.9 min 5% B→2.0 min 5% B; flow rate: 1.50 ml/min; UV detection: 190-400 nm; temperature: 40° C.

Method 15 (LC-MS):
Instrument: Shimadzu LCMS-2020; column Kinetex 2.6 m XB-C18 H16-198547, 50 mm×3.0 mm; mobile phase A: water with 0.05% trifluoroacetic acid, mobile phase B: acetonitrile; gradient: 0.0 min 5% B→4.0 min 80% B→4.8 min 80% B→4.9 min 5% B→5.0 min 5% B; flow rate: 1.50 ml/min; UV detection: 190-400 nm; temperature: 40° C.

Further Details:
The percentages in the example and test descriptions which follow are, unless indicated otherwise, percentages by weight; parts are parts by weight. Solvent ratios, dilution ratios and concentration data for liquid/liquid solutions are based in each case on volume.

Purity figures are generally based on corresponding peak integrations in the LC/MS chromatogram, but may additionally also have been determined with the aid of the $^1$H NMR spectrum. If no purity is stated, the purity is generally >95% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

In cases where the reaction products were obtained by trituration, stirring or recrystallization, it was frequently possible to isolate further amounts of product from the respective mother liquor by chromatography. However, a description of this chromatography is dispensed with hereinbelow unless a large part of the total yield could only be isolated in this step.

Melting points and melting point ranges, if stated, are uncorrected.

The descriptions of the coupling patterns of $^1$H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the center of the signal in question. In the case of broad multiplets, an interval is given. Signals obscured by solvent or water were either tentatively assigned or have not been listed.

The $^1$H NMR data of synthesis intermediates and working examples can also be stated in the form of $^1$H NMR peak lists. Here, for each signal peak, first the δ value in ppm and then the signal intensity in round brackets are listed. The δ value/signal intensity number pairs of different signal peaks are listed separated by commas; accordingly, the peak list for a compound has the form: $δ_1$ (intensity$_1$), $δ_2$ (intensity$_2$), . . . , $δ_i$ (intensity$_i$), . . . , $δ_n$(intensity$_n$).

The intensity of sharp signals correlates with the height of the signals (in cm) in a printed example of an NMR spectrum and shows the true ratios of the signal intensities in comparison with other signals. In the case of broad signals, several peaks or the middle of the signal and their relative intensity may be given in comparison to the most intense signal in the spectrum. The lists of the $^1$H NMR peaks are similar to the conventional $^1$H NMR printouts and thus usually contain all peaks listed in a conventional NMR interpretation. In addition, like classic $^1$H NMR printouts, they may comprise solvent signals, signals of stereoisomers of the target compound in question, peaks of impurities, $^{13}$C satellite peaks and/or rotation side bands. Peaks of stereoisomers of the target compound and/or peaks of impurities usually have a lower intensity on average than the peaks of the target compound (for example with a purity of >90%). Such stereoisomers and/or impurities may be typical of the particular preparation process. Their peaks can thus help in identifying reproduction of the preparation process with reference to "by-product fingerprints". An expert calculating the peaks of a target compound by known methods (MestreC, ACD simulation, or using empirically determined expected values) can, if required, isolate the peaks of the target compound, optionally using additional intensity filters. This isolation would be similar to the peak picking in question in conventional ¹H NMR interpretation.

A detailed description of the presentation of NMR data in the form of peak lists can be found in the publication "Citation of NMR Peaklist Data within Patent Applications" (see http://www.researchdisclosure.com/searching-disclosures, Research Disclosure Database Number 605005, 2014, 1 Aug. 2014). In the peak picking routine described in the stated Research Disclosure, the parameter "MinimumHeight" can be set between 1% and 4%. However, depending on the type of chemical structure and/or on the concentration of the compound to be analysed, it may also be advisable to set the parameter "MinimumHeight" to values of <1%.

All reactants or reagents whose preparation is not described explicitly hereinafter were purchased commercially from generally accessible sources. For all other reactants or reagents whose preparation is likewise not described hereinafter and which were not commercially obtainable or were obtained from sources which are not generally accessible, a reference is given to the published literature in which their preparation is described.

Starting Compounds and Intermediates:

Example 1A 2-(4-Chlorophenyl)imidazo[1,2-a]pyrimidine

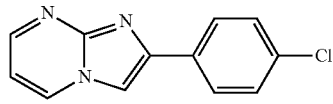 [SMILES: Clc1ccc(-c2cn3cccnc3n2)cc1]

Sodium bicarbonate (10.8 g, 128 mmol) was added to a solution of 2-bromo-1-(4-chlorophenyl)ethanone (20.0 g, 85.7 mmol) and pyrimidin-2-amine (8.96 g, 94.2 mmol) in 200 ml of ethanol, and the mixture was stirred at 80° C. for 5 hours. The batch was then cooled to 0° C. (ice bath). The resulting precipitate was filtered off and washed twice with an ethanol/water mixture (1:1). The solid was then dried under reduced pressure at 40° C. overnight. This gave 15.9 g (69.23 mmol, 80.8% of theory) of the target product.

LC-MS (method 2): $R_t$=1.25 min; m/z=230 (M+H)⁺.

¹H-NMR (400 MHz, DMSO-d₆, δ/ppm): 7.07 (dd, 1H), 7.53 (d, 2H), 8.03 (d, 2H), 8.41 (s, 1H), 8.54 (dd, 1H), 8.97 (dd, 1H).

Example 2A 2-(4-Isopropylphenyl)imidazo[1,2-a]pyrimidine

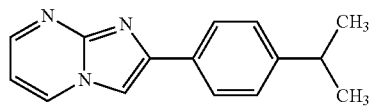

Sodium bicarbonate (0.52 g, 6.22 mmol) was added to a solution or 2-bromo-1-(4-isopropylphenyl)ethanone (1.0 g, 4.15 mmol) and pyrimidin-2-amine (0.43 g, 4.6 mmol) in 50 ml of ethanol, and the mixture was stirred at 80° C. for 5 hours. The mixture was then concentrated to dryness. The residue was stirred with diethyl ether and the solid that remained was filtered off and dried at 40° C. under reduced pressure overnight. This gave 1.15 g of the crude target product, which was used in the subsequent reactions without further purification.

LC-MS (method 2): $R_t$=1.48 min; m/z=238 (M+H)⁺.

¹H-NMR (400 MHz, DMSO-d₆, δ/ppm): 1.24 (d, 6H), 2.87-3.00 (m, 1H), 7.04 (dd, 1H), 7.34 (d, 2H), 7.92 (d, 2H), 8.21 (d, 1H), 8.33 (s, 1H), 8.51 (dd, 1H).

Example 3A 2-(4-Chlorophenyl)imidazo[1,2-a]pyridine

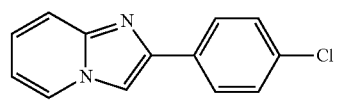 [SMILES: Clc1ccc(-c2cn3ccccc3n2)cc1]

To a solution of 20 g (85.65 mmol) of 2-bromo-1-(4-chlorophenyl)ethanone and 8.87 g (94.22 mmol) of pyridin-2-amine in 200 ml of ethanol were added 10.95 g (130 mmol) of sodium hydrogencarbonate, and the mixture was stirred at 80° C. for 5 hours. The mixture was then cooled, first to room temperature and then to 0° C. (ice bath). The resulting precipitate was filtered off and washed repeatedly with an ethanol/water mixture (2:1). The solid was then dried under reduced pressure at 40° C. overnight. This gave 19.8 g of the target product, which was used in the subsequent reactions without further purification.

¹H-NMR (400 MHz, DMSO-d₆, δ/ppm): 6.87-6.94 (m, 1H), 7.23-7.29 (m, 1H), 7.50 (d, 2H), 7.58 (d, 1H), 7.99 (d, 2H), 8.43 (s, 1H), 8.53 (d, 1H).

LC-MS (method 1): $R_t$=0.58 min; m/z=229/231 (M+H)⁺.

Example 4A 2-(5-Chloropyridin-2-yl)imidazo[1,2-a]pyridine

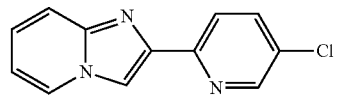

5 g (32.14 mmol) of 1-(5-chloropyridin-2-yl)ethanone, 6.96 g (73.92 mmol) of pyridin-2-amine and 9.79 g (38.56 mmol) of iodine were stirred at 120° C. for 2 h. After cooling to room temperature, 15 ml of water and 1.93 g (48 mmol) of sodium hydroxide were added and then the reaction mixture was stirred at 100° C. for another 1 h. Thereafter, the mixture was cooled to room temperature and the precipitate obtained was filtered off and washed repeatedly with water. The solid was dissolved in cyclohexane/ethyl acetate (1:1), silica gel was added, the mixture was concentrated to dryness again and the residue was purified by column chromatography on silica gel (mobile phase: cyclohexane/ethyl acetate 1:1). 4.32 g (18.81 mmol, 59% of theory) of the target compound were obtained.

¹H-NMR (400 MHz, DMSO-d₆, δ/ppm): 6.95 (t, 1H), 7.30 (t, 1H), 7.61 (d, 1H), 8.00 (dd, 1H), 8.12 (d, 1H), 8.50 (s, 1H), 8.59 (d, 1H), 8.65 (d, 1H).

LC-MS (method 1): $R_t$=0.50 min; m/z=230/232 (M+H)⁺.

Analogously to Examples 1A-4A, the following compounds were prepared from the starting materials specified in each case:

¹H-NMR (400 MHz, DMSO-d₆): δ [ppm]=7.46 (dd, 1H), 7.65 (d, 2H), 8.01 (d, 2H), 8.91 (dd, 1H), 9.83 (dd, 1H), 10.07 (s, 1H).

| Example | Name/Structure/Starting materials | Analytical data |
|---|---|---|
| 5A | 2-(4-bromophenyl)imidazo[1,2-a]pyrimidine 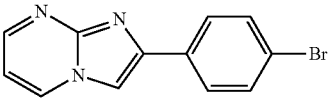 from 2-bromo-1-(4-bromophenyl) ethanone and pyrimidin-2-amine | ¹H-NMR (400 MHz, DMSO-d₆): δ [ppm] = 7.07 (dd, 1H), 7.67 (d, 2H), 7.97 (d, 2H), 8.42 (s, 1H), 8.54 (dd, 1H), 8.97 (dd, 1H). LC-MS (method 2): R$_t$ = 1.34 min; m/z = 274/276 (M + H)⁺. |
| 6A | 2-(4-bromophenyl)imidazo[1,2-a]pyridine 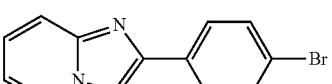 from 2-bromo-1-(4-bromophenyl) ethanone and pyridin-2-amine | ¹H-NMR (400 MHz, DMSO-d₆, δ/ppm): 6.88-6.94 (m, 1H), 7.23-7.29 (m, 1H), 7.58 (d, 1H), 7.63 (d, 2H), 7.92 (d, 2H), 8.44 (s, 1H), 8.53 (d, 1H). LC-MS (method 1): R$_t$ = 0.63 min; m/z = 273/275 (M + H)⁺. |
| 7A | 2-(4-isopropylphenyl)imidazo[1,2-a]pyridine 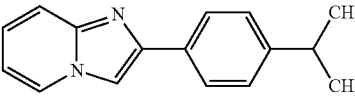 from 2-bromo-1-(4-isopropylphenyl) ethanone and pyridin-2-amine | ¹H-NMR (400 MHz, DMSO-d₆, δ/ppm): 1.23 (d, 6H), 2.85-2.96 (m, 1H), 6.88 (t, 1H), 7.19-7.26 (m, 1H), 7.31 (d, 2H), 7.56 (d, 1H), 7.88 (d, 2H), 8.34 (s, 1H), 8.51 (d, 1H). LC-MS (method 1): R$_t$ = 0.68 min; m/z = 237 (M + H)⁺. |

Example 8A 2-(4-Chlorophenyl)imidazo[1,2-a]pyrimidine-3-carbaldehyde

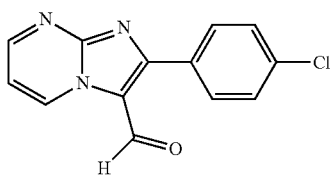 [SMILES: O=Cc1c(-c2ccc(Cl)cc2)nc2ncccn12]

300 ml of DMF were initially charged and cooled to 0° C. Phosphorus oxychloride (16 ml, 173 mmol) was then slowly added dropwise. The solution was then slowly warmed to room temperature and stirred at this temperature for another hour. 2-(4-Chlorophenyl)imidazo[1,2-a]pyrimidine (15.9 g, 69.2 mmol) was then added a little at a time. After the addition had ended, the reaction mixture was heated to 80° C. and stirred at this temperature for 1 hour. The batch was then cooled to 0° C. (ice bath). The resulting solid was filtered off with suction, washed repeatedly with water and dried in a high-vacuum drying cabinet at 40° C. overnight. 13.75 g (53.36 mmol, 77% of theory) of the target product were obtained.

LC-MS (method 2): R$_t$=1.44 min; m/z=258 (M+H)⁺.

Example 9A 2-(4-Isopropylphenyl)imidazo[1,2-a]pyrimidine-3-carbaldehyde

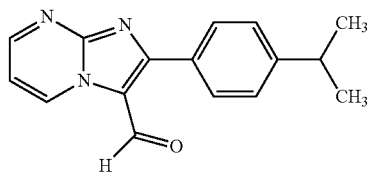 [SMILES: CC(C)c1ccc(-c2nc3ncccn3c2C=O)cc1]

50 ml of DMF were initially charged and cooled to 0° C. Phosphorus oxychloride (2.86 ml, 30.66 mmol) was then slowly added dropwise. The solution was then slowly warmed to room temperature and stirred at this temperature for another hour. 2-(4-Isopropylphenyl)imidazo[1,2-a]pyrimidine (2.91 g, 12.26 mmol) was then added a little at a time. After the addition had ended, the reaction mixture was heated to 80° C. and stirred at this temperature for 1 hour. The batch was then cooled to 0° C. (ice bath). The solid obtained was filtered off with suction and dried under reduced pressure. The resulting crude product was subsequently purified twice by column chromatography (Biotage Isolera, Biotage SNAP-KP-NH column, mobile phase cyclohexane/ethyl acetate gradient). 3 g (11.3 mmol, 92% of theory) of the target compound were obtained.

LC-MS (method 2): R$_t$=1.75 min; m/z=266 (M+H)⁺.

$^1$H-NMR (400 MHz, DMSO-d$_6$): δ [ppm]=1.27 (d, 6H), 3.00 (dt, 1H), 7.39-7.52 (m, 3H), 7.90 (d, 2H), 8.89 (dd, 1H), 9.83 (dd, 1H), 10.08 (s, 1H).

Example 10A 2-(4-Chlorophenyl)imidazo[1,2-a]pyridine-3-carbaldehyde

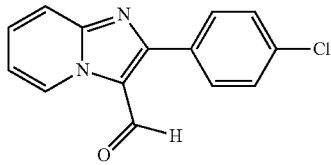 [SMILES: O=Cc1c(-c2ccc(Cl)cc2)nc2ccccn12]

300 ml of DMF were cooled to 0° C. 44 ml (470.08 mmol) of phosphorus oxychloride were then slowly added dropwise. The reaction solution was then slowly warmed to room temperature and stirred at this temperature for another hour. 43 g (188.03 mmol) of 2-(4-chlorophenyl)imidazo[1,2-a]pyridine were then added in portions. During the addition, the reaction solution warmed to 35° C. After the addition had ended, the reaction mixture was heated to 80° C. and stirred at this temperature for 2 hours. After cooling to room temperature, the solution was slowly added to 3 litres of ice-water. The resulting solid was filtered off with suction, washed repeatedly with water and dried in a high-vacuum drying cabinet at 40° C. overnight. 39.6 g (154.27 mmol, 82% of theory) of the target product were obtained.

$^1$H-NMR (400 MHz, DMSO-d$_6$, δ/ppm): 7.37 (t, 1H), 7.63 (d, 2H), 7.78 (t, 1H), 7.90-7.99 (m, 3H), 9.58 (d, 1H), 10.02 (s, 1H).

LC-MS (method 1): R$_t$=0.97 min; m/z=257/259 (M+H)$^+$.

Example 11A 2-(5-Chloropyridin-2-yl)imidazo[1,2-a]pyridine-3-carbaldehyde

80 ml of DMF were cooled to 0° C. 4.4 ml (47.02 mmol) of phosphorus oxychloride were then slowly added dropwise. The reaction solution was then slowly warmed to room temperature and stirred at this temperature for another hour. 4.32 g (18.81 mmol) of 2-(5-chloropyridin-2-yl)imidazo[1,2-a]pyridine were then added in portions. When the addition had ended, the reaction mixture was heated to 80° C. and stirred at this temperature for 1 h. After cooling to room temperature, the solution was gradually added to ice-water. Ethyl acetate was added and, after thorough shaking, the organic phase was removed. The latter was washed with saturated sodium chloride solution, dried over magnesium sulfate, filtered and concentrated to dryness. The residue obtained was purified by column chromatography on silica gel (mobile phase: cyclohexane/ethyl acetate 2:1). cyclohexane/ethyl acetate 2:1). 4.46 g (17.31 mmol, 92% of theory) of the target compound were obtained.

$^1$H-NMR (400 MHz, DMSO-d$_6$, δ/ppm): 7.36 (td, 1H), 7.76 (ddd, 1H), 7.94 (d, 1H), 8.15 (dd, 1H), 8.35 (d, 1H), 8.81 (d, 1H), 9.60 (d, 1H), 10.87 (s, 1H).

LC-MS (method 1): R$_t$=0.92 min; m/z=258/260 (M+H)$^+$.

Analogously to Examples 8A-11A, the following compounds were prepared from the starting material specified in each case:

| Example | Name/Structure/Starting material | Analytical data |
|---|---|---|
| 12A | 2-(4-bromophenyl)imidazo[1,2-a]pyrimidine-3-carbaldehyde<br><br>from 2-(4-bromophenyl)imidazo[1,2-a]pyrimidine | $^1$H-NMR (400 MHz, DMSO-d$_6$): δ [ppm] = 7.46 (dd, 1H), 7.79 (d, 2H), 7.94 (d, 2H), 8.91 (dd, 1H), 9.83 (dd, 1H), 10.07 (s, 1H).<br>LC-MS (method 1): R$_t$ = 0.78 min; m/z = 302/304 (M + H)$^+$. |
| 13A | 2-(4-bromophenyl)imidazo[1,2-a]pyridine-3-carbaldehyde<br><br>from 2-(4-bromophenyl)imidazo[1,2-a]pyridine | $^1$H-NMR (400 MHz, DMSO-d$_6$, δ/ppm): 7.35 (t, 1H), 7.72-7.80 (m, 3H), 7.85-7.95 (m, 3H), 9.58 (d, 1H), 10.02 (s, 1H).<br>LC-MS (method 2): R$_t$ = 1.76 min; m/z = 301/303 (M + H)$^+$. |

| Example | Name/Structure/Starting material | Analytical data |
|---|---|---|
| 14A | 2-(4-isopropylphenyl)imidazo[1,2-a]pyridine-3-carbaldehyde<br />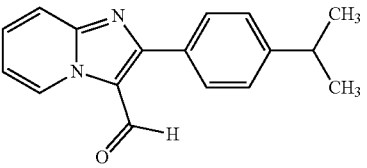<br />from 2-(4-isopropylphenyl)imidazo[1,2-a]pyridine | $^1$H-NMR (400 MHz, DMSO-$d_6$, δ/ppm): 1.27 (d, 6H), 2.93-3.05 (m, 1H), 7.33 (t, 1H), 7.44 (d, 2H), 7.74 (t, 1H), 7.85 (d, 2H), 7.91 (d, 1H), 9.58 (d, 1H), 10.03 (s, 1H).<br />LC-MS (method 1):<br />$R_t$ = 1.03 min; m/z = 265 (M + H)$^+$. |

Example 15A 2,2'-Oxydiacetaldehyde

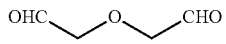

With stirring, a solution of 2,5-dihydrofuran (50 g, 713.37 mmol) in 1.2 litres of dichloromethane was cooled to −78° C. Excess ozone was then introduced into the reaction solution until the blue colour remained. Thereafter, nitrogen was introduced for 30 min. When the introduction of nitrogen had ended, 185.8 g (218.6 ml, 2.99 mol) of dimethyl sulfide were added to the reaction solution. The reaction mixture was then slowly warmed to room temperature and stirred for 15 hours (reaction monitored by TLC: mobile phase petroleum ether/ethyl acetate 2:1; starting material 2,5-dihydrofuran $R_f$=0.3, target product $R_f$=0.1). The reaction mixture was then concentrated to dryness under reduced pressure. This gave 100 g of the title compound as a yellowish oil which was used in the subsequent reaction without further purification.

Example 16A

9-Benzyl-3-oxa-9-azabicyclo[3.3.1]nonan-7-one

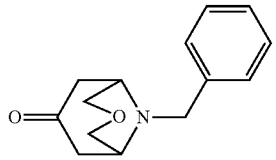 [SMILES: O=C1CC2COCC(C1)N2Cc1ccccc1]

71.5 g (490 mmol) of 3-oxopentanedicarboxylic acid and 40.1 g (490 mmol) of sodium acetate were added to a solution of 2,2'-oxydiacetaldehyde (100 g, about 980 mmol) in 600 ml of water. A little at a time, 52.5 g (490 mmol) of benzylamine, dissolved in 200 ml of 3 N hydrochloric acid, were then added and the mixture was stirred at 25° C. for 16 h. The pH of the reaction mixture was then adjusted to pH 10 using 1 N aqueous sodium hydroxide solution and the solution was extracted three times with 1 litre of ethyl acetate. The combined organic phases were concentrated to dryness under reduced pressure. The residue obtained was separated into its components on silica gel (mobile phase: dichloromethane). This gave 36 g (155.65 mmol, 16% of theory) of the title compound.

$^1$H-NMR (400 MHz, CDCl$_3$): δ [ppm]=7.44-7.31 (m, 5H), 3.92 (s, 2H), 3.84 (d, 2H), 3.72 (d, 2H), 3.18-3.16 (m, 2H), 2.78-2.73 (m, 2H), 2.36 (s, 1H), 2.33 (s, 1H).

Example 17A (E/Z)-9-Benzyl-N-hydroxy-3-oxa-9-azabicyclo[3.3.1]nonan-7-imine

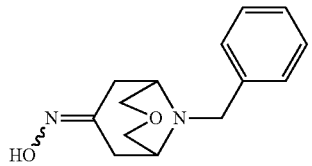 [SMILES: ON=C1CC2COCC(C1)N2Cc1ccccc1]

At 20°-30° C., 22.8 g (329 mmol) of hydroxylamine hydrochloride were metered into a solution of 38 g (164 mmol) of 9-benzyl-3-oxa-9-azabicyclo[3.3.1]nonan-7-one and 53.9 g (657 mmol) of sodium acetate in 600 ml of ethanol and 200 ml of water. The reaction mixture was then heated to 70°-80° C. and stirred at this temperature for 3 h. After cooling, the reaction mixture was concentrated under reduced pressure, i.e. part of the solvent was removed on a rotary evaporator. The reaction solution that remained was extracted three times with 500 ml of ethyl acetate. The combined organic phases were dried over sodium sulfate, filtered and concentrated to dryness. This gave 35 g (142.1 mmol, 87% of theory) of the title compound, which was used in the subsequent reaction without further purification.

$^1$H-NMR (400 MHz, CDCl$_3$): δ [ppm]=7.37-7.18 (m, 5H), 3.82-3.76 (m, 4H), 3.69-3.61 (m, 2H), 3.08-3.04 (d, 1H), 2.83-2.81 (m, 2H), 2.68-2.63 (m, 1H), 2.35-2.24 (m, 2H).

Example 18A

10-Benzyl-8-oxa-3,10-diazabicyclo[4.3.1]decan-4-one (racemate)

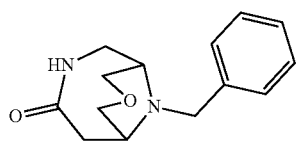 [SMILES: O=C1CC2COCC(CN1)N2Cc1ccccc1]

With stirring at 20°-30° C., 40.6 g (213 mmol) of 4-methylbenzenesulfonyl chloride were added to a solution of 35 g (142 mmol) of (E/Z)-9-benzyl-N-hydroxy-3-oxa-9-azabicyclo[3.3.1]nonan-7-imine and 45.2 g (426 mmol) of sodium carbonate in 525 ml of acetonitrile and 175 ml of water. The reaction mixture was then heated to 70°-80° C. and stirred at this temperature for 15 h. After cooling to room temperature, the reaction mixture was concentrated under reduced pressure (acetonitrile was removed under reduced pressure). The remaining aqueous phase was extracted three times with 1000 ml of ethyl acetate. The combined organic phases were washed with 300 ml of saturated sodium chloride solution, dried over sodium sulfate, filtered and concentrated to dryness. This gave 25 g (101.5 mmol, 71% of theory) of the title compound which was reacted without further purification.

$^1$H-NMR (400 MHz, CDCl$_3$): δ [ppm]=7.37-7.18 (m, 5H), 6.00 (br. s, 1H), 3.90-3.78 (m, 7H), 3.07-3.03 (m, 2H), 2.71 (br. s, 1H), 2.61 (br. s, 1H), 2.41-2.37 (m, 1H).

Example 19A

10-Benzyl-8-oxa-3,10-diazabicyclo[4.3.1]decane (racemate)

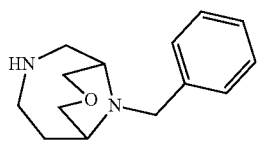 [SMILES: c1ccc(CN2C3CCNCC2COC3)cc1]

Under argon and at a temperature of 20°-30° C., 4.62 g (122 mmol) of lithium aluminium hydride were added a little at a time to a solution of 10 g (40.6 mmol) of 10-benzyl-8-oxa-3,10-diazabicyclo[4.3.1]decan-4-one (racemate) in 800 ml of dry THF. The reaction mixture was then stirred at this temperature for 12 h. In parallel, this reaction was carried out a second time. Both reaction mixtures were then cooled to 0° C., and 10 ml of water, 10 ml of 10% strength aqueous sodium hydroxide solution and 30 ml of water were successively added to each mixture. After filtration of the reaction mixtures, the filtrates were combined and extracted three times with 1 litre of ethyl acetate. The combined organic phases were washed with 200 ml of saturated sodium chloride solution, dried over sodium sulfate, filtered and concentrated to dryness. This gave 22 g of the title compound as a brown oil which was used in the subsequent reaction without further purification.

Example 20A tert-Butyl 10-benzyl-8-oxa-3,10-diazabicyclo[4.3.1]decane-3-carboxylate (racemate)

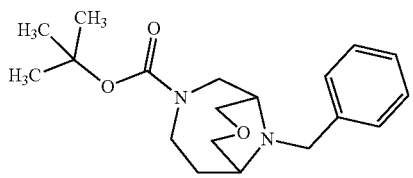 [SMILES: CC(C)(C)OC(=O)N1CCC2COCC(C1)N2Cc1ccccc1]

With stirring and at a temperature of 20°-30° C., 14.1 g (64.6 mmol) of di-tert-butyl dicarbonate were metered into a mixture consisting of 10 g (43.0 mmol) of 10-benzyl-8-oxa-3,10-diazabicyclo[4.3.1]decane (racemate) and 17.9 ml (129 mmol) of triethylamine in 250 ml of dichloromethane. The reaction mixture was then stirred at this temperature for 5 h. The reaction solution was subsequently concentrated to dryness under reduced pressure.

In parallel, this reaction was carried out a second time in exactly the same size. The crude products obtained in this manner were combined and then purified together by column chromatography on silica gel (mobile phase: petroleum ether/ethyl acetate 50:1→3:1). This gave in total 24 g (70.8 mmol, 82% of theory) of the title compound.

$^1$H-NMR (400 MHz, CDCl$_3$): δ [ppm]=7.33-7.21 (m, 5H), 3.9-3.7 (m, 2H), 3.75-3.40 (m, 7H), 3.30-3.20 (m, 1H), 2.78-2.74 (m, 2H), 2.00-2.20 (m, 1H), 1.75-1.60 (m, 1H), 1.50-1.40 (m, 9H).

Example 21A tert-Butyl 8-oxa-3,10-diazabicyclo[4.3.1]decane-3-carboxylate (racemate)

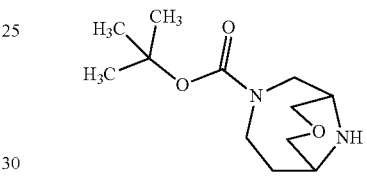

At a temperature of 20°-30° C., 2 g (64.6 mmol) of palladium hydroxide were added to a solution of 10 g (30.1 mmol) of tert-butyl 10-benzyl-8-oxa-3,10-diazabicyclo[4.3.1]decane-3-carboxylate in 500 ml of methanol. With stirring, the reaction mixture was subsequently hydrogenated at this temperature under 50 psi (about 3.45 bar) of hydrogen for 4 h. The reaction solution was subsequently filtered and the filtrate was concentrated to dryness under reduced pressure. On silica gel (mobile phase: petroleum ether/ethyl acetate 50:1→1:1), the residue obtained was separated into its components. This gave 5 g (20.6 mmol, 69% of theory) of the title compound.

$^1$H-NMR (400 MHz, CDCl$_3$): δ [ppm]=3.92-3.85 (m, 2H), 3.71-3.59 (m, 4H), 3.37-3.24 (m, 2H), 3.07-3.00 (m, 1H), 2.82-2.81 (m, 1H), 2.04-1.99 (m, 2H), 1.48 (s, 9H).

Example 22A and Example 23A tert-Butyl 8-oxa-3,10-diazabicyclo[4.3.1]decane-3-carboxylate (Enantiomers 1 and 2)

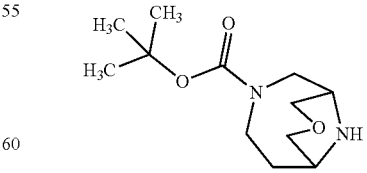

5.91 g (24.4 mmol) of the racemic tert-butyl 8-oxa-3,10-diazabicyclo[4.3.1]decane-3-carboxylate (Example 21A) were separated into the enantiomers by preparative HPLC on a chiral phase [column: YMC Chiral Art Cellulose, 5 μm, 250 mm×20 mm; mobile phase: n-heptane/isopropanol 60:40 (v/v)+0.2% diethylamine; flow rate: 15 ml/min; UV detection: 220 nm; temperature: 45° C.]:

Example 22A (Enantiomer 1)

Yield: 2.95 g $R_t$=4.95 min; chemical purity >99%; >99% ee

[column: Daicel Chiralpak IC, 5 μm, 250 mm×4.6 mm; mobile phase: isohexane/isopropanol 60:40 (v/v)+0.2% diethylamine; flow rate: 1 ml/min; temperature: 50° C.; UV detection: 235 nm].

LC-MS (method 4): $R_t$=1.12 min; m/z=242 (M+H)⁺

¹H-NMR (400 MHz, DMSO-d₆): δ [ppm]=1.38 (d, 9H), 1.77-1.88 (m, 2H), 2.68-2.79 (m, 1H), 2.88-2.97 (m, 1H), 3.04-3.76 (m, 9H).

Example 23A (Enantiomer 2)

Yield: 2.85 g $R_t$=6.47 min; chemical purity >99%; >99% ee

[column: Daicel Chiralpak IC, 5 μm, 250 mm×4.6 mm; mobile phase: isohexane/isopropanol 60:40 (v/v)+0.2% diethylamine; flow rate: 1 ml/min; temperature: 50° C.; UV detection: 235 nm].

LC-MS (method 4): $R_t$=1.12 min; m/z=242 (M+H)⁺

¹H-NMR (400 MHz, DMSO-d₆): δ [ppm]=1.38 (d, 9H), 1.76-1.88 (m, 2H), 2.66-2.81 (m, 1H), 2.87-2.98 (m, 1H), 3.04-3.79 (m, 9H).

Example 24A 2-(4-Methoxyphenyl)-2-azabicyclo[2.2.2]octan-5-one (racemate)

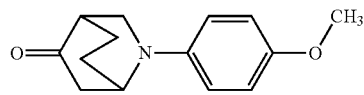

Under an atmosphere of nitrogen, 20 litres of DMSO, 1759 g (14.28 mol) of 4-methoxyaniline, 1083 g (37% strength aqueous solution, 13.0 mol) of formaldehyde, 2496 g (26 mol) of cyclohex-2-en-1-one and 448.5 g (3.9 mol) of DL-proline were introduced into a 50 litre reactor. The reaction mixture was then heated to 50° C. and stirred at this temperature for 30 h. The reaction mixture was subsequently cooled to room temperature using a water/ice bath and transferred into a larger vessel, and 100 litres of water were added. The reaction mixture was extracted three times with 20 litres of ethyl acetate. The combined organic phases were washed once with 30 litres of saturated sodium chloride solution. After the organic phase had been removed, it was concentrated to dryness under reduced pressure. On silica gel (mobile phase: petroleum ether/ethyl acetate 15:1), the residue obtained was separated into its components. This gave 600 g (2.60 mol, 18% of theory) of the title compound.

LC-MS (method 11): $R_t$=0.913 min; m/z=232 (M+H)⁺.

Example 25A (E/Z)-N-Hydroxy-2-(4-methoxyphenyl)-2-azabicyclo[2.2.2]octan-5-imine (racemate)

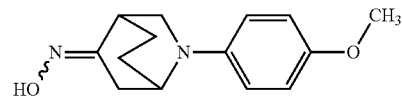

Under an atmosphere of nitrogen, 600 g (2.59 mol) of 2-(4-methoxyphenyl)-2-azabicyclo[2.2.2]octan-5-one (racemate), 10 litres of THF, 688 g (6.43 mol) of sodium carbonate and 197 g (2.86 mol) of hydroxylamine hydrochloride were introduced into a 20 litre four-necked flask. The reaction mixture was then stirred at room temperature overnight. The reaction mixture was subsequently filtered and the filtrate was concentrated to dryness under reduced pressure. This gave 700 g of the title compound which was used in the subsequent reaction without further purification.

LC-MS (method 11): $R_t$=0.71 min; m/z=247 (M+H)⁺.

Example 26A 6-(4-Methoxyphenyl)-2,6-diazabicyclo[3.2.2]nonan-3-one (racemate)

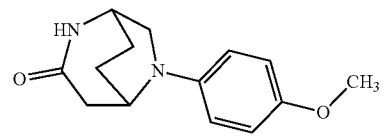 [SMILES: COc1ccc(N2CC3CCC2CC(=O)N3)cc1]

Under an atmosphere of nitrogen, 700 g (2.84 mol) of (E/Z)-N-hydroxy-2-(4-methoxyphenyl)-2-azabicyclo[2.2.2]octan-5-imine (racemate), 3500 g of polyphosphoric acid and 1 litre of toluene were introduced into a 5 litre four-necked flask. The resulting reaction solution was heated to 100° C. with stirring and stirred at this temperature for 5 h. The reaction mixture was subsequently cooled to room temperature using a water bath. After transfer to a larger vessel, 10 litres of water were added. The resulting mixture was extracted with 10 litres of ethyl acetate. After removal of the organic phase, the aqueous phase was adjusted to a pH of 10 using aqueous sodium hydroxide solution. The solution was then extracted twice with 10 litres of dichloromethane, and the combined organic phases were dried over sodium sulfate, filtered and concentrated to dryness under reduced pressure. This gave 270 g (1.12 mmol, 39% of theory) of the title compound.

LC-MS (method 11): $R_t$=0.76 min; m/z=247 (M+H)⁺.

Example 27A 2,6-Diazabicyclo[3.2.2]nonan-3-one (racemate)

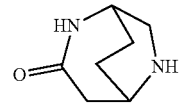

Under an atmosphere of nitrogen, 225 g (914 mmol) of 6-(4-methoxyphenyl)-2,6-diazabicyclo[3.2.2]nonan-3-one (racemate), 2.2 litres of acetonitrile and 440 ml of water were introduced into a 10 litre four-necked flask. At room temperature and with stirring, 1254 g (2.29 mol) of cerium (IV) ammonium nitrate were then added to the reaction mixture a little at a time and stirring was continued overnight. 3 litres of water were then added to the solution and the pH was adjusted to 10 by addition of sodium carbonate. The solution obtained in this manner was used directly, without further work-up, in the next reaction.

LC-MS (method 11): $R_t$=0.17 min; m/z=141 (M+H)$^+$.

Example 28A

Benzyl 3-oxo-2,6-diazabicyclo[3.2.2]nonane-6-carboxylate (racemate)

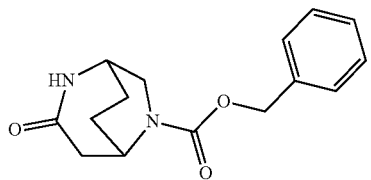 [SMILES: O=C1CC2CCC(CN2C(=O)OCc2ccccc2)N1]

The solution obtained in Example 27A was transferred into a 20 litre flask, and 310 g (1.82 mol) of benzyl carbonochloridate were added a little at a time with stirring. Stirring of the resulting reaction solution was continued at room temperature overnight. The solution was then filtered, and the filtrate obtained was extracted three times with 3 litres of dichloromethane. The combined organic phases were concentrated to dryness under reduced pressure. On silica gel (mobile phase: dichloromethane/methanol 10:1), the residue obtained was separated into its components. This gave 120 g of the title compound (438 mmol, 48% of theory based on 225 g (914 mmol) of 6-(4-methoxyphenyl)-2,6-diazabicyclo[3.2.2]nonan-3-one).

LC-MS (method 11): $R_t$=0.81 min; m/z=275 (M+H)$^+$.

Example 29A

Benzyl 2,6-diazabicyclo[3.2.2]nonane-6-carboxylate (racemate)

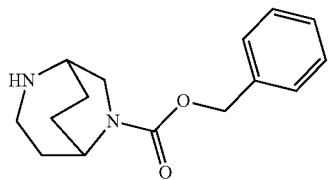 [SMILES: O=C(OCc1ccccc1)N1CC2CCC1CCN2]

Under an atmosphere of nitrogen, 120 g (438 mmol) of benzyl 3-oxo-2,6-diazabicyclo[3.2.2]nonane-6-carboxylate (racemate) and 1.5 litres of dry THF were introduced into a 5 litre four-necked flask. With stirring, 547 ml (1.1 mol) of a 2 M solution of borane/dimethyl sulfide complex in THF were metered in a little at a time. The reaction solution was then heated to 65° C. and stirred at this temperature overnight. Using an ice/water bath, the reaction solution was then cooled to 0° C., and the reaction was stopped by addition of 3 M hydrochloric acid. Hydrochloric acid was added until a pH of 2 had been reached. The resulting solution was heated to 70° C. and stirred at this temperature for 1 h. The solution was subsequently cooled to room temperature, and sodium carbonate was added carefully until a pH of 10 had been reached. The solution obtained in this manner was used directly, without further work-up, in the next reaction.

LC-MS (method 11): $R_t$=0.67 min; m/z=261 (M+H)$^+$.

Example 30A

6-Benzyl 2-tert-butyl 2,6-diazabicyclo[3.2.2]nonane-2,6-dicarboxylate (racemate)

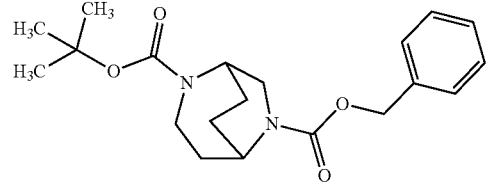 [SMILES: CC(C)(C)OC(=O)N1CCC2CCC1CN2C(=O)OCc1ccccc1]

Under an atmosphere of nitrogen, the solution obtained in Example 29A was transferred into a 5 litre four-necked flask, and 191 g (875 mmol) of di-tert-butyl dicarbonate were added. The resulting solution was stirred at room temperature for 3 h. 3 litres of water were then added slowly. The solution was extracted three times with ethyl acetate, and the organic phases were combined and concentrated to dryness under reduced pressure. On silica gel (mobile phase: petroleum ether/ethyl acetate 10:1), the residue obtained was separated into its components. This gave 100 g of the title compound (278 mmol, 63% of theory based on 120 g (438 mmol) of benzyl 3-oxo-2,6-diazabicyclo[3.2.2]nonane-6-carboxylate).

LC-MS (method 11): $R_t$=1.23 min; m/z=361 (M+H)$^+$.

$^1$H-NMR (300 MHz, CDCl$_3$): δ [ppm]=7.37 (s, 5H), 5.16 (s, 2H), 4.53-4.28 (m, 2H), 3.93-3.75 (m, 2H), 3.35-3.19 (m, 2H), 2.06-1.70 (m, 6H), 1.48 (s, 9H).

Example 31A and Example 32A

6-Benzyl 2-tert-butyl 2,6-diazabicyclo[3.2.2]nonane-2,6-dicarboxylate (Enantiomers 1 and 2)

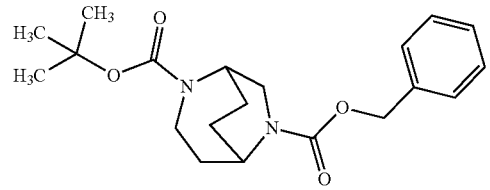 [SMILES: CC(C)(C)OC(=O)N1CCC2CCC1CN2C(=O)OCc1ccccc1]

100 g (277 mmol) of racemic 6-benzyl 2-tert-butyl 2,6-diazabicyclo[3.2.2]nonane-2,6-dicarboxylate (Example 30A) were separated into the enantiomers by preparative SFC-HPLC on a chiral phase [column: ColumnTEK EnantioPak-Al, 5 µm, 250 mm×50 mm; mobile phase: carbon dioxide/ethanol 50:50 (v/v); flow rate: 150 ml/min; pressure: 100 bar; UV detection: 220 nm; temperature: 35° C.]:

Example 31A (Enantiomer 1)

Yield: 30 g
$R_t$=1.88 min; >98% ee
[column: Daicel Chiralpak ID-H, 5 µm, 150 mm×4.6 mm; mobile phase: carbon dioxide/methanol 10:90 (v/v)+0.1% diethylamine; flow rate: 4 ml/min; pressure: 100 bar; UV detection: 210 nm; temperature: 35.8° C.].

Example 32A (Enantiomer 2)

Yield: 30 g
$R_t$=2.29 min; >99% ee
[column: Daicel Chiralpak ID-H, 5 µm, 150 mm×4.6 mm; mobile phase: carbon dioxide/methanol 10:90 (v/v)+0.1% diethylamine; flow rate: 4 ml/min; pressure: 100 bar; UV detection: 210 nm; temperature: 35.8° C.].

Example 33A tert-Butyl 2,6-diazabicyclo[3.2.2]nonane-2-carboxylate (Enantiomer 1)

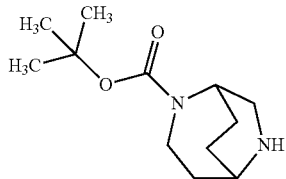 [SMILES: CC(C)(C)OC(=O)N1CCC2CCC1CN2]

At room temperature, 25 g (69.4 mmol) of 6-benzyl 2-tert-butyl 2,6-diazabicyclo[3.2.2]nonane-2,6-dicarboxylate (enantiomer 1), 250 ml of methanol and 4 g (3.7 mmol) of palladium on carbon (10%) were introduced into a 1 litre flask. With stirring, the reaction mixture was subsequently hydrogenated at room temperature under 1 bar of hydrogen overnight. The reaction solution was subsequently filtered and the filtrate was concentrated under reduced pressure. The residue was then washed once with 50 ml of hexane. The precipitate that remained was filtered off and dried in a vacuum drying oven at 40° C. This gave 10.1 g (44.4 mmol, 64% of theory) of the title compound.

LC-MS (method 12): $R_t$=0.85 min; m/z=227 (M+H)$^+$.
$^1$H-NMR (300 MHz, D$_2$O): δ [ppm]=4.21-4.15 (m, 1H), 3.90-3.34 (m, 2H), 3.26-2.82 (m, 3H), 1.88-1.65 (m, 6H), 1.35 (s, 9H). $[α]_D^{27.2}$=−17.41° (c=0.494 g/100 ml in methanol).

Example 34A tert-Butyl 2,6-diazabicyclo[3.2.2]nonane-2-carboxylate (Enantiomer 2)

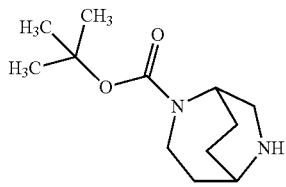 [SMILES: CC(C)(C)OC(=O)N1CCC2CCC1CN2]

At room temperature, 25 g (69.4 mmol) of 6-benzyl 2-tert-butyl 2,6-diazabicyclo[3.2.2]nonane-2,6-dicarboxylate (enantiomer 2), 250 ml of methanol and 4 g (3.7 mmol) of palladium on carbon (10%) were introduced into a 1 litre flask. With stirring, the reaction mixture was subsequently hydrogenated at room temperature under 1 bar of hydrogen overnight. The reaction solution was subsequently filtered and the filtrate was concentrated under reduced pressure. The residue was then washed once with 50 ml of hexane. The precipitate that remained was filtered off and dried in a vacuum drying oven at 40° C. This gave 10.9 g (47.8 mmol, 69% of theory) of the title compound.

LC-MS (method 12): $R_t$=0.84 min; m/z=227 (M+H)$^+$.
$^1$H-NMR (300 MHz, D$_2$O): δ [ppm]=4.31-4.21 (m, 1H), 4.10-3.41 (m, 2H), 3.22-3.04 (m, 3H), 1.97-1.63 (m, 6H), 1.36 (s, 9H).
$[α]_D^{27.2}$=+16.590 (c=0.476 g/100 ml in methanol).

Example 35A

3-Benzyl-(E/Z)-N-hydroxy-3-azabicyclo[3.2.1]octan-8-imine

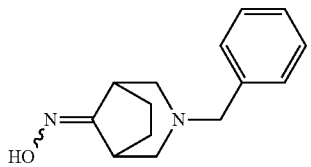 [SMILES: ON=C1C2CCC1CN(Cc1ccccc1)C2]

200 g (930 mmol) of 3-benzyl-3-azabicyclo[3.2.1]octan-8-one, 64.6 g (930 mmol) of hydroxylamine hydrochloride, 120 g (929 mmol) of diisopropylethylamine and 1 litre of ethanol were introduced into a 1 litre flask. The resulting solution was heated to 35° C. and stirred at this temperature for 2 h. After cooling to room temperature, the solution was concentrated under reduced pressure and transferred into a larger vessel, and 2 litres of water were added. The solution was then extracted three times with 800 ml of dichloromethane. The organic phases were combined and the solution was then concentrated to dryness under reduced pressure. On silica gel (mobile phase: petroleum ether/ethyl acetate 4:1 to 15:1), the residue obtained was separated into its components. This gave 179 g (780 mmol, 84% of theory) of the title compound.

$^1$H-NMR (300 MHz, CDCl$_3$): δ [ppm]=9.53 (s, 1H), 7.39-7.26 (m, 3H), 7.20 (d, 2H), 6.96 (d, 2H), 5.55 (s, 2H).
LC-MS (method 11): $R_t$=0.54 min; m/z=231 (M+H)$^+$.

Example 36A

3-Benzyl-3,6-diazabicyclo[3.2.2]nonan-7-one (racemate)

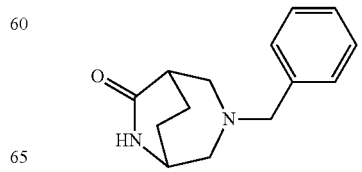

800 g of polyphosphoric acid were introduced into a 3 litre four-necked flask and heated to 50° C. 178 g (773 mmol) of 8-benzyl-(E/Z)-N-hydroxy-8-azabicyclo[3.2.1]octan-3-imine, dissolved in 300 ml of toluene, were then added a little at a time with stirring. After the addition had ended, the reaction mixture was heated to 110°-120° C. and stirred at this temperature for 2 h. The solution was then cooled to 80° C., and the reaction was stopped by addition of 500 ml of water. The resulting solution was slowly taken up in 5 litres of water. While stirring, the pH was adjusted to 10-11 by addition of 2 M aqueous sodium hydroxide solution. The solution was then extracted four times with 2 litres of dichloromethane. The combined organic phases were dried over sodium sulfate and the solution was, after filtration, concentrated to dryness under reduced pressure. The solid obtained was washed three times with 400 ml of diethyl ether and, after another filtration, dried. This gave 88 g (379 mmol, 49% of theory) of the title compound.

LC-MS (method 11): $R_t$=0.49 min; m/z=231 $(M+H)^+$.

Example 37A

3-Benzyl-3,6-diazabicyclo[3.2.2]nonane (racemate)

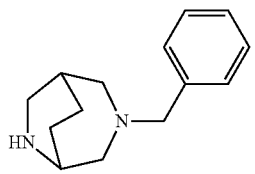 [SMILES: c1ccc(CN2CC3CCC(C2)NC3)cc1]

Under an atmosphere of nitrogen, a solution of 331 g (1.64 mol) of sodium bis(2-methoxyethoxy)aluminiumhydride (Red-Al®) in 150 ml of dry THF was introduced into a 3 litre four-necked flask. 88 g (382.1 mmol) of 3-benzyl-3,6-diazabicyclo[3.2.2]nonan-7-one (racemate), dissolved in 1 litre of dry THF, were then added dropwise over 30 min with stirring. During the addition, the temperature of the reaction solution was kept below 5° C. After the addition had ended, the reaction solution was heated to 50° C. and stirred at this temperature for 3 h. The reaction mixture was cooled to 30° C., and 1 litre of ice-water was then added slowly to stop the reaction. The pH was then adjusted to 10 by addition of 1 M aqueous sodium hydroxide solution. The resulting solution was extracted with 500 ml of toluene. The organic phase was separated off and then washed successively with in each case 500 ml of 1 M aqueous sodium hydroxide solution, water and saturated sodium chloride solution. The organic phase was then dried over sodium sulfate, filtered and concentrated to dryness under reduced pressure. This gave 89.7 g (crude product) of the title compound as a yellowish oil which was used in the subsequent reaction without further purification.

LC-MS (method 11): $R_t$=0.46 min; m/z=217 $(M+H)^+$.

Example 38A

Benzyl 3-benzyl-3,6-diazabicyclo[3.2.2]nonane-6-carboxylate (racemate)

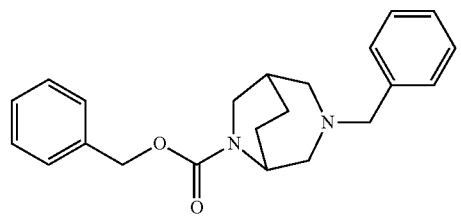 [SMILES: O=C(OCc1ccccc1)N1CC2CCC1CN(Cc1ccccc1)C2]

Under an atmosphere of nitrogen, 89.7 g (about 379 mmol, crude material) of 3-benzyl-3,6-diazabicyclo[3.2.2]nonane (racemate) in 1 litre of dichloromethane and 57.6 g (569 mmol) of triethylamine were introduced into a 3 litre four-necked flask. Over a period of 20 min, 64.6 g (379 mmol) of benzyl carbonochloridate were then added dropwise with stirring. During the addition, the temperature of the reaction solution was kept below 10° C. The resulting reaction solution was stirred at 10° C. for 1 h. The solution was then diluted with 1 litre of water and extracted twice with 300 ml of dichloromethane. The combined organic phases were dried over sodium sulfate, filtered and concentrated to dryness under reduced pressure. This gave 147 g (crude product) of the title compound as a yellowish oil which was used in the subsequent reaction without further purification.

LC-MS (method 13): $R_t$=1.05 min; m/z=351 $(M+H)^+$.

Example 39A

Benzyl 3,6-diazabicyclo[3.2.2]nonane-6-carboxylate (racemate)

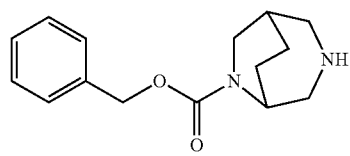 [SMILES: O=C(OCc1ccccc1)N1CC2CCC1CNC2]

Under an atmosphere of nitrogen, 147 g (about 378 mmol, crude material) of benzyl 3-benzyl-3,6-diazabicyclo[3.2.2]nonane-6-carboxylate (racemate) were introduced into 1 litre of 1,2-dichloroethane in a 2 litre flask. 269.8 g (1.89 mol) of 1-chloroethyl carbonochloridate were then slowly added dropwise with stirring. The resulting reaction solution was heated to 85° C. and stirred at this temperature for 5 h. The reaction solution was then concentrated under reduced pressure, and 500 ml of methanol were added a little at a time. The solution was subsequently stirred at 85° C. for a further hour. Then the reaction mixture was cooled to room temperature and concentrated to dryness under reduced pressure. This gave 150 g (crude product) of the title compound as a brownish oil which was used in the subsequent reaction without further purification.

LC-MS (method 13): $R_t$=0.95 min; m/z=261 $(M+H)^+$.

Example 40A

6-Benzyl 3-tert-butyl 3,6-diazabicyclo[3.2.2]nonane-3,6-dicarboxylate (racemate)

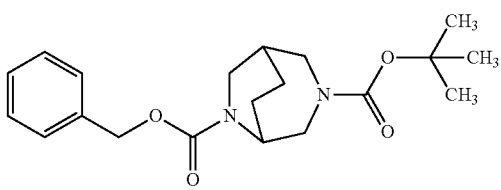 [SMILES: CC(C)(C)OC(=O)N1CC2CCC(C1)N(C(=O)OCc1ccccc1)C2]

150 g (about 379 mmol, crude material) of benzyl 3,6-diazabicyclo[3.2.2]nonane-6-carboxylate (racemate) in 800 ml of dichloromethane, 96 g (949 mmol) of triethylamine and 2.3 g (18.8 mmol) of 4-dimethylaminopyridine were introduced into a 3 litre four-necked flask. Over a period of 40 min, 82.8 g (379.4 mmol) of di-tert-butyl dicarbonate in 400 ml of dichloromethane were then added dropwise. During the addition, the temperature of the reaction solution was kept below 10° C. After the addition had ended, the reaction solution was stirred at 10° C. for another 2 h. Thereafter, 1 litre of water was added to the solution. The organic phase was removed and then washed successively with 1 litre of water and 500 ml of saturated sodium chloride solution, dried over sodium sulfate, filtered and concentrated to dryness under reduced pressure. On silica gel (mobile phase: petroleum ether/THF 15:1), the residue obtained was separated into its components. This gave 95 g (263 mmol, 69% of theory) of the title compound.

LC-MS (method 11): $R_t$=1.24 min; m/z=361 (M+H)$^+$.

$^1$H-NMR (300 MHz, CDCl$_3$): δ [ppm]=7.40-7.29 (m, 5H), 5.17 (s, 2H), 4.53-4.03 (m, 3H), 3.66-3.51 (m, 1H), 3.39-3.29 (m, 2H), 2.33-2.26 (m, 1H), 1.90-1.59 (m, 4H), 1.49 (s, 9H).

Example 41A and Example 42A

6-Benzyl 3-tert-butyl 3,6-diazabicyclo[3.2.2]nonane-3,6-dicarboxylate (Enantiomer 1 and 2)

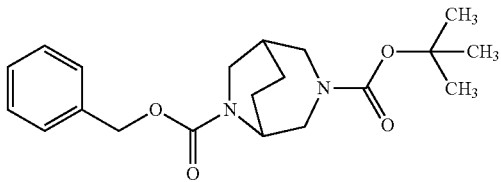 [SMILES: CC(C)(C)OC(=O)N1CC2CCC(C1)N(C(=O)OCc1ccccc1)C2]

84 g (233 mmol) of racemic 6-benzyl 3-tert-butyl 3,6-diazabicyclo[3.2.2]nonane-3,6-dicarboxylate (Example 40A) in methanol were separated into the enantiomers by preparative SFC-HPLC on a chiral phase [column: Daicel Chiralpak AD-H, 5 μm, 250 mm×50 mm; mobile phase: carbon dioxide/ethanol 70:30 (v/v); flow rate: 150 ml/min; pressure: 100 bar; UV detection: 220 nm; temperature: 35° C.]:

Example 41A (Enantiomer 1)

Yield: 38.8 g
$R_t$=7.15 min; >95.5% ee
[column: Daicel Chiralpak AD-H, 5 μm, 100 mm×4.6 mm; mobile phase: n-hexane/isopropanol (+0.1% diethylamine) 95:5 (v/v); flow rate: 1 ml/min; UV detection: 190-500 nm; temperature: 25° C.].

LC-MS (method 14): $R_t$=1.25 min; m/z=361 (M+H)$^+$.

$^1$H-NMR (300 MHz, CDCl$_3$): δ [ppm]=7.38-7.29 (m, 5H), 5.17 (s, 2H), 4.53-4.03 (m, 3H), 3.66-3.51 (m, 1H), 3.39-3.29 (m, 2H), 2.33-2.26 (m, 1H), 1.90-1.59 (m, 4H), 1.49 (s, 9H).

Example 42A (Enantiomer 2)

Yield: 36.9 g
$R_t$=5.15 min; >95.5% ee
[column: Daicel Chiralpak AD-H, 5 μm, 100 mm×4.6 mm; mobile phase: n-hexane/isopropanol (+0.1% diethylamine) 95:5 (v/v); flow rate: 1 ml/min; UV detection: 190-500 nm; temperature: 25° C.].

LC-MS (method 14): $R_t$=1.25 min; m/z=361 (M+H)$^+$.

$^1$H-NMR (300 MHz, CDCl$_3$): δ [ppm]=7.40-7.29 (m, 5H), 5.17 (s, 2H), 4.53-4.03 (m, 3H), 3.66-3.51 (m, 1H), 3.39-3.29 (m, 2H), 2.33-2.26 (m, 1H), 1.90-1.59 (m, 4H), 1.49 (s, 9H).

Example 43A tert-Butyl 3,6-diazabicyclo[3.2.2]nonane-3-carboxylate (Enantiomer 1)

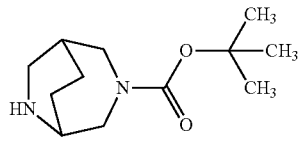

3 g (2.8 mmol) of palladium on carbon (10%) were introduced into a solution of 25.8 g (71.6 mmol) of 6-benzyl 3-tert-butyl 3,6-diazabicyclo[3.2.1]nonane-3,6-dicarboxylate (enantiomer 1) in 250 ml of methanol. With stirring, the reaction mixture was subsequently hydrogenated at room temperature under 1 atm of hydrogen overnight. The reaction solution was subsequently filtered and the filtrate was concentrated under reduced pressure. The residue obtained was dried under an infrared lamp. This gave 16.0 g (70.9 mmol, 99% of theory) of the title compound.

LC-MS (method 15): $R_t$=1.13 min; m/z=227 (M+H)$^+$.

$^1$H-NMR (300 MHz, CDCl$_3$): δ [ppm]=5.06 (s, 2H), 4.06-4.49 (m, 2.4H), 3.47-3.76 (m, 1H), 2.80-3.46 (m, 3.7H), 2.04-2.36 (m, 1H), 1.76-2.04 (m, 1.8H), 1.56-1.72 (m, 1H), 1.48 (s, 9.2H).

$[α]_D^{27.2}$=+9.130 (c=0.51 g/100 ml in chloroform).

Example 44A tert-Butyl 3,6-diazabicyclo[3.2.2]nonane-3-carboxylate (Enantiomer 2)

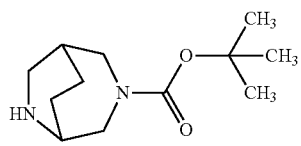

3 g (2.8 mmol) of palladium on carbon (10%) were introduced into a solution of 25 g (69.36 mmol) of 6-benzyl 3-tert-butyl 3,6-diazabicyclo[3.2.2]nonane-3,6-dicarboxylate (enantiomer 2) in 250 ml of methanol. With stirring, the reaction mixture was subsequently hydrogenated at room temperature under 1 atm of hydrogen overnight. The reaction solution was subsequently filtered and the filtrate was concentrated under reduced pressure. The residue obtained was dried under an infrared lamp. This gave 10.6 g (47.2 mmol, 68% of theory) of the title compound.

LC-MS (method 15): $R_t$=1.14 min; m/z=227 (M+H)$^+$.

$^1$H-NMR (300 MHz, CDCl$_3$): δ [ppm]=4.08-4.44 (m, 2H), 3.39-3.71 (m, 2H), 2.84-3.39 (m, 4.7H), 1.83-2.37 (m, 2H), 1.74 (s, 2.6H), 1.49 (s, 9H).

$[α]_D^{27.2}$=−11.59° (c=0.52 g/100 ml in chloroform).

Example 45A 2-(4-Chlorophenyl)-3-(2,6-diazabicyclo[3.2.2]non-6-ylmethyl)imidazo[1,2-a]pyrimidine bis(trifluoroacetic acid) salt (Enantiomer 2)×

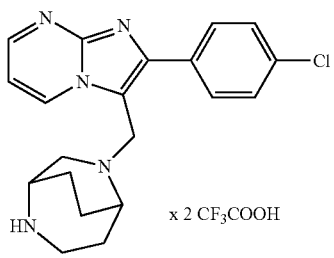 [SMILES: Clc1ccc(-c2nc3ncccn3c2CN2CC3CCC2CCN3)cc1]

tert-Butyl 6-{[2-(4-chlorophenyl)imidazo[1,2-a]pyrimidin-3-yl]methyl}-2,6-diazabicyclo[3.2.2]nonane-2-carboxylate (enantiomer 2; 1.05 g, 2.25 mmol) was initially charged in 15 ml of dichloromethane and 7.6 ml of trifluoroacetic acid and stirred at room temperature overnight. The reaction mixture was then concentrated to dryness. The crude product obtained in this manner was used in subsequent reactions without further purification.

LC-MS (method 2): $R_t$=0.84 min; m/z=368 (M+H)$^+$.

Example 46A 3-(3,9-Diazabicyclo[4.2.1]non-9-ylmethyl)-2-(4-isopropylphenyl)imidazo[1,2-a]pyrimidine dihydrochloride (Enantiomer 1)

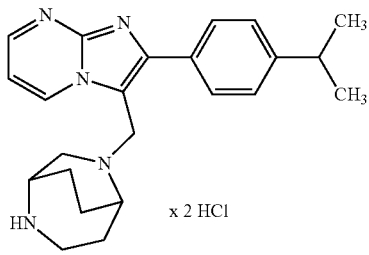 [SMILES: CC(C)c1ccc(-c2nc3ncccn3c2CN2CC3CCC2CCN3)cc1]

745 mg (1.57 mmol) of tert-butyl 9-{[2-(4-isopropylphenyl)imidazo[1,2-a]pyrimidin-3-yl]methyl}-3,9-diazabicyclo[4.2.1]nonane-3-carboxylate (enantiomer 1) were dissolved in 3 ml of dioxane, and 3.92 ml of a 4 M solution of hydrogen chloride in dioxane were added with stirring. The mixture was stirred at room temperature overnight. The solids obtained were then filtered off with suction, washed repeatedly with diethyl ether and dried under high vacuum at 40° C. 720 mg of a solid material were obtained, which was used in subsequent reactions without further purification.

LC-MS (method 1): $R_t$=0.6 min; m/z=376 (M+H)$^+$.

Analogously to Examples 45A and 46A, the following compounds were prepared from the starting material specified in each case:

| Example | Name/Structure/Starting material | Analytical data |
|---|---|---|
| 47A | 2-(4-chlorophenyl)-3-(2,6-diazabicyclo[3.2.2]non-6-ylmethyl)imidazo[1,2-a]pyrimidine bis(trifluoroacetic acid) salt (enantiomer 1)<br><br>from tert-butyl {[2-(4-chlorophenyl)imidazo[1,2-a]pyrimidin-3-yl]methyl}-2,6-diazabicyclo[3.2.2]nonane-2-carboxylate (enantiomer 1) | LC-MS (method 1): $R_t$ = 0.50 min; m/z = 368 (M + H)$^+$. |
| 48A | 2-(5-chloropyridin-2-yl)-3-(2,6-diazabicyclo[3.2.2]non-6-ylmethyl)imidazo[1,2-a]pyridine bis(trifluoroacetic acid) salt (enantiomer 1)<br><br>from tert-butyl 6-{[2-(5-chloropyridin-2-yl)imidazo[1,2-a]pyridin-3-yl]methyl}-2,6-diazabicyclo[3.2.2]nonane-2-carboxylate (enantiomer 1) | LC-MS (method 1): $R_t$ = 0.38 min; m/z = 368 (M + H)$^+$. |

| Example | Name/Structure/Starting material | Analytical data |
|---|---|---|
| 49A | 2-(4-chlorophenyl)-3-(2,6-diazabicyclo[3.2.2]non-6-ylmethyl)imidazo[1,2-a]pyridine bis(trifluoroacetic acid) salt (enantiomer 1)<br><br>× 2 CF₃COOH<br><br>from tert-butyl 6-{[2-(4-chlorophenyl)imidazo[1,2-a]pyridin-3-yl]methyl}-2,6-diazabicyclo[3.2.2]nonane-2-carboxylate (enantiomer 1) | LC-MS (method 2): $R_t = 0.67$ min; m/z = 367 (M + H)⁺. |
| 50A | 2-(4-chlorophenyl)-3-(2,6-diazabicyclo[3.2.2]non-6-ylmethyl)imidazo[1,2-a]pyridine bis(trifluoroacetic acid) salt (enantiomer 2)<br><br>× 2 CF₃COOH<br><br>from tert-butyl 6-{[2-(4-chlorophenyl)imidazo[1,2-a]pyridin-3-yl]methyl}-2,6-diazabicyclo[3.2.2]nonane-2-carboxylate (enantiomer 2) | LC-MS (method 1): $R_t = 0.42$ min; m/z = 367 (M + H)⁺. |
| 51A | 3-(3,9-diazabicyclo[4.2.1]non-9-ylmethyl)-2-(4-isopropylphenyl)imidazo[1,2-a]pyrimidine dihydrochloride (enantiomer 2)<br><br>× 2 HCl<br><br>from tert-butyl 9-{[2-(4-isopropylphenyl)imidazo[1,2-a]pyrimidin-3-yl]methyl}-3,9-diazabicyclo[4.2.1]nonane-3-carboxylate (enantiomer 2) | LC-MS (method 1): $R_t = 0.6$ min; m/z = 376 (M + H)⁺. |
| 52A | 3-(2,6-diazabicyclo[3.2.2]non-6-ylmethyl)-2-(4-isopropylphenyl)imidazo[1,2-a]pyrimidine dihydrochloride (enantiomer 1)<br><br>× 2 HCl<br><br>from tert-butyl 6-{[2-(4-isopropylphenyl)imidazo[1,2-a]pyrimidin-3-yl]methyl}-2,6-diazabicyclo[3.2.2]nonane-2-carboxylate (enantiomer 1) | LC-MS (method 2): $R_t = 0.97$ min; m/z = 376 (M − H + HCOOH)⁻. |
| 53A | 3-(2,6-diazabicyclo[3.2.2]non-6-ylmethyl)-2-(4-isopropylphenyl)imidazo[1,2-a]pyrimidine dihydrochloride (enantiomer 2)<br><br>× 2 HCl<br><br>from tert-butyl 6-{[2-(4-isopropylphenyl)imidazo[1,2-a]pyrimidin-3-yl]methyl}-2,6-diazabicyclo[3.2.2]nonane-2-carboxylate (enantiomer 2) | LC-MS (method 2): $R_t = 0.97$ min; m/z = 376 (M − H + HCOOH)⁻. |

Example 54A

[2-(4-Chlorophenyl)imidazo[1,2-a]pyridin-3-yl]methano1

2-(4-Chlorophenyl)imidazo[1,2-a]pyridine-3-carbaldehyde (15.0 g, 58.4 mmol) was initially charged in 100 ml of ethanol and cooled to 0° C. in an ice bath. A solution of sodium borohydride (4.42 g, 117 mmol) in 50 ml of ethanol was then slowly added dropwise. The mixture was stirred at room temperature and subsequently diluted with saturated ammonium chloride solution and with water. The precipitate formed was filtered off with suction and washed with water. The residue was then suspended in a little 2-methoxy-2-methylpropane and a little methanol and then once more evaporated to dryness. This gave 14.2 g (content 100%, 54.7 mmol, 94% of theory) of the title compound.

LC-MS (method 1): $R_t$=0.49 min; m/z=259/261 (M+H)$^+$.

$^1$H-NMR (400 MHz, DMSO-d$_6$): δ [ppm]=4.91 (d, 2H), 5.44 (t, 1H), 7.00 (t, 1H), 7.33 (t, 1H), 7.55 (d, 2H), 7.62 (d, 1H), 7.87 (d, 2H), 8.47 (d, 1H).

Example 55A tert-Butyl 9-[(3-fluoro-6-methoxypyridin-2-yl)carbonyl]-3,9-diazabicyclo[4.2.1]nonane-3-carboxylate (Racemate)

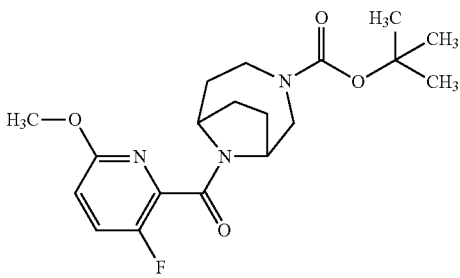 [SMILES: COc1ccc(F)c(C(=O)N2C3CCC2CN(C(=O)OC(C)(C)C)CC3)n1]

tert-Butyl 3,9-diazabicyclo[4.2.1]nonane-3-carboxylate (1.00 g, 4.42 mmol), 3-fluoro-6-methoxypyridine-2-carboxylic acid (907 mg, 5.30 mmol) and 1-[bis(dimethylamino)methylene]-1H-[1,2,3]triazolo[4,5-b]pyridin-1-ium 3-oxide hexafluorophosphate (2.18 g, 5.74 mmol) were initially charged in 10 ml of DMF. N-Ethyl-N-isopropylpropan-2-amine (2.3 ml, 13.2 mmol) was then added, and the mixture was stirred at room temperature overnight. The reaction mixture was then diluted with ethyl acetate and the organic phase was washed with water. The organic phase was dried over magnesium sulfate, filtered and concentrated to dryness. On silica gel (mobile phase: cyclohexane/ethyl acetate gradient), the residue obtained was separated into its components. This gave 1.47 g (96% pure, 3.72 mmol, 84% of theory) of the title compound.

LC-MS (method 1): $R_t$=0.98 min; m/z=380 (M+H)$^+$ $^1$H-NMR (400 MHz, DMSO-d$_6$): δ [ppm]=1.35-1.46 (m, 9H), 1.47-1.61 (m, 1.5H), 1.63-1.84 (m, 2H), 1.84-2.25 (m, 2H), 2.28-2.40 (m, 0.5H), 2.74-3.07 (m, 1.7H), 3.26 (br. dd, 0.3H), 3.71-3.80 (m, 1H), 3.81-3.85 (m, 3H), 3.86-4.06 (m, 2H), 4.57-4.76 (m, 1H), 6.97 (dt, 1H), 7.65-7.94 (m, 1H).

Example 56A and Example 57A tert-Butyl 9-[(3-fluoro-6-methoxypyridin-2-yl)carbonyl]-3,9-diazabicyclo[4.2.1]nonane-3-carboxylate (Enantiomers 1 and 2)

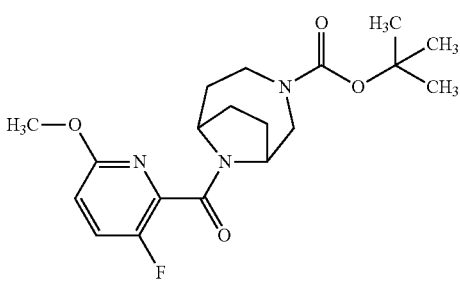 [SMILES: COc1ccc(F)c(C(=O)N2C3CCC2CN(C(=O)OC(C)(C)C)CC3)n1]

1.47 g (3.72 mmol) of racemic tert-butyl 9-[(3-fluoro-6-methoxypyridin-2-yl)carbonyl]-3,9-diazabicyclo[4.2.1]nonane-3-carboxylate (Example 55A) were separated into the enantiomers by preparative SFC-HPLC on a chiral phase [column: Chiralcel AD-H, 5 μm, 250 mm×30 mm; mobile phase: carbon dioxide/isopropanol 91:9 (v/v); flow rate: 125 g/min; pressure: 135 bar; UV detection: 210 nm; temperature: 38° C.]:

Example 56A (Enantiomer 1)

Yield: 711 mg $R_t$=0.93 min; chemical purity >99%; >99% ee [column: Chiralpak AD-3, 3 μm, 100 mm×4.6 mm; mobile phase: carbon dioxide/isopropanol 95:5→1:1 (v/v); flow rate: 3 ml/min; pressure: 135 bar; UV detection: 220 nm; temperature: 60° C.].

LC-MS (method 2): $R_t$=1.87 min; m/z=380 (M+H)$^+$.

$^1$H-NMR (400 MHz, DMSO-d$_6$): δ [ppm]=1.33-1.45 (m, 9H), 1.47-1.61 (m, 1.5H), 1.62-1.81 (m, 2H), 1.83-2.25 (m, 2H), 2.28-2.40 (m, 0.5H), 2.74-3.06 (m, 1.7H), 3.26 (br. dd, 0.3H), 3.73-3.80 (m, 1H), 3.81-3.85 (m, 3H), 3.87-4.06 (m, 2H), 4.56-4.77 (m, 1H), 6.97 (dt, 1H), 7.72-7.87 (m, 1H).

Example 57A (Enantiomer 2)

Yield: 695 mg $R_t$=1.07 min; chemical purity >99%; >92% ee [column: Chiralpak AD-3, 3 μm, 100 mm×4.6 mm; mobile phase: carbon dioxide/isopropanol 95:5-1:1 (v/v); flow rate: 3 ml/min; pressure: 135 bar; UV detection: 220 nm; temperature: 60° C.].

LC-MS (method 2): $R_t$=1.87 min; m/z=380 (M+H)$^+$.

$^1$H-NMR (400 MHz, DMSO-d$_6$): δ [ppm]=1.35-1.44 (m, 9H), 1.47-1.61 (m, 1.5H), 1.62-1.81 (m, 2H), 1.84-2.23 (m, 2H), 2.27-2.41 (m, 0.5H), 2.72-3.08 (m, 1.7H), 3.26 (br. dd, 0.3H), 3.72-3.80 (m, 1H), 3.81-3.85 (m, 3H), 3.87-4.06 (m, 2H), 4.55-4.77 (m, 1H), 6.97 (dt, 1H), 7.75-7.84 (m, 1H).

Example 58A 3,9-Diazabicyclo[4.2.1]non-9-yl(3-fluoro-6-methoxypyridin-2-yl)methanone (Enantiomer 2)

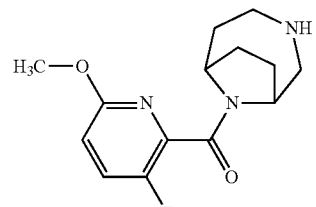

tert-Butyl 9-[(3-fluoro-6-methoxypyridin-2-yl)carbonyl]-3,9-diazabicyclo[4.2.1]nonane-3-carboxylate (695 mg, 1.83 mmol, enantiomer 2) was initially charged in 12 ml of dichloromethane and 6.2 ml of trifluoroacetic acid and stirred at room temperature overnight. The reaction mixture was subsequently diluted with ethyl acetate and 1 N aqueous sodium hydroxide solution, the organic phase was removed and the aqueous phase was extracted with ethyl acetate. The combined organic phases were dried over magnesium sulfate, filtered and concentrated to dryness (LC/MS analysis was carried out at this point). The residue obtained was dissolved in ethyl acetate and washed with 1 N aqueous sodium hydroxide solution. The organic phase was separated off and the aqueous phase was once more extracted with ethyl acetate. Again, the combined organic phases were dried over magnesium sulfate, filtered and concentrated to dryness. This gave 258 mg (100% pure, 0.93 mmol, 51% of theory) of the title compound.

LC-MS (method 1): R$_t$=0.38 min; m/z=280 (M+H)$^+$ $^1$H-NMR (400 MHz, DMSO-d$_6$): δ [ppm]=1.25-1.78 (m, 3H), 1.80-2.28 (m, 4H), 2.57-2.83 (m, 2H), 2.89-3.10 (m, 1H), 3.76-3.93 (d, 4H), 4.47-4.68 (m, 1H), 6.95 (dt, 1H), 7.67-7.85 (m, 1H).

Example 59A 3,9-Diazabicyclo[4.2.1]non-9-yl(3-fluoro-6-methoxypyridin-2-yl)methanone (Enantiomer 1)

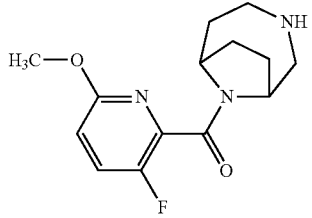 [SMILES: COc1ccc(F)c(C(=O)N2C3CCNCC2CC3)n1]

tert-Butyl 9-[(3-fluoro-6-methoxypyridin-2-yl)carbonyl]-3,9-diazabicyclo[4.2.1]nonane-3-carboxylate (711 mg, 1.87 mmol, enantiomer 1) was initially charged in 13 ml of dichloromethane and 6.3 ml of trifluoroacetic acid and stirred at room temperature overnight. The reaction mixture was subsequently diluted with ethyl acetate and 1 N aqueous sodium hydroxide solution, the organic phase was removed and the aqueous phase was extracted with ethyl acetate. The combined organic phases were dried over magnesium sulfate, filtered and concentrated to dryness (LC/MS analysis was carried out at this point). The residue obtained was dissolved in ethyl acetate and washed with 1 N aqueous sodium hydroxide solution. The organic phase was separated off and the aqueous phase was once more extracted with ethyl acetate. Again, the combined organic phases were dried over magnesium sulfate, filtered and concentrated to dryness. This gave 309 mg (100% pure, 1.11 mmol, 59% of theory) of the title compound.

LC-MS (method 1): R$_t$=0.37 min; m/z=280 (M+H)$^+$ $^1$H-NMR (400 MHz, DMSO-d$_6$): δ [ppm]=1.25-1.78 (m, 3H), 1.81-2.27 (m, 4H), 2.57-2.78 (m, 2H), 2.90-3.09 (m, 1H), 3.75-3.93 (d, 4H), 4.50-4.66 (m, 1H), 6.95 (dt, 1H), 7.68-7.85 (m, 1H).

Example 60A tert-Butyl 10-[(3-fluoro-6-methoxypyridin-2-yl)carbonyl]-8-oxa-3,10-diazabicyclo[4.3.1]decane-3-carboxylate (Enantiomer 1)

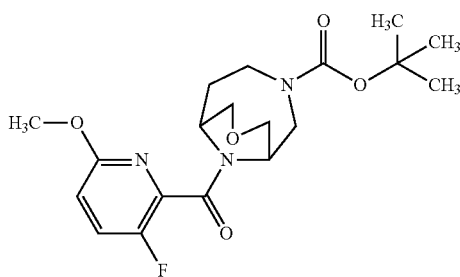 [SMILES: COc1ccc(F)c(C(=O)N2C3CCN(C(=O)OC(C)(C)C)CC2COC3)n1]

3-Fluoro-6-methoxypyridine-2-carboxylic acid (169 mg, 990 μmol) and 1-[bis(dimethylamino)methylene]-1H-[1,2,3]triazolo[4,5-b]pyridin-1-ium 3-oxide hexafluorophosphate (408 mg, 1.07 mmol) were initially charged in 1.0 ml of DMF. N-Ethyl-N-isopropylpropan-2-amine (430 μl, 2.5 mmol) was then added, and the mixture was stirred at room temperature for 1 h. tert-Butyl 8-oxa-3,10-diazabicyclo[4.3.1]decane-3-carboxylate (200 mg, 825 μmol, enantiomer 1) in 1 ml of DMF was then added, and stirring of the reaction mixture was continued at room temperature overnight. The reaction mixture was then diluted with tert-butyl methyl ether and saturated sodium carbonate solution, the organic phase was removed and the aqueous phase was extracted twice with ethyl acetate. The combined organic phases were dried over magnesium sulfate, filtered and concentrated to dryness under reduced pressure. On silica gel (mobile phase: cyclohexane/ethyl acetate 10:1), the residue obtained was separated into its components. This gave 301 mg (100% pure, 0.76 mmol, 92% of theory) of the title compound.

LC-MS (method 1): R$_t$=1.72 min; m/z=396 (M+H)$^+$ $^1$H-NMR (400 MHz, DMSO-d$_6$): δ [ppm]=1.30-1.48 (m, 9H), 1.81-2.29 (m, 2H), 2.62-2.80 (m, 0.2H), 2.90-3.18 (m, 1.5H), 3.27 (br. dd, 0.4H), 3.38-3.43 (m, 0.7H), 3.48-4.03 (m, 9.2H), 4.44-4.62 (m, 1H), 6.92-7.01 (m, 1H), 7.81 (td, 1H).

Example 61A tert-Butyl 10-[(3-fluoro-6-methoxypyridin-2-yl)carbonyl]-8-oxa-3,10-diazabicyclo[4.3.1]decane-3-carboxylate (Enantiomer 2)

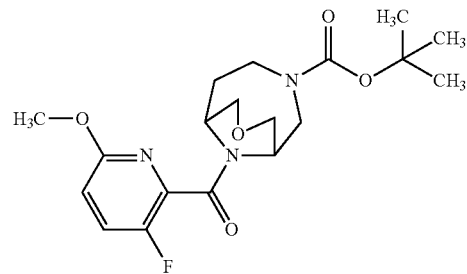 [SMILES: COc1ccc(F)c(C(=O)N2C3CCN(C(=O)OC(C)(C)C)CC2COC3)n1]

3-Fluoro-6-methoxypyridine-1-carboxylic acid (2 mg, 1.49 mmol) and 1-[bis(dimethylamino)methylene]-1H-[1,2,3]triazolo[4,5-b]pyridin-1-ium 3-oxide hexafluorophosphate (612 mg, 1.61 mmol) were initially charged in 1.0 ml of DMF. N-Ethyl-N-isopropylpropan-2-amine (650 μl, 3.7 mmol) was then added, and the mixture was stirred at room temperature for 1 h. tert-Butyl 8-oxa-3,10-diazabicyclo[4.3.1]decane-3-carboxylate (300 mg, 1.24 mmol, enantiomer 2) in 1 ml of DMF was then added, and stirring of the reaction mixture was continued at room temperature overnight. The reaction mixture was then diluted with tert-butyl methyl ether and saturated sodium carbonate solution, the organic phase was removed and the aqueous phase was extracted twice with ethyl acetate. The combined organic phases were dried over magnesium sulfate, filtered and concentrated to dryness under reduced pressure. On silica gel (mobile phase: cyclohexane/ethyl acetate 10:1), the residue obtained was separated into its components. This gave 443 mg (100% pure, 1.12 mmol, 90% of theory) of the title compound.

LC-MS (method 1): R$_t$=1.72 min; m/z=396 (M+H)$^+$.

¹H-NMR (400 MHz, DMSO-d₆): δ [ppm]=1.29-1.47 (m, 9H), 1.81-2.29 (m, 2H), 2.62-2.81 (m, 0.2H), 2.89-3.21 (m, 1.5H), 3.27 (br. dd, 0.4H), 3.37-3.45 (m, 0.7H), 3.47-4.03 (m, 9.2H), 4.44-4.62 (m, 1H), 6.87-7.05 (m, 1H), 7.81 (td, 1H).

Example 62A (3-Fluoro-6-methoxypyridin-2-yl)(8-oxa-3,10-diazabicyclo[4.3.1]dec-10-yl)methanone (Enantiomer 1)

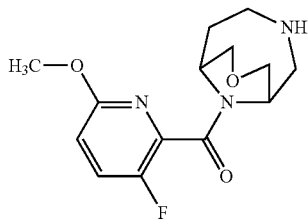 [SMILES: COc1ccc(F)c(C(=O)N2C3CCNCC2COC3)n1]

tert-Butyl 10-[(3-fluoro-6-methoxypyridin-2-yl)carbonyl]-8-oxa-3,10-diazabicyclo[4.3.1]decane-3-carboxylate (4.53 g, 11.5 mmol, enantiomer 1) was initially charged in 40 ml of dichloromethane and 20 ml of trifluoroacetic acid and stirred at room temperature for 2 h. The reaction mixture was then concentrated to dryness and the residue was taken up in ethyl acetate. The organic phase was washed with saturated sodium carbonate solution, dried over magnesium sulfate, filtered and concentrated to dryness under reduced pressure. This gave 2.36 g (content 100%, 7.98 mmol, 70% of theory) of the title compound.

LC-MS (method 6): $R_t$=1.00 min; m/z=296 (M+H)⁺.

¹H-NMR (400 MHz, DMSO-d₆): δ [ppm]=1.57-1.80 (m, 1H), 1.82-2.11 (m, 1H), 2.61-2.81 (m, 1.5H), 2.83-3.10 (m, 2.5H), 3.40-3.73 (m, 4H), 3.79-4.01 (m, 4H), 4.33-4.59 (m, 1H), 6.96 (dd, 1H), 7.80 (t, 1H).

Example 63A (3-Fluoro-6-methoxypyridin-2-yl)(8-oxa-3,10-diazabicyclo[4.3.1]dec-10-yl)methanone (Enantiomer 2)

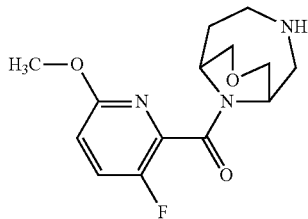 [SMILES: COc1ccc(F)c(C(=O)N2C3CCNCC2COC3)n1]

tert-Butyl 10-[(3-fluoro-6-methoxypyridin-2-yl)carbonyl]-8-oxa-3,10-diazabicyclo[4.3.1]decane-3-carboxylate (3.88 g, 9.80 mmol, enantiomer 2) was initially charged in 40 ml of dichloromethane and 20 ml of trifluoroacetic acid and stirred at room temperature for 2 h. The reaction mixture was then concentrated to dryness and the residue was taken up in ethyl acetate. The organic phase was washed with saturated sodium carbonate solution, dried over magnesium sulfate, filtered and concentrated to dryness under reduced pressure. This gave 1.95 g (content 100%, 6.59 mmol, 67% of theory) of the title compound.

LC-MS (method 6): $R_t$=1.00 min; m/z=296 (M+H)⁺.

¹H NMR (400 MHz, DMSO-d₆): δ [ppm]=1.55-1.80 (m, 1H), 1.83-2.11 (m, 1H), 2.63-2.81 (m, 1.5H), 2.82-3.11 (m, 2.5H), 3.39-3.73 (m, 4H), 3.79-4.01 (m, 4H), 4.35-4.61 (m, 1H), 6.96 (dd, 1H), 7.80 (t, 1H).

Analogously to Examples 55A, 60A and 61A, the following compounds were prepared from the starting materials specified in each case:

| Example | Name/Structure/Starting materials Analytical data |
|---|---|
| 64A | tert-butyl 9-(2-fluorobenzyl)-3,9-diazabicyclo[4.2.1]nonane-3-carboxylate (racemate)<br><br>from tert-butyl 3,9-diazabicyclo[4.2.1]nonane-3-carboxylate (racemate) and 2-fluorobenzoic acid<br><br>¹H-NMR (400 MHz, DMSO-d₆): δ [ppm] = 1.379 (5.77), 1.406 (9.63), 1.419 (16.00), 1.504 (0.63), 1.528 (0.86), 1.548 (0.74), 1.571 (0.47), 1.689 (0.45), 1.712 (0.83), 1.721 (0.85), 1.739 (0.90), 1.756 (0.54), 2.305 (0.48), 2.336 (0.46), 2.952 (0.53), 3.699 (0.58), 3.736 (1.15), 3.770 (0.64), 3.822 (0.82), 3.842 (0.79), 3.864 (0.54), 3.887 (0.48), 4.638 (0.42), 4.695 (0.55), 5.755 (0.58), 7.263 (0.54), 7.270 (0.56), 7.282 (1.88), 7.289 (1.90), 7.307 (1.87), 7.328 (0.70), 7.336 (0.64), 7.386 (0.50), 7.403 (0.85), 7.474 (0.83), 7.488 (1.58), 7.508 (1.25).<br>LC-MS (method 1): $R_t$ = 0.99 min; m/z = 349 (M + H)⁺. |
| 65A | tert-butyl 9-[(6-methoxypyridin-2-yl)carbonyl]-3,9 diazabicyclo[4.2.1]nonane-3-carboxylate (racemate)<br>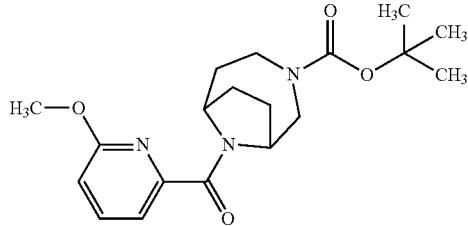<br>from tert-butyl 3,9-diazabicyclo[4.2.1]nonane-3-carboxylate (racemate) and 6-methoxypyridine-2-carboxylate acid<br><br>¹H-NMR (400 MHz, DMSO-d₆): δ [ppm] = 1.375 (6.26), 1.403 (16.00), 1.422 (8.86), 1.544 (0.54), 1.558 (0.59), 1.730 (0.41), 1.744 (0.50), 1.770 (0.48), 1.959 (0.41), 3.702 (0.41), 3.738 (0.54), 3.825 (0.46), 3.854 (6.39), 3.867 (8.26), 4.694 (0.64), 4.708 (0.73), 4.732 (0.42), 4.761 (0.40), 5.754 (1.87), 6.919 (0.65), 6.938 (0.92), 6.952 (0.72), 7.333 (0.49), 7.351 (0.56), 7.800 (0.58), 7.808 (0.54), 7.819 (0.92), 7.827 (0.91), 7.838 (0.57), 7.846 (0.47).<br>LC-MS (method 1): $R_t$ = 1.00 min; m/z = 362 (M + H)⁺. |

| Ex-ample | Name/Structure/Starting materials Analytical data |
|---|---|
| 66A | tert-Butyl 10-(2-fluorobenzoyl)-8-oxa-3,10-diazabicyclo[4.3.1]decane-3-carboxylate (racemate) 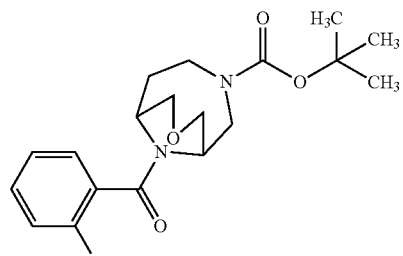 from tert-butyl 8-oxa-3,10-diazabicyclo[4.3.1]decane-3-carboxylate (racemate) and 2-fluorobenzoic acid <br> $^1$H-NMR (400 MHz, DMSO-$d_6$): δ [ppm] = 1.358 (5.09), 1.395 (8.29), 1.411 (16.00), 1.988 (0.57), 3.437 (0.45), 3.445 (0.50), 3.466 (0.70), 3.473 (0.78), 3.501 (0.46), 3.569 (1.26), 3.588 (1.02), 3.597 (0.86), 3.614 (0.67), 3.728 (0.58), 3.949 (0.63), 3.982 (0.47), 4.523 (0.48), 7.287 (0.67), 7.296 (1.06), 7.304 (1.21), 7.318 (1.15), 7.322 (1.36), 7.341 (0.54), 7.440 (0.52), 7.489 (0.40), 7.504 (0.65), 7.520 (0.52). <br> LC-MS (method 2): $R_t$ = 1.87 min; m/z = 307 (M − $C_4H_9$)$^+$. |
| 67A | tert-butyl 10-[(6-methoxypyridin-2-yl)carbonyl]-8-oxa-3,10-diazabicyclo[4.3.1]decane-3-carboxylate (racemate) 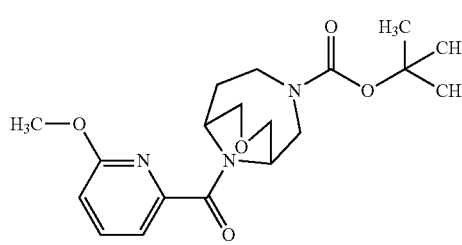 from tert-butyl 8-oxa-3,10-diazabicyclo[4.3.1]decane-3-carboxylate (racemate) and 6-methoxypyridine-2-carboxylic acid <br> $^1$H-NMR (400 MHz, DMSO-$d_6$): δ [ppm] = 1.339 (5.79), 1.391 (11.49), 1.400 (11.63), 1.404 (16.00), 1.989 (0.57), 3.141 (0.47), 3.152 (0.46), 3.412 (0.46), 3.418 (0.49), 3.428 (0.54), 3.439 (0.62), 3.447 (0.50), 3.523 (1.11), 3.551 (0.93), 3.567 (0.80), 3.578 (0.65), 3.587 (0.46), 3.597 (0.63), 3.607 (0.67), 3.618 (0.60), 3.685 (0.77), 3.718 (0.50), 3.756 (0.58), 3.787 (0.82), 3.829 (0.99), 3.847 (14.55), 3.864 (0.78), 3.959 (0.89), 3.988 (0.69), 4.103 (0.46), 4.524 (0.85), 5.754 (0.42), 6.894 (1.33), 6.915 (1.68), 7.112 (0.78), 7.131 (0.94), 7.153 (0.63), 7.162 (0.44), 7.180 (0.44), 7.803 (0.77), 7.823 (1.33), 7.842 (0.70). <br> LC-MS (method 2): $R_t$ = 1.86 min; m/z = 378 (M + H)$^+$. |
| 68A | tert-butyl 10-[(4-methyl-1,2,5-oxadiazol-3-yl)carbonyl]-8-oxa-3,10-diazabicyclo[4.3.1]decane-3-carboxylate (racemate) 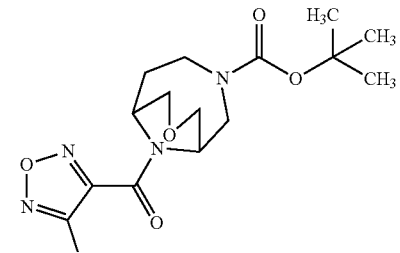 from tert-butyl 8-oxa-3,10-diazabicyclo[4.3.1]decane-3-carboxylate (racemate) and 4-methyl-1,2,5-oxadiazole-3-carboxylic acid <br> $^1$H-NMR (400 MHz, DMSO-$d_6$): δ [ppm] = 1.227 (0.42), 1.335 (5.04), 1.387 (16.00), 1.948 (0.40), 3.162 (1.47), 3.175 (1.54), 3.278 (0.42), 3.290 (0.47), 3.325 (0.55), 3.498 (0.50), 3.519 (0.53), 3.527 (0.67), 3.537 (0.50), 3.575 (0.53), 3.584 (0.62), 3.600 (1.23), 3.626 (1.15), 3.652 (0.74), 3.692 (0.45), 3.816 (0.41), 3.841 (0.69), 3.974 (0.81), 4.002 (0.83), 4.074 (0.40), 4.575 (0.75). <br> LC-MS (method 2): $R_t$ = 1.92 min; m/z = 297 [M − $C_4H_9$]$^+$. |
| 69A | tert-butyl 10-[(4-amino-1,2,5-oxadiazol-3-yl)carbonyl]-8-oxa-3,10-diazabicyclo[4.3.1]decane-3-carboxylate (racemate) 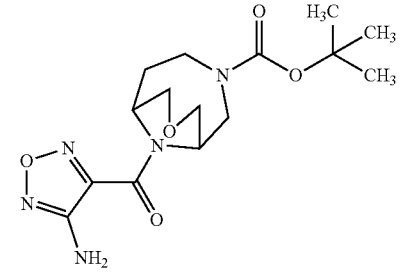 from tert-butyl 8-oxa-3,10-diazabicyclo[4.3.1]decane-3-carboxylate (racemate) and 4-amino-1,2,5-oxadiazole-3-carboxylic acid <br> $^1$H-NMR (400 MHz, DMSO-$d_6$): δ [ppm] = −0.008 (1.17), 0.008 (0.89), 1.106 (0.61), 1.157 (0.55), 1.175 (1.09), 1.193 (0.56), 1.290 (10.65), 1.359 (9.07), 1.369 (13.06), 1.385 (16.00), 1.398 (0.84), 1.911 (0.44), 1.944 (0.46), 1.988 (2.14), 2.037 (0.52), 2.048 (0.50), 2.066 (0.42), 3.267 (0.54), 3.279 (0.59), 3.510 (0.59), 3.519 (0.76), 3.528 (0.57), 3.539 (0.79), 3.548 (0.99), 3.558 (0.58), 3.587 (0.47), 3.596 (0.51), 3.618 (2.61), 3.630 (1.64), 3.643 (2.27), 3.657 (1.45), 3.670 (1.11), 3.778 (0.45), 3.790 (0.57), 3.830 (1.06), 3.859 (0.76), 3.877 (0.57), 3.951 (0.55), 3.978 (1.00), 4.004 (0.65), 4.021 (0.50), 4.039 (0.49), 4.180 (0.63), 4.548 (1.30), 5.754 (0.53), 6.389 (3.00), 6.442 (1.00). <br> LC-MS (method 1): $R_t$ = 0.85 min; m/z = 354 (M + H)$^+$. |

Analogously to Examples 58A, 59A, 62A and 63A, the following compounds were prepared from the starting material specified in each case:

| Example | Name/Structure/Starting material | Analytical data |
|---|---|---|
| 70A | 3,9-diazabicyclo[4.2.1]non-9-yl(2-fluorophenyl)methanone (racemate)<br><br>from tert-butyl 9-(2-fluorobenzoyl)-3,9-diazabicyclo[4.2.1]nonane-3-carboxylate (racemate) | $^1$H-NMR (400 MHz, DMSO-$d_6$): δ [ppm] = 1.13-1.54 (m, 2H), 1.65-2.37 (m, 5H), 2.39-2.60 (m, 2H), 2.64-3.08 (m, 2H), 3.67-3.83 (m, 1H), 4.51-4.65 (m, 1H), 7.18-7.34 (m, 2H), 7.34-7.58 (m, 2H).<br>LC-MS (method 2): $R_t$ = 0.58 min; m/z = 249 (M + H)$^+$. |
| 71A | 3,9-diazabicyclo[4.2.1]non-9-yl(6-methoxypyridin-2-yl)methanone (racemate)<br><br>from tert-butyl 9-[(6-methoxypyridin-2-yl)carbonyl]-3,9-diazabicyclo[4.2.1]nonane-3-carboxylate (racemate) | $^1$H-NMR (400 MHz, DMSO-$d_6$): δ [ppm] = 1.28-1.60 (m, 1H), 1.66-2.24 (m, 5H), 2.40-2.48 (m, 0.8H), 2.59-2.70 (m, 1.2H), 2.72-2.86 (m, 1H), 2.88-3.05 (m, 1H), 3.11-3.22 (m, 0.7H), 3.85 (d, 3H), 4.08 (q, 0.3H), 4.35-4.58 (m, 1H), 4.56-4.70 (m, 2H), 6.90 (dd, 1H), 7.25 (dd, 1H), 7.80 (td, 1H).<br>LC-MS (method 2): $R_t$ = 0.61 min; m/z = 262 (M + H)$^+$. |
| 72A | (2-fluorophenyl)(8-oxa-3,10-diazabicyclo[4.3.1]dec-10-yl)methanone trifluoroacetic acid salt (racemate)<br><br>from tert-butyl 9-(2-fluorobenzoyl)-3,9-diazabicyclo[4.2.1]nonane-3-carboxylate (racemate) | LC-MS (method 6): $R_t$ = 0.94 min; m/z = 265 (M + H)$^+$. |
| 73A | (6-methoxypyridin-2-yl)(8-oxa-3,10-diazabicyclo[4.3.1]dec-10-yl)methanone bis(trifluoroacetic acid) salt (racemate)<br><br>from tert-butyl 10-[(6-methoxypyridin-2-yl)carbonyl]-8-oxa-3,10-diazabicyclo[4.3.1]decane-3-carboxylate (racemate) | LC-MS (method 6): $R_t$ = 0.91 min; m/z = 278 (M + H)$^+$. |
| 74A | (4-methyl-1,2,5-oxadiazol-3-yl)(8-oxa-3,10-diazabicyclo[4.3.1]dec-10-yl)methanone trifluoroacetic acid salt (racemate)<br><br>from tert-butyl 10-[(4-methyl-1,2,5-oxadiazol-3-yl)carbonyl]-8-oxa-3,10-diazabicyclo[4.3.1]decane-3-carboxylate (racemate) | LC-MS (method 6): $R_t$ = 0.94 min; m/z = 253 (M + H)$^+$. |
| 75A | (4-amino-1,2,5-oxadiazol-3-yl)(8-oxa-3,10-diazabicyclo[4.3.1]dec-10-yl)methanone bis(trifluoroacetic acid) salt (racemate)<br><br>from tert-butyl 10-[(4-amino-1,2,5-oxadiazol-3-yl)carbonyl]-8-oxa-3,10-diazabicyclo[4.3.1]decane-3-carboxylate (racemate) | LC-MS (method 6): $R_t$ = 0.79 min; m/z = 254 (M + H)$^+$. |

Example 76A and Example 77A tert-Butyl 9-[(6-methoxypyridin-2-yl)carbonyl]-3,9-diazabicyclo[4.2.1]nonane-3-carboxylate (Enantiomers 1 and 2)

83

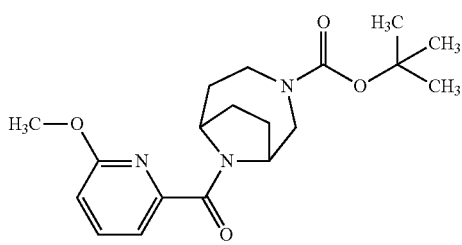 [SMILES: COc1cccc(C(=O)N2C3CCC2CN(C(=O)OC(C)(C)C)CC3)n1]

553 mg (1.53 mmol) of racemic tert-butyl 9-[(6-methoxypyridin-2-yl)carbonyl]-3,9-diazabicyclo[4.2.1]nonane-3-carboxylate (Example 65A) were separated into the enantiomers by preparative SFC-HPLC on a chiral phase [column: Chiralcel AD-H, 5 μm, 250 mm×30 mm; mobile phase: carbon dioxide/isopropanol 88:12 (v/v); flow rate: 125 g/min; pressure: 135 bar; UV detection: 210 nm; temperature: 38° C.]:

Example 76A (Enantiomer 1)

Yield: 274 mg
$R_t$=1.69 min; chemical purity >98%; >99% ee
[column: Chiralpak AD-3, 3 μm, 100 mm×4.6 mm; mobile phase: carbon dioxide/isopropanol 85:15 (v/v); flow rate: 3 ml/min; pressure: 130 bar; UV detection: 210 nm; temperature: 60° C.].
$^1$H-NMR (400 MHz, DMSO-$d_6$): δ [ppm]=1.36-1.46 (m, 9H), 1.49-1.62 (m, 1.5H), 1.62-1.84 (m, 1.5H), 1.84-2.30 (m, 3H), 2.76-3.00 (m, 1H), 3.05-3.44 (m, 1H), 3.65-3.95 (m, 5H), 4.49-4.81 (m, 2H), 6.94 (dd, 1H), 7.20-7.42 (m, 1H), 7.69-7.90 (m, 1H).
LC-MS (method 1): $R_t$=0.97 min; m/z=362 (M+H)$^+$.

Example 77A (Enantiomer 2)

Yield: 273 mg
$R_t$=1.82 min; chemical purity >96%; >92% ee
[column: Chiralpak AD-3, 3 μm, 100 mm×4.6 mm; mobile phase: carbon dioxide/isopropanol 85:15 (v/v); flow rate: 3 ml/min; pressure: 130 bar; UV detection: 210 nm; temperature: 60° C.].
$^1$H-NMR (400 MHz, DMSO-$d_6$): δ [ppm]=1.33-1.47 (m, 9H), 1.48-1.63 (m, 1.5H), 1.64-1.81 (m, 1.5H), 1.84-2.36 (m, 3H), 2.77-3.00 (m, 1H), 3.04-3.45 (m, 1H), 3.68-3.98 (m, 5H), 4.50-4.81 (m, 2H), 6.94 (dd, 1H), 7.20-7.45 (m, 1H), 7.82 (td, 1H).
LC-MS (method 2): $R_t$=1.90 min; m/z=362 (M+H)$^+$.

Example 78A and Example 79A tert-Butyl 9-(2-fluorobenzoyl)-3,9-diazabicyclo[4.2.1]nonane-3-carboxylate (Enantiomers 1

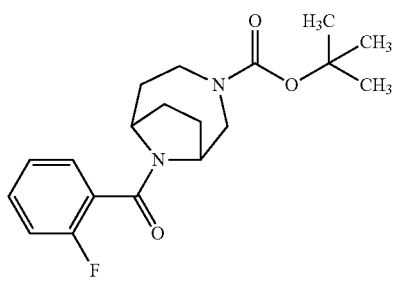 [SMILES: CC(C)(C)OC(=O)N1CCC2CCC(C1)N2C(=O)c1ccccc1F]

84

1.27 g (3.65 mmol) of racemic tert-butyl 9-(2-fluorobenzoyl)-3,9-diazabicyclo[4.2.1]nonane-3-carboxylate (Example 64A) were separated into the enantiomers by preparative SFC-HPLC on a chiral phase [column: Chiralpak OX-H, 5 μm, 250 mm×30 mm; mobile phase: carbon dioxide/isopropanol 85:15 (v/v); pressure: 120 bar; flow rate: 120 g/min; UV detection: 210 nm; temperature: 38° C.]:

Example 78A (Enantiomer 1)

Yield: 628 mg
$R_t$=2.14 min; chemical purity >99%; >99% ee
[Aligent SFC; column: Chiralpak OX-3, 50 mm×4.6 mm; mobile phase: carbon dioxide/isopropanol, gradient: 0 min 5% isopropanol, 0.5 min 5% isopropanol, 5 min 50% isopropanol, 6 min 50% isopropanol, 6.01 min 5% isopropanol, 7 min 5% isopropanol; flow rate: 3 ml/min; temperature: 40° C.; UV detection: 220 nm].
LC-MS (method 1): $R_t$=1.00 min; m/z=349 (M+H)$^+$.
$[α]_D^{20}$=−23.33° (c=0.41, methanol).

Example 79A (Enantiomer 2)

Yield: 602 mg
$R_t$=2.415 min; chemical purity >99%; >99% ee
[Aligent SFC; column: Chiralpak OX-3, 50 mm×4.6 mm; mobile phase: carbon dioxide/isopropanol, gradient: 0 min 5% isopropanol, 0.5 min 5% isopropanol, 5 min 50% isopropanol, 6 min 50% isopropanol, 6.01 min 5% isopropanol, 7 min 5% isopropanol; flow rate: 3 ml/min; temperature: 40° C.; UV detection: 220 nm].
LC-MS (method 1): $R_t$=1.00 min; m/z=349 (M+H)$^+$.
$[α]_D^{20}$=+22.5° (c=0.41, methanol).

Example 80A 3,9-diazabicyclo[4.2.1]non-9-yl(2-fluorophenyl)methanone (Enantiomer 1)

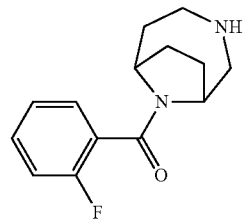 [SMILES: O=C(c1ccccc1F)N1C2CCNCC1CC2]

With stirring, 4.5 ml of dioxane and 4.5 ml of a 4 M solution of hydrogen chloride in dioxane were added to tert-butyl 9-(2-fluorobenzoyl)-3,9-diazabicyclo[4.2.1]nonane-3-carboxylate (628 mg, 1.80 mmol, enantiomer 1), and the mixture was stirred at room temperature overnight. The reaction mixture was then concentrated to dryness and the residue was taken up in 10 ml of THF. 0.33 ml of triethylamine was then added with stirring, and the mixture was stirred at room temperature for 1 h. The mixture was then diluted with water and ethyl acetate. The organic phase was removed, washed with water, dried over magnesium sulfate and concentrated to dryness. This gave 153 mg (content 100%, 0.61 mmol, 40% of theory) of the title compound.
LC-MS (method 1): $R_t$=0.32 min; m/z=249 (M+H)$^+$.

Analogously to Example 80A, the following compound was prepared from the starting material stated:

| Example | Name/Structure/Starting material | Analytical data |
|---|---|---|
| 81A | 3,9-diazabicyclo[4.2.1]non-9-yl(2-fluorophenyl)methanone (enantiomer 2)<br>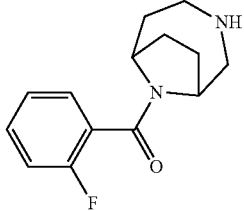<br>from tert-butyl 9-(2-fluorobenzoyl)-3,9-diazabicyclo[4.2.1]nonane-3-carboxylate (enantiomer 2) | LC-MS (method 1): $R_t$ = 0.32 min; m/z = 249 (M + H)$^+$. |

Analogously to Examples 62A and 63A, the following compound was prepared from the starting material specified:

| Example | Name/Structure/Starting material | Analytical data |
|---|---|---|
| 82A | (3-Fluoro-6-methoxypyridin-2-yl)(8-oxa-3,10-diazabicyclo[4.3.1]dec-10-yl)methanone (racemate)<br>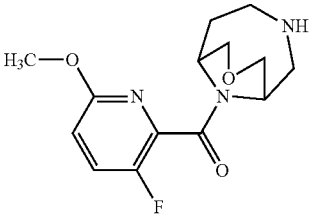<br>from tert-butyl 10-[(3-fluoro-6-methoxy-pyridin-2-yl)carbonyl]-8-oxa-3,10-diazabicyclo[4.3.1]decane-3-carboxylate (racemate) | LC-MS (method 2): $R_t$ = 0.49 min; m/z = 296 (M + H)$^+$. |

Analogously to Examples 55A, 60A and 61A, the following compounds were prepared from the starting materials specified in each case:

| Example | Name/Structure/Starting materials | Analytical data |
|---|---|---|
| 83A | tert-butyl 6-[(6-methoxypyridin-2-yl)carbonyl]-3,6-diazabicyclo[3.2.2]nonane-3-carboxylate (enantiomer 1)<br><br>from tert-butyl 3,6-diazabicyclo[3.2.2]nonane-3-carboxylate (enantiomer 1) and 6-methoxypyridine-2-carboxylate acid | $^1$H-NMR (500 MHz, DMSO-$d_6$): δ [ppm] = 1.29-1.49 (m, 9H), 1.51-1.71 (m, 3H), 1.72-1.95 (m, 1.25H), 2.18-2.29 (m, 0.25H), 2.30-2.42 (m, 0.75H), 2.81-3.00 (m, 0.25H), 3.02-3.26 (m, 1H), 3.35-3.52 (m, 1.5H), 3.52-3.64 (m, 1H), 3.79-3.89 (m, 3H), 3.90-4.22 (m, 2.75H), 4.57 (br. s, 0.25H), 6.90 (d, 1H), 7.12-7.26 (m, 1H), 7.75-7.86 (m, 1H).<br>LC-MS (method 1): $R_t$ = 0.98 min; m/z = 362 (M + H)$^+$. |
| 84A | tert-butyl 3-[(3-fluoro-6-methoxypyridin-2-yl)carbonyl]-3,6-diazabicyclo[3.2.2]nonane-3-carboxylate (enantiomer 1)<br><br>from tert-butyl 3,6-diazabicyclo[3.2.2]nonane-3-carboxylate (enantiomer 1) and 3-fluoro-6-methoxypyridine-2-carboxylic acid | $^1$H-NMR (500 MHz, DMSO-$d_6$): δ [ppm] = 1.32-1.48 (m, 9H), 1.51-1.72 (m, 3H), 1.72-1.93 (m, 1.25H), 2.20-2.28 (m, 0.25H), 2.30-2.42 (m, 0.75H), 3.02-3.26 (m, 2H), 3.48 (br. d, 0.75H), 3.62 (br. d, 0.75H), 3.76-3.89 (m, 3.75H), 3.90-4.23 (m, 2.25H), 4.56-4.68 (m, 0.25H), 6.91-6.99 (m, 1H), 7.73-7.85 (m, 1H).<br>LC-MS (method 1): $R_t$ = 0.93 min; m/z = 380 (M + H)$^+$. |

| Example | Name/Structure/Starting materials | Analytical data |
|---|---|---|
| 85A | tert-Butyl 9-[(3-chloro-6-methoxypyridin-2-yl)carbonyl]-3,9-diazabicyclo[4.2.1]nonane-3-carboxylate (racemate) 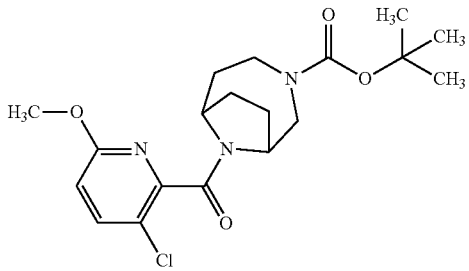 from tert-butyl 3,9-diazabicyclo[4.2.1]nonane-3-carboxylate (racemate) and 3-chloro-6-methoxypyridine-2-carboxylic acid | LC-MS (method 1): $R_t$ = 1.04 min; m/z = 396/398 (M + H)$^+$. |

Example 86A

3,6-Diazabicyclo[3.2.2]non-6-yl(3-fluoro-6-methoxypyridin-2-yl)methanone hydrochloride (Enantiomer 1)

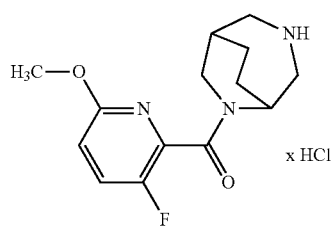 [SMILES: COc1ccc(F)c(C(=O)N2CC3CCC2CNC3)n1]

With stirring, 7 ml of a 4 M solution of hydrogen chloride in dioxane were added to tert-butyl 6-[(3-fluoro-6-methoxypyridin-2-yl)carbonyl]-3,6-diazabicyclo[3.2.2]nonane-3-carboxylate (enantiomer 1) (1060 mg, 2.79 mmol). The mixture was stirred at room temperature overnight. The reaction solution was then concentrated to dryness and the resulting residue was dried under high vacuum at 40° C. This gave 763 mg of the target product.

LC-MS (method 2): $R_t$=0.54 min; m/z=280 (M+H)$^+$.

Analogously to Example 86A, the following compounds were prepared from the starting material specified in each case:

| Example | Name/Structure/Starting material | Analytical data |
|---|---|---|
| 87A | 3,6-Diazabicyclo[3.2.2]non-6-yl (6-methoxypyridin-2-yl)methanone hydrochloride (enantiomer 1) 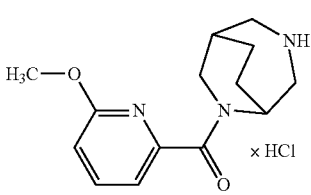 from tert-butyl 6-[(6-methoxypyridin-2-yl)carbonyl]-3,6-diazabicyclo[3.2.2]nonane-3-carboxylate (enantiomer 1) | LC-MS (method 2): $R_t$ = 0.54 min; m/z = 262 (M + H)$^+$. |
| 88A | (3-chloro-6-methoxypyridin-2-yl)(3,9-diazabicyclo[4.2.1]non-9-yl)methanone hydrochloride (racemate) 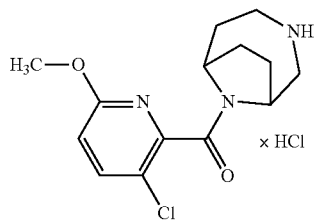 from tert-butyl 9-[(3-chloro-6-methoxypyridin-2-yl)carbonyl]-3,9-diazabicyclo[4.2.1]nonane-3-carboxylate (racemate) | LC-MS (method 1): $R_t$ = 0.40 min; m/z = 296/298 (M + H)$^+$. |

Example 89A and Example 90A

9-Benzyl 3-tert-butyl 3,9-diazabicyclo[4.2.1]nonane-3,9-dicarboxylate (Enantiomer 1 and 2)

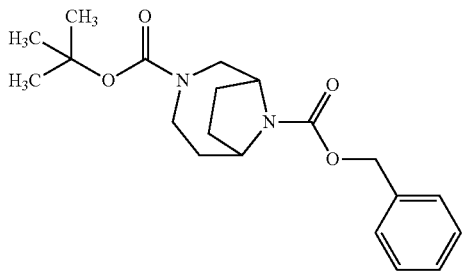 [SMILES: CC(C)(C)OC(=O)N1CCC2CCC(C1)N2C(=O)OCc1ccccc1]

135.7 g (376 mmol) of the racemic 9-benzyl 3-tert-butyl 3,9-diazabicyclo[4.2.1]nonane-3,9-dicarboxylate (prepared according to the original synthesis procedure US 20150132258) were separated into the enantiomers by preparative SFC-HPLC on a chiral phase (column: Chiralcel AZ, 20 m, 360 mm×50 mm; mobile phase: carbon dioxide/MeOH 90:10 (v/v); flow rate: 400 ml/min; pressure: 110 bar; UV detection: 210 nm; temperature: 40° C.]:

Example 89A (Enantiomer 1)

Yield: 57.7 g $R_t$=1.92 min; chemical purity >×100%; >99% ee
[Column: Chiralpak AZ-H, 5 μm, 150 mm×4.6 mm; mobile phase: carbon dioxide/methanol 90:10; flow rate: 3 ml/min; pressure: 130 bar; UV detection: 210 nm; temperature: 40° C.].

LC-MS (Method 2): $R_t$=2.22 min; m/z=305 (M+H-C4H8)$^+$.

$^1$H NMR (500 MHz, DMSO-d$_6$) δ ppm 1.33-1.45 (m, 9H), 1.49 (br s, 1H), 1.57-1.75 (m, 2H), 1.81-2.07 (m, 2H), 2.14-2.34 (m, 1H), 2.57-2.84 (m, 1H), 2.87-3.18 (m, 1H), 3.52-3.89 (m, 2H), 4.16-4.28 (m, 2H), 4.96-5.17 (m, 2H), 7.24-7.46 (m, 5H).

Example 90A (Enantiomer 2)

Yield: 62.1 g $R_t$=2.31 min; chemical purity >99%; >94% ee
[Column: Chiralpak AZ-H, 5 μm, 150 mm×4.6 mm; mobile phase: carbon dioxide/methanol 90:10; flow rate: 3 ml/min; pressure: 130 bar; UV detection: 210 nm; temperature: 40° C.].

LC-MS (Method 2): $R_t$=2.22 min; m/z=305 (M+H-C4H8)$^+$.

$^1$H NMR (500 MHz, DMSO-d$_6$) δ ppm 1.33-1.44 (m, 9H), 1.48 (br s, 1H), 1.55-1.74 (m, 2H), 1.78-2.06 (m, 2H), 2.12-2.32 (m, 1H), 2.56-2.86 (m, 1H), 2.90-3.18 (m, 1H), 3.50-3.88 (m, 2H), 4.24 (br t, 2H), 4.98-5.18 (m, 2H), 7.25-7.43 (m, 5H).

Example 91A tert-Butyl 3,9-diazabicyclo[4.2.1]nonane-3-carboxylate (Enantiomer 2)

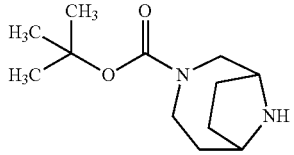 [SMILES: CC(C)(C)OC(=O)N1CCC2CCC(C1)N2]

9-Benzyl 3-tert-butyl 3,9-diazabicyclo[4.2.1]nonane-3,9-dicarboxylate (Enantiomer 2) (62.0 g, 172 mmol) was initially charged in ethanol (500 ml) and flushed with argon. Pd/C 5 mol % (3.66 g, 1.72 mmol) was then added and the mixture was stirred overnight at room temperature and under a hydrogen atmosphere (1 bar). More Pd/C 5 mol % (3.66 g, 1.72 mmol) was then added and the mixture was stirred at room temperature for another 7 h (hydrogen 1 bar). The mixture was then filtered and concentrated to dryness under reduced pressure. This gave 25.6 mg (content 100%, 157 mmol, 91% of theory) of the title compound.

GC-MS (Method 3): $R_t$=5.23, min; m/z=226 (M$^+$)

$^1$H NMR (500 MHz, DMSO-d$_6$) δ ppm 1.24-1.34 (m, 1H), 1.39 (s, 9H), 1.47-1.74 (m, 4H), 1.86-2.01 (m, 1H), 2.55-2.65 (br. s, 1H), 2.67-2.81 (m, 1H), 2.97-3.16 (m, 1H), 3.35-3.45 (m, 1H), 3.49-3.59 (m, 1.5H), 3.60-3.78 (m, 1.5H).

Example 92A tert-Butyl 3,9-diazabicyclo[4.2.1]nonane-3-carboxylate (Enantiomer 1)

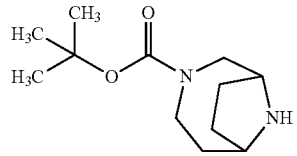

9-Benzyl 3-tert-butyl 3,9-diazabicyclo[4.2.1]nonane-3,9-dicarboxylate (Enantiomer 1) (57.7 g, 160 mmol) was initially charged in ethanol (500 ml) and flushed with argon. Pd/C 5 mol % (3.41 g, 1.60 mmol) was then added and the mixture was stirred overnight at room temperature and under a hydrogen atmosphere (1 bar). Pd/C 5 mol % (3.41 g, 1.60 mmol) was then added and stirring of the mixture at room temperature was continued overnight (hydrogen 1 bar). The mixture was then filtered and concentrated to dryness under reduced pressure. This gave 35.5 g (content 100%, 157 mmol, 98% of theory) of the title compound.

GC-MS (Method 3): $R_t$=5.24, min; m/z=226 (M$^{+)}$ $^1$H NMR (500 MHz, DMSO-d$_6$) δ ppm 1.24-1.32 (m, 1H), 1.39 (s, 9H), 1.47-1.73 (m, 4H), 1.84-2.01 (m, 1H), 2.67-2.82 (m, 1H), 2.96-3.17 (m, 1H), 3.36-3.41 (m, 1H), 3.50-3.58 (m, 1.5H), 3.61-3.79 (m, 1.5H).

Analogously to Examples 55A, 60A and 61A, the following compounds were prepared from the starting materials stated in each case:

| Example | Name/Structure/Starting material | Analytical data |
| --- | --- | --- |
| 94A | tert-Butyl 9-[(3-chloro-6-methoxypyridin-2-yl)carbonyl]-3,9-diazabicyclo[4.2.1]nonane-3-carboxylate (Enantiomer 2)<br><br>from tert-Butyl 3,9-diazabicyclo[4.2.1]nonane-3-carboxylate (Enantiomer 2) and 3-chloro-6-methoxypyridine-2-carboxylic acid | 1H NMR (500 MHz, DMSO-d6) δ ppm 1.36-1.45 (m, 9H), 1.48-1.66 (m, 1.5H), 1.67-2.25 (m, 4H), 2.29-2.41 (m, 0.5H), 2.75-3.26 (m, 2H), 3.80-3.87 (m, 6H), 4.57-4.75 (m, 1H), 6.95 (dd, 1H), 7.91 (t, 1H) LC-MS (Method 1): Rt = 1.04 min; MS (ESIpos): m/z = 396 (M + H)$^+$ |

Analogously to Example 86A, the following compounds were prepared from the starting material stated in each case:

| Example | Name/Structure/Starting material | Analytical data |
|---|---|---|
| 96A | 3,9-Diazabicyclo[4.2.1]nonan-9-yl-(3-fluoro-6-methoxypyridin-2-yl)methanone hydrochloride (1:1) (Enantiomer 2) 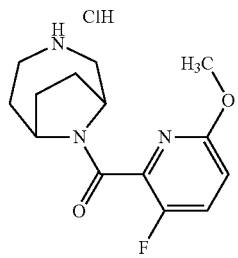 from tert-butyl 9-(3-fluoro-6-methoxypyridine-2-carbonyl)-3,9-diazabicyclo[4.2.1]nonane-3-carboxylate (Enantiomer 2) | LC-MS (Method 1): $R_t$ = 0.37 min; MS (ESIpos): m/z = 280 (M + H)$^+$ |
| 97A | 3,9-Diazabicyclo[4.2.1]nonan-9-yl(6-methoxypyridin-2-yl)methanone hydrochloride (1:1) (Enantiomer 1) 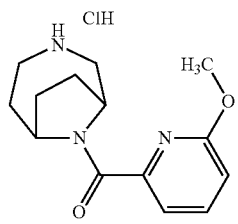 from tert-butyl 9-(6-methoxypyridine-2-carbonyl)-3,9-diazabicyclo[4.2.1]nonane-3-carboxylate (Enantiomer 1) | LC-MS (Method 1): $R_t$ = 0.38 min; MS (ESIpos): m/z = 262 (M + H)$^+$ |
| 98A | 3,9-Diazabicyclo[4.2.1]nonan-9-yl-(6-methoxypyridin-2-yl)methanone hydrochloride (1:1) (Enantiomer 2) 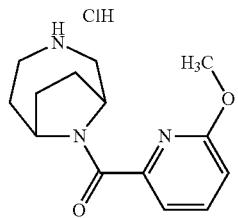 from tert-butyl 9-(6-methoxypyridine-2-carbonyl)-3,9-diazabicyclo[4.2.1]nonane-3-carboxylate (Enantiomer 2) | LC-MS (Method 1): $R_t$ = 0.41 min; MS (ESIpos): m/z = 262 (M + H)$^+$ |

-continued

| Example | Name/Structure/Starting material | Analytical data |
|---|---|---|
| 99A | (3-Chloro-6-methoxypyridin-2-yl)[3,9-diazabicyclo[4.2.1]nonan-9-yl]methanone hydrochloride (1:1) (Enantiomer 1) from tert-butyl (1R,6S)-9-(3-chloro-6-methoxypyridine-2-carbonyl)-3,9-diazabicyclo[4.2.1]nonane-3-carboxylate (Enantiomer 1) | LC-MS (Method 1): $R_t$ = 0.46 min; MS (ESIpos): m/z = 296 (M + H)$^+$ |
| 100A | (3-Chloro-6-methoxypyridin-2-yl)[3,9-diazabicyclo[4.2.1]nonan-9-yl]methanone hydrochloride (1:1) (Enantiomer 1) from tert-butyl (1R,6S)-9-(3-chloro-6-methoxypyridine-2-carbonyl)-3,9-diazabicyclo[4.2.1]nonane-3-carboxylate (Enantiomer 2) | LC-MS (Method 1): $R_t$ = 0.46 min; MS (ESIpos): m/z = 296 (M + H)$^+$ |

WORKING EXAMPLES

Example 1 tert-Butyl 6-{[2-(4-chlorophenyl)imidazo[1,2-a]pyrimidin-3-yl]methyl}-2,6-diazabicyclo[3.2.2]nonane-2-carboxylate (Enantiomer 2)

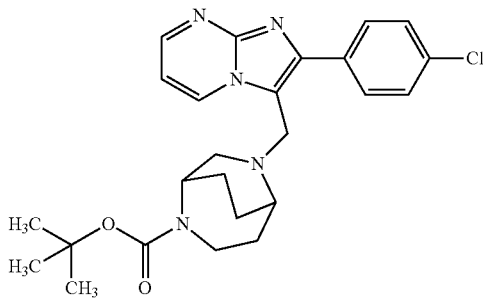 [SMILES: CC(C)(C)OC(=O)N1CCC2CCC1CN2Cc1c(-c2ccc(Cl)cc2)nc2ncccn12]

Under argon, 2-(4-chlorophenyl)imidazo[1,2-a]pyrimidine-3-carbaldehyde (1.00 g, 3.88 mmol), tert-butyl 2,6-diazabicyclo[3.2.2]nonane-2-carboxylate (enantiomer 2; 1.05 g, 4.66 mmol) and acetic acid (440 μl, 7.8 mmol) were initially charged in 26 ml of THF. Subsequently, sodium triacetoxyborohydride (1.23 g, 5.82 mmol) was added and the mixture was stirred at room temperature overnight. The reaction mixture was then first diluted with saturated ammonium chloride solution, and saturated sodium carbonate solution was then added. The organic phase was separated off and the aqueous phase was extracted with ethyl acetate. The combined organic phases were dried over magnesium sulfate, filtered and concentrated to dryness under reduced pressure. On silica gel (mobile phase: dichloromethane/methanol 50:1), the residue obtained was separated into its components. This gave 1,056 g (content 100%, 2.25 mmol, 58% of theory) of the title compound.

LC-MS (method 2): $R_t$=1.50 min; m/z=468/470 (M+H)$^+$ $^1$H-NMR (400 MHz, DMSO-d$_6$): δ [ppm]=1.23-1.46 (m, 10H), 1.52-1.99 (m, 5H), 2.56-2.73 (m, 2H), 2.93-3.08 (m, 1H), 3.12-3.28 (m, 1H), 3.51-3.75 (m, 1H), 3.94-4.14 (m, 1H), 4.22 (br. s, 2H), 7.11 (dd, 1H), 7.55 (d, 2H), 7.89 (d, 2H), 8.58 (dd, 1H), 8.85-9.04 (m, 1H).

Analogously to Example 1, the following compounds were prepared from the starting materials specified in each case:

| Example | Name/Structure/Starting materials Analytical data |
|---|---|
| 2 | tert-butyl 6-{[2-(4-chlorophenyl)imidazo[1,2-a]pyrimidin-3-yl]methyl}-2,6-diazabicyclo[3.2.2]nonane-2-carboxylate (enantiomer 1)<br><br>from 2-(4-chlorophenyl)imidazo[1,2-a]pyrimidine-3-carbaldehyde and tert-butyl 2,6-diazabicyclo[3.2.2]nonane-2-carboxylate (enantiomer 1)<br><br>$^1$H-NMR (400 MHz, DMSO-d$_6$): δ [ppm] = −0.008 (1.65), 0.008 (1.51), 1.272 (16.00), 1.360 (10.16), 1.393 (5.02), 1.599 (1.53), 1.629 (1.48), 1.784 (1.07), 1.916 (0.99), 2.328 (0.91), 2.566 (0.99), 2.617 (1.38), 2.670 (1.65), 2.970 (0.69), 3.029 (0.97), 3.209 (0.61), 3.636 (0.87), 3.990 (1.03), 4.111 (0.73), 4.220 (4.73), 5.754 (2.55), 7.092 (3.52), 7.103 (3.60), 7.109 (3.61), 7.120 (3.58), 7.537 (8.91), 7.558 (10.30), 7.881 (7.18), 7.902 (6.41), 8.573 (3.56), 8.578 (4.01), 8.583 (3.80), 8.588 (3.65), 8.947 (1.80).<br><br>LC-MS (method 2): $R_t$ = 1.52 min; m/z = 468/470 (M + H)$^+$. |

| Example | Name/Structure/Starting materials<br>Analytical data |
|---|---|
| 3 | tert-butyl 6-{[2-(5-chloropyridin-2-yl)imidazo[1,2-a]pyridin-3-yl]methyl}-2,6-diazabicyclo[3.2.2]nonane-2-carboxylate (enantiomer 1)<br>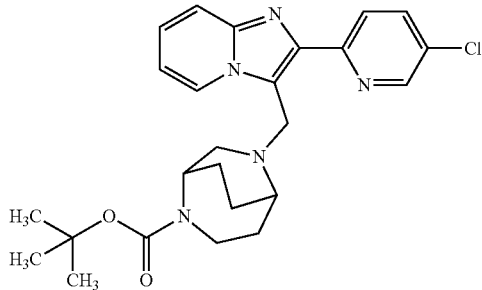<br>from 2-(5-chloropyridin-2-yl)imidazo[1,2-a]pyridine-3-carbaldehyde and tert-butyl 2,6-diazabicyclo[3.2.2]nonane-2-carboxylate (enantiomer 1)<br><br>$^1$H-NMR (400 MHz, DMSO-$d_6$): δ [ppm] = −0.149 (0.44), −0.008 (4.22), 0.008 (3.54), 0.146 (0.46), 1.234 (0.51), 1.316 (16.00), 1.390 (11.89), 1.568 (0.98), 1.597 (0.86), 1.670 (1.53), 1.814 (0.82), 1.924 (0.77), 2.328 (0.41), 2.680 (0.64), 2.711 (1.05), 2.749 (0.60), 2.859 (2.45), 2.888 (1.71), 3.048 (1.40), 3.287 (1.03), 3.622 (1.09), 3.657 (0.92), 4.021 (0.99), 4.123 (0.72), 4.515 (2.25), 4.550 (3.12), 4.676 (0.72), 4.719 (1.20), 4.754 (0.73), 5.755 (0.55), 6.951 (1.59), 6.968 (3.23), 6.984 (1.78), 7.311 (1.85), 7.314 (1.88), 7.334 (2.46), 7.337 (2.29), 7.351 (2.05), 7.353 (1.96), 7.599 (4.37), 7.622 (3.69), 7.982 (3.36), 7.989 (3.41), 8.004 (4.10), 8.010 (4.21), 8.193 (5.92), 8.215 (4.84), 8.411 (2.13), 8.428 (2.11), 8.653 (3.32).<br>LC-MS (method 2): $R_t$ = 1.26 min; m/z = 468/470 (M + H)$^+$. |
| 4 | tert-butyl 6-{[2-(4-chlorophenyl)imidazo[1,2-a]pyridin-3-yl]methyl}-2,6-diazabicyclo[3.2.2]nonane-2-carboxylate (enantiomer 1)<br>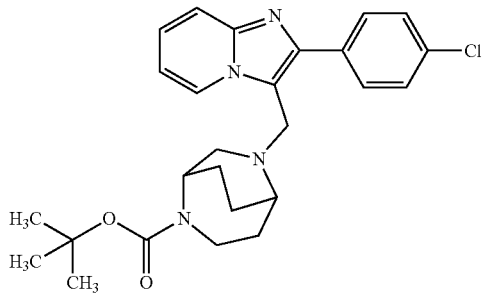<br>from 2-(4-chlorophenyl)imidazo[1,2-a]pyridine-3-carbaldehyde and tert-butyl 2,6-diazabicyclo[3.2.2]nonane-2-carboxylate (enantiomer 1)<br><br>$^1$H-NMR (400 MHz, DMSO-$d_6$): δ [ppm] = −0.008 (0.68), 0.008 (0.80), 1.285 (16.00), 1.365 (10.59), 1.419 (1.11), 1.597 (1.40), 1.659 (1.45), 1.762 (1.01), 1.909 (0.91), 2.367 (0.70), 2.523 (1.33), 2.526 (1.26), 2.558 (1.09), 2.561 (1.04), 2.563 (1.08), 2.587 (0.99), 2.615 (0.56), 2.655 (1.28), 2.670 (0.97), 2.675 (0.89), 2.694 (0.94), 2.710 (1.16), 2.961 (0.70), 3.015 (0.96), 3.170 (0.60), 3.203 (0.60), 3.236 (0.46), 3.643 (0.85), 3.677 (0.51), 4.000 (1.02), 4.120 (0.73), 4.194 (4.78), 5.755 (0.65), 6.932 (1.71), 6.949 (3.48), 6.966 (1.88), 7.277 (1.84), 7.280 (1.96), 7.299 (2.53), 7.302 (2.46), 7.316 (2.03), 7.319 (2.05), 7.507 (8.35), 7.524 (3.12), 7.528 (9.53), 7.579 (4.15), 7.602 (3.55), 7.855 (6.76), 7.876 (6.10), 8.491 (1.21), 8.508 (1.88).<br>LC-MS (method 2): $R_t$ = 1.56 min; m/z = 467/469 (M + H)$^+$. |

| Example | Name/Structure/Starting materials Analytical data |
|---|---|
| 5 | tert-butyl 6-{[2-(4-chlorophenyl)imidazo[1,2-a]pyridin-3-yl]methyl}-2,6-diazabicyclo[3.2.2]nonane-2-carboxylate (enantiomer 2)<br>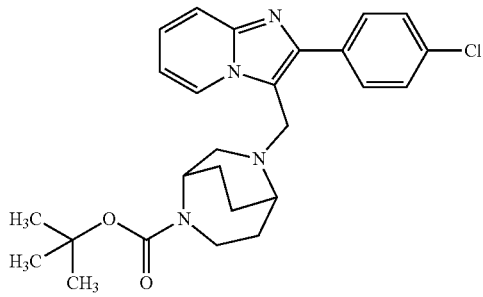<br>from 2-(4-chlorophenyl)imidazo[1,2-a]pyridine-3-carbaldehyde and tert-butyl 2,6-diazabicyclo[3.2.2]nonane-2-carboxylate (enantiomer 2)<br><br>$^1$H-NMR (400 MHz, DMSO-$d_6$): δ [ppm] = −0.008 (1.76), 0.008 (1.74), 1.285 (16.00), 1.365 (10.49), 1.597 (1.39), 1.662 (1.44), 1.764 (1.00), 1.903 (0.88), 2.328 (0.41), 2.367 (0.44), 2.588 (0.96), 2.651 (1.32), 2.670 (1.03), 2.690 (0.93), 2.710 (0.88), 2.963 (0.67), 3.014 (0.93), 3.171 (0.60), 3.201 (0.59), 3.236 (0.47), 3.643 (0.84), 4.002 (1.00), 4.120 (0.71), 4.194 (4.70), 6.933 (1.70), 6.950 (3.46), 6.966 (1.87), 7.280 (1.96), 7.300 (2.49), 7.302 (2.39), 7.317 (2.05), 7.319 (2.03), 7.507 (8.31), 7.528 (9.38), 7.579 (4.11), 7.602 (3.50), 7.855 (6.76), 7.876 (6.04), 8.491 (1.19), 8.508 (1.85).<br>LC-MS (method 1): $R_t$ = 0.80 min; m/z = 467/469 (M + H)$^+$. |
| 6 | (−)-tert-butyl 6-{[2-(4-isopropylphenyl)imidazo[1,2-a]pyrimidin-3-yl]methyl}-2,6-diazabicyclo[3.2.2]nonane-2-carboxylate (enantiomer 1)<br>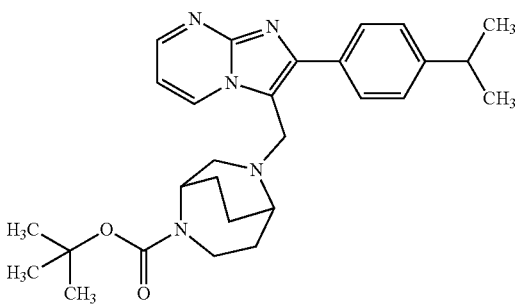<br>from 2-(4-isopropylphenyl)imidazo[1,2-a]pyrimidine-3-carbaldehyde and tert-butyl 2,6-diazabicyclo[3.2.2]nonane-2-carboxylate (enantiomer 1)<br><br>$^1$H-NMR (400 MHz, DMSO-$d_6$): δ [ppm] = 1.20-1.48 (m, 16H), 1.53-1.84 (m, 4H), 1.86-1.98 (m, 1H), 2.47-2.77 (m, 2H, partially covered by DMSO signal), 2.88-3.09 (m, 2H), 3.12-3.29 (m, 1H), 3.56-3.73 (m, 1H), 3.96-4.07 (m, 0.5H), 4.07-4.16 (m, 0.5H), 4.22 (br. s, 2H), 7.08 (dd, 1H), 7.36 (d, 2H), 7.78 (br. d, 2H), 8.55 (dd, 1H), 8.86-8.97 (m, 1H).<br>LC-MS (method 2): $R_t$ = 1.60 min; m/z = 476 (M + H)$^+$.<br>$[α]_D^{20}$ = −9.42° (c = 0.29, Methanol). |

| Example | Name/Structure/Starting materials Analytical data |
|---|---|
| 7 | (+)-tert-butyl 6-{[2-(4-isopropylphenyl)imidazo[1,2-a]pyrimidin-3-yl]methyl}-2,6-diazabicyclo[3.2.2]nonane-2-carboxylate (enantiomer 2) 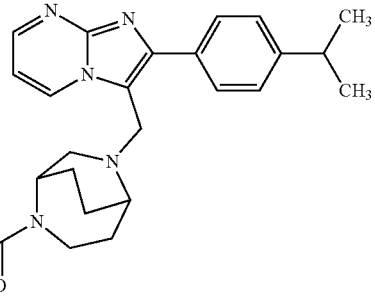 from 2-(4-isopropylphenyl)imidazo[1,2-a]pyrimidine-3-carbaldehyde and tert-butyl 2,6-diazabicyclo[3.2.2]nonane-2-carboxylate (enantiomer 2) $^1$H-NMR (400 MHz, DMSO-$d_6$): δ [ppm] = 1.20-1.48 (m, 16H), 1.53-1.84 (m, 4H), 1.86-1.98 (m, 1H), 2.47-2.77 (m, 2H, partially covered by DMSO signal), 2.88-3.09 (m, 2H), 3.12-3.29 (m, 1H), 3.56-3.72 (m, 1H), 3.96-4.07 (m, 0.5H), 4.07-4.16 (m, 0.5H), 4.22 (br. s, 2H), 7.08 (dd, 1H), 7.36 (d, 2H), 7.78 (br. d, 2H), 8.55 (dd, 1H), 8.87-8.96 (m, 1H). LC-MS (method 2): $R_t$ = 1.61 min; m/z = 476 (M + H)$^+$. $[α]_D^{20}$ = +9.49° (c = 0.33, Methanol). |

Example 8 tert-Butyl 9-{[2-(4-isopropylphenyl)imidazo[1,2-a]pyrimidin-3-yl]methyl}-3,9-diazabicyclo[4.2.1]nonane-3-carboxylate (racemate)

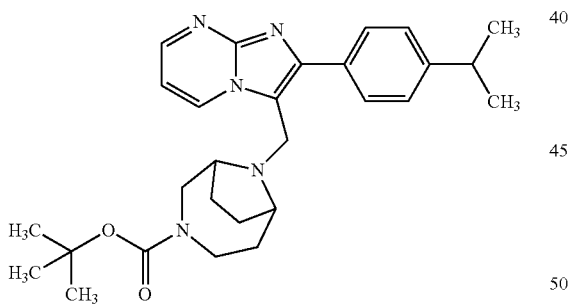

Under argon and at room temperature, 1.465 g (5.52 mmol) of 2-(4-isopropylphenyl)imidazo[1,2-a]pyrimidine-3-carbaldehyde were dissolved in 20 ml of THF, and 1.5 g (6.63 mmol) of tert-butyl 3,9-diazabicyclo[4.2.1]nonane-3-carboxylate (racemate) and 0.63 ml (11.05 mmol) of acetic acid were added. Subsequently, 1.756 g (8.29 mmol) of sodium triacetoxyborohydride were added in portions, and the reaction solution was stirred at room temperature overnight. Then water was gradually and carefully added dropwise (caution: evolution of gas), and subsequently ethyl acetate was added. The resulting organic phase was removed and the aqueous phase was extracted twice with ethyl acetate. The combined organic phases were washed with saturated sodium chloride solution, dried over magnesium sulfate, filtered and concentrated to dryness under reduced pressure on a rotary evaporator. The residue obtained was purified by column chromatography (Biotage Isolera, Biotage SNAP-KP-NH column; mobile phase: cyclohexane/ethyl acetate gradient 2:1→1:1). This gave 1.75 g (content 96%, 3.53 mmol, 64% of theory) of the target compound.

LC-MS (method 2): $R_t$=2.06 min; m/z=476 (M+H)$^+$.

Example 9 and Example 10 tert-Butyl 9-{[2-(4-isopropylphenyl)imidazo[1,2-a]pyrimidin-3-yl]methyl}-3,9-diazabicyclo[4.2.1]nonane-3-carboxylate (Enantiomer 1 and 2)

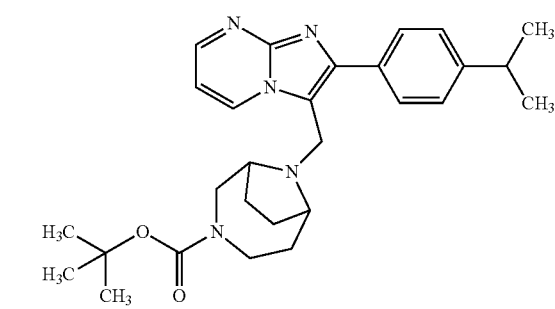 [SMILES: CC(C)c1ccc(-c2nc3ncccn3c2CN2C3CCC2CN(C(=O)OC(C)(C)C)CC3)cc1]

1.75 g (3.68 mmol) of racemic tert-butyl 9-{[2-(4-isopropylphenyl)imidazo[1,2-a]pyrimidin-3-yl]methyl}-3,9-diazabicyclo[4.2.1]nonane-3-carboxylate (Example 8) were separated into the enantiomers by preparative HPLC on a chiral phase [column: Daicel Chiralpak IC, 5 μm, 250 mm×20 mm; mobile phase: isopropanol+0.2% diethylamine (v/v); flow rate: 15 ml/min; UV detection: 220 nm; temperature: 40° C.]:

Example 9 (Enantiomer 1)

Yield: 745 mg
$R_t$=7.652 min; chemical purity >98.9%; >99% ee
[column: Daicel Chiralpak ID, 5 μm, 250 mm×4.6 mm; mobile phase: isohexane/isopropanol 50:50+0.2% diethylamine (v/v); flow rate: 1 ml/min; temperature: 50° C.; UV detection: 235 nm].
LC-MS (method 2): $R_t$=2.04 min; m/z=476 (M+H)$^+$.
$^1$H-NMR (400 MHz, DMSO-d$_6$): δ [ppm]=1.25 (d, 6H), 1.29-1.56 (m, 12H), 1.56-1.67 (m, 1H), 1.92-2.07 (m, 1H), 2.14-2.28 (m, 1H), 2.79 (br. d, 1H), 2.88-3.01 (m, 1.5H), 3.01-3.13 (m, 0.5H), 3.17-3.35 (m, 2H, partially covered by H$_2$O signal), 3.47 (br. d, 0.5H), 3.61 (br. d, 1.5H), 4.16-4.30 (m, 2H), 7.05-7.14 (m, 1H), 7.37 (d, 2H), 7.79 (d, 2H), 8.52-8.61 (m, 1H), 9.02-9.12 (m, 1H).

Example 10 (Enantiomer 2)

Yield: 751 mg
$R_t$=6.945 min; chemical purity >99%; >99% ee
[column: Daicel Chiralpak ID, 5 μm, 250 mm×4.6 mm; mobile phase: isohexane/isopropanol 50:50+0.2% diethylamine (v/v); flow rate: 1 ml/min; temperature: 50° C.; UV detection: 235 nm].
LC-MS (method 2): $R_t$=2.04 min; m/z=476 (M+H)$^+$.
$^1$H-NMR (400 MHz, DMSO-d$_6$): δ [ppm]=1.25 (d, 6H), 1.29-1.56 (m, 12H), 1.56-1.67 (m, 1H), 1.92-2.07 (m, 1H), 2.14-2.27 (m, 1H), 2.79 (br. d, 1H), 2.88-3.01 (m, 1.5H), 3.01-3.12 (m, 0.5H), 3.17-3.35 (m, 2H, partially covered by H$_2$O signal), 3.47 (br. d, 0.5H), 3.61 (br. d, 1.5H), 4.16-4.29 (m, 2H), 7.05-7.14 (m, 1H), 7.37 (d, 2H), 7.79 (d, 2H), 8.53-8.61 (m, 1H), 9.03-9.12 (m, 1H).

Example 11

3-{[2-(4-Chlorophenyl)imidazo[1,2-a]pyridin-3-yl]methyl}-8-oxa-3,10-diazabicyclo[4.3.1]dec-10-yl](3-fluoro-6-methoxypyridin-2-yl)methanone (Enantiomer 1)

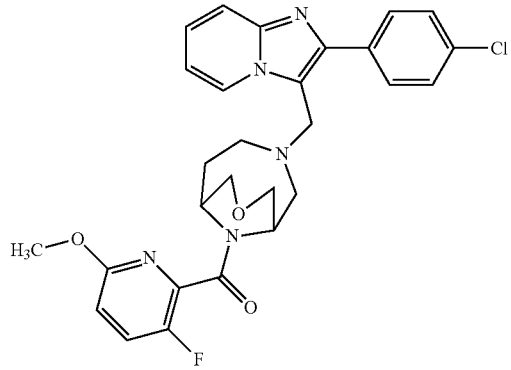 [SMILES: COc1ccc(F)c(C(=O)N2C3CCN(Cc4c(-c5ccc(Cl)cc5)nc5ccccn45)CC2COC3)n1]

Under argon, [2-(4-chlorophenyl)imidazo[1,2-a]pyridin-3-yl]methanol (2.48 g, 9.58 mmol) and triethylamine (10 ml, 72 mmol) were initially charged in 40 ml of dichloromethane. In an ice bath, the mixture was cooled to 0° C., and methanesulfonyl chloride (1.9 ml, 24 mmol) was then added slowly. The mixture was stirred in the ice bath for 30 min. (3-Fluoro-6-methoxypyridin-2-yl)[8-oxa-3,10-diazabicyclo[4.3.1]dec-10-yl]methanone (2.36 g, 7.98 mmol, enantiomer 1) in 40 ml of acetonitrile was then added slowly. The reaction solution was then heated to 40° C. and stirred at this temperature for 2 h. The reaction mixture was subsequently diluted with 1 N aqueous sodium hydroxide solution and the aqueous phase was extracted with ethyl acetate. The combined organic phases were dried over magnesium sulfate, filtered and concentrated. On silica gel (mobile phase: cyclohexane/ethyl acetate 5:2), the residue obtained was separated into its components. The mixed fraction obtained was then re-purified by preparative HPLC (Method 10). The product fractions obtained in this manner were taken up in ethyl acetate, and the organic phase was washed with saturated sodium carbonate solution, dried over magnesium sulfate, filtered and once more concentrated to dryness. This gave 3.00 g (content 100%, 5.58 mmol, 70% of theory) of the title compound.

LC-MS (method 2): $R_t$=1.44 min; m/z=536/538 (M+H)$^+$.
$^1$H-NMR (400 MHz, DMSO-d$_6$): δ [ppm]=1.47-1.65 (m, 1H), 1.72-1.88 (m, 1H), 2.31-2.46 (m, 0.4H), 2.58-2.89 (m, 3H), 2.90-2.98 (m, 0.6H), 3.41 (dd, 0.6H), 3.47-3.82 (m, 7.4H), 4.10-4.29 (m, 2H), 4.38-4.58 (m, 1H), 6.83-7.02 (m, 2H), 7.22-7.36 (m, 1H), 7.45-7.54 (m, 2H), 7.55-7.63 (m, 1H), 7.72-7.84 (m, 1H), 7.85-8.04 (m, 2H), 8.69-8.92 (m, 1H).
$[α]_D^{20}$=−5.85° (c=0.410, methanol).

Example 12

3-{[2-(4-Chlorophenyl)imidazo[1,2-a]pyridin-3-yl]methyl}-8-oxa-3,10-diazabicyclo[4.3.1]dec-10-yl](3-fluoro-6-methoxypyridin-2-yl)methanone (Enantiomer 2)

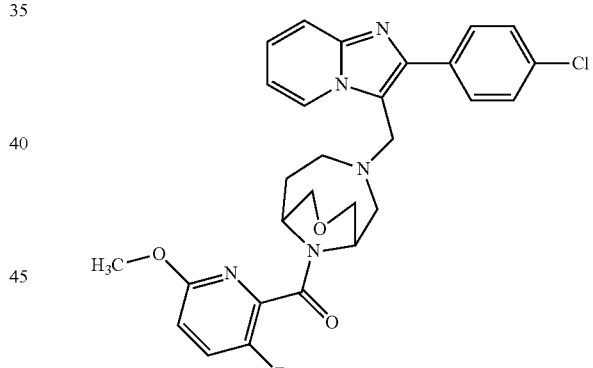

Under argon, [2-(4-chlorophenyl)imidazo[1,2-a]pyridin-3-yl]methanol (2.05 g, 7.91 mmol) and triethylamine (8.3 ml, 59 mmol) were initially charged in 40 ml of dichloromethane. In an ice bath, the mixture was cooled to 0° C., and methanesulfonyl chloride (1.5 ml, 20 mmol) was then added slowly. The mixture was stirred in the ice bath for 30 min. (3-Fluoro-6-methoxypyridin-2-yl)[8-oxa-3,10-diazabicyclo[4.3.1]dec-10-yl]methanone (1.95 g, 6.59 mmol, enantiomer 2) in 40 ml of acetonitrile was then added slowly. The reaction solution was then heated to 40° C. and stirred at this temperature for 2 h. The reaction mixture was subsequently diluted with 1 N aqueous sodium hydroxide solution and the aqueous phase was extracted with ethyl acetate. The combined organic phases were dried over magnesium sulfate, filtered and concentrated. On silica gel (mobile phase: cyclohexane/ethyl acetate 5:2), the residue obtained was separated into its components. The mixed fraction obtained was then re-purified by preparative HPLC (Method 10). The product fractions obtained in this manner were taken up in ethyl acetate, and the organic phase was washed with saturated sodium carbonate solution, dried over magnesium sulfate, filtered and once more concentrated to dryness. This gave 2.35 g (content 100%, 4.39 mmol, 67% of theory) of the title compound.

LC-MS (method 1): $R_t$=0.77 min; m/z=536/538 (M+H)$^+$.

$^1$H-NMR (400 MHz, DMSO-d$_6$): δ [ppm]=1.35-1.63 (m, 1H), 1.68-1.87 (m, 1H), 2.31-2.46 (m, 0.4H), 2.58-2.88 (m, 3H), 2.89-3.02 (m, 0.6H), 3.41 (dd, 0.6H), 3.46-3.86 (m, 7.4H), 4.07-4.30 (m, 2H), 4.40-4.57 (m, 1H), 6.75-7.02 (m, 2H), 7.13-7.37 (m, 1H), 7.42-7.53 (m, 2H), 7.56-7.67 (m, 1H), 7.72-7.83 (m, 1H), 7.84-8.04 (m, 2H), 8.62-8.94 (m, 1H).

$[α]_D^{20}$=+8.10° (c=0.395, methanol).

Example 13

3-{[2-(4-Chlorophenyl)imidazo[1,2-a]pyrimidin-3-yl]methyl}-8-oxa-3,10-diazabicyclo[4.3.1]dec-10-yl] (3-fluoro-6-methoxypyridin-2-yl)methanone (Enantiomer 1)

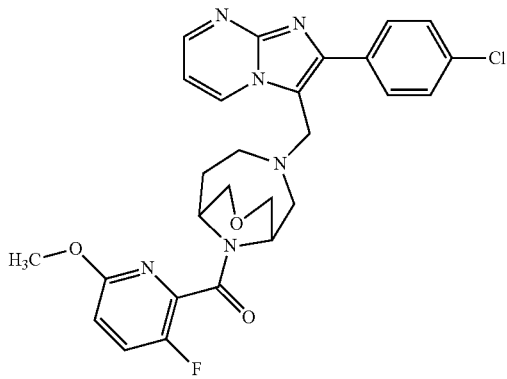 [SMILES: COc1ccc(F)c(C(=O)N2C3CCN(Cc4c(-c5ccc(Cl)cc5)nc5ncccn45)CC2COC3)n1]

Under argon, (3-fluoro-6-methoxypyridin-2-yl) [8-oxa-3,1-diazabicyclo[4.3.1]dec-10-yl]methanone (780 mg, 2.64 mmol, enantiomer 1), 2-(4-chlorophenyl)imidazo[1,2-a]pyrimidine-3-carbaldehyde (817 mg, 3.17 mmol) and acetic acid (360 µl, 6.3 mmol) were initially charged in 30 ml of THF. Sodium triacetoxyborohydride (1.01 g, 4.75 mmol) was then added, and the reaction mixture was stirred at room temperature overnight. The reaction mixture was then diluted with saturated sodium carbonate solution, the organic phase was removed and the aqueous phase was extracted twice with ethyl acetate. The combined organic phases were dried over magnesium sulfate, filtered and concentrated to dryness. On neutral alumina (mobile phase: dichloromethane/methanol 50:1), the residue obtained was separated into its components. 100 mg of the product obtained in this manner were then re-purified by preparative HPLC (Method 9). This gave 81 mg (content 100%, 0.150 mmol, 6% of theory) of the title compound.

LC-MS (method 2): $R_t$=1.65 min; m/z=537/539 (M+H)$^+$.

$^1$H-NMR (400 MHz, DMSO-d$_6$): δ [ppm]=1.47-1.66 (m, 1H), 1.73-1.88 (m, 1H), 2.30-2.44 (m, 0.4H), 2.58-2.87 (m, 3H), 2.87-2.97 (m, 0.75H), 3.41 (dd, 0.75H), 3.49-3.83 (m, 7.1H), 4.15-4.30 (m, 2H), 4.40-4.50 (m, 1H), 6.91-6.99 (m, 1H), 7.01-7.08 (m, 1H), 7.54 (d, 2H), 7.73-7.85 (m, 1H), 7.87-8.01 (m, 2H), 8.58 (dd, 1H), 9.15-9.36 (m, 1H).

Example 14

3-{[2-(4-Chlorophenyl)imidazo[1,2-a]pyrimidin-3-yl]methyl}-8-oxa-3,10-diazabicyclo[4.3.1]dec-10-yl] (3-fluoro-6-methoxypyridin-2-yl)methanone (Enantiomer 2)

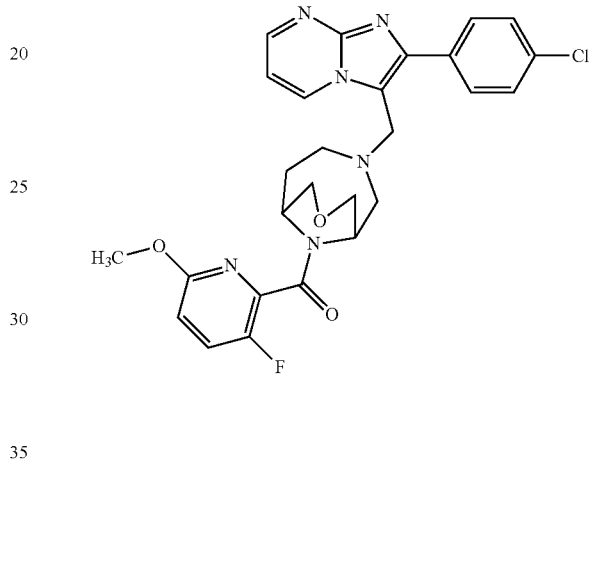

Under argon, (3-fluoro-6-methoxypyridin-2-yl)[8-oxa-3,10-diazabicyclo[4.3.1]dec-10-yl]methanone (575 mg, 1.95 mmol, enantiomer 2), 2-(4-chlorophenyl)imidazo[1,2-a]pyrimidine-3-carbaldehyde (602 mg, 2.34 mmol) and acetic acid (270 µl, 4.7 mmol) were initially charged in 22 ml of THF. Sodium triacetoxyborohydride (743 mg, 3.50 mmol) was then added, and the reaction mixture was stirred at room temperature overnight. The reaction mixture was then diluted with saturated sodium carbonate solution, the organic phase was removed and the aqueous phase was extracted twice with ethyl acetate. The combined organic phases were dried over magnesium sulfate, filtered and concentrated to dryness. On neutral alumina (mobile phase: dichloromethane/methanol 50:1), the residue obtained was separated into its components. 100 mg of the product obtained in this manner were then re-purified by preparative HPLC (Method 9). This gave 85 mg (content 100%, 0.160 mmol, 8% of theory) of the title compound.

LC-MS (method 2): $R_t$=1.65 min; m/z=537/539 (M+H)$^+$.

$^1$H-NMR (400 MHz, DMSO-d$_6$): δ [ppm]=1.50-1.62 (m, 1H), 1.70-1.88 (m, 1H), 2.35-2.43 (m, 0.4H), 2.56-2.87 (m, 3H), 2.87-2.95 (m, 0.75H), 3.41 (dd, 0.75H), 3.47-3.69 (m, 3.1H), 3.70-3.81 (m, 4H), 4.14-4.31 (m, 2H), 4.39-4.50 (m, 1H), 6.89-7.00 (m, 1H), 7.01-7.12 (m, 1H), 7.49-7.59 (m, 2H), 7.72-7.84 (m, 1H), 7.87-8.04 (m, 2H), 8.58 (dd, 1H), 9.10-9.38 (m, 1H).

Example 15

[3-{[2-(5-Chloropyridin-2-yl)imidazo[1,2-a]pyridin-3-yl]methyl}-3,9-diazabicyclo[4.2.1]non-9-yl](3-fluoro-6-methoxypyridin-2-yl)methanone (Enantiomer 1)

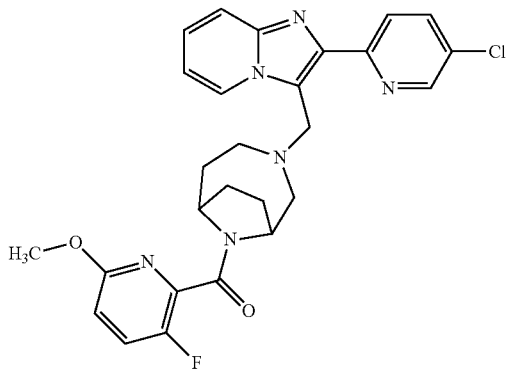 [SMILES: COc1ccc(F)c(C(=O)N2C3CCC2CN(Cc2c(-c4ccc(Cl)cn4)nc4ccccn24)CC3)n1]

Under argon, 3,9-diazabicyclo[4.2.1]non-9-yl(3-fluoro-6-methoxypyridin-2-yl)methanone (65.0 mg, 233 µmol, enantiomer 1), 2-(5-chloropyridin-2-yl)imidazo[1,2-a]pyridine-3-carbaldehyde (50.0 mg, 194 µmol) and acetic acid (22 µl, 390 µmol) were initially charged in 1.2 ml of THF. Sodium triacetoxyborohydride (62 mg, 291 µmol) was then added, and the mixture was stirred at room temperature overnight. Thereafter, methanol was added and the reaction mixture was separated directly into its components via preparative HPLC (Method 9). This gave 79 mg (100% pure, 0.151 mmol, 78% of theory) of the title compound.

LC-MS (method 2): $R_t$=1.22 min; m/z=521/523 (M+H)$^+$.
$^1$H-NMR (400 MHz, DMSO-d$_6$): δ [ppm]=1.21-1.37 (m, 1H), 1.42-1.51 (m, 0.5H), 1.50-1.59 (m, 0.5H), 1.59-1.69 (m, 1H), 1.70-1.90 (m, 1.5H), 1.90-2.05 (m, 1H), 2.08-2.17 (m, 0.5H), 2.35-2.70 (m, 3H), 2.81-3.05 (m, 1H), 3.74-3.83 (m, 3H), 3.84-3.90 (m, 1H), 4.39-4.60 (m, 2H), 4.68 (dd, 1H), 6.94 (ddd, 1H), 7.01 (qd, 1H), 7.30-7.41 (m, 1H), 7.62 (ddt, 1H), 7.77 (dt, 1H), 8.00 (td, 1H), 8.21 (td, 1H), 8.59 (dd, 1H), 8.62-8.71 (m, 1H).

Example 16

[3-{[2-(5-Chloropyridin-2-yl)imidazo[1,2-a]pyridin-3-yl]methyl}-3,9-diazabicyclo[4.2.1]non-9-yl](3-fluoro-6-methoxypyridin-2-yl)methanone (Enantiomer 2)

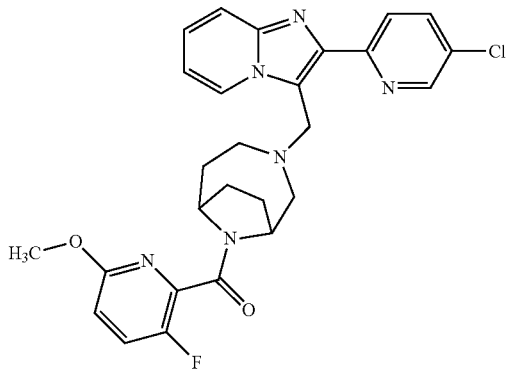 [SMILES: COc1ccc(F)c(C(=O)N2C3CCC2CN(Cc2c(-c4ccc(Cl)cn4)nc4ccccn24)CC3)n1]

Under argon, 3,9-diazabicyclo[4.2.1]non-9-yl(3-fluoro-6-methoxypyridin-2-yl)methanone (65.0 mg, 233 µmol, enantiomer 2), 2-(5-chloropyridin-2-yl)imidazo[1,2-a]pyridine-3-carbaldehyde (50.0 mg, 194 µmol) and acetic acid (22 µl, 390 µmol) were initially charged in 1.2 ml of THF. Sodium triacetoxyborohydride (62 mg, 291 µmol) was then added, and the mixture was stirred at room temperature overnight. Thereafter, methanol was added and the reaction mixture was separated directly into its components via preparative HPLC (Method 9). This gave 80 mg (100% pure, 0.154 mmol, 79% of theory) of the title compound.

LC-MS (method 2): $R_t$=1.23 min; m/z=521/523 (M+H)$^+$.
$^1$H-NMR (400 MHz, DMSO-d$_6$): δ [ppm]=1.23-1.37 (m, 1H), 1.41-1.50 (m, 0.5H), 1.51-1.59 (m, 0.5H), 1.58-1.69 (m, 1H), 1.71-1.88 (m, 1.5H), 1.89-2.06 (m, 1H), 2.06-2.19 (m, 0.5H), 2.35-2.46 (dt, 3H), 2.84-3.03 (m, 1H), 3.74-3.83 (m, 3H), 3.84-3.90 (m, 1H), 4.36-4.59 (m, 2H), 4.68 (dd, 1H), 6.93 (ddd, 1H), 7.01 (qd, 1H), 7.27-7.42 (m, 1H), 7.62 (dtt, 1H), 7.77 (dt, 1H), 8.00 (td, 1H), 8.21 (td, 1H), 8.59 (dd, 1H), 8.62-8.74 (m, 1H).

Example 17

[6-{[2-(4-Chlorophenyl)imidazo[1,2-a]pyrimidin-3-yl]methyl}-2,6-diazabicyclo[3.2.2]non-2-yl](3-fluoro-6-methoxypyridin-2-yl)methanone (Enantiomer 2)

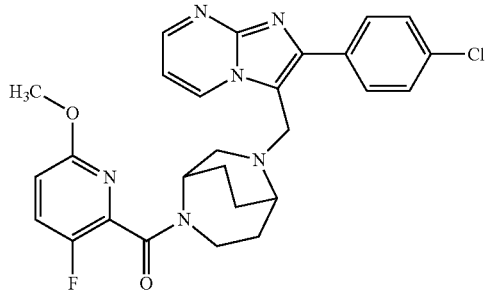 [SMILES: COc1ccc(F)c(C(=O)N2CCC3CCC2CN3Cc2c(-c3ccc(Cl)cc3)nc3ncccn23)n1]

2-(4-Chlorophenyl)-3-(2,6-diazabicyclo[3.2.2]non-6-ylmethyl)imidazo[1,2-a]pyrimidine bis(trifluoroacetic acid) salt (enantiomer 2; 153 mg, 141 µmol), 3-fluoro-6-methoxypyridine-2-carboxylic acid (29.0 mg, 169 µmol) and 1-[bis(dimethylamino)methylene]-1H-[1,2,3]triazolo[4,5-b]pyridin-1-ium 3-oxide hexafluorophosphate (69.8 mg, 184 µmol) were dissolved in 1.7 ml of DMF. N-Ethyl-N-isopropylpropan-2-amine (170 µl, 990 µmol) was then added. The mixture was stirred at room temperature overnight. Thereafter, methanol was added and the reaction mixture was separated directly into its components via preparative HPLC (Method 9). This gave 58.5 mg (100% pure, 0.112 mmol, 80% of theory) of the title compound.

LC-MS (method 2): $R_t$=1.40 min; m/z=521/523 (M+H)$^+$.
$^1$H-NMR (400 MHz, DMSO-d$_6$): δ [ppm]=1.33-1.48 (m, 0.6H), 1.59-1.93 (m, 4.4H), 1.93-2.11 (m, 1H), 2.58-2.80 (m, 1.6H), 2.93 (br. d, 0.6H), 2.98-3.16 (m, 1H), 3.24-3.41 (m, 1.4H), 3.60 (s, 1.2H), 3.70 (br. s, 0.4H), 3.78 (s, 1.8H), 4.04-4.16 (m, 0.4H), 4.20-4.37 (m, 2H), 4.57 (br. s, 0.6H), 6.81-6.99 (m, 1H), 7.11 (dd, 1H), 7.49-7.59 (m, 2H), 7.66-7.83 (m, 1H), 7.85-7.98 (m, 2H), 8.53-8.63 (m, 1H), 8.94-9.03 (m, 1H).

Analogously to Example 17, the following compounds were prepared from the starting materials specified in each case:

| Example | Name/Structure/Starting materials<br>Analytical data |
|---|---|
| 18 | [6-{[2-(5-chloropyridin-2-yl)imidazo[1,2-a]pyridin-3-yl]methyl}-2,6-diazabicyclo[3.2.2]non-2-yl](6-methoxypyridin-2-yl)methanone (enantiomer 1)<br>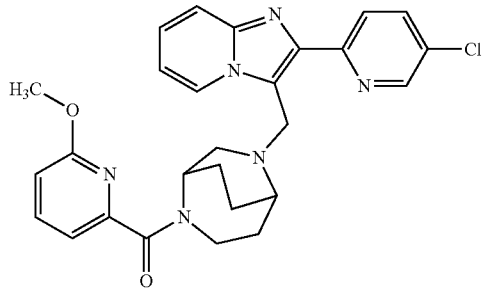<br>from 2-(5-chloropyridin-2-yl)-3-(2,6-diazabicyclo[3.2.2]non-6-ylmethyl)imidazo[1,2-a]pyridine bis(trifluoroacetic acid) salt (enantiomer 1) and 6-methoxypyridine-2-carboxylic acid<br><br>$^1$H-NMR (400 MHz, DMSO-d$_6$): δ [ppm] = 1.37-1.53 (m, 0.3H), 1.56-2.12 (m, 5.7H), 2.71-2.87 (m, 1H), 2.96 (br. d, 0.4H), 3.03-3.20 (m, 1.6H), 3.33-3.55 (m, 1.4H), 3.61 (s, 1.2H), 3.85 (s, 1.8H), 3.87-3.93 (m, 0.6H), 4.00-4.11 (m, 0.4H), 4.49-4.73 (m, 2H), 4.82 (d, 0.6H), 6.77-6.94 (m, 1H), 6.93-7.15 (m, 2H), 7.27-7.40 (m, 1H), 7.62 (br. d, 1H), 7.68-7.88 (m, 1H), 7.93-8.09 (m, 1H), 8.21 (d, 1H), 8.46 (d, 1H), 8.53-8.72 (m, 1H).<br>LC-MS (method 2): R$_t$ = 1.16 min; m/z = 503/505 (M + H)$^+$. |
| 19 | [6-{[2-(5-Chloropyridin-2-yl)imidazo[1,2-a]pyridin-3-yl]methyl}-2,6-diazabicyclo[3.2.2]non-2-yl](3-fluoro-6-methoxypyridin-2-yl)methanone (enantiomer 1)<br>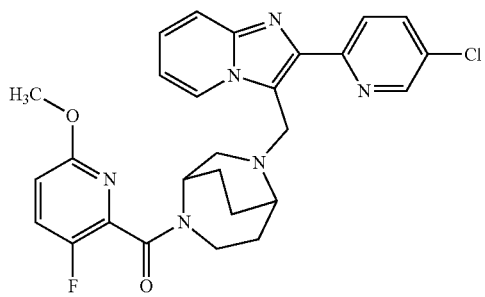<br>from 2-(5-chloropyridin-2-yl)-3-(2,6-diazabicyclo[3.2.2]non-6-ylmethyl)imidazo[1,2-a]pyridine bis(trifluoroacetic acid) salt (enantiomer 1) and 3-fluoro-6-methoxypyridine-2-carboxylic acid<br><br>$^1$H-NMR (400 MHz, DMSO-d$_6$): δ [ppm] = 1.37-1.48 (m, 0.7H), 1.56-2.11 (m, 5.3H), 2.69-2.94 (m, 1.6H), 3.03-3.20 (m, 1.8H), 3.32-3.48 (m, 1.2H), 3.61 (s, 1H), 3.71 (br. s, 0.4H), 3.83 (s, 2H), 4.08 (dt, 0.3H), 4.49-4.74 (m, 2H), 4.81 (d, 0.7H), 6.77-7.05 (m, 2H), 7.20-7.41 (m, 1H), 7.57-7.66 (m, 1H), 7.66-7.86 (m, 1H), 7.90-8.04 (m, 1H), 8.21 (d, 1H), 8.45 (d, 1H), 8.54-8.71 (m, 1H).<br>LC-MS (method 2): R$_t$ = 1.11 min; m/z = 521/523 (M + H)$^+$. |

| Example | Name/Structure/Starting materials<br>Analytical data |
|---|---|
| 20 | (3-Chloro-6-methoxypyridin-2-yl)[6-{[2-(5-chloropyridin-2-yl)imidazo[1,2-a]pyridin-3-yl]methyl}-2,6-diazabicyclo[3.2.2]non-2-yl]methanone (enantiomer 1)<br>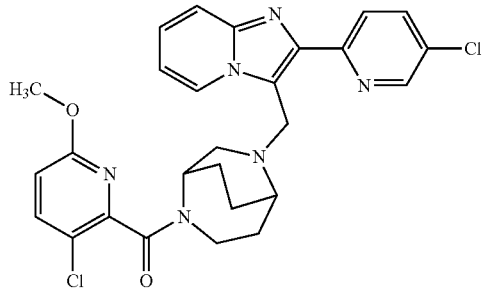<br>from 2-(5-chloropyridin-2-yl)-3-(2,6-diazabicyclo[3.2.2]non-6-ylmethyl)imidazo[1,2-a]pyridine bis(trifluoroacetic acid) salt (enantiomer 1) and 3-chloro-6-methoxypyridine-2-carboxylic acid<br><br>$^1$H-NMR (400 MHz, DMSO-$d_6$): δ [ppm] = 1.37-1.49 (m, 0.8H), 1.57-2.08 (m, 5.2H), 2.63-2.93 (m, 1.6H), 3.03-3.26 (m, 2.7H), 3.35-3.48 (m, 0.4H), 3.56 (br. s, 0.3H), 3.64 (s, 1H), 3.84 (s, 2H), 4.05-4.15 (m, 0.3H), 4.51-4.62 (m, 1.7H), 4.66-4.84 (m, 1H), 6.80-7.04 (m, 2H), 7.29-7.39 (m, 1H), 7.58-7.69 (m, 1H), 7.76-7.95 (m, 1H), 8.00 (dd, 1H), 8.21 (d, 1H), 8.45 (d, 1H), 8.56-8.74 (m, 1H).<br>LC-MS (method 2): $R_t$ = 1.19 min; m/z = 537/539 (M + H)$^+$. |
| 21 | [6-{[2-(4-Chlorophenyl)imidazo[1,2-a]pyrimidin-3-yl]methyl}-2,6-diazabicyclo[3.2.2]non-2-yl](6-methoxy-pyridin-2-yl)methanone (enantiomer 2)<br>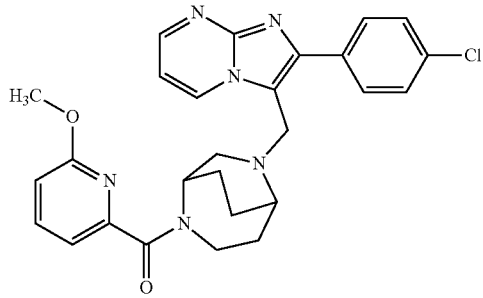<br>from 2-(4-chlorophenyl)-3-(2,6-diazabicyclo[3.2.2]non-6-ylmethyl)imidazo[1,2-a]pyrimidine bis(trifluoro-acetic acid) salt (enantiomer 2) and 6-methoxypyridine-2-carboxylic acid<br><br>$^1$H-NMR (400 MHz, DMSO-$d_6$): δ [ppm] = 1.36-1.49 (m, 0.6H), 1.57-2.13 (m, 5.4H), 2.62-2.85 (m, 1.6H), 2.90 (br. d, 0.6H), 3.03 (br. d, 0.6H), 3.14 (br. s, 0.4H), 3.22-3.40 (m, 0.8H), 3.42-3.52 (m, 0.6H), 3.58 (s, 1.3H), 3.80 (s, 1.7H), 3.88 (br. s, 0.4H), 4.08 (dt, 0.4H), 4.18-4.37 (m, 2H), 4.56 (br. s, 0.6H), 6.70-6.92 (m, 1H), 6.96-7.16 (m, 2H), 7.42-7.61 (m, 2H), 7.68-7.85 (m, 1H), 7.86-7.99 (m, 2H), 8.58 (td, 1H), 9.01 (ddd, 1H).<br>LC-MS (method 2): $R_t$ = 1.28 min; m/z = 503/505 (M + H)$^+$. |

| Example | Name/Structure/Starting materials Analytical data |
|---|---|
| 22 | [6-{[2-(4-Chlorophenyl)imidazo[1,2-a]pyrimidin-3-yl]methyl}-2,6-diazabicyclo[3.2.2]non-2-yl](2-fluorophenyl)methanone (enantiomer 2)<br>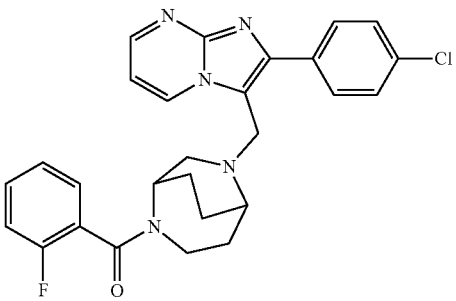<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 2) and 2-fluorobenzoic acid<br><br>$^1$H-NMR (400 MHz, DMSO-$d_6$): δ [ppm] = −0.149 (0.45), −0.008 (3.62), 0.008 (3.77), 1.355 (1.77), 1.367 (1.97), 1.378 (1.57), 1.389 (2.27), 1.401 (2.12), 1.558 (0.70), 1.570 (0.82), 1.596 (1.85), 1.622 (2.85), 1.652 (4.27), 1.731 (2.00), 1.756 (2.70), 1.767 (2.77), 1.795 (3.50), 1.805 (3.15), 1.948 (1.70), 1.979 (2.37), 2.073 (2.50), 2.328 (0.95), 2.366 (0.70), 2.585 (1.45), 2.670 (1.25), 2.716 (2.20), 2.726 (2.42), 2.745 (3.12), 2.755 (2.90), 2.888 (3.85), 2.916 (2.85), 2.975 (3.32), 3.063 (1.10), 3.260 (4.75), 3.653 (1.20), 4.098 (0.52), 4.196 (5.40), 4.232 (0.85), 4.270 (16.00), 4.308 (0.57), 4.598 (3.52), 5.754 (1.20), 7.105 (2.05), 7.122 (4.47), 7.133 (5.02), 7.148 (3.20), 7.197 (2.10), 7.219 (2.30), 7.243 (1.90), 7.270 (5.72), 7.289 (7.35), 7.312 (3.37), 7.393 (0.63), 7.406 (0.97), 7.414 (1.17), 7.427 (1.12), 7.454 (1.65), 7.468 (2.42), 7.475 (2.65), 7.489 (2.80), 7.498 (1.67), 7.511 (1.10), 7.546 (11.40), 7.562 (9.30), 7.567 (14.40), 7.583 (5.00), 7.898 (10.60), 7.901 (10.70), 7.919 (10.67), 8.572 (2.07), 8.577 (2.35), 8.587 (7.40), 8.592 (6.20), 8.597 (5.85), 8.602 (5.40), 8.963 (2.07), 8.968 (2.20), 8.985 (4.55), 9.004 (3.10).<br>LC-MS (method 2): $R_t$ = 1.39 min; m/z = 490/492 (M + H)$^+$. |
| 23 | (3-chloro-6-methoxypyridin-2-yl)[6-{[2-(4-chlorophenyl)imidazo[1,2-a]pyrimidin-3-yl]methyl}2,6-diazabicyclo[3.2.2]non-2-yl]methanone (enantiomer 2)<br>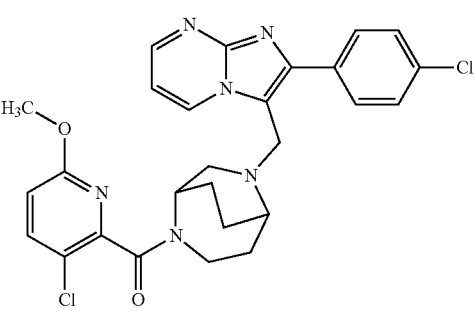<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 2) and 3-chloro-6-methoxypyridine-2-carboxylic acid<br><br>$^1$H-NMR (400 MHz, DMSO-$d_6$): δ [ppm] = −0.008 (1.27), 0.008 (1.34), 1.405 (0.51), 1.416 (0.57), 1.429 (0.45), 1.440 (0.65), 1.451 (0.58), 1.614 (0.50), 1.625 (0.62), 1.648 (1.06), 1.679 (1.30), 1.756 (0.50), 1.766 (0.55), 1.794 (0.86), 1.807 (1.03), 1.819 (0.96), 1.843 (0.91), 1.970 (0.48), 2.002 (0.74), 2.074 (0.44), 2.566 (0.41), 2.583 (0.57), 2.594 (0.52), 2.642 (0.68), 2.671 (0.67), 2.714 (0.74), 2.723 (0.78), 2.743 (1.09), 2.753 (0.99), 2.844 (1.12), 2.873 (0.74), 3.040 (0.94), 3.127 (0.80), 3.149 (0.76), 3.163 (1.05), 3.179 (0.80), 3.191 (0.68), 3.202 (0.62), 3.215 (0.71), 3.540 (0.53), 3.623 (5.48), 3.798 (16.00), 4.234 (2.53), 4.274 (2.71), 4.285 (2.72), 4.321 (0.46), 4.563 (1.13), 6.829 (1.52), 6.851 (1.61), 6.902 (3.28), 6.924 (3.42), 7.099 (2.02), 7.109 (2.12), 7.116 (2.10), 7.126 (2.07), 7.523 (3.92), 7.544 |

| Example | Name/Structure/Starting materials Analytical data |
|---|---|
| | (6.35), 7.566 (2.14), 7.789 (1.55), 7.811 (1.49), 7.869 (3.53), 7.878 (4.61), 7.891 (3.62), 7.899 (4.20), 7.908 (2.41), 7.930 (1.90), 8.567 (0.74), 8.572 (0.85), 8.577 (0.85), 8.585 (1.77), 8.590 (1.78), 8.595 (1.67), 8.600 (1.60), 8.968 (1.48), 8.973 (1.54), 8.986 (1.85), 8.990 (1.90), 9.005 (0.73), 9.009 (0.69). LC-MS (method 1): $R_t$ = 0.75 min; m/z = 537/539 (M + H)$^+$. |
| 24 | (4-amino-1,2-oxadiazol-3-yl)[6-{[2-(4-chlorophenyl) imidazo[1,2-a]pyrimidin-3-yl]methyl}-2,6-diazabicyclo [3.2.2]non-2-yl]methanone (enantiomer 2) 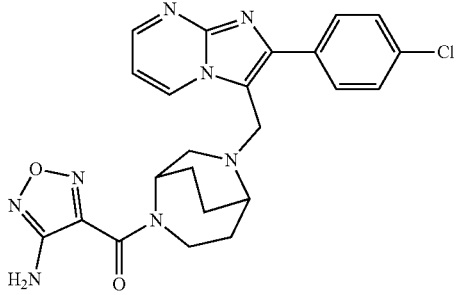 from 2-(4-chlorophenyl)-3-(2,6-diazabicyclo[3.2.2]non-6-ylmethyl)imidazo[1,2-a]pyrimidine bis(trifluoroacetic acid) salt (enantiomer 2) and 4-amino-1,2,5-oxadiazole-3-carboxylic acid $^1$H-NMR (400 MHz, DMSO-d$_6$): δ [ppm] = 1.41-1.69 (m, 2H), 1.72-2.05 (m, 4H), 2.70-2.85 (m, 1.4H), 2.91-3.10 (m, 1.6H), 3.38-3.60 (m, 1H), 3.71 (dt, 0.6H), 3.96-4.07 (m, 0.4H), 4.16 (br. s, 0.4H), 4.24 (d, 2H), 4.59 (br. s, 0.6H), 6.31 (br. d, 2H), 7.01-7.13 (m, 1H), 7.42-7.63 (m, 2H), 7.82-7.98 (m, 2H), 8.58 (dd, 1H), 9.00 (dd, 1H). LC-MS (method 2): $R_t$ = 1.25 min; m/z = 479/481 (M + H)$^+$. |
| 25 | [6-{[2-(4-Chlorophenyl)imidazo[1,2-a]pyridin-3-yl]methyl}-2,6-diazabicyclo[3.2.2]non-2-yl](2-fluorophenyl) methanone (enantiomer 2) 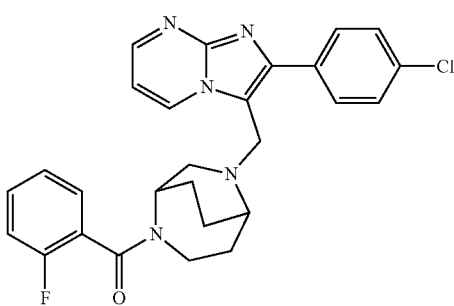 from 2-(4-chlorophenyl)-3-(2,6-diazabicyclo[3.2.2] non-6-ylmethyl)imidazo[1,2-a]pyridine bis(trifluoroacetic acid) salt (enantiomer 2) and 2-fluorobenzoic acid $^1$H-NMR (400 MHz, DMSO-d$_6$): δ [ppm] = −0.149 (1.11), −0.008 (9.05), 0.008 (8.48), 0.146 (1.05), 1.345 (1.96), 1.356 (2.14), 1.379 (2.51), 1.390 (2.31), 1.563 (0.94), 1.600 (2.11), 1.626 (2.99), 1.656 (4.84), 1.773 (2.76), 1.800 (4.30), 1.945 (1.94), 1.975 (2.56), 2.073 (2.48), 2.328 (1.88), 2.367 (0.88), 2.603 (1.40), 2.670 (2.16), 2.711 (1.31), 2.733 (2.08), 2.756 (2.59), 2.911 (4.33), 2.940 (3.25), 2.970 (3.81), 3.059 (1.14), 3.260 (4.95), 3.661 (1.31), 4.171 (6.80), 4.206 (1.31), 4.242 (9.00), 4.250 (11.27), 4.286 (1.40), 4.604 (3.67), 5.755 (0.63), 6.951 (1.34), 6.968 (4.81), 6.984 (5.98), 7.001 (2.76), 7.203 (2.28), 7.226 (2.51), 7.249 (2.85), 7.270 (6.52), 7.291 (10.65), 7.314 (8.34), 7.331 (4.75), 7.417 (1.28), 7.431 (1.14), 7.453 (2.11), 7.467 (2.56), 7.475 (2.99), 7.488 (3.07), 7.516 (12.44), 7.537 (16.00), 7.554 (5.75), 7.577 (3.10), 7.589 (8.00), 7.600 (2.79), 7.611 (6.78), 7.871 (9.59), 7.877 (13.04), 7.893 (10.51), 7.898 (10.88), 8.524 (2.45), 8.541 (2.70), 8.553 (4.90), 8.571 (4.70). LC-MS (method 1): $R_t$ = 0.73 min; m/z = 489/491 (M + H)$^+$. |

| Example | Name/Structure/Starting materials Analytical data |
|---|---|
| 26 | [6-{[2-(4-chlorophenyl)imidazo[1,2-a]pyridin-3-yl]methyl}-2,6-diazabicyclo[3.2.2]non-2-yl](6-methoxypyridin-2-yl)methanone (enantiomer 2) 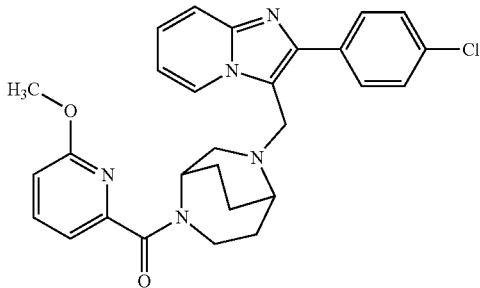 from 2-(4-chlorophenyl)-3-(2,6-diazabicyclo[3.2.2]non-6-ylmethyl)imidazo[1,2-a]pyridine bis(trifluoroacetic acid) salt (enantiomer 2) and 6-methoxypyridine-2-carboxylic acid |

$^1$H-NMR (400 MHz, DMSO-$d_6$): δ [ppm] = −0.008 (2.10), 0.008 (2.26), 1.396 (0.45), 1.407 (0.51), 1.431 (0.57), 1.442 (0.55), 1.611 (0.44), 1.636 (0.92), 1.648 (0.85), 1.662 (1.28), 1.694 (1.28), 1.727 (0.53), 1.765 (0.55), 1.792 (0.46), 1.864 (1.08), 1.994 (0.51), 2.073 (2.51), 2.328 (0.51), 2.653 (0.45), 2.666 (0.86), 2.682 (0.71), 2.695 (0.62), 2.711 (1.07), 2.720 (0.80), 2.740 (0.97), 2.749 (0.88), 2.793 (0.80), 2.822 (0.54), 2.916 (1.00), 2.944 (0.76), 3.018 (0.84), 3.135 (0.61), 3.339 (0.97), 3.352 (0.52), 3.363 (0.53), 3.450 (0.83), 3.463 (0.47), 3.486 (0.51), 3.589 (10.16), 3.794 (16.00), 3.894 (0.72), 4.063 (0.49), 4.098 (0.45), 4.207 (1.33), 4.217 (3.00), 4.243 (2.05), 4.289 (2.03), 4.326 (0.92), 4.573 (0.98), 6.794 (1.43), 6.815 (1.47), 6.873 (2.08), 6.893 (2.15), 6.944 (1.18), 6.961 (2.39), 6.978 (1.30), 6.996 (1.43), 7.014 (1.47), 7.039 (2.09), 7.057 (2.13), 7.279 (0.69), 7.283 (0.90), 7.286 (0.91), 7.301 (1.52), 7.318 (0.72), 7.323 (0.93), 7.462 (3.80), 7.483 (4.27), 7.523 (2.58), 7.545 (2.88), 7.583 (1.80), 7.585 (1.99), 7.608 (1.68), 7.703 (1.13), 7.721 (1.24), 7.724 (1.27), 7.742 (1.03), 7.779 (1.65), 7.798 (1.82), 7.800 (1.86), 7.819 (1.51), 7.869 (4.32), 7.890 (3.96), 7.902 (3.04), 7.923 (2.60), 8.557 (1.62), 8.574 (1.88), 8.587 (1.08).
LC-MS (method 1): $R_t$ = 0.70 min; m/z = 502/504 (M + H)$^+$.

| 27 | [6-{[2-(4-chlorophenyl)imidazo[1,2-a]pyridin-3-yl]methyl}-2,6-diazabicyclo[3.2.2]non-2-yl](3-fluoro-6-methoxy-pyridin-2-yl)methanone (enantiomer 2) 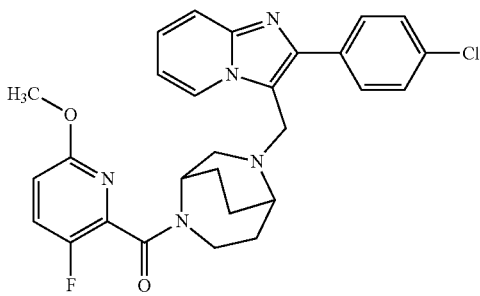 from 2-(4-chlorophenyl)-3-(2,6-diazabicyclo[3.2.2]non-6-ylmethyl)imidazo[1,2-a]pyridine bis(trifluoroacetic acid) salt (enantiomer 2) and 3-fluoro-6-methoxypyridine-2-carboxylic acid |

$^1$H-NMR (400 MHz, DMSO-$d_6$): δ [ppm] = 1.34-1.47 (m, 0.6H), 1.57-2.05 (m, 5.4H), 2.61-2.79 (m, 1.5H), 2.96 (br. d, 0.6H), 2.99-3.15 (m, 1H), 3.25-3.40 (m, 1.5H), 3.60 (s, 1.1H), 3.71 (br. s, 0.4H), 3.78 (s, 1.9H), 4.11 (dt, 0.4H), 4.18-4.33 (m, 2H), 4.58 (br. s, 0.6H), 6.81-7.01 (m, 2H), 7.19-7.38 (m, 1H), 7.46-7.55 (m, 2H), 7.56-7.63 (m, 1H), 7.68-7.83 (m, 1H), 7.85-7.95 (m, 2H), 8.47-8.63 (m, 1H).
LC-MS (method 1): $R_t$ = 0.73 min; m/z = 520/522 (M + H)$^+$.

| Example | Name/Structure/Starting materials Analytical data |
|---|---|
| 28 | (3-chloro-6-methoxypyridin-2-yl)[6-{[2-(4-chlorophenyl)imidazo[1,2-a]pyridin-3-yl]methyl}-2,6-diazabicyclo[3.2.2]non-2-yl]methanone (enantiomer 2) 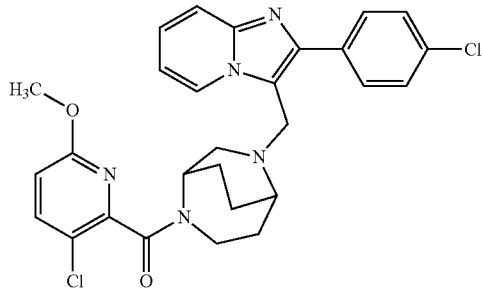 from 2-(4-chlorophenyl)-3-(2,6-diazabicyclo[3.2.2]non-6-ylmethyl)imidazo[1,2-a]pyridine bis(trifluoroacetic acid) salt (enantiomer 2) and 3-chloro-6-methoxypyridine-2-carboxylic acid |

$^1$H-NMR (400 MHz, DMSO-$d_6$): δ [ppm] = −0.008 (2.32), 0.008 (2.30), 1.396 (0.46), 1.407 (0.53), 1.418 (0.41), 1.431 (0.59), 1.443 (0.56), 1.618 (0.47), 1.629 (0.51), 1.652 (0.98), 1.679 (1.19), 1.764 (0.46), 1.773 (0.53), 1.815 (1.01), 1.843 (0.82), 1.963 (0.47), 1.994 (0.67), 2.073 (0.77), 2.328 (0.49), 2.600 (0.54), 2.612 (0.45), 2.675 (0.94), 2.710 (0.56), 2.721 (0.67), 2.731 (0.75), 2.750 (1.01), 2.760 (0.88), 2.872 (1.05), 2.901 (0.73), 3.033 (0.85), 3.125 (0.68), 3.147 (0.55), 3.161 (0.95), 3.182 (0.57), 3.194 (0.63), 3.205 (0.56), 3.217 (0.65), 3.553 (0.49), 3.632 (5.46), 3.798 (16.00), 4.206 (3.17), 4.242 (2.22), 4.266 (2.24), 4.302 (0.70), 4.573 (1.05), 5.754 (1.12), 6.831 (1.54), 6.853 (1.63), 6.900 (3.32), 6.923 (3.45), 6.940 (1.19), 6.957 (2.40), 6.974 (1.30), 7.274 (0.44), 7.288 (1.25), 7.291 (1.31), 7.311 (1.50), 7.313 (1.48), 7.328 (0.93), 7.330 (0.93), 7.493 (3.95), 7.498 (1.31), 7.514 (6.19), 7.535 (2.12), 7.573 (0.94), 7.588 (1.91), 7.596 (0.84), 7.610 (1.59), 7.794 (1.57), 7.816 (1.54), 7.854 (4.54), 7.858 (1.49), 7.868 (3.83), 7.875 (4.11), 7.886 (2.47), 7.890 (3.92), 7.907 (1.88), 8.533 (1.62), 8.550 (1.75), 8.573 (0.73).
LC-MS (method 1): $R_t$ = 0.77 min; m/z = 536/538 (M + H)$^+$.

| 29 | (4-amino-1,2,5-oxadiazol-3-yl)[6-{[2-(4-chlorophenyl)imidazo[1,2-a]pyridin-3-yl]methyl}-2,6-diazabicyclo[3.2.2]non-2-yl]methanone (enantiomer 2) 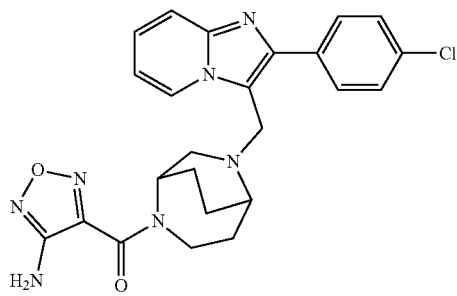 from 2-(4-chlorophenyl)-3-(2,6-diazabicyclo[3.2.2]non-6-ylmethyl)imidazo[1,2-a]pyridine bis(trifluoroacetic acid) salt (enantiomer 2) and 4-amino-1,2,5-oxadiazole-3-carboxylic acid |

$^1$H-NMR (400 MHz, DMSO-$d_6$): δ [ppm] = 1.43-1.70 (m, 2H), 1.73-2.04 (m, 4H), 2.73-2.86 (m, 1.4H), 2.91-3.08 (m, 1.6H), 3.37-3.59 (m, 1H), 3.71 (dt, 0.6H), 4.02 (dt, 0.4H), 4.13-4.29 (m, 2.4H), 4.61 (br. s, 0.6H), 6.32 (br. d, 2H), 6.82-7.06 (m, 1H), 7.20-7.39 (m, 1H), 7.44-7.63 (m, 3H), 7.89 (dd, 2H), 8.56 (d, 1H).
LC-MS (method 2): $R_t$ = 1.31 min; m/z = 478/480 (M + H)$^+$.

| Example | Name/Structure/Starting materials Analytical data |
|---|---|
| 30 | [6-{[2-(5-Chloropyridin-2-yl)imidazo[1,2-a]pyridin-3-yl]methyl}-2,6-diazabicyclo[3.2.2]non-2-yl](2-fluorophenyl)methanone (enantiomer 1)<br>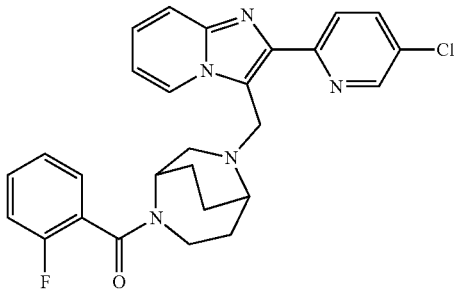<br>from 2-(5-chloropyridin-2-yl)-3-(2,6-diazabicyclo[3.2.2]non-6-ylmethyl)imidazo[1,2-a]pyridine bis(trifluoroacetic acid) salt (enantiomer 1) and 2-fluorobenzoic acid<br><br>$^1$H-NMR (400 MHz, DMSO-d$_6$): δ [ppm] = −0.120 (0.50), 0.116 (0.46), 1.034 (0.99), 1.045 (0.95), 1.231 (2.16), 1.360 (3.32), 1.369 (3.61), 1.378 (2.86), 1.387 (3.85), 1.397 (3.61), 1.590 (3.19), 1.619 (4.68), 1.638 (3.15), 1.673 (2.69), 1.778 (3.90), 1.801 (4.19), 1.848 (5.72), 1.906 (2.20), 1.979 (3.40), 2.003 (3.85), 2.362 (1.49), 2.636 (1.45), 2.756 (1.78), 2.850 (3.61), 2.867 (4.19), 3.076 (12.19), 3.100 (7.09), 3.448 (0.95), 3.677 (2.07), 4.067 (0.66), 4.553 (3.52), 4.595 (11.03), 4.611 (6.92), 4.755 (4.93), 4.782 (3.77), 6.968 (1.82), 6.982 (3.90), 6.995 (5.06), 7.007 (5.93), 7.019 (3.52), 7.213 (2.16), 7.231 (3.32), 7.250 (2.90), 7.317 (6.92), 7.333 (13.26), 7.349 (16.00), 7.363 (8.79), 7.420 (1.91), 7.435 (1.82), 7.486 (4.89), 7.498 (4.77), 7.601 (4.52), 7.611 (11.52), 7.619 (4.48), 7.629 (9.82), 7.986 (8.54), 7.991 (8.87), 7.996 (4.10), 8.003 (11.44), 8.008 (10.49), 8.013 (4.06), 8.019 (3.40), 8.192 (5.39), 8.203 (13.89), 8.209 (5.72), 8.220 (11.52), 8.422 (3.15), 8.437 (3.19), 8.455 (9.87), 8.468 (9.37), 8.635 (9.08), 8.687 (4.44), 8.691 (4.35).<br>LC-MS (method 1): R$_t$ = 0.66 min; m/z = 490/492 (M + H)$^+$. |
| 31 | [6-{[2-(4-Chlorophenyl)imidazo[1,2-a]pyrimidin-3-yl]methyl}-2,6-diazabicyclo[3.2.2]non-2-yl](2-fluorophenyl)methanone (enantiomer 1)<br>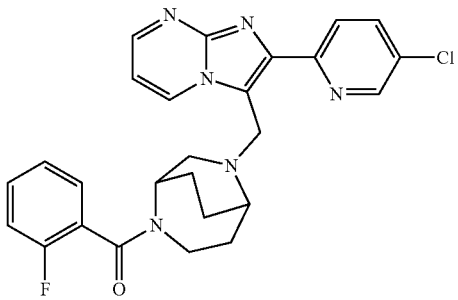<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 1) and 2-fluorobenzoic acid<br><br>$^1$H-NMR (400 MHz, DMSO-d$_6$): δ [ppm] = −0.150 (0.47), −0.008 (4.05), 0.008 (4.47), 0.146 (0.53), 1.355 (1.74), 1.367 (2.00), 1.378 (1.53), 1.389 (2.32), 1.401 (2.21), 1.621 (2.84), 1.653 (4.16), 1.756 (2.74), 1.766 (2.74), 1.795 (3.53), 1.947 (1.63), 1.980 (2.37), 1.988 (2.47), 2.073 (4.79), 2.328 (1.63), 2.367 (0.84), 2.670 (1.89), 2.716 (2.21), 2.726 (2.47), 2.746 (3.16), 2.755 (2.84), 2.887 (3.89), 2.917 (2.89), 2.985 (3.32), 3.063 (1.11), 3.261 (5.00), 3.652 (1.26), 4.101 (0.53), 4.196 (5.37), 4.232 (0.89), 4.271 (16.00), 4.308 (0.63), 4.597 (3.53), 5.754 (0.47), 7.106 (2.16), 7.122 (4.53), 7.133 (5.11), 7.148 (3.21), 7.198 (2.16), 7.219 (2.21), 7.243 (1.95), 7.270 (5.68), 7.289 (7.37), 7.312 (3.42), 7.407 (1.11), 7.414 (1.16), 7.428 (1.16), 7.454 (1.84), 7.468 (2.53), 7.476 (2.74), 7.489 (2.79), 7.498 (1.79), 7.511 |

| Example | Name/Structure/Starting materials<br>Analytical data |
|---|---|
| | (1.21), 7.546 (11.79), 7.562 (9.37), 7.567 (14.89), 7.583 (5.21), 7.898 (10.68), 7.901 (10.79), 7.919 (10.68), 8.572 (2.16), 8.577 (2.53), 8.587 (7.84), 8.592 (6.58), 8.597 (6.21), 8.602 (5.74), 8.963 (2.11), 8.968 (2.21), 8.985 (4.58), 9.005 (3.11).<br>LC-MS (method 2): R$_t$ = 1.41 min; m/z = 490/492 (M + H)$^+$. |
| 32 | [6-{[2-(4-Chlorophenyl)imidazo[1,2-a]pyrimidin-3-yl]methyl}-2,6-diazabicyclo[3.2.2]non-2-yl](6-methoxypyridin-2-yl)methanone (enantiomer 1)<br><br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 1) and 6-methoxypyridine-2-carboxylic acid<br><br>$^1$H-NMR (400 MHz, DMSO-d$_6$): δ [ppm] = 1.33-1.50 (m, 0.6H), 1.58-2.12 (m, 5.4H), 2.60-2.84 (m, 1.6H), 2.90 (br. d, 0.6H), 3.03 (br. d, 0.6H), 3.14 (br. s, 0.4H), 3.23-3.40 (m, 0.8H), 3.42-3.53 (m, 0.6H), 3.58 (s, 1.25H), 3.80 (s, 1.75H), 3.88 (br. s, 0.4H), 4.00-4.13 (m, 0.4H), 4.17-4.38 (m, 2H), 4.56 (br. s, 1.6H), 6.74-6.94 (m, 1H), 6.97-7.22 (m, 2H), 7.43-7.63 (m, 2H), 7.66-7.85 (m, 1H), 7.86-7.99 (m, 2H), 8.53-8.65 (m, 1H), 9.01 (ddd, 1H).<br>LC-MS (method 2): R$_t$ = 1.30 min; m/z = 503/505 (M + H)$^+$. |
| 33 | [6-{[2-(4-Chlorophenyl)imidazo[1,2-a]pyrimidin-3-yl]methyl}-2,6-diazabicyclo[3.2.2]non-2-yl](3-fluoro-6-methoxypyridin-2-yl)methanone (enantiomer 1)<br><br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 1) and 3-fluoro-6-methoxypyridine-2-carboxylic acid<br><br>$^1$H-NMR (400 MHz, DMSO-d$_6$): δ [ppm] = −0.008 (1.18), 0.008 (1.18), 1.393 (0.49), 1.405 (0.56), 1.416 (0.44), 1.428 (0.65), 1.439 (0.61), 1.615 (0.65), 1.639 (1.17), 1.672 (1.48), 1.684 (1.31), 1.771 (0.74), 1.798 (0.98), 1.830 (0.85), 1.851 (0.70), 1.901 (0.43), 1.975 (0.53), 2.006 (0.82), 2.073 (2.43), 2.615 (0.40), 2.631 (0.72), 2.644 (0.67), 2.670 (0.50), 2.687 (0.92), 2.717 (1.20), 2.725 (0.93), 2.746 (1.07), 2.755 (0.94), 2.916 (1.10), 2.946 (0.83), 3.022 (0.96), 3.121 (0.60), 3.276 (1.37), 3.293 (2.27), 3.343 (0.70), 3.594 (9.37), 3.695 (0.70), 3.783 (16.00), 4.092 (0.48), 4.127 (0.45), 4.230 (4.17), 4.267 (2.36), 4.297 (2.33), 4.333 (0.84), 4.567 (1.14), 6.850 (0.78), 6.858 (0.79), 6.873 (0.89), 6.881 (0.85), 6.928 (1.26), 6.935 (1.29), 6.950 (1.45), 6.958 (1.40), 7.097 (1.77), 7.107 (1.90), 7.114 (1.94), 7.124 (1.86), 7.513 (3.82), 7.535 (4.30), 7.547 (2.43), 7.568 (2.63), 7.683 (0.84), 7.705 |

| Example | Name/Structure/Starting materials Analytical data |
|---|---|
| | (1.42), 7.727 (0.82), 7.766 (1.37), 7.788 (2.24), 7.809 (1.31), 7.889 (4.49), 7.911 (4.36), 7.917 (3.30), 7.938 (2.43), 8.569 (0.93), 8.574 (1.06), 8.583 (2.29), 8.587 (1.80), 8.593 (1.62), 8.598 (1.49), 8.977 (1.46), 8.982 (1.53), 8.995 (2.11), 8.999 (2.10), 9.013 (0.94), 9.018 (0.87).<br>LC-MS (method 2): $R_t$ = 1.41 min; m/z = 521/523 (M + H)⁺. |
| 34 | (3-chloro-6-methoxypyridine-2-yl)[6-{[2-(4-chlorophenyl)imidazo[1,2-a]pyrimidin-3-yl]methyl}-2,6-diazabicyclo[3.2.2]non-2-yl]methanone (enantiomer 1)<br>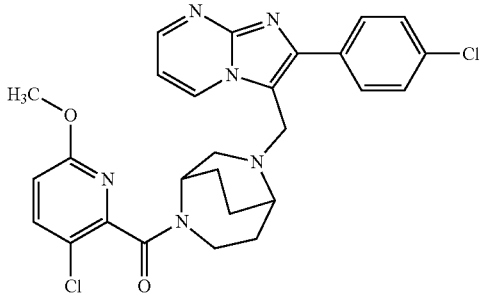<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 1) and 3-chloro-6-methoxypyridine-2-carboxylic acid |
| | ¹H-NMR (400 MHz, DMSO-$d_6$): δ [ppm] = −0.008 (1.24), 0.008 (1.35), 1.405 (0.46), 1.416 (0.53), 1.427 (0.40), 1.439 (0.60), 1.451 (0.56), 1.624 (0.60), 1.648 (0.96), 1.677 (1.24), 1.755 (0.49), 1.765 (0.51), 1.807 (0.97), 1.842 (0.85), 1.970 (0.46), 2.000 (0.70), 2.328 (0.47), 2.582 (0.51), 2.594 (0.47), 2.641 (0.63), 2.670 (0.81), 2.712 (0.72), 2.723 (0.72), 2.742 (1.04), 2.752 (0.92), 2.844 (1.04), 2.872 (0.71), 3.039 (0.89), 3.127 (0.77), 3.148 (0.72), 3.162 (1.02), 3.177 (0.75), 3.191 (0.65), 3.202 (0.58), 3.214 (0.67), 3.538 (0.50), 3.622 (5.31), 3.797 (16.00), 4.233 (2.41), 4.274 (2.59), 4.284 (2.60), 4.320 (0.45), 4.560 (1.09), 6.828 (1.52), 6.850 (1.60), 6.902 (3.31), 6.924 (3.42), 7.098 (1.96), 7.109 (2.03), 7.116 (2.06), 7.126 (2.02), 7.522 (3.95), 7.544 (6.30), 7.565 (2.11), 7.789 (1.56), 7.811 (1.49), 7.868 (3.52), 7.877 (4.58), 7.890 (3.60), 7.898 (4.13), 7.908 (2.35), 7.929 (1.85), 8.567 (0.75), 8.572 (0.83), 8.577 (0.83), 8.585 (1.71), 8.590 (1.78), 8.595 (1.70), 8.600 (1.57), 8.968 (1.46), 8.973 (1.52), 8.985 (1.82), 8.990 (1.85), 9.004 (0.70), 9.009 (0.68).<br>LC-MS (method 2): $R_t$ = 1.55 min; m/z = 537/539 (M + H)⁺. |
| 35 | (4-amino-1,2,5-oxadiazol-3-yl)[6-{[2-(4-chlorophenyl)imidazo[1,2-a]pyrimidin-3-yl]methyl}-2,6-diazabicyclo[3.2.2]non-2-yl]methanone (enantiomer 1)<br>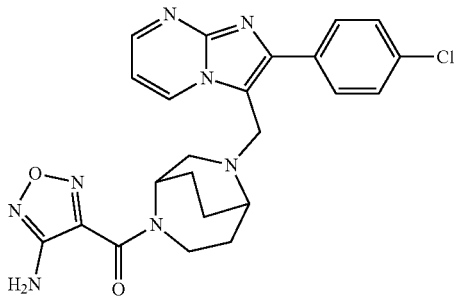<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 1) and 4-amino-1,2,5-oxadiazole-3-carboxylic acid |
| | ¹H-NMR (400 MHz, DMSO-$d_6$): δ [ppm] = −0.149 (1.14), −0.008 (8.80), 0.008 (8.65), 0.146 (1.08), 1.465 (0.97), 1.476 (1.11), 1.487 (0.91), 1.500 (1.25), 1.511 (1.22), 1.557 (0.65), 1.570 (0.77), 1.604 (1.51), 1.633 (1.77), 1.656 (1.28), 1.776 (2.62), 1.805 (1.48), 1.850 (2.02), 1.875 (2.02), 1.946 (1.31), 1.978 (1.45), 2.073 (16.00), 2.328 (1.62), 2.366 (0.68), 2.670 (1.77), 2.710 (0.83), 2.731 (1.57), 2.740 (1.71), 2.760 (2.08), 2.769 (1.88), 2.807 (3.76), 2.813 (3.93), 2.932 (2.22), 2.961 |

| Example | Name/Structure/Starting materials<br>Analytical data |
|---|---|
| | (1.65), 3.018 (1.99), 3.418 (0.68), 3.442 (1.02), 3.466 (0.71), 3.502 (0.63), 3.514 (0.80), 3.525 (0.71), 3.538 (1.48), 3.551 (1.05), 3.561 (1.11), 3.572 (0.80), 3.687 (1.82), 3.700 (1.00), 3.723 (1.28), 4.002 (1.08), 4.038 (1.00), 4.156 (1.59), 4.227 (7.09), 4.258 (10.16), 4.594 (2.19), 6.307 (7.12), 6.320 (5.69), 7.081 (3.02), 7.091 (3.13), 7.098 (3.16), 7.108 (4.47), 7.117 (2.05), 7.124 (2.05), 7.134 (2.02), 7.527 (7.97), 7.541 (6.23), 7.548 (9.79), 7.562 (6.01), 7.895 (9.42), 7.904 (6.60), 7.911 (3.84), 7.916 (8.57), 7.926 (5.67), 8.576 (4.90), 8.581 (5.38), 8.586 (5.18), 8.591 (4.87), 8.987 (4.47), 8.992 (3.73), 9.004 (4.38).<br>LC-MS (method 2): $R_t$ = 1.26 min; m/z = 479/481 (M + H)⁺. |
| 36 | [6-{[2-(4-Chlorophenyl)imidazo[1,2-a]pyridin-3-yl]methyl}-2,6-diazabicyclo[3.2.2]non-2-yl](2-fluorophenyl)methanone (enantiomer 1)<br>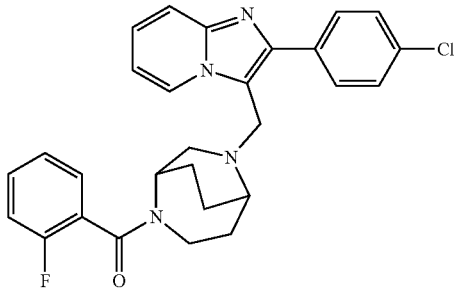<br>from 2-(4-chlorophenyl)-3-(2,6-diazabicyclo[3.2.2]non-6-ylmethyl)imidazo[1,2-a]pyridine bis(trifluoroacetic acid) salt (enantiomer 1) and 2-fluorobenzoic acid |
| | ¹H-NMR (400 MHz, DMSO-d₆): δ [ppm] = −0.149 (0.91), −0.008 (7.77), 0.008 (7.45), 0.146 (0.86), 1.233 (0.55), 1.345 (2.00), 1.356 (2.23), 1.367 (1.68), 1.379 (2.45), 1.391 (2.41), 1.562 (0.86), 1.600 (2.14), 1.624 (3.05), 1.656 (4.82), 1.763 (2.59), 1.773 (2.82), 1.801 (4.27), 1.944 (1.91), 1.975 (2.64), 2.073 (0.55), 2.328 (1.68), 2.366 (0.59), 2.601 (1.23), 2.670 (1.82), 2.711 (1.00), 2.734 (2.09), 2.757 (2.50), 2.911 (4.41), 2.940 (3.36), 2.969 (3.86), 3.054 (1.18), 3.260 (5.18), 3.663 (1.27), 4.083 (0.59), 4.171 (6.91), 4.206 (1.32), 4.242 (9.14), 4.250 (11.64), 4.286 (1.36), 4.604 (3.73), 6.950 (1.32), 6.967 (4.86), 6.984 (6.14), 7.001 (2.73), 7.204 (2.27), 7.226 (2.59), 7.249 (2.86), 7.270 (6.68), 7.291 (10.59), 7.314 (8.36), 7.333 (4.64), 7.409 (1.05), 7.417 (1.27), 7.431 (1.23), 7.453 (2.09), 7.467 (2.73), 7.475 (2.95), 7.488 (3.23), 7.497 (2.05), 7.516 (12.32), 7.537 (16.00), 7.554 (5.59), 7.577 (3.09), 7.589 (7.82), 7.599 (2.86), 7.611 (6.68), 7.871 (9.55), 7.876 (13.14), 7.893 (10.55), 7.898 (11.05), 8.524 (2.41), 8.541 (2.73), 8.553 (5.00), 8.570 (4.77).<br>LC-MS (method 2): $R_t$ = 1.43 min; m/z = 489/491 (M + H)⁺. |
| 37 | [6-{[2-(4-chlorophenyl)imidazo[1,2-a]pyridin-3-yl]methyl}-2,6-diazabicyclo[3.2.2]non-2-yl](6-methoxypyridin-2-yl)methanone (enantiomer 1)<br>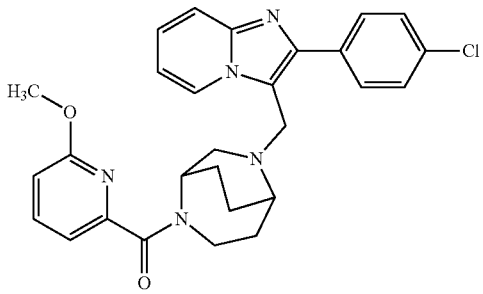<br>from 2-(4-chlorophenyl)-3-(2,6-diazabicyclo[3.2.2]non-6-ylmethyl)imidazo[1,2-a]pyridine bis(trifluoroacetic acid) salt (enantiomer 1) and 6-methoxypyridine-2-carboxylic acid |
| | ¹H-NMR (400 MHz, DMSO-d₆): δ [ppm] = −0.149 (0.42), 0.146 (0.42), 1.396 (0.57), 1.407 (0.59), 1.418 (0.48), 1.432 (0.67), 1.441 (0.65), 1.635 (1.14), 1.662 (1.54), 1.694 (1.55), 1.726 (0.65), 1.761 (0.64), 1.791 (0.56), 1.864 (1.35), 1.992 (0.64), 2.073 (0.61), 2.327 (0.71), 2.653 (0.55), 2.665 (1.20), 2.681 (0.89), 2.695 |

| Example | Name/Structure/Starting materials Analytical data |
|---|---|
| | (0.76), 2.710 (1.19), 2.720 (0.95), 2.740 (1.14), 2.748 (1.06), 2.793 (1.02), 2.822 (0.68), 2.915 (1.25), 2.944 (0.95), 3.017 (1.06), 3.137 (0.77), 3.338 (1.25), 3.363 (0.71), 3.375 (0.51), 3.449 (0.97), 3.462 (0.57), 3.486 (0.59), 3.589 (10.54), 3.794 (16.00), 3.893 (0.88), 4.063 (0.57), 4.098 (0.56), 4.216 (3.51), 4.242 (2.30), 4.289 (2.26), 4.325 (1.03), 4.570 (1.25), 6.793 (1.61), 6.814 (1.66), 6.871 (2.31), 6.892 (2.48), 6.943 (1.29), 6.960 (2.65), 6.977 (1.46), 6.995 (1.65), 7.013 (1.76), 7.038 (2.43), 7.055 (2.52), 7.283 (1.06), 7.300 (1.79), 7.315 (0.94), 7.323 (1.11), 7.461 (3.84), 7.482 (4.24), 7.523 (2.64), 7.544 (2.93), 7.584 (2.27), 7.606 (1.96), 7.702 (1.08), 7.722 (1.45), 7.741 (0.98), 7.779 (1.49), 7.798 (2.09), 7.818 (1.41), 7.869 (4.48), 7.890 (4.13), 7.901 (3.28), 7.923 (2.76), 8.557 (1.78), 8.573 (2.23), 8.586 (1.24). LC-MS (method 2): $R_t$ = 1.35 min; m/z = 502/504 (M + H)$^+$. |
| 38 | [6-{[2-(4-chlorophenyl)imidazo[1,2-a]pyridin-3-yl]methyl}-2,6-diazabicyclo[3.2.2]non-2-yl](3-fluoro-6-methoxypyridin-2-yl)methanone (enantiomer 1) |
| | from 2-(4-chlorophenyl)-3-(2,6-diazabicyclo[3.2.2]non-6-ylmethyl)imidazo[1,2-a]pyridine bis(trifluoroacetic acid) salt (enantiomer 1) and 3-fluoro-6-methoxypyridine-2-carboxylic acid |
| | $^1$H-NMR (400 MHz, DMSO-d$_6$): δ [ppm] = 1.30-1.48 (m, 0.6H), 1.54-2.05 (m, 5.4H), 2.60-2.82 (m, 1.6H), 2.89-3.16 (m, 1.6H), 3.21-3.42 (m, 1.4H), 3.60 (s, 1.1H), 3.71 (br. s, 0.4H), 3.78 (s, 1.9H), 4.03-4.16 (m, 0.4H), 4.17-4.36 (m, 2H), 4.58 (br. s, 0.6H), 6.81-7.08 (m, 2H), 7.16-7.36 (m, 1H), 7.46-7.56 (m, 2H), 7.55-7.64 (m, 1H), 7.66-7.83 (m, 1H), 7.83-7.95 (m, 2H), 8.48-8.64 (m, 1H). LC-MS (method 2): $R_t$ = 1.44 min; m/z = 520/522 (M + H)$^+$. |
| 39 | (3-chloro-6-methoxypyridin-2-yl)[6-{[2-(4-chlorophenyl)imidazol[1,2-a]pyridin-3-yl]methyl}-2,6-diazabicyclo[3.2.2]non-2-yl]methanone (enantiomer 1) |
| | from 2-(4-chlorophenyl)-3-(2,6-diazabicyclo[3.2.2]non-6-ylmethyl)imidazo[1,2-a]pyridine bis(trifluoroacetic acid) salt (enantiomer 1) and 3-fluoro-6-methoxypyridine-2-carboxylic acid |
| | $^1$H-NMR (400 MHz, DMSO-d$_6$): δ [ppm] = −0.008 (2.44), 0.008 (2.27), 1.396 (0.53), 1.408 (0.60), 1.419 (0.47), 1.431 (0.67), 1.442 (0.62), 1.618 (0.53), 1.629 (0.57), 1.652 (1.07), 1.678 (1.32), 1.764 (0.53), 1.774 (0.61), 1.803 (1.18), 1.842 (0.95), 1.963 (0.51), 1.995 (0.78), 2.328 (0.58), 2.600 (0.55), 2.612 (0.49), 2.675 (1.05), 2.710 (0.58), 2.722 (0.73), 2.731 (0.81), 2.750 (1.12), 2.760 (1.00), 2.872 (1.16), 2.901 (0.81), 3.040 (0.98), 3.125 (0.75), 3.148 (0.61), 3.161 (1.06), 3.181 (0.63), 3.194 (0.68), 3.205 (0.61), 3.217 (0.73), 3.556 (0.52), 3.632 (5.59), 3.798 (16.00), 4.206 (3.35), 4.242 (2.43), 4.266 (2.44), 4.302 (0.76), 4.572 (1.18), 6.831 (1.41), 6.853 (1.48), 6.900 (3.11), 6.923 (3.26), 6.940 (1.23), 6.957 (2.52), 6.974 |

| Example | Name/Structure/Starting materials Analytical data |
|---|---|
| | (1.38), 7.274 (0.46), 7.291 (1.41), 7.313 (1.62), 7.329 (1.00), 7.493 (3.98), 7.514 (6.24), 7.535 (2.09), 7.573 (0.92), 7.588 (2.04), 7.596 (0.90), 7.610 (1.70), 7.794 (1.45), 7.816 (1.39), 7.854 (4.57), 7.868 (3.74), 7.875 (4.21), 7.886 (2.49), 7.890 (3.83), 7.907 (1.88), 8.533 (1.75), 8.551 (1.89), 8.573 (0.78). LC-MS (method 2): $R_t$ = 1.52 min; m/z = 536/538 (M + H)$^+$. |
| 40 | (4-amino-1,2,5-oxadiazol-3-yl)[6-{[2-(4-chlorophenyl)imidazo[1,2-a]pyridin-3-yl]methyl}-2,6-diazabicyclo[3.2.2]non-2-yl]methanone (enantiomer 1) 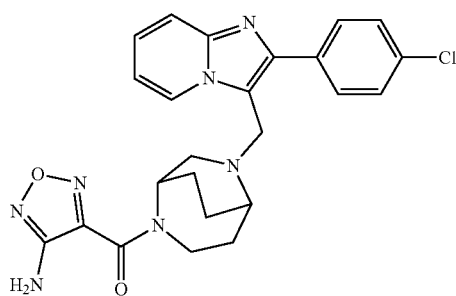 from 2-(4-chlorophenyl)-3-(2,6-diazabicyclo[3.2.2]non-6-ylmethyl)imidazo[1,2-a]pyridine bis(trifluoroacetic acid) salt (enantiomer 1) and 4-amino-1,2,5-oxadiazole-3-carboxylic acid $^1$H-NMR (400 MHz, DMSO-d$_6$): δ [ppm] = 1.43-1.69 (m, 2H), 1.70-2.03 (m, 4H), 2.73-2.86 (m, 1.4H), 2.92-3.07 (m, 1.6H), 3.39-3.59 (m, 1H), 3.71 (dt, 0.6H), 4.02 (dt, 0.4H), 4.10-4.32 (m, 2.4H), 4.60 (br. s, 0.6H), 6.32 (br. d, 2H), 6.87-7.07 (m, 1H), 7.22-7.37 (m, 1H), 7.44-7.55 (m, 2H), 7.59 (d, 1H), 7.89 (dd, 2H), 8.56 (d, 1H). LC-MS (method 2): $R_t$ = 1.30 min; m/z = 478/480 (M + H)$^+$. |
| 41 | [6-{[2-(4-isopropylphenyl)imidazo[1,2-a]pyrimidin-3-yl]methyl}-2,6-diazabicyclo[3.2.2]non-2-yl](6-methoxypyridin-2-yl)methanone (enantiomer 1) 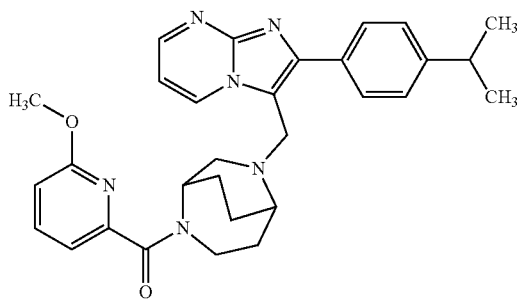 from 3-(2,6-diazabicyclo[3.2.2]non-6-ylmethyl)-2-(4-isopropylphenyl)imidazo[1,2-a]pyrimidine dihydrochloride (enantiomer 1) and 6-methoxypyridine-2-carboxylic acid $^1$H-NMR (400 MHz, DMSO-d$_6$): δ [ppm] = 1.24 (dd, 6H), 1.41-1.53 (m, 0.6H), 1.59-2.13 (m, 5.4H), 2.58-2.85 (m, 1.5H), 2.86-3.00 (m, 1.6H), 3.03-3.21 (m, 1H), 3.23-3.40 (m, 0.9H), 3.49 (dt, 0.6H), 3.57 (s, 1.25H), 3.79 (s, 1.75H), 3.88 (br. s, 0.4H), 4.09 (dt, 0.4H), 4.21-4.42 (m, 2H), 4.58 (br. s, 0.6H), 6.73-6.92 (m, 1H), 6.94-7.14 (m, 2H), 7.24-7.43 (m, 2H), 7.61-7.86 (m, 3H), 8.55 (td, 1H), 8.98 (dt, 1H). LC-MS (method 1): $R_t$ = 0.72 min; m/z = 511 (M + H)$^+$. |

| Example | Name/Structure/Starting materials Analytical data |
|---|---|
| 42 | (3-fluoro-6-methoxypyridin-2-yl)[6-{[2-(4-isopropylphenyl)imidazo[1,2-a]pyrimidin-3-yl]methyl}-2,6-diazabicyclo[3.2.2]non-2-yl]methanone (enantiomer 1) |

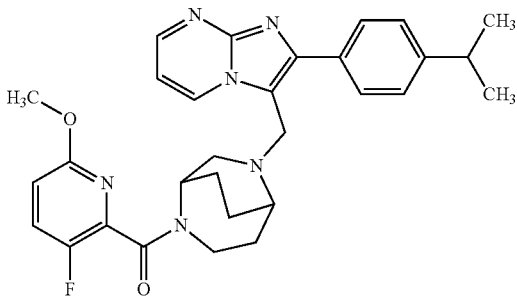

from 3-(2,6-diazabicyclo[3.2.2]non-6-ylmethyl)-2-(4-isopropylphenyl)imidazo[1,2-a]pyrimidine dihydrochloride (enantiomer 1) and 3-fluoro-6-methoxypyridine-2-carboxylic acid $^1$H-NMR (400 MHz, DMSO-$d_6$): δ [ppm] = −0.008 (0.92), 0.008 (0.89), 1.224 (11.24), 1.242 (16.00), 1.261 (7.98), 1.404 (0.42), 1.415 (0.49), 1.438 (0.52), 1.450 (0.47), 1.627 (0.47), 1.638 (0.50), 1.662 (0.90), 1.685 (1.25), 1.694 (1.29), 1.788 (0.46), 1.804 (0.52), 1.826 (0.85), 1.861 (0.67), 1.992 (0.51), 2.009 (0.46), 2.023 (0.53), 2.524 (0.63), 2.638 (0.52), 2.650 (0.47), 2.711 (0.84), 2.720 (0.72), 2.730 (0.77), 2.749 (0.87), 2.759 (0.74), 2.915 (0.92), 2.933 (1.42), 2.950 (1.88), 2.967 (0.81), 2.983 (0.84), 3.061 (0.75), 3.155 (0.46), 3.284 (1.02), 3.582 (7.67), 3.698 (0.52), 3.777 (13.47), 4.238 (2.65), 4.267 (1.72), 4.314 (1.71), 4.350 (0.80), 4.581 (0.88), 6.846 (0.66), 6.854 (0.67), 6.868 (0.76), 6.877 (0.72), 6.928 (1.09), 6.936 (1.11), 6.950 (1.26), 6.958 (1.22), 7.069 (1.30), 7.073 (1.01), 7.080 (1.39), 7.086 (1.52), 7.090 (1.05), 7.097 (1.37), 7.100 (0.97), 7.316 (2.86), 7.337 (3.12), 7.360 (1.73), 7.381 (1.90), 7.680 (0.70), 7.702 (1.15), 7.724 (0.67), 7.765 (1.90), 7.769 (3.53), 7.789 (4.21), 7.795 (2.71), 7.809 (1.50), 7.816 (1.87), 8.540 (0.77), 8.545 (0.87), 8.551 (0.96), 8.555 (1.91), 8.559 (1.51), 8.565 (1.34), 8.570 (1.26), 8.951 (1.25), 8.957 (1.63), 8.963 (0.93), 8.968 (1.33), 8.974 (1.55), 8.980 (0.76). LC-MS (method 1): $R_t$ = 0.76 min; m/z = 529 (M + H)$^+$.

| | |
|---|---|
| 43 | (3-chloro-6-methoxypyridin-2-yl)[6-{[2-(4-isopropylphenyl)imidazo[1,2-a]pyrimidin-3-yl]methyl}-2,6-diazabicyclo[3.2.2]non-2-yl]methanone (enantiomer 1) |

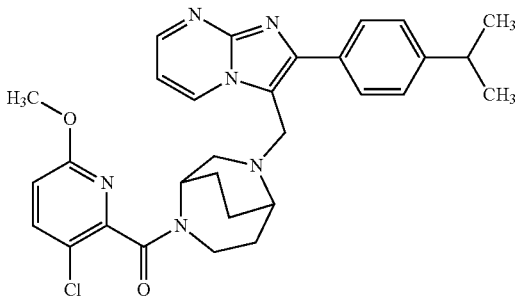

from 3-(2,6-diazabicyclo[3.2.2]non-6-ylmethyl)-2-(4-isopropylphenyl)imidazo[1,2-a]pyrimidine dihydrochloride (enantiomer 1) and 3-chloro-6-methoxypyridine-2-carboxylic acid $^1$H-NMR (400 MHz, DMSO-$d_6$): δ [ppm] = −0.008 (1.19), 0.008 (0.97), 1.237 (15.38), 1.243 (7.80), 1.254 (15.99), 1.260 (7.51), 1.409 (0.54), 1.419 (0.54), 1.431 (0.41), 1.443 (0.60), 1.455 (0.54), 1.647 (0.54), 1.672 (0.96), 1.691 (1.24), 1.780 (0.53), 1.808 (1.02), 1.820 (1.03), 1.843 (0.86), 1.988 (0.52), 2.019 (0.61), 2.524 (0.77), 2.583 (0.43), 2.661 (0.61), 2.670 (0.46), 2.718 (0.66), 2.728 (0.75), 2.747 (0.99), 2.757 (0.87), 2.868 (1.04), 2.898 (0.78), 2.910 (0.50), 2.927 (1.02), 2.944 (1.31), 2.962 (0.97), 3.087 (0.88), 3.124 (0.40), 3.148 (0.68), 3.160 (1.25), 3.184 (0.63), 3.196 (0.60), 3.207 (0.56), 3.219 (0.68), 3.546 (0.41), 3.608 (4.29), 3.793 (16.00), 4.240 (2.20), 4.271 (2.17), 4.299 (2.16), 4.334 (0.77), 4.572 (1.05), 6.823 (1.36), 6.845 (1.39), 6.900 (3.42), 6.922 (3.56), 7.072 (2.11), 7.082 (2.14), 7.089 (2.13), 7.099 (2.13), 7.330 (3.44), 7.351 (4.00), 7.356 (2.05), 7.377 (1.55), 7.756 (4.04), 7.776 (3.70), 7.785 (2.39), 7.807 (2.75), 7.854 (3.49), 7.877 (3.29),

| Example | Name/Structure/Starting materials Analytical data |
|---|---|
| | 8.538 (0.63), 8.542 (0.72), 8.548 (0.71), 8.556 (1.69), 8.561 (1.77), 8.567 (1.68), 8.572 (1.60), 8.941 (1.45), 8.946 (1.60), 8.958 (1.63), 8.963 (1.51), 8.972 (0.62). LC-MS (method 1): $R_t$ = 0.81 min; m/z = 545/547 (M + H)$^+$. |
| 44 | cyclopentyl[6-{[2-(4-isopropylphenyl)imidazo[1,2-a]pyrimidin-3-yl]methyl}-2,6-diazabicyclo[3.2.2]non-2-yl]methanone (enantiomer 1) 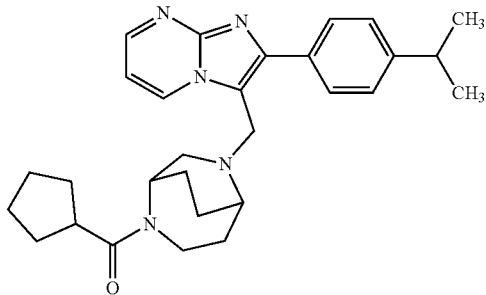 from 3-(2,6-diazabicyclo[3.2.2]non-6-ylmethyl)-2-(4-isopropylphenyl)imidazo[1,2-a]pyrimidine dihydrochloride (enantiomer 1) and cyclopentanecarboxylic acid |
| | $^1$H-NMR (400 MHz, DMSO-d$_6$): δ [ppm] = −0.008 (0.83), 0.008 (0.75), 1.243 (15.81), 1.260 (16.00), 1.435 (0.68), 1.446 (0.73), 1.457 (0.68), 1.470 (0.87), 1.482 (1.00), 1.488 (1.10), 1.509 (1.23), 1.526 (1.52), 1.546 (1.93), 1.556 (1.63), 1.566 (1.53), 1.608 (0.59), 1.652 (1.31), 1.685 (1.96), 1.734 (0.65), 1.753 (0.65), 1.765 (0.64), 1.932 (0.43), 1.949 (0.40), 2.574 (0.66), 2.583 (0.70), 2.602 (0.93), 2.611 (0.85), 2.747 (0.93), 2.775 (0.73), 2.914 (0.42), 2.932 (1.05), 2.949 (1.42), 2.966 (1.40), 2.976 (1.03), 2.983 (1.09), 3.387 (0.46), 3.647 (0.50), 4.172 (0.57), 4.209 (2.03), 4.218 (2.51), 4.426 (0.76), 7.059 (0.99), 7.069 (1.04), 7.076 (1.10), 7.086 (1.10), 7.097 (0.41), 7.341 (2.40), 7.352 (1.22), 7.361 (2.72), 7.373 (1.08), 7.771 (3.08), 7.775 (2.15), 7.792 (2.92), 8.546 (1.52), 8.551 (1.67), 8.557 (1.61), 8.561 (1.51), 8.909 (1.01), 8.914 (1.03), 8.926 (1.04), 8.931 (1.11), 8.938 (0.46). LC-MS (method 1): $R_t$ = 0.76 min; m/z = 472 (M + H)$^+$. |
| 45 | [6-(difluoromethoxy)pyridin-2-yl][6-{[2-(4-isopropylphenyl)imidazo[1,2-a]pyrimidin-3-yl]methyl}-2,6-diazabicyclo[3.2.2]non-2-yl]methanone (enantiomer 1) 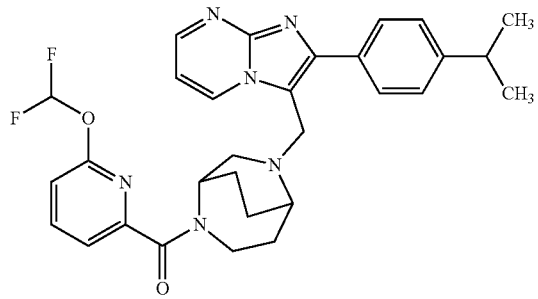 from 3-(2,6-diazabicyclo[3.2.2]non-6-ylmethyl)-2-(4-isopropylphenyl)imidazo[1,2-a]pyrimidine dihydrochloride (enantiomer 1) and 6-(difluoromethoxy)pyridine-2-carboxylic acid |
| | $^1$H-NMR (400 MHz, DMSO-d$_6$): δ [ppm] = 1.17-1.29 (m, 6H), 1.36-1.50 (m, 0.7H), 1.55-1.92 (m, 4.3H), 1.95-2.10 (m, 1H), 2.62-2.79 (m, 1.4H), 2.86-3.00 (m, 1.6H), 3.04-3.16 (m, 1H), 3.35-3.52 (m, 1.4H), 3.90 (br. s, 0.4H), 3.95-4.07 (m, 0.4H), 4.17-4.38 (m, 2H), 4.58 (br. s, 0.6H), 7.03-7.22 (m, 2H), 7.24-7.40 (m, 3.2H), 7.41-7.75 (m, 0.8H), 7.78-7.84 (m, 2H), 7.88-8.09 (m, 1H), 8.56 (td, 1H), 8.90-9.04 (m, 1H). LC-MS (method 1): $R_t$ = 0.79 min; m/z = 547 (M + H)$^+$. |

| Example | Name/Structure/Starting materials Analytical data |
|---|---|
| 46 | (2-fluorophenyl)[6-{[2-(4-isopropylphenyl)imidazo[1,2-a]pyrimidin-3-yl]methyl}-2,6-diazabicyclo[3.2.2]non-2-yl]methanone (enantiomer 2)<br>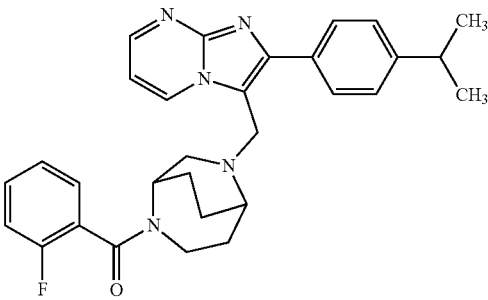<br>from 3-(2,6-diazabicyclo[3.2.2]non-6-ylmethyl)-2-(4-isopropylphenyl)imidazo[1,2-a]pyrimidine dihydrochloride (enantiomer 2) and 2-fluorobenzoic acid<br><br>$^1$H-NMR (400 MHz, DMSO-d$_6$): δ [ppm] = −0.008 (0.90), 0.008 (0.94), 1.238 (15.45), 1.247 (7.17), 1.255 (16.00), 1.264 (6.62), 1.362 (0.49), 1.374 (0.55), 1.385 (0.44), 1.396 (0.65), 1.408 (0.61), 1.601 (0.49), 1.613 (0.55), 1.662 (1.26), 1.746 (0.50), 1.773 (0.63), 1.783 (0.66), 1.811 (1.08), 1.965 (0.51), 1.979 (0.54), 1.995 (0.55), 2.723 (0.65), 2.733 (0.72), 2.752 (0.89), 2.761 (0.81), 2.916 (0.51), 2.933 (1.80), 2.942 (0.68), 2.951 (1.66), 2.959 (1.37), 2.967 (1.17), 2.977 (0.47), 2.985 (0.44), 3.010 (0.92), 3.269 (1.33), 4.199 (1.88), 4.320 (0.46), 4.266 (2.60), 4.277 (2.30), 4.612 (1.00), 7.079 (0.63), 7.090 (0.81), 7.096 (1.34), 7.106 (1.48), 7.123 (0.82), 7.193 (0.49), 7.216 (0.59), 7.239 (0.47), 7.251 (0.52), 7.268 (1.73), 7.287 (2.55), 7.311 (1.40), 7.355 (3.35), 7.376 (4.38), 7.399 (1.37), 7.454 (0.44), 7.474 (0.79), 7.490 (0.78), 7.777 (1.87), 7.792 (2.10), 7.797 (2.40), 7.809 (1.67), 8.544 (0.62), 8.549 (0.71), 8.554 (0.78), 8.559 (2.15), 8.564 (1.83), 8.569 (1.69), 8.574 (1.58), 8.925 (0.57), 8.930 (0.59), 8.943 (0.65), 8.947 (0.69), 8.961 (0.93), 8.975 (0.90).<br>LC-MS (method 1): R$_t$ = 0.77 min; m/z = 498 (M + H)$^+$. |
| 47 | (2-fluorophenyl)[6-{[2-(4-isopropylphenyl)imidazo[1,2-a]pyrimidin-3-yl]methyl}-2,6-diazabicyclo[3.2.2]non-2-yl]methanone (enantiomer 1)<br>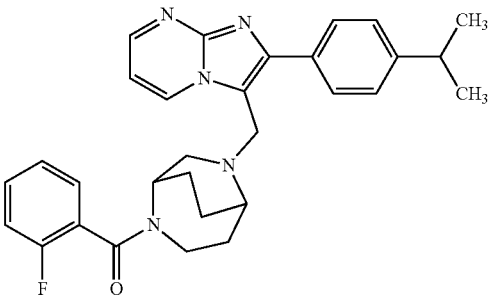<br>from 3-(2,6-diazabicyclo[3.2.2]non-6-ylmethyl)-2-(4-isopropylphenyl)imidazo[1,2-a]pyrimidine dihydrochloride (enantiomer 1) and 2-fluorobenzoic acid<br><br>$^1$H-NMR (400 MHz, DMSO-d$_6$): δ [ppm] = −0.008 (0.95), 0.008 (1.00), 1.238 (15.47), 1.247 (7.15), 1.255 (16.00), 1.264 (6.67), 1.363 (0.47), 1.374 (0.53), 1.385 (0.44), 1.397 (0.65), 1.409 (0.62), 1.601 (0.50), 1.614 (0.55), 1.662 (1.22), 1.736 (0.49), 1.773 (0.62), 1.784 (0.66), 1.811 (1.04), 1.965 (0.50), 1.993 (0.54), 2.724 (0.64), 2.732 (0.73), 2.752 (0.87), 2.761 (0.81), 2.916 (0.51), 2.933 (1.77), 2.951 (1.64), 2.959 (1.34), 2.967 (1.14), 2.976 (0.47), 2.985 (0.44), 3.008 (0.90), 3.268 (1.30), 4.199 (1.84), 4.230 (0.45), 4.267 (2.58), 4.277 (2.27), 4.611 (0.97), 7.079 (0.62), 7.090 (0.79), 7.096 (1.32), 7.107 (1.48), 7.123 (0.80), 7.194 (0.49), 7.216 (0.60), 7.240 (0.45), 7.252 (0.50), 7.268 (1.71), 7.288 (2.54), 7.311 (1.41), 7.356 (3.33), 7.377 (4.34), 7.399 (1.36), 7.454 (0.44), 7.475 (0.77), 7.490 (0.77), 7.777 (1.86), 7.792 (2.08), 7.797 (2.39), 7.809 (1.66), 8.544 (0.62), 8.549 (0.69), 8.554 (0.77), 8.559 (2.20), 8.564 (1.84), 8.569 (1.70), 8.574 (1.58), 8.925 (0.57), 8.930 (0.58), 8.943 (0.64), 8.948 (0.68), 8.959 (0.92), 8.975 (0.89).<br>LC-MS (method 1): R$_t$ = 0.76 min; m/z = 498 (M + H)$^+$. |

| Example | Name/Structure/Starting materials Analytical data |
|---|---|
| 48 | [6-{[2-(4-isopropylphenyl)imidazo[1,2-a]pyrimidin-3-yl]methyl}-2,6-diazabicyclo[3.2.2]non-2-yl](6-methoxypyridin-2-yl)methanone (enantiomer 2)<br>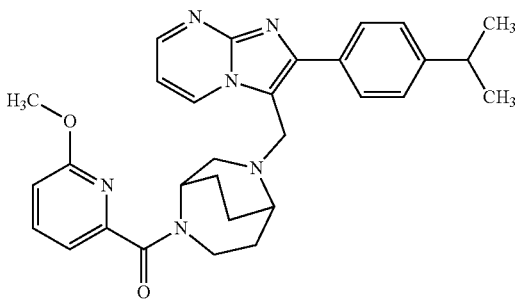<br>from 3-(2,6-diazabicyclo[3.2.2]non-6-ylmethyl)-2-(4-isopropylphenyl)imidazo[1,2-a]pyrimidine dihydrochloride (enantiomer 2) and 6-methoxypyridine-2-carboxylic acid<br><br>$^1$H-NMR (400 MHz, DMSO-$d_6$): δ [ppm] = 1.24 (dd, 6H), 1.39-1.50 (m, 0.6H), 1.58-2.10 (m, 5.4H), 2.60-2.84 (m, 1.5H), 2.85-3.00 (m, 1.6H), 3.09 (br. s, 0.6H), 3.18 (br. s, 0.4H), 3.22-3.40 (m, 0.9H), 3.43-3.54 (m, 0.6H), 3.57 (s, 1.3H), 3.79 (s, 1.7H), 3.88 (br. s, 0.4H), 4.02-4.15 (m, 0.4H), 4.20-4.40 (m, 2H), 4.58 (br. s, 0.6H), 6.72-6.92 (m, 1H), 6.96-7.13 (m, 2H), 7.24-7.43 (m, 2H), 7.63-7.86 (m, 3H), 8.55 (td, 1H), 8.98 (dt, 1H).<br>LC-MS (method 1): $R_t$ = 0.74 min; m/z = 511 (M + H)$^+$. |
| 49 | (3-fluoro-6-methoxypyridin-2-yl)[6-{[2-(4-isopropylphenyl)imidazo[1,2-a]pyrimidin-3-yl]methyl}-2,6-diazabicyclo[3.2.2]non-2-yl]methanone (enantiomer 2)<br>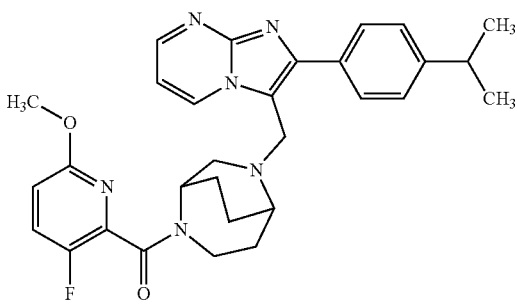<br>from 3-(2,6-diazabicyclo[3.2.2]non-6-ylmethyl)-2-(4-isopropylphenyl)imidazo[1,2-a]pyrimidine dihydrochloride (enantiomer 2) and 3-fluoro-6-methoxypyridine-2-carboxylic acid<br><br>$^1$H-NMR (400 MHz, DMSO-$d_6$): δ [ppm] = 1.15-1.32 (m, 6H), 1.33-1.53 (m, 0.6H), 1.57-2.11 (m, 5.4H), 2.58-2.81 (m, 1.4H), 2.86-3.01 (m, 1.6H), 3.03-3.21 (m, 1H), 3.24-3.43 (m, 1.2H), 3.58 (s, 1.2H), 3.70 (br. s, 0.4H), 3.78 (s, 1.8H), 4.05-4.17 (m, 0.4H), 4.17-4.39 (m, 2H), 4.58 (br. s, 0.6H), 6.80-7.00 (m, 1H), 7.08 (ddd, 1H), 7.27-7.44 (m, 2H), 7.63-7.69 (m, 3H), 8.49-8.59 (m, 1H), 8.97 (dt, 1H).<br>LC-MS (method 1): $R_t$ = 0.77 min; m/z = 529 (M + H)$^+$. |

-continued

| Example | Name/Structure/Starting materials<br>Analytical data |
|---|---|
| 50 | (3-chloro-6-methoxypyridin-2-yl)[6-{[2-(4-isopropylphenyl)imidazo[1,2-a]pyrimidin-3-yl]methyl}-2,6-diazabicyclo[3.2.2]non-2-yl]methanone (enantiomer 2) 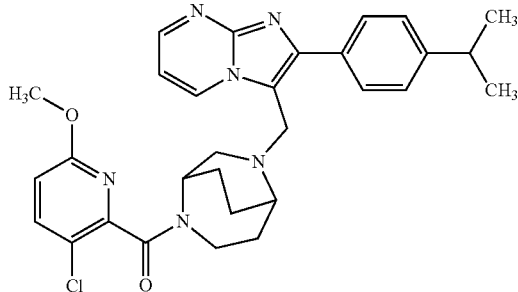 from 3-(2,6-diazabicyclo[3.2.2]non-6-ylmethyl)-2-(4-isopropylphenyl)imidazo[1,2-a]pyrimidine dihydrochloride (enantiomer 2) and 3-chloro-6-methoxypyridine-2-carboxylic acid<br><br>$^1$H-NMR (400 MHz, DMSO-d$_6$): δ [ppm] = −0.008 (1.20), 0.008 (1.19), 1.237 (15.36), 1.243 (7.29), 1.254 (16.00), 1.260 (7.11), 1.408 (0.52), 1.419 (0.55), 1.431 (0.42), 1.443 (0.61), 1.455 (0.55), 1.646 (0.48), 1.671 (0.89), 1.691 (1.13), 1.769 (0.44), 1.780 (0.51), 1.807 (0.99), 1.820 (1.01), 1.844 (0.84), 1.988 (0.50), 2.001 (0.50), 2.018 (0.57), 2.524 (0.88), 2.582 (0.41), 2.661 (0.59), 2.670 (0.48), 2.718 (0.67), 2.727 (0.74), 2.747 (1.00), 2.756 (0.88), 2.868 (1.01), 2.897 (0.74), 2.910 (0.49), 2.927 (0.98), 2.944 (1.27), 2.962 (0.94), 3.077 (0.86), 3.147 (0.66), 3.160 (1.18), 3.184 (0.59), 3.196 (0.60), 3.207 (0.54), 3.219 (0.65), 3.608 (3.83), 3.792 (15.73), 4.239 (1.97), 4.271 (2.12), 4.298 (2.12), 4.334 (0.76), 4.572 (1.02), 6.823 (1.23), 6.845 (1.27), 6.900 (3.37), 6.922 (3.48), 7.072 (2.09), 7.082 (2.12), 7.089 (2.08), 7.099 (2.09), 7.330 (3.38), 7.351 (3.88), 7.356 (1.84), 7.377 (1.40), 7.755 (4.00), 7.776 (3.62), 7.785 (2.25), 7.807 (2.51), 7.854 (3.36), 7.877 (3.23), 8.538 (0.58), 8.542 (0.63), 8.548 (0.64), 8.556 (1.61), 8.561 (1.70), 8.566 (1.61), 8.571 (1.49), 8.941 (1.49), 8.946 (1.57), 8.958 (1.62), 8.963 (1.47), 8.972 (0.58). LC-MS (method 1): R$_t$ = 0.81 min; m/z = 545/547 (M + H)$^+$. |
| 51 | [6-(difluoromethoxy)pyridin-2-yl][6-{[2-(4-isopropylphenyl)imidazo[1,2-a]pyrimidin-3-yl]methyl}-2,6-diazabicyclo[3.2.2]non-2-yl]methanone (enantiomer 2) 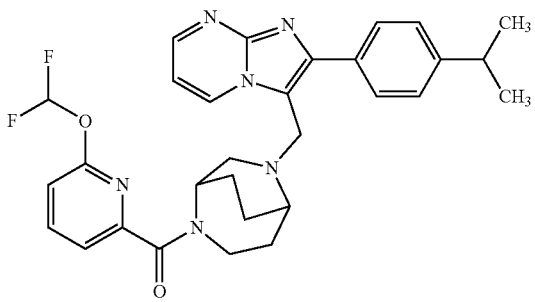 from 3-(2,6-diazabicyclo[3.2.2]non-6-ylmethyl)-2-(4-isopropylphenyl)imidazo[1,2-a]pyrimidine dihydrochloride (enantiomer 2) and 6-(difluoromethoxy)pyridine-2-carboxylic acid<br><br>$^1$H-NMR (400 MHz, DMSO-d$_6$): δ [ppm] = −0.008 (0.80), 0.008 (0.84), 1.218 (15.11), 1.236 (16.00), 1.242 (9.88), 1.260 (9.22), 1.423 (0.48), 1.435 (0.54), 1.446 (0.42), 1.458 (0.61), 1.470 (0.56), 1.625 (0.62), 1.651 (0.84), 1.676 (1.00), 1.690 (0.77), 1.703 (0.72), 1.742 (0.48), 1.770 (0.52), 1.779 (0.57), 1.795 (0.42), 1.807 (0.52), 1.845 (0.89), 1.866 (1.09), 1.980 (0.49), 1.996 (0.59), 2.010 (0.75), 2.524 (0.60), 2.665 (0.52), 2.682 (0.65), 2.694 (0.58), 2.731 (1.44), 2.738 (1.09), 2.759 (1.30), 2.767 (1.01), 2.907 (0.93), 2.925 (1.94), 2.934 (1.33), 2.942 (1.09), 2.952 (1.25), 2.958 (1.16), 2.968 (0.65), 3.067 (0.91), 3.076 (0.88), 3.119 (0.52), 3.357 (0.84), 3.369 (0.65), 3.380 (0.77), 3.390 (0.77), 3.426 (0.61), 3.440 (0.93), 3.452 (0.50), 3.475 (0.49), 3.902 (0.61), 3.991 (0.46), 4.026 (0.41), 4.220 (2.90), 4.236 (0.86), 4.272 (2.20), 4.297 (2.24), 4.333 (0.72), 4.577 (1.05), 7.072 (1.55), 7.077 (1.10), 7.082 (1.67), 7.088 (2.22), 7.094 (2.24), 7.099 (1.71), 7.104 (1.03), 7.113 (1.32), 7.161 (2.10), 7.181 (2.21), 7.252 (0.77), 7.266 (1.24), 7.284 (1.31), |

| Example | Name/Structure/Starting materials Analytical data |
|---|---|
| | 7.311 (3.44), 7.331 (3.73), 7.357 (2.31), 7.366 (2.23), 7.370 (2.30), 7.375 (2.59), 7.386 (2.22), 7.433 (1.55), 7.552 (2.69), 7.615 (0.72), 7.734 (1.26), 7.787 (4.08), 7.800 (2.78), 7.808 (3.87), 7.820 (2.15), 7.934 (0.93), 7.954 (1.24), 7.974 (0.84), 8.013 (1.64), 8.033 (2.12), 8.052 (1.47), 8.543 (0.89), 8.548 (1.04), 8.553 (2.38), 8.558 (2.44), 8.563 (1.63), 8.568 (1.46), 8.962 (1.49), 8.967 (1.57), 8.973 (1.08), 8.979 (2.10), 8.984 (1.51), 8.990 (0.95), 8.995 (0.81).<br>LC-MS (method 1): $R_t$ = 0.79 min; m/z = 547 (M + H)$^+$. |
| 52 | cyclopentyl[6-{[2-(4-isopropylphenyl)imidazo[1,2-a]pyrimidin-3-yl]methyl}-2,6-diazabicyclo[3.2.2]non-2-yl]methanone (enantiomer-2)<br>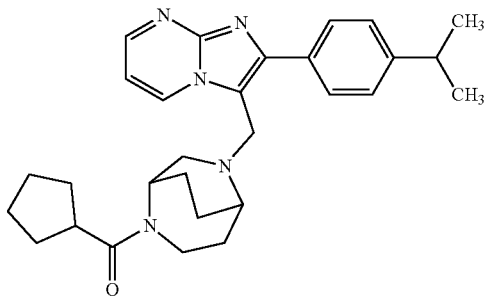<br>from 3-(2,6-diazabicyclo[3.2.2]non-6-ylmethyl)-2-(4-isopropylphenyl)imidazo[1,2-a]pyrimidine dihydrochloride (enantiomer 2) and cyclopentanecarboxylic acid<br>$^1$H-NMR (400 MHz, DMSO-d$_6$): δ [ppm] = −0.008 (0.63), 0.008 (0.57), 1.243 (15.74), 1.261 (16.00), 1.434 (0.72), 1.447 (0.75), 1.457 (0.70), 1.470 (0.91), 1.481 (1.03), 1.489 (1.15), 1.509 (1.28), 1.526 (1.57), 1.546 (2.00), 1.556 (1.68), 1.566 (1.60), 1.610 (0.62), 1.652 (1.36), 1.685 (2.06), 1.701 (1.19), 1.734 (0.69), 1.753 (0.67), 1.765 (0.66), 1.776 (0.58), 1.931 (0.45), 1.947 (0.42), 2.523 (0.41), 2.574 (0.70), 2.583 (0.73), 2.602 (0.97), 2.611 (0.89), 2.747 (0.97), 2.775 (0.78), 2.914 (0.42), 2.932 (1.07), 2.949 (1.46), 2.966 (1.43), 2.976 (1.07), 2.983 (1.12), 3.387 (0.49), 3.647 (0.52), 3.684 (0.42), 4.173 (0.58), 4.209 (2.11), 4.218 (2.62), 4.426 (0.80), 7.059 (0.98), 7.070 (1.04), 7.076 (1.09), 7.087 (1.11), 7.097 (0.41), 7.341 (2.44), 7.353 (1.24), 7.361 (2.76), 7.373 (1.09), 7.771 (3.12), 7.776 (2.19), 7.792 (2.96), 8.547 (1.46), 8.551 (1.61), 8.557 (1.55), 8.562 (1.45), 8.909 (1.01), 8.914 (1.04), 8.926 (1.06), 8.931 (1.13), 8.938 (0.46), 8.951 (0.40).<br>LC-MS (method 1): $R_t$ = 0.75 min; m/z = 472 (M + H)$^+$. |
| 53 | (3-fluoro-6-methoxypyridin-2-yl)[9-{[2-(4-isopropylphenyl)imidazo[1,2-a]pyrimidin-2-yl]methyl}-3,9-diazabicyclo[4.2.1]non-3-yl]methanone (enantiomer 1)<br>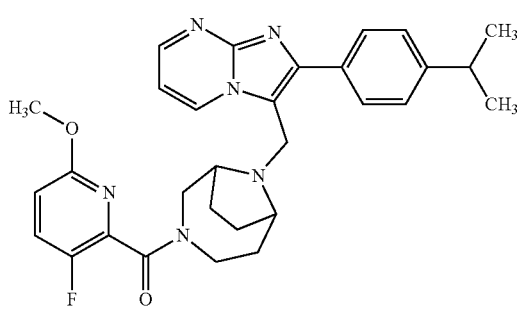<br>from 3-(3,9-diazabicyclo[4.2.1]non-9-ylmethyl)-2-(4-isopropylphenyl)imidazo[1,2-a]pyrimidine dihydrochloride (enantiomer 1) and 3-fluoro-6-methoxypyridine-2-carboxylic acid<br>$^1$H-NMR (400 MHz, DMSO-d$_6$): δ [ppm] = 1.24 (dd, 6H), 1.29-1.40 (m, 0.5H), 1.41-1.57 (m, 2H), 1.59-1.82 (m, 1.5H), 1.90-2.30 (m, 2H), 2.88-3.01 (m, 1.5H), 3.06-3.14 (m, 0.5H), 3.16-3.36 (m, 3.4H, partially covered by H$_2$O signal), 3.44 (br. d, 0.6H), 3.78 (d, 3H), 3.93 (br. d, 0.5H), 4.11-4.33 (m, 2.5H), 6.92 (dd, 1H), 7.04-7.14 (m, 1H), 7.31-7.41 (m, 2H), 7.71-7.84 (m, 3H), 8.52-8.60 (m, 1H), 9.12 (dd, 1H).<br>LC-MS (method 2): $R_t$ = 1.80 min; m/z = 529 (M + H)$^+$. |

| Example | Name/Structure/Starting materials<br>Analytical data |
|---|---|
| 54 | (3-chloro-6-methoxypyridin-2-yl)[9-{[2-(4-isopropylphenyl)imidazo[1,2-a]pyrimidin-3-yl]methyl}-3,9-diazabicyclo[4.2.1]non-3-yl]methanone (enantiomer 1)<br>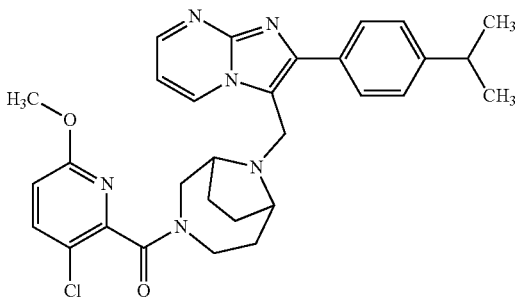<br>from 3-(3,9-diazabicyclo[4.2.1]non-9-ylmethyl)-2-(4-isopropylphenyl)imidazo[1,2-a]pyrimidine dihydrochloride (enantiomer 1) and 3-chloro-6-methoxypyridine-2-carboxylic acid<br><br>$^1$H-NMR (400 MHz, DMSO-d$_6$): δ [ppm] = 1.13-1.36 (m, 6.5H), 1.38-1.58 (m, 1.5H), 1.58-1.73 (m, 1.5H), 1.78-1.90 (m, 0.5H), 1.90-2.14 (m, 1H), 2.14-2.30 (m, 1H), 2.87-3.00 (m, 1.5H), 3.02-3.14 (m, 1.4H), 3.15-3.37 (m, 2.5H, partially covered by H$_2$O signal), 3.44 (br. d, 0.6H), 3.79 (d, 3H), 3.94-4.05 (m, 0.5H), 4.12-4.36 (m, 2.5H), 6.90 (dd, 1H), 7.04-7.14 (m, 1H), 7.28-7.42 (m, 2H), 7.70-7.90 (m, 3H), 8.50-8.62 (m, 1H), 9.06-9.19 (m, 1H).<br>LC-MS (method 2): R$_t$ = 1.88 min; m/z = 545/547 (M + H)$^+$. |
| 55 | [9-{[2-(4-isopropylphenyl)imidazo[1,2-a]pyrimidin-3-yl]methyl}-3,9-diazabicyclo[4.2.1]non-3-yl](6-methoxypyridin-2-yl)methanone (enantiomer 1)<br>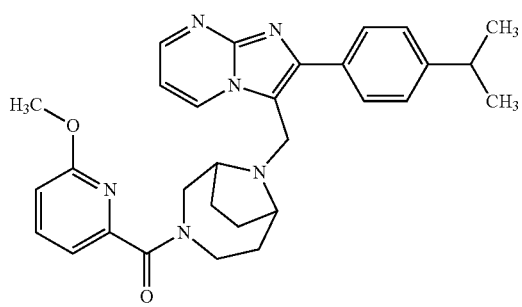<br>from 3-(3,9-diazabicyclo[4.2.1]non-9-ylmethyl)-2-(4-isopropylphenyl)imidazo[1,2-a]pyrimidine dihydrochloride (enantiomer 1) and 6-methoxypyridine-2-carboxylic acid<br><br>$^1$H-NMR (400 MHz, DMSO-d$_6$): δ [ppm] = 1.24 (d, 6H), 1.40-1.57 (m, 2.5H), 1.59-1.70 (m, 1H), 1.70-1.81 (m, 0.5H), 1.91-2.12 (m, 1H), 2.12-2.29 (m, 1H), 2.87-3.01 (m, 1.5H), 3.10-3.47 (m, 4H, partially covered by H$_2$O signal), 3.52 (br. d, 0.5H), 3.75-3.86 (m, 3.5H), 4.12-4.33 (m, 2.5H), 6.86 (dd, 1H), 7.03 (dd, 1H), 7.10 (td, 1H), 7.36 (dd, 2H), 7.70-7.85 (m, 3H), 8.56 (dt, 1H), 9.07-9.15 (m, 1H).<br>LC-MS (method 2): R$_t$ = 1.72 min; m/z = 511 (M + H)$^+$. |

| Example | Name/Structure/Starting materials<br>Analytical data |
|---|---|
| 56 | [6-(difluoromethoxy)pyridin-2-yl][9-{[2-(4-isopropylphenyl)imidazo[1,2-a]pyrimidin-3-yl]methyl}-3,9-diazabicyclo[4.2.1]non-3-yl]methanone (enantiomer 1)<br>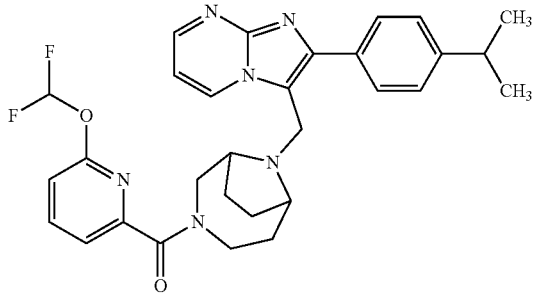<br>from 3-(3,9-diazabicyclo[4.2.1]non-9-ylmethyl)-2-(4-isopropylphenyl)imidazo[1,2-a]pyrimidine dihydrochloride (enantiomer 1) and 6-(difluoromethoxy)pyridine-2-carboxylic acid<br><br>$^1$H-NMR (400 MHz, DMSO-$d_6$): δ [ppm] = 1.24 (d, 6H), 1.31-1.56 (m, 2.5H), 1.59-1.75 (m, 1.5H), 1.89-2.11 (m, 1H), 2.12-2.29 (m, 1H), 2.88-3.01 (m, 1.5H), 3.05-3.39 (m, 3.5H, partially covered by H$_2$O signal), 3.40-3.51 (m, 1H), 3.81 (br. d, 0.5H), 4.14 (br. d, 0.5H), 4.24 (br. d, 2H), 7.03-7.19 (m, 2H), 7.30-7.41 (m, 3.25H), 7.54 (d, 0.5H), 7.72 (d, 0.25H), 7.79 (dd, 2H), 7.99 (q, 1H), 8.53-8.62 (m, 1H), 9.10 (ddd, 1H).<br>LC-MS (method 2): R$_t$ = 1.83 min; m/z = 547 (M + H)$^+$. |
| 57 | cyclopentyl[9-{[2-(4-isopropylphenyl)imidazo[1,2-a]pyrimidin-3-yl]methyl}-3,9-diazabicyclo[4.2.1]non-3-yl]methanone (enantiomer 1)<br>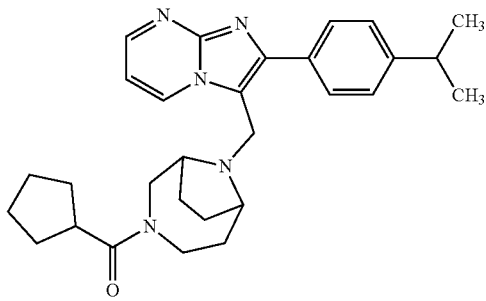<br>from 3-(3,9-diazabicyclo[4.2.1]non-9-ylmethyl)-2-(4-isopropylphenyl)imidazo[1,2-a]pyrimidine dihydrochloride (enantiomer 1) and cyclopentanecarboxylic acid<br><br>$^1$H-NMR (400 MHz, DMSO-$d_6$): δ [ppm] = 1.19-1.36 (m, 7.5H), 1.36-1.84 (m, 11H), 1.88-2.24 (m, 2H), 2.72 (dd, 0.75H), 2.81-3.02 (m, 2H), 3.07-3.19 (m, 0.75H), 3.21-3.36 (m, 2H, partially covered by H$_2$O signal), 3.52 (br. d, 0.4H), 3.57-3.70 (m, 1H), 4.03 (br. d, 0.6H), 4.17-4.30 (m, 2H), 7.09 (dd, 1H), 7.37 (d, 2H), 7.79 (d, 2H), 8.57 (dd, 1H), 9.03-9.13 (m, 1H).<br>LC-MS (method 2): R$_t$ = 1.83 min; m/z = 472 (M + H)$^+$. |

| Example | Name/Structure/Starting materials<br>Analytical data |
| --- | --- |
| 58 | (3-fluoro-6-methoxypyridin-2-yl)[9-{[2-(4-isopropylphenyl)imidazo[1,2-a]pyrimidin-3-yl]methyl}-3,9-diazabicyclo[4.2.1]non-3-yl]methanone (enantiomer 2)<br>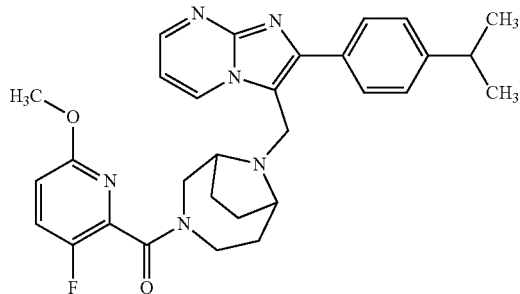<br>from 3-(3,9-diazabicyclo[4.2.1]non-9-ylmethyl)-2-(4-isopropylphenyl)imidazo[1,2-a]pyrimidine dihydrochloride (enantiomer 2) and 3-fluoro-6-methoxypyridine-2-carboxylic acid<br><br>$^1$H-NMR (400 MHz, DMSO-$d_6$): δ [ppm] = 1.24 (dd, 6H), 1.29-1.40 (m, 0.5H), 1.41-1.56 (m, 2H), 1.59-1.82 (m, 1.5H), 1.91-2.29 (m, 2H), 2.88-3.01 (m, 1.5H), 3.06-3.15 (m, 0.5H), 3.16-3.37 (m, 3.4H, partially covered by H$_2$O signal ), 3.44 (br. d, 0.6H), 3.78 (d, 3H), 3.93 (br. d, 0.5H), 4.12-4.33 (m, 2.5H), 6.92 (dd, 1H), 7.05-7.14 (m, 1H), 7.32-7.41 (m, 2H), 7.71-7.84 (m, 3H), 8.52-8.60 (m, 1H), 9.12 (dd, 1H).<br>LC-MS (method 1): R$_t$ = 0.92 min; m/z = 529 (M + H)$^+$. |
| 59 | (3-chloro-6-methoxypyridin-2-yl)[9-{[2-(4-isopropylphenyl)imidazo[1,2-a]pyrimidin-3-yl]methyl}-3,9-diazabicyclo[4.2.1]non-3-yl]methanone (enantiomer 2)<br>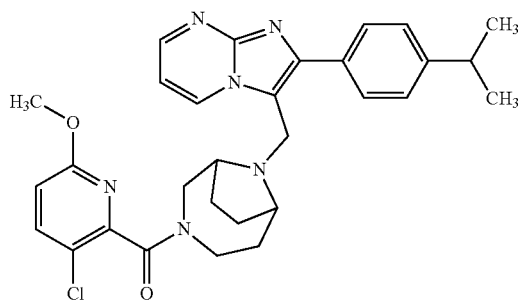<br>from 3-(3,9-diazabicyclo[4.2.1]non-9-ylmethyl)-2-(4-isopropylphenyl)imidazo[1,2-a]pyrimidine dihydrochloride (enantiomer 2) and 3-chloro-6-methoxypyridine-2-carboxylic acid<br><br>$^1$H-NMR (400 MHz, DMSO-$d_6$): δ [ppm] = 1.19-1.36 (m, 6.5H), 1.38-1.58 (m, 1.5H), 1.58-1.72 (m, 1.5H), 1.78-1.90 (m, 0.5H), 1.91-2.14 (m, 1H), 2.14-2.29 (m, 1H), 2.88-3.00 (m, 1.5H), 3.02-3.14 (m, 1.4H), 3.15-3.36 (m, 2.5H, partially covered by H$_2$O signal), 3.44 (br. d, 0.6H), 3.79 (d, 3H), 3.94-4.05 (m, 0.5H), 4.13-4.36 (m, 2.5H), 6.90 (dd, 1H), 7.05-7.14 (m, 1H), 7.32-7.42 (m, 2H), 7.73-7.90 (m, 3H), 8.52-8.62 (m, 1H), 9.08-9.19 (m, 1H).<br>LC-MS (method 1): R$_t$ = 0.96 min; m/z = 545/547 (M + H)$^+$. |

| Example | Name/Structure/Starting materials<br>Analytical data |
|---|---|
| 60 | [9-{[2-(4-isopropylphenyl)imidazo[1,2-a]pyrimidin-3-yl]methyl}-3,9-diazabicyclo[4.2.1]non-3-yl](6-methoxypyridin-2-yl)methanone (enantiomer 2)<br>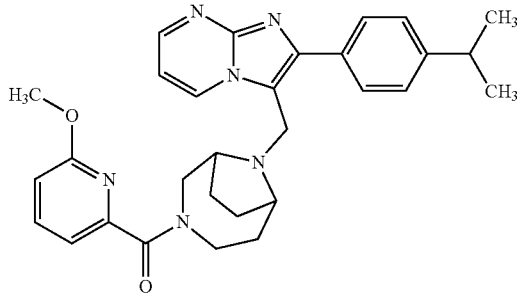<br>from 3-(3,9-diazabicyclo[4.2.1]non-9-ylmethyl)-2-(4-isopropylphenyl)imidazo[1,2-a]pyrimidine dihydrochloride (enantiomer 2) and 6-methoxypyridine-2-carboxylic acid<br><br>$^1$H-NMR (400 MHz, DMSO-$d_6$): δ [ppm] = 1.24 (d, 6H), 1.39-1.57 (m, 2.5H), 1.59-1.70 (m, 1H), 1.70-1.81 (m, 0.5H), 1.89-2.12 (m, 1H), 2.12-2.29 (m, 1H), 2.87-3.01 (m, 1.5H), 3.10-3.47 (m, 4H, partially covered by H$_2$O signal), 3.52 (br. d, 0.5H), 3.75-3.88 (m, 3.5H), 4.12-4.34 (m, 2.5H), 6.86 (dd, 1H), 7.03 (dd, 1H), 7.10 (td, 1H), 7.36 (dd, 2H), 7.71-7.84 (m, 3H), 8.57 (dt, 1H), 9.06-9.15 (m, 1H).<br>LC-MS (method 1): R$_t$ = 0.88 min; m/z = 511 (M + H)$^+$. |
| 61 | [6-(difluoromethoxy)pyridin-2-yl][9-{[2-(4-isopropylphenyl)imidazo[1,2-a]pyrimidin-3-yl]methyl}-3,9-diazabicyclo[4.2.1]non-3-yl]methanone (enantiomer 2)<br>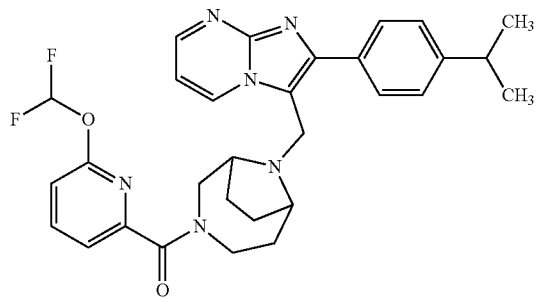<br>from 3-(3,9-diazabicyclo[4.2.1]non-9-ylmethyl)-2-(4-isopropylphenyl)imidazo[1,2-a]pyrimidine dihydrochloride (enantiomer 2) and 6-(difluoromethoxy)pyridine-2-carboxylic acid<br><br>$^1$H-NMR (400 MHz, DMSO-$d_6$): δ [ppm] = 1.24 (dd, 6H), 1.31-1.57 (m, 2.5H), 1.59-1.75 (m, 1.5H), 1.89-2.11 (m, 1H), 2.12-2.29 (m, 1H), 2.87-3.01 (m, 1.5H), 3.04-3.39 (m, 3.5H, partially covered by H$_2$O signal), 3.39-3.51 (m, 1H), 3.81 (br. d, 0.5H), 4.14 (br. d, 0.5H), 4.25 (br. d, 2H), 7.05-7.19 (m, 2H), 7.29-7.41 (m, 3.5H), 7.54 (d, 0.5H), 7.72 (d, 0.25H), 7.79 (dd, 2H), 7.99 (q, 1H), 8.53-8.62 (m, 1H), 9.10 (ddd, 1H).<br>LC-MS (method 2): R$_t$ = 1.82 min; m/z = 547 (M + H)$^+$. |

| Example | Name/Structure/Starting materials<br>Analytical data |
|---|---|
| 62 | cyclopentyl[9-{[2-(4-isopropylphenyl)imidazo[1,2-a]pyrimidin-3-yl]methyl}-3,9-diazabicyclo[4.2.1]non-3-yl]methanone (enantiomer 2)<br>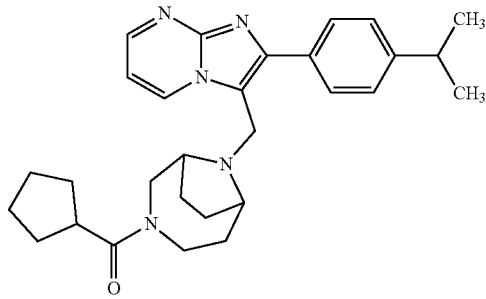<br>from 3-(3,9-diazabicyclo[4.2.1]non-9-ylmethyl)-2-(4-isopropylphenyl)imidazo[1,2-a]pyrimidine dihydrochloride (enantiomer 2) and cyclopentanecarboxylic acid<br><br>$^1$H-NMR (400 MHz, DMSO-d$_6$): δ [ppm] = 1.20-1.36 (m, 7.5H), 1.36-1.83 (m, 11H), 1.88-2.24 (m, 2H), 2.72 (dd, 0.75H), 2.81-3.02 (m, 2H), 3.07-3.18 (m, 0.75H), 3.21-3.36 (m, 2H, partially covered by H$_2$O signal), 3.52 (br. d, 0.4H), 3.57-3.70 (m, 1H), 4.03 (br. d, 0.6H), 4.16-4.30 (m, 2H), 7.09 (dd, 1H), 7.37 (d, 2H), 7.79 (d, 2H), 8.57 (dd, 1H), 9.03-9.13 (m, 1H).<br>LC-MS (method 2): R$_t$ = 1.82 min; m/z = 472 (M + H)$^+$. |
| 63 | (−)-(2-fluorophenyl)[9-{[2-(4-isopropylphenyl)imidazo[1,2-a]pyrimidin-3-yl]methyl}-3,9-diazabicyclo[4.2.1]non-3-yl]methanone (enantiomer 1)<br>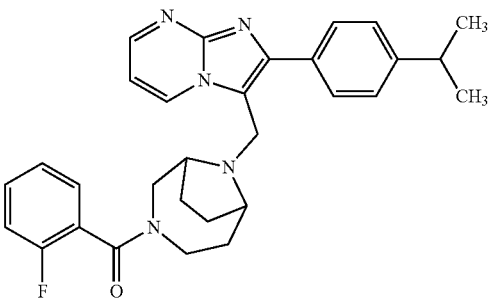<br>from 3-(3,9-diazabicyclo[4.2.1]non-9-ylmethyl)-2-(4-isopropylphenyl)imidazo[1,2-a]pyrimidine dihydrochloride (enantiomer 1) and 2-fluorobenzoic acid<br><br>$^1$H-NMR (400 MHz, DMSO-d$_6$): δ [ppm] = 1.00-1.12 (m, 0.5H), 1.16-1.36 (m, 7H), 1.37-1.74 (m, 3.25H), 1.89-2.29 (m, 2H), 2.87-3.39 (m, 5.25H, partially covered by H$_2$O signal), 3.45 (br. d, 0.5H), 4.07 (br. d, 0.5H), 4.23 (br. d, 2H), 7.05-7.16 (m, 1H), 7.16-7.32 (m, 3H), 7.37 (t, 2H), 7.41-7.51 (m, 1H), 7.78 (dd, 2H), 8.53-8.61 (m, 1H), 9.04-9.15 (m, 1H).<br>LC-MS (method 2): R$_t$ = 1.81 min; m/z = 498 (M + H)$^+$.<br>$[α]_D^{20}$ = −8.72° (c = 0.260, Methanol). |

| Example | Name/Structure/Starting materials<br>Analytical data |
|---|---|
| 64 | (+)-(2-fluorophenyl)[9-{[2-(4-isopropylphenyl)imidazo[1,2-a]pyrimidin-3-yl]methyl}-3,9-diazabicyclo[4.2.1]non-3-yl]methanone (enantiomer 2)<br>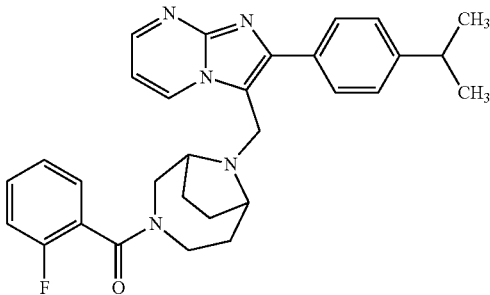<br>from 3-(3,9-diazabicyclo[4.2.1]non-9-ylmethyl)-2-(4-isopropylphenyl)imidazo[1,2-a]pyrimidine dihydrochloride (enantiomer 2) and 2-fluorobenzoic acid<br><br>$^1$H-NMR (400 MHz, DMSO-d$_6$): δ [ppm] = 1.00-1.12 (m, 0.5H), 1.17-1.36 (m, 7H), 1.38-1.74 (m, 3.25H), 1.89-2.29 (m, 2H), 2.87-3.40 (m, 5.25H, partially covered by H$_2$O signal), 3.45 (br. d, 0.5H), 4.07 (br. d, 0.5H), 4.23 (br. d, 2H), 7.05-7.16 (m, 1H), 7.16-7.32 (m, 3H), 7.37 (t, 2H), 7.41-7.51 (m, 1H), 7.78 (dd, 2H), 8.54-8.61 (m, 1H), 9.03-9.15 (m, 1H).<br>LC-MS (method 2): R$_t$ = 1.82 min; m/z = 498 (M + H)$^+$.<br>[α]$_D^{20}$ = +7.98° (c = 0.280, Methanol). |
| 65 | [6-{[2-(4-chlorophenyl)imidazo[1,2-a]pyrimidin-3-yl]methyl}-2,6-diazabicyclo[3.2.2]non-2-yl][6-(trifluoromethoxy)pyridin-2-yl]methanone (enantiomer 2)<br>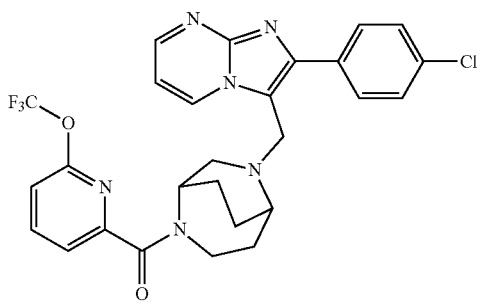<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 2) and 6-(trifluoromethoxy)pyridine-2-carboxylic acid<br><br>$^1$H-NMR (400 MHz, DMSO-d$_6$): δ [ppm] = −0.149 (0.67), −0.008 (4.28), 0.008 (4.04), 0.147 (0.54), 1.401 (1.79), 1.413 (1.82), 1.435 (2.05), 1.446 (2.05), 1.651 (5.25), 1.681 (3.33), 1.724 (1.68), 1.762 (1.95), 1.790 (1.89), 1.853 (3.67), 1.995 (2.19), 2.328 (1.35), 2.367 (1.25), 2.581 (1.45), 2.594 (1.58), 2.610 (2.09), 2.623 (1.85), 2.671 (1.48), 2.710 (5.39), 2.718 (3.17), 2.738 (5.09), 2.747 (3.54), 2.865 (3.77), 2.894 (2.73), 3.039 (3.23), 3.118 (2.05), 3.330 (3.77), 3.343 (2.80), 3.353 (3.60), 3.364 (2.63), 3.411 (3.40), 3.424 (1.92), 3.447 (1.58), 3.819 (2.22), 4.033 (1.58), 4.067 (1.45), 4.221 (10.91), 4.238 (2.53), 4.274 (8.66), 4.290 (8.56), 4.326 (2.12), 4.569 (3.74), 7.084 (5.22), 7.094 (6.84), 7.101 (5.83), 7.107 (4.01), 7.112 (6.80), 7.123 (3.37), 7.288 (4.95), 7.309 (5.42), 7.376 (8.35), 7.396 (8.62), 7.465 (4.72), 7.484 (6.37), 7.491 (14.18), 7.512 (16.00), 7.527 (8.49), 7.545 (15.43), 7.566 (9.30), 7.882 (15.66), 7.904 (14.28), 7.922 (9.87), 7.943 (8.39), 8.050 (3.60), 8.070 (5.05), 8.089 (3.13), 8.126 (5.89), 8.146 (8.45), 8.166 (5.09), 8.569 (3.40), 8.574 (3.84), 8.580 (8.62), 8.585 (8.89), 8.590 (6.27), 8.595 (5.66), 8.982 (5.12), 8.987 (5.25), 8.999 (5.29), 9.004 (5.29), 9.010 (3.50), 9.015 (3.27), 9.028 (3.03), 9.032 (3.03).<br>LC-MS (method 1): R$_t$ = 0.81 min; m/z = 557/559 (M + H)$^+$. |

| Example | Name/Structure/Starting materials<br>Analytical data |
|---|---|
| 66 | [6-{[2-(4-chlorophenyl)imidazo[1,2-a]pyrimidin-3-yl]methyl}-2,6-diazabicyclo[3.2.2]non-2-yl][6-(trifluoromethoxy)pyridin-2-yl]methanone (enantiomer 1)<br>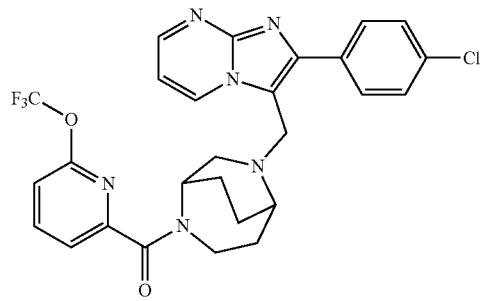<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 1) and 6-(trifluoromethoxy)pyridine-2-carboxylic acid<br><br>$^1$H-NMR (400 MHz, DMSO-$d_6$): δ [ppm] = 1.36-1.50 (m, 0.6H), 1.55-2.06 (m, 5.4H), 2.57-2.93 (m, 2H), 2.99-3.18 (m, 1H), 3.35-3.49 (m, 1.6H), 3.77-3.86 (m, 0.4H), 4.01-4.11 (m, 0.4H), 4.20-4.36 (m, 2H), 4.52-4.61 (m, 0.6H), 7.10 (dt, 1H), 7.24-7.43 (m, 1H), 7.44-7.62 (m, 3H), 7.84-8.00 (m, 2H), 8.02-8.19 (m, 1H), 8.51-8.64 (m, 1H), 8.91-9.10 (m, 1H).<br>LC-MS (method 2): $R_t$ = 1.57 min; m/z = 557/559 (M + H)$^+$. |
| 67 | [6-{[2-(4-chlorophenyl)imidazo[1,2-a]pyrimidin-3-yl]methyl}-2,6-diazabicyclo[3.2.2]non-2-yl][6-(difluoromethoxy)pyridin-2-yl]methanone (enantiomer 2)<br>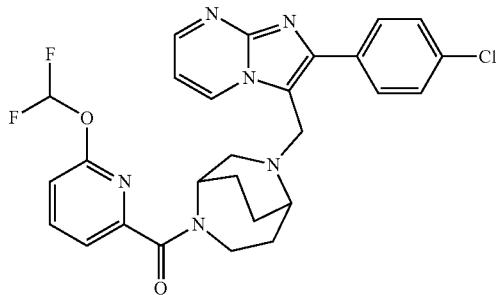<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 2) and 6-(difluoromethoxy)pyridine-2-carboxylic acid<br><br>$^1$H-NMR (400 MHz, DMSO-$d_6$): δ [ppm] = −0.150 (0.63), 0.008 (3.74), 1.423 (1.51), 1.447 (1.69), 1.622 (2.57), 1.637 (3.51), 1.673 (2.97), 1.760 (1.71), 1.852 (2.80), 1.989 (2.37), 2.073 (2.66), 2.327 (1.23), 2.366 (1.00), 2.650 (1.03), 2.679 (2.34), 2.690 (1.80), 2.722 (4.06), 2.750 (3.69), 2.887 (2.97), 2.917 (2.17), 3.021 (2.63), 3.107 (1.63), 3.351 (2.49), 3.373 (2.23), 3.424 (2.89), 3.461 (1.31), 3.893 (1.91), 3.985 (1.31), 4.022 (1.34), 4.221 (8.97), 4.241 (1.51), 4.278 (7.77), 4.286 (7.74), 4.323 (1.09), 4.559 (3.03), 7.094 (4.77), 7.097 (5.06), 7.108 (5.20), 7.114 |

| Example | Name/Structure/Starting materials Analytical data |
|---|---|
| | (9.40), 7.125 (4.69), 7.160 (6.40), 7.180 (6.71), 7.232 (2.20), 7.293 (3.86), 7.311 (4.11), 7.338 (6.34), 7.356 (6.54), 7.406 (3.89), 7.414 (4.66), 7.508 (11.46), 7.529 (12.60), 7.550 (7.23), 7.571 (7.77), 7.588 (7.89), 7.596 (2.40), 7.769 (3.63), 7.900 (12.77), 7.922 (16.00), 7.940 (5.40), 7.944 (7.00), 7.960 (3.94), 7.980 (2.49), 8.010 (4.74), 8.030 (6.14), 8.050 (4.14), 8.571 (2.71), 8.575 (3.51), 8.581 (7.37), 8.586 (7.54), 8.591 (4.91), 8.596 (4.31), 8.988 (4.20), 8.993 (4.11), 9.005 (4.37), 9.010 (4.60), 9.018 (2.77), 9.031 (2.51).<br>LC-MS (method 1): $R_t$ = 0.76 min; m/z = 539/541 (M + H)$^+$. |
| 68 | [6-{[2-(4-chlorophenyl)imidazo[1,2-a]pyrimidin-3-yl]methyl}-2,6-diazabicyclo[3.2.2]non-2-yl][6-(difluoromethoxy)pyridin-2-yl]methanone (enantiomer 1)<br>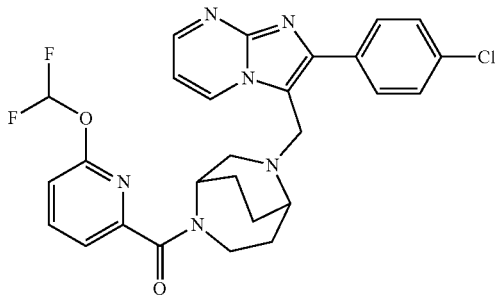<br>from 2-(4-chlorophenyl)-3-(2,6-diazabicyclo[3.2.2]non-6-ylmethyl)imidazo[1,2-a]pyrimidine bis(trifluoroacetic acid) salt (enantiomer 1) and 6-(difluoromethoxy)pyridine-2-carboxylic acid<br>$^1$H-NMR (400 MHz, DMSO-d$_6$): δ [ppm] = −0.149 (0.59), −0.008 (4.53), 0.008 (4.08), 0.146 (0.52), 1.412 (1.34), 1.423 (1.45), 1.435 (1.23), 1.446 (1.71), 1.459 (1.60), 1.623 (2.56), 1.648 (3.53), 1.673 (3.04), 1.759 (1.60), 1.853 (2.82), 1.990 (1.82), 2.073 (3.19), 2.328 (1.11), 2.366 (1.30), 2.524 (3.53), 2.650 (0.89), 2.678 (2.26), 2.691 (1.86), 2.711 (1.82), 2.722 (4.08), 2.750 (3.64), 2.760 (3.04), 2.888 (3.08), 2.916 (2.19), 3.031 (2.52), 3.104 (1.52), 3.350 (2.38), 3.373 (2.26), 3.425 (2.78), 3.438 (1.60), 3.461 (1.30), 3.892 (1.78), 3.986 (1.41), 4.021 (1.26), 4.221 (8.98), 4.241 (1.34), 4.278 (7.76), 4.286 (7.83), 4.322 (1.08), 4.558 (3.04), 7.097 (5.53), 7.101 (3.56), 7.107 (5.16), 7.114 (9.50), 7.124 (4.90), 7.128 (3.23), 7.160 (6.50), 7.181 (6.79), 7.232 (2.34), 7.293 (3.97), 7.312 (4.08), 7.338 (6.46), 7.357 (6.61), 7.406 (4.12), 7.414 (4.94), 7.508 (11.62), 7.529 (13.10), 7.550 (7.20), 7.571 (8.13), 7.588 (8.32), 7.596 (2.41), 7.769 (3.71), 7.900 (13.07), 7.922 (16.00), 7.940 (5.46), 7.945 (7.31), 7.960 (3.94), 7.980 (2.60), 8.010 (4.86), 8.030 (6.27), 8.049 (4.34), 8.570 (2.82), 8.575 (3.42), 8.581 (7.42), 8.586 (7.61), 8.591 (4.94), 8.596 (4.45), 8.988 (4.23), 8.993 (4.34), 9.005 (4.38), 9.010 (4.60), 9.018 (2.67), 9.030 (2.60), 9.035 (2.30).<br>LC-MS (method 1): $R_t$ = 0.75 min; m/z = 539/541 (M + H)$^+$. |

Analogously to Examples 13-16, the following compounds were prepared from the starting materials specified in each case:

| Example | Name/Structure/Starting materials Analytical data |
|---|---|
| 69 | [3-{[2-(4-chlorophenyl)imidazo[1,2-a]pyridin-3-yl]methyl}-3,9-diazabicyclo[4.2.1]non-9-yl](2-fluorophenyl)methanone (racemtate)<br><br>from 2-(4-chlorophenyl)imidazo[1,2-a]pyridine-3-carbaldehyde and 3,9-diazabicyclo[4.2.1]non-9-yl (2-fluorophenyl)methanone (racemate)<br><br>¹H-NMR (400 MHz, DMSO-d₆): δ [ppm] = 1.21-1.35 (m, 0.5H), 1.35-1.47 (m, 1.5H), 1.51-1.67 (m, 1H), 1.68-1.79 (m, 0.5H), 1.79-1.93 (m, 1H), 1.93-2.20 (m, 2H), 2.30-2.45 (m, 1.5H), 2.55-2.68 (m, 1H), 2.70-2.85 (m, 1H), 3.62-3.81 (m, 1H), 3.99-4.24 (m, 2H), 4.43-4.64 (m, 1H), 6.91-7.03 (m, 1H), 7.18-7.28 (m, 2H), 7.28-7.37 (m, 2H), 7.42-7.48 (m, 1H), 7.53 (dd, 2H), 7.60 (dd, 1H), 7.93 (dd, 2H), 8.60 (dd, 1H).<br>LC-MS (method 2): R_t = 1.60 min; m/z = 489/491 (M + H)⁺. |
| 70 | [3-{[2-(4-chlorophenyl)imidazo[1,2-a]pyridin-3-yl]methyl}-3,9-diazabicyclo[4.2.1]non-9-yl](6-methoxypyridin-2-yl)methanone (racemate)<br><br>from 2-(4-chlorophenyl)imidazo[1,2-a]pyridine-3-carbaldehyde and 3,9-diazabicyclo[4.2.1]non-9-yl (6-methoxypyridin-2-yl)methanone (racemate)<br><br>¹H-NMR (400 MHz, DMSO-d₆): δ [ppm] = −0.008 (2.46), 0.008 (2.02), 1.328 (0.55), 1.365 (0.56), 1.393 (0.56), 1.478 (0.46), 1.633 (1.82), 1.654 (0.70), 1.746 (0.52), 1.776 (0.43), 1.806 (0.48), 1.828 (0.83), 1.856 (1.18), 1.875 (1.04), 1.893 (0.57), 1.989 (0.96), 2.009 (0.83), 2.058 (0.53), 2.092 (0.46), 2.328 (0.66), 2.367 (0.96), 2.390 (0.67), 2.423 (0.72), 2.459 (1.06), 2.524 (1.29), 2.568 (1.07), 2.598 (0.92), 2.621 (0.65), 2.664 (1.20), 2.686 (0.68), 2.710 (0.51), 2.738 (0.62), 2.771 (0.52), 2.826 (0.47), 2.849 (0.41), 3.755 (14.92), 3.791 (16.00), 4.095 (4.59), 4.134 (2.13), 4.154 (2.17), 4.190 (0.61), 4.430 (0.57), 4.451 (1.12), 4.471 (0.60), 4.583 (0.45), 4.611 (1.18), 4.640 (1.06), 4.667 (0.81), 6.890 (3.80), 6.910 (3.98), 6.942 (0.82), 6.957 (2.25), 6.959 (2.26), 6.974 (2.33), 6.991 (0.82), 7.228 (2.00), 7.245 (2.10), 7.286 (2.22), 7.290 (1.87), 7.305 (2.73), 7.312 (2.17), 7.329 (1.71), 7.506 (3.92), 7.513 (4.20), 7.527 (4.44), 7.535 (4.43), 7.585 (2.00), 7.588 (2.02), 7.591 (2.02), 7.608 (1.71), 7.611 (1.73), 7.614 (1.73), 7.765 (1.61), 7.778 (1.79), 7.783 (1.86), 7.786 (1.91), 7.796 (1.95), 7.798 (2.00), 7.804 (1.50), 7.817 (1.48), 7.912 (3.91), 7.934 (3.50), 7.952 (4.15), 7.973 (3.67), 8.587 (1.44), 8.608 (2.15), 8.626 (1.46).<br>LC-MS (method 2): R_t = 1.60 min; m/z = 502/504 (M + H)⁺. |
| 71 | (3-{[2-(4-chlorophenyl)imidazo[1,2-a]pyridin-3-yl]methyl}-8-oxa-3,10-diazabicyclo[4.3.1]dec-10-yl)(2-fluorophenyl)methanone (racemate)<br><br>from 2-(4-chlorophenyl)imidazo[1,2-a]pyridine-3-carbaldehyde and (2-fluorophenyl)[8-oxa-3,10-diazabicyclo[4.3.1]dec-10-yl]methanone trifluoroacetic acid salt (racemate)<br><br>¹H-NMR (400 MHz, DMSO-d₆): δ [ppm] = 1.488 (2.65), 1.661 (1.13), 2.028 (0.96), 2.440 (1.00), 2.456 (1.59), 2.473 (2.09), 2.524 (3.57), 2.671 (0.68), 2.711 (0.81), 2.767 (2.29), 2.780 (1.79), 2.802 (2.15), 2.815 (3.34), 2.848 (3.60), 3.039 (1.18), 3.387 (2.69), 3.416 (2.28), 3.448 (5.59), 3.472 (5.42), 3.538 (2.11), 3.546 (2.32), 3.567 (4.55), 3.576 (5.40), 3.604 (6.93), 3.632 (3.21), 3.784 (5.22), 3.813 (4.14), 4.125 (1.55), 4.131 (1.57), 4.161 (8.90), 4.170 (11.10), 4.188 (4.21), 4.207 (1.61), 4.225 (1.14), 4.466 (2.02), 4.484 (2.03), 4.515 (3.24), 4.908 (0.64), 6.854 (0.54), 6.934 (2.39), 6.951 (5.95), 6.968 (5.63), 6.984 (2.15), 7.187 (1.02), 7.210 (1.94), 7.240 (5.01), 7.262 (5.03), 7.285 (5.16), 7.305 (5.49), 7.324 (6.57), 7.341 (4.97), 7.371 (1.56), 7.448 (1.16), 7.462 (2.18), 7.470 (2.52), 7.491 (9.03), 7.514 (16.00), 7.536 (10.46), 7.565 (0.67), 7.595 (5.16), 7.617 (4.66), 7.629 (3.69), 7.652 (2.95), 7.861 (0.58), 7.882 (0.51), 7.944 (5.98), 7.965 (7.09), 7.972 (12.53), 7.993 (10.26), 8.638 (2.48), 8.656 (2.46), 8.733 (3.86), 8.750 (3.82).<br>LC-MS (method 2): R_t = 1.48 min; m/z = 505/507 (M + H)⁺. |

| Example | Name/Structure/Starting materials Analytical data |
|---|---|
| 72 | [3-{[2-(4-chlorophenyl)imidazo[1,2-a]pyridin-3-yl]methyl}-8-oxa-3,10-diazabicyclo[4.3.1]dec-10-yl](6-methoxypyridin-2-yl)methanone (racemate)

from 2-(4-chlorophenyl)imidazo[1,2-a]pyridine-3-carbaldehyde and (6-methoxypyridin-2-yl)[8-oxa-3,10-diazabicyclo[4.3.1]dec-10-yl]methanone bis(trifluoroacetic acid) salt (racemate)

$^1$H-NMR (400 MHz, DMSO-d$_6$): δ [ppm] = 1.567 (0.87), 1.592 (0.80), 1.788 (0.52), 2.608 (1.26), 2.638 (1.30), 2.657 (0.64), 2.834 (1.95), 2.858 (2.13), 2.884 (0.69), 2.966 (0.86), 2.980 (0.97), 2.996 (0.69), 3.011 (0.60), 3.430 (1.06), 3.437 (1.03), 3.459 (1.38), 3.466 (1.31), 3.484 (0.59), 3.492 (0.60), 3.513 (0.82), 3.521 (0.77), 3.551 (1.85), 3.579 (1.68), 3.598 (1.83), 3.604 (1.80), 3.625 (1.64), 3.741 (16.00), 3.755 (10.52), 3.768 (2.31), 3.798 (1.62), 3.826 (0.99), 3.844 (1.13), 4.030 (0.59), 4.144 (0.83), 4.162 (1.98), 4.171 (2.27), 4.179 (2.74), 4.201 (2.58), 4.237 (0.72), 4.420 (0.60), 4.514 (1.25), 6.831 (1.53), 6.852 (1.73), 6.865 (3.41), 6.880 (3.01), 6.887 (3.01), 6.895 (1.71), 6.912 (1.93), 6.929 (1.02), 7.089 (2.50), 7.106 (2.60), 7.271 (0.69), 7.283 (1.18), 7.297 (1.37), 7.305 (1.44), 7.321 (1.10), 7.469 (2.60), 7.484 (4.84), 7.489 (3.91), 7.505 (4.37), 7.584 (3.37), 7.606 (3.06), 7.620 (1.39), 7.640 (0.89), 7.773 (1.60), 7.792 (2.16), 7.812 (1.47), 7.911 (2.78), 7.932 (2.50), 7.959 (4.47), 7.980 (4.02), 8.728 (2.05), 8.745 (1.91).
LC-MS (method 2): R$_t$ = 1.44 min; m/z = 518 (M + H)$^+$. |
| 73 | [3-{[2-(4-chlorophenyl)imidazo[1,2-a]pyridin-3-yl]methyl}-8-oxa-3,10-diazabicyclo[4.3.1]dec-10-yl](4-methyl-1,2,5-oxadiazol-3-yl)methanone (racemate)

from 2-(4-chlorophenyl)imidazo[1,2-a]pyridine-3-carbaldehyde and (4-methyl-1,2,5-oxadiazol-3-yl)[8-oxa-3,10-diazabicyclo[4.3.1]dec-10-yl]methanone trifluoroacetic acid salt (racemate)

$^1$H-NMR (400 MHz, DMSO-d$_6$): δ [ppm] = 0.008 (0.45), 1.596 (0.63), 1.631 (0.49), 1.658 (0.43), 1.867 (0.57), 1.888 (0.61), 2.397 (14.19), 2.407 (16.00), 2.616 (0.46), 2.638 (0.42), 2.661 (1.05), 2.666 (0.98), 2.690 (0.81), 2.697 (0.78), 2.815 (0.74), 2.846 (1.68), 2.879 (1.06), 2.897 (0.53), 2.905 (0.65), 2.961 (0.75), 2.977 (0.84), 2.992 (0.60), 3.008 (0.54), 3.124 (0.58), 3.146 (0.76), 3.153 (0.68), 3.175 (0.60), 3.502 (1.34), 3.530 (1.75), 3.603 (1.20), 3.634 (2.86), 3.661 (1.94), 3.688 (0.96), 3.789 (1.53), 3.818 (1.34), 3.826 (1.51), 3.856 (1.09), 3.874 (0.83), 3.896 (0.80), 4.006 (0.71), 4.027 (0.66), 4.143 (0.55), 4.174 (5.38), 4.194 (2.21), 4.230 (0.50), 4.460 (0.74), 4.540 (0.97), 6.709 (0.73), 6.726 (1.45), 6.743 (0.79), 6.819 (0.81), 6.836 (1.65), 6.853 (0.90), 7.197 (0.76), 7.219 (0.96), 7.236 (0.83), 7.268 (0.86), 7.290 (1.09), 7.307 (0.95), 7.451 (3.37), 7.467 (5.00), 7.472 (4.76), 7.488 (4.09), 7.544 (1.78), 7.566 (1.57), 7.578 (1.88), 7.601 (1.61), 7.908 (3.71), 7.929 (3.34), 7.946 (4.19), 7.967 (3.71), 8.545 (1.42), 8.562 (1.36), 8.666 (1.59), 8.683 (1.53).
LC-MS (method 1): R$_t$ = 0.80 min; m/z = 493/495 (M + H)$^+$. |
| 74 | [3-{[2-(4-chlorophenyl)imidazo[1,2-a]pyrimidin-3-yl]methyl}-8-oxa-3,10-diazabicyclo[4.3.1]dec-10-yl](2-fluorophenyl)methanone (racemate)

from 2-(4-chlorophenyl)imidazo[1,2-a]pyrimidine-3-carbaldehyde and (2-fluorophenyl)[8-oxa-3,10-diazabicyclo[4.3.1]dec-10-yl]methanone trifluoroacetic acid salt (racemate)

$^1$H-NMR (400 MHz, DMSO-d$_6$): δ [ppm] = 1.500 (2.79), 1.621 (0.96), 2.019 (0.78), 2.074 (0.43), 2.440 (1.66), 2.462 (2.53), 2.479 (2.61), 2.594 (1.63), 2.623 (1.35), 2.670 (0.79), 2.711 (0.53), 2.757 (2.07), 2.770 (1.35), 2.792 (1.80), 2.825 (2.83), 2.852 (3.46), 2.972 (1.24), 3.387 (1.98), 3.441 (3.65), 3.467 (5.66), 3.524 (1.84), 3.533 (1.91), 3.562 (3.97), 3.569 (4.03), 3.589 (3.16), 3.607 (4.51), 3.637 (2.37), 3.762 (1.88), 3.778 (3.80), 3.808 (2.72), 4.157 (1.54), 4.193 (9.08), 4.203 (10.44), 4.239 (1.92), 4.482 (4.20), 6.950 (0.61), 7.082 (2.69), 7.098 (4.45), 7.109 (4.38), 7.124 (1.90), 7.207 (1.12), 7.231 (2.74), 7.251 (5.42), 7.264 (5.91), 7.286 (5.03), 7.309 (3.28), 7.403 (1.40), 7.417 (1.47), 7.452 (1.51), 7.466 (2.25), 7.473 (2.88), 7.486 (2.71), 7.495 (1.60), 7.509 (1.08), 7.523 (6.63), 7.544 (16.00), 7.566 (9.86), 7.601 (0.43), 7.948 (4.54), 7.970 (5.54), 7.976 (10.99), 7.998 (8.96), 8.590 (6.44), 8.595 (6.11), 8.600 (6.16), 9.116 (2.08), 9.131 (2.05), 9.172 (3.27), 9.176 (3.32), 9.190 (3.27).
LC-MS (method 2): R$_t$ = 1.69 min; m/z = 506/508 (M +H)$^+$. |

| Example | Name/Structure/Starting materials Analytical data |
|---|---|
| 75 | [3-{[2-(4-chlorophenyl)imidazo[1,2-a]pyrimidin-3-yl]methyl}-8-oxa-3,10-diazabicyclo[4.3.1]dec-10-yl](6-methoxypyridin-2-yl)methanone (racemate)

from 2-(4-chlorophenyl)imidazo[1,2-a]pyrimidine-3-carbaldehyde and (6-methoxypyridin-2-yl)[8-oxa-3,10-diazabicyclo[4.3.1]dec-10-yl]methanone bis(trifluoroacetic acid) salt (racemate)

$^1$H-NMR (400 MHz, DMSO-$d_6$): δ [ppm] = 1.570 (0.60), 1.593 (0.57), 1.645 (0.41), 1.825 (0.43), 2.628 (0.86), 2.660 (0.80), 2.805 (1.01), 2.824 (1.36), 2.855 (1.36), 2.919 (0.72), 2.932 (0.88), 2.948 (0.49), 2.964 (0.45), 3.287 (1.05), 3.357 (0.74), 3.371 (0.52), 3.429 (0.89), 3.451 (1.04), 3.457 (1.04), 3.491 (0.52), 3.499 (0.56), 3.520 (0.69), 3.529 (0.67), 3.546 (1.40), 3.576 (1.47), 3.596 (1.73), 3.612 (1.16), 3.624 (1.37), 3.746 (16.00), 3.762 (2.17), 3.791 (1.61), 3.814 (1.06), 3.842 (2.71), 3.870 (0.43), 4.056 (0.41), 4.189 (1.31), 4.197 (1.28), 4.218 (1.73), 4.236 (1.80), 4.272 (0.46), 4.422 (0.49), 4.488 (0.94), 6.848 (0.97), 6.869 (2.62), 6.890 (1.83), 6.951 (0.96), 6.969 (1.00), 7.010 (0.63), 7.020 (0.69), 7.027 (0.69), 7.037 (0.72), 7.045 (1.05), 7.055 (1.10), 7.062 (1.09), 7.072 (1.06), 7.087 (1.75), 7.105 (1.81), 7.503 (1.66), 7.515 (2.91), 7.523 (2.10), 7.536 (3.02), 7.558 (0.49), 7.590 (0.44), 7.655 (0.68), 7.674 (0.88), 7.694 (0.59), 7.777 (1.12), 7.797 (1.58), 7.816 (1.10), 7.915 (1.73), 7.936 (1.54), 7.963 (2.90), 7.984 (2.61), 8.553 (0.73), 8.558 (0.81), 8.569 (1.60), 8.574 (1.32), 8.580 (1.22), 8.584 (1.10), 9.172 (1.05), 9.176 (1.19), 9.188 (1.22), 9.194 (1.15).
LC-MS (method 2): $R_t$ = 1.61 min; m/z = 519/521 (M +H)$^+$. |
| 76 | [3-{[2-(4-chlorophenyl)imidazo[1,2-a]pyrimidin-3-yl]methyl}-8-oxa-3,10-diazabicyclo[4.3.1]dec-10-yl](4-methyl-1,2,5-oxadiazol-3-yl)methanone (racemate)

from 2-(4-chlorophenyl)imidazo[1,2-a]pyrimidine-3-carbaldehyde and (4-methyl-1,2,5-oxadiazol-3-yl)[8-oxa-3,10-diazabicyclo[4.3.1]dec-10-yl]methanone trifluoroacetic acid salt (racemate)

$^1$H-NMR (400 MHz, DMSO-$d_6$): δ [ppm] = 1.607 (0.86), 1.622 (0.95), 1.658 (0.51), 1.909 (0.93), 1.924 (0.91), 2.389 (14.10), 2.407 (16.00), 2.479 (0.60), 2.525 (0.91), 2.639 (1.35), 2.662 (1.45), 2.669 (1.53), 2.814 (0.78), 2.845 (1.77), 2.873 (1.03), 2.900 (1.15), 2.910 (1.31), 2.926 (1.43), 2.941 (0.71), 2.957 (0.58), 3.046 (0.67), 3.067 (0.86), 3.075 (0.77), 3.097 (0.62), 3.475 (0.83), 3.482 (0.97), 3.491 (0.99), 3.503 (1.40), 3.512 (1.24), 3.520 (1.40), 3.527 (1.26), 3.586 (0.91), 3.595 (1.55), 3.626 (3.60), 3.637 (2.10), 3.655 (1.38), 3.668 (1.21), 3.782 (1.80), 3.812 (1.40), 3.829 (1.64), 3.859 (1.91), 3.886 (0.98), 3.940 (0.86), 3.962 (0.82), 4.185 (0.63), 4.209 (6.10), 4.220 (2.95), 4.234 (2.63), 4.270 (0.55), 4.470 (0.91), 4.511 (1.21), 6.875 (1.29), 6.885 (1.37), 6.892 (1.33), 6.902 (1.31), 6.978 (1.43), 6.988 (1.52), 6.995 (1.47), 7.005 (1.45), 7.490 (3.56), 7.502 (4.28), 7.511 (4.08), 7.523 (4.26), 7.924 (4.03), 7.946 (4.01), 7.954 (4.78), 7.975 (3.99), 8.477 (1.41), 8.482 (1.51), 8.487 (1.51), 8.492 (1.39), 8.561 (1.58), 8.565 (1.68), 8.571 (1.66), 8.575 (1.46), 8.948 (1.40), 8.953 (1.38), 8.965 (1.42), 8.970 (1.30), 9.103 (1.56), 9.108 (1.54), 9.120 (1.58), 9.125 (1.43).
LC-MS (method 2): $R_t$ = 1.73 min; m/z = 494/496 (M +H)$^+$. |
| 77 | (4-amino-1,2,5-oxadiazol-3-yl)[3-{[2-(4-chlorophenyl)imidazo[1,2-a]pyrimidin-3-yl]methyl}-8-oxa-3,10-diazabicyclo[4.3.1]dec-10-yl]methanone (racemate)

from 2-(4-chlorophenyl)imidazo[1,2-a]pyrimidine-3-carbaldehyde and (4-amino-1,2,5-oxadiazol-3-yl)[8-oxa-3,10-diazabicyclo[4.3.1]dec-10-yl]methanone bis(trifluoroacetic acid) salt (racemate)

$^1$H-NMR (500 MHz, DMSO-$d_6$): δ [ppm] = 1.234 (1.70), 1.567 (1.12), 1.596 (1.63), 1.623 (1.40), 1.834 (1.28), 1.892 (1.22), 2.075 (1.63), 2.365 (0.43), 2.607 (1.25), 2.635 (1.73), 2.664 (1.94), 2.688 (1.96), 2.782 (1.95), 2.807 (2.40), 2.829 (1.46), 2.848 (2.34), 2.869 (2.53), 2.891 (1.06), 2.957 (1.60), 2.970 (1.86), 2.981 (1.60), 2.993 (1.52), 3.052 (1.37), 3.069 (1.87), 3.092 (1.25), 3.377 (2.05), 3.525 (2.11), 3.543 (3.97), 3.561 (2.67), 3.620 (2.85), 3.633 (3.17), 3.644 (3.61), 3.669 (3.93), 3.680 (3.80), 3.691 (3.10), 3.704 (2.75), 3.777 (3.33), 3.801 (2.62), 3.821 (3.15), 3.844 (2.43), 4.108 (2.18), 4.124 (2.09), 4.161 (0.99), 4.193 (16.00), 4.224 (2.81), 4.451 (2.06), 4.494 (2.45), 6.348 (7.64), 6.390 (7.95), 6.888 (2.17), 6.897 (2.48), 6.902 (2.55), 6.910 (2.28), 6.969 (2.37), 6.977 (2.68), 6.982 (2.78), 6.990 (2.49), 7.455 (0.57), 7.486 (6.37), 7.504 (11.79), 7.521 (7.81), 7.571 (0.59), 7.584 (0.57), 7.601 (0.49), 7.830 (0.66), 7.847 (0.50), 7.909 (6.89), 7.926 (7.00), 7.936 (8.05), 7.953 (7.00), 8.002 (0.44), 8.493 (3.05), 8.498 (3.03), 8.501 (2.86), 8.564 (3.37), 8.568 (3.40), 8.572 (3.22), 8.899 (2.70), 8.913 (2.68), 9.066 (3.05), 9.076 (2.91), 9.079 (2.96).
LC-MS (method 2): $R_t$ = 1.57 min; m/z = 495/497 (M + H)$^+$. |

| Example | Name/Structure/Starting materials Analytical data |
|---|---|
| 78 | [3-{[2-(4-chlorophenyl)imidazo[1,2-a]pyridin-3-yl]methyl}-3,9-diazabicyclo[4.2.1]non-9-yl](3-fluoro-6-methoxypyridin-2-yl)methanone (enantiomer 1)

from 2-(4-chlorophenyl)imidazo[1,2-a]pyridine-3-carbaldehyde and 3,9-diazabicyclo[4.2.1]non-9-yl (3-fluoro-6-methoxypyridin-2-yl)methanone (enantiomer 1)

$^1$H-NMR (500 MHz, DMSO-$d_6$): δ [ppm] = 1.28-1.40 (m, 1H), 1.43-1.52 (m, 0.5H), 1.53-1.91 (m, 3H), 1.92-2.05 (m, 1H), 2.08-2.19 (m, 0.5H), 2.31-2.45 (m, 1.5H), 2.46-2.53 (m, 0.5H, partially covered by DMSO signal), 2.53-2.65 (m, 1H), 2.76-2.89 (m, 1H), 3.78 (m, 3H), 3.82-3.94 (m, 1H), 4.07-4.24 (m, 2H), 4.49-4.61 (m, 1H), 6.94 (dt, 1H), 6.98 (td, 1H), 7.32 (ddt, 1H), 7.49-7.56 (m, 2H), 7.56-7.63 (m, 1H), 7.72-7.81 (m, 1H), 7.85-8.02 (m, 2H), 8.58-8.66 (m, 1H).
LC-MS (method 2): $R_t$ = 1.59 min; m/z = 520/522 (M + H)$^+$. |
| 79 | [3-{[2-(4-chlorophenyl)imidazo[1,2-a]pyridin-3-yl]methyl}-3,9-diazabicyclo[4.2.1]non-9-yl](3-fluoro-6-methoxypyridin-2-yl)methanone (enantiomer 2)

from 2-(4-chlorophenyl)imidazo[1,2-a]pyridine-3-carbaldehyde and 3,9-diazabicyclo[4.2.1]non-9-yl (3-fluoro-6-methoxypyridin-2-yl)methanone (enantiomer 2)

$^1$H-NMR (500 MHz, DMSO-$d_6$): δ [ppm] = 1.29-1.40 (m, 1H), 1.43-1.52 (m, 0.5H), 1.53-1.91 (m, 3H), 1.91-2.06 (m, 1H), 2.08-2.17 (m, 0.5H), 2.33-2.45 (m, 1.5H), 2.47-2.53 (m, 0.5H, partially covered by DMSO signal), 2.53-2.65 (m, 1H), 2.75-2.89 (m, 1H), 3.78 (m, 3H), 3.83-3.93 (m, 1H), 4.07-4.22 (m, 2H), 4.50-4.61 (m, 1H), 6.94 (dt, 1H), 6.98 (td, 1H), 7.32 (ddt, 1H), 7.48-7.56 (m, 2H), 7.57-7.62 (m, 1H), 7.71-7.81 (m, 1H), 7.84-8.10 (m, 2H), 8.45-8.72 (m, 1H).
LC-MS (method 2): $R_t$ = 1.59 min; m/z = 520/522 (M +H)$^+$. |
| 80 | (+)-[3-{[2-(4-chlorophenyl)imidazo[1,2-a]pyrimidin-3-yl+methyl}-3,9-diazabicyclo[4.2.1]non-9-yl](2-fluorophenyl)methanone (enantiomer 1)

from 2-(4-chlorophenyl)imidazo[1,2-a]pyrimidine-3-carbaldehyde and 3,9-diazabicyclo[4.2.1]non-9-yl (2-fluorophenyl)methanone (enantiomer 1)

$^1$H-NMR (500 MHz, DMSO-$d_6$): δ [ppm] = 1.21-1.35 (m, 0.5H), 1.35-1.50 (m, 1.5H), 1.51-1.65 (m, 1H), 1.65-1.76 (m, 0.5H), 1.78-1.93 (m, 1H), 1.94-2.20 (m, 2H), 2.31-2.46 (m, 1.5H), 2.55-2.69 (m, 1H, partially covered by DMSO signal), 2.70-2.83 (m, 1H), 3.66-3.79 (m, 1H), 4.04-4.24 (m, 2H), 4.47-4.62 (m, 1H), 7.11-7.18 (m, 1H), 7.19-7.39 (m, 3H), 7.42-7.51 (m, 1H), 7.52-7.61 (m, 2H), 7.89-8.04 (m, 2H), 8.56-8.63 (m, 1H), 8.98-9.09 (m, 1H).
LC-MS (method 2): $R_t$ = 1.77 min; m/z = 490/492 (M + H)$^+$.
$[\alpha]_D^{20}$ = +18.1° (c = 0.35, Methanol). |
| 81 | (−)-[3-{[2-(4-chlorophenyl)imidazo[1,2-a]pyrimidin-3-yl]methyl}-3,9-diazabicyclo[4.2.1]non-9-yl](2-fluorophenyl)methanone (enantiomer 2)

from 2-(4-chlorophenyl)imidazo[1,2-a]pyrimidine-3-carbaldehyde and 3,9-diazabicyclo[4.2.1]non-9-yl (2-fluorophenyl)methanone (enantiomer 2)

$^1$H-NMR (500 MHz, DMSO-$d_6$): δ [ppm] = 1.24-1.36 (m, 0.5H), 1.36-1.48 (m, 1.5H), 1.50-1.65 (m, 1H), 1.65-1.76 (m, 0.5H), 1.77-1.92 (m, 1H), 1.93-2.20 (m, 2H), 2.31-2.46 (m, 1.5H), 2.55-2.69 (m, 1H, partially covered by DMSO signal), 2.70-2.83 (m, 1H), 3.65-3.78 (m, 1H), 4.04-4.24 (m, 2H), 4.47-4.62 (m, 1H), 7.11-7.18 (m, 1H), 7.19-7.39 (m, 3H), 7.41-7.51 (m, 1H), 7.52-7.61 (m, 2H), 7.90-8.04 (m, |

| Example | Name/Structure/Starting materials Analytical data |
|---|---|
| | 2H), 8.55-8.63 (m, 1H), 8.97-9.08 (m, 1H).<br>LC-MS (method 2): $R_t$ = 1.77 min; m/z = 490/492 (M + H)$^+$.<br>$[\alpha]_D^{20}$ = −17.69° (c = 0.26, Methanol). |
| 82 | [3-{[2-(4-chlorophenyl)imidazo[1,2-a]pyrimidin-3-yl]methyl}-3,9-diazabicyclo[4.2.1]non-9-yl](3-fluoro-6-methoxypyridin-2-yl)methanone (enantiomer 1)<br><br>from 2-(4-chlorophenyl)imidazo[1,2-a]pyrimidine-3-carbaldehyde and 3,9-diazabicyclo[4.2.1]non-9-yl (3-fluoro-6-methoxypyridin-2-yl)methanone (enantiomer 1)<br><br>$^1$H-NMR (400 MHz, DMSO-d$_6$): δ [ppm] = −0.008 (1.33), 0.008 (1.51), 1.323 (0.51), 1.351 (1.00), 1.375 (0.65), 1.481 (0.40), 1.597 (1.68), 1.620 (0.66), 1.714 (0.70), 1.805 (0.44), 1.864 (0.57), 1.887 (0.76), 1.988 (0.67), 2.143 (0.41), 2.328 (0.76), 2.350 (0.98), 2.407 (1.09), 2.437 (0.49), 2.569 (1.19), 2.614 (1.24), 2.637 (0.56), 2.670 (0.40), 2.762 (0.64), 2.796 (0.81), 3.761 (16.00), 3.788 (12.13), 3.842 (0.60), 3.862 (1.14), 3.882 (0.67), 3.904 (0.66), 3.923 (0.67), 4.116 (3.08), 4.133 (0.87), 4.168 (2.04), 4.196 (2.11), 4.231 (0.77), 4.540 (0.67), 4.562 (1.14), 4.581 (0.77), 6.923 (1.52), 6.931 (1.89), 6.936 (1.30), 6.946 (1.75), 6.954 (1.91), 6.958 (1.27), 7.124 (1.78), 7.134 (1.89), 7.141 (1.98), 7.151 (1.84), 7.541 (3.17), 7.557 (4.99), 7.562 (4.59), 7.578 (4.61), 7.743 (1.54), 7.754 (1.20), 7.765 (2.47), 7.776 (1.94), 7.787 (1.47), 7.798 (1.10), 7.921 (3.28), 7.943 (2.94), 7.998 (4.43), 8.019 (3.95), 8.594 (2.40), 8.599 (2.44), 9.040 (1.10), 9.045 (1.12), 9.060 (2.05), 9.077 (1.40), 9.082 (1.37).<br>LC-MS (method 2): $R_t$ = 1.76 min; m/z = 521/523 (M + H)$^+$. |
| 83 | [3-{[2-(4-chlorophenyl)imidazo[1,2-a]pyrimidin-3-yl]methyl}-3,9-diazabicyclo[4.2.1]non-9-yl](3-fluoro-6-methoxypyridin-2-yl)methanone (enantiomer 2)<br><br>from 2-(4-chlorophenyl)imidazo[1,2-a]pyrimidine-3-carbaldehyde and 3,9-diazabicyclo[4.2.1]non-9-yl(3-fluoro-6-methoxypyridin-2-yl)methanone (enantiomer 2)<br><br>$^1$H-NMR (400 MHz, DMSO-d$_6$): δ [ppm] = −0.008 (1.78), 1.325 (0.60), 1.351 (1.03), 1.482 (0.41), 1.597 (1.78), 1.624 (0.69), 1.693 (0.75), 1.784 (0.40), 1.803 (0.49), 1.835 (0.44), 1.864 (0.60), 1.887 (0.80), 1.987 (0.71), 2.328 (0.88), 2.350 (1.02), 2.407 (1.18), 2.435 (0.54), 2.569 (1.28), 2.613 (1.33), 2.637 (0.62), 2.670 (0.46), 2.764 (0.65), 2.798 (0.87), 3.761 (16.00), 3.788 (12.13), 3.840 (0.66), 3.862 (1.20), 3.881 (0.69), 3.903 (0.71), 3.922 (0.70), 4.115 (3.28), 4.132 (0.89), 4.168 (2.16), 4.196 (2.26), 4.232 (0.79), 4.540 (0.71), 4.562 (1.22), 4.582 (0.86), 6.923 (1.53), 6.931 (1.89), 6.935 (1.31), 6.945 (1.74), 6.953 (1.94), 6.958 (1.38), 7.124 (1.83), 7.134 (1.93), 7.141 (2.04), 7.151 (1.88), 7.541 (3.16), 7.556 (5.03), 7.562 (4.70), 7.578 (4.61), 7.743 (1.53), 7.754 (1.17), 7.765 (2.58), 7.776 (2.00), 7.787 (1.54), 7.798 (1.08), 7.921 (3.42), 7.943 (3.01), 7.998 (4.52), 8.019 (4.03), 8.593 (2.48), 8.599 (2.52), 9.040 (1.05), 9.045 (1.12), 9.060 (2.18), 9.077 (1.45), 9.082 (1.42).<br>LC-MS (method 2): $R_t$ = 1.77 min; m/z = 521/523 (M + H)$^+$. |
| 84 | [3-{[2-(5-chloropyridin-2-yl)imidazo[1,2-a]pyridin-3-yl]methyl}-3,9-diazabicyclo[4.2.1]non-9-yl](6-methoxypyridin-2-yl)methanone (enantiomer 1)<br><br>from 2-(5-chloropyridin-2-yl)imidazo[1,2-a]pyridine-3-carbaldehyde and 3,9-diazabicyclo[4.2.1]non-9-yl(6-methoxypyridin-2-yl)methanone (enantiomer 1)<br><br>$^1$H-NMR (400 MHz, DMSO-d$_6$): δ [ppm] = 0.008 (1.08), 1.234 (0.44), 1.272 (0.56), 1.296 (0.47), 1.338 (0.72), 1.369 (0.41), 1.455 (0.49), 1.618 (1.49), 1.643 (0.64), 1.759 (0.89), 1.776 (1.43), 1.798 (1.23), 1.826 (1.18), 1.852 (0.79), 1.979 (1.03), 1.999 (0.87), 2.045 (0.74), 2.074 (2.25), 2.367 (0.82), 2.379 (0.83), 2.413 (0.91), 2.576 (1.39), 2.609 (1.34), 2.653 (2.98), 2.711(0.41), 2.827 (0.71), 2.861 (0.55), 2.949 (0.55), 2.971 (0.46), 3.751 (16.00), 3.780 (15.67), 4.421 (1.64), 4.437 (1.22), 4.455 (2.27), 4.503 (1.21), 4.537 (1.75), 4.565 (1.37), 4.586 (2.44), 4.607 (1.32), 4.634 (1.76), 4.661 (2.00), 4.667 (1.62), 4.694 (1.23), 6.882 (3.25), 6.903 (3.37), 6.955 (0.80), 6.970 (1.63), 6.988 (1.68), 7.005 (1.72), 7.020 (0.93), 7.225 (2.06), 7.243 (2.21), 7.254 (2.17), 7.271 (2.27), 7.320 (0.91), 7.329 (1.02), 7.343 (1.88), 7.357 (1.06), 7.366 (1.00), 7.604 (3.20), 7.627 (2.70), 7.765 (1.68), 7.773 (1.69), 7.785 (2.17), 7.791 (2.06), 7.804 (1.55), 7.812 (1.46), 7.978 (1.43), 7.985 (2.22), 7.992 (1.50), 7.999 (1.81), 8.006 (2.76), 8.013 (1.72), 8.188 (2.55), 8.206 (3.33), 8.226 (2.09), 8.560 (2.92), 8.577 (2.85), 8.623 (2.28), 8.628 (2.25), 8.666 (2.15), 8.671 (2.13).<br>LC-MS (method 2): $R_t$ = 1.19 min; m/z = 503/505 (M + H)$^+$. |

| Example | Name/Structure/Starting materials Analytical data |
|---|---|
| 85 | [3-{[2-(5-chloropyridin-2-yl)imidazo[1,2-a]pyridin-3-yl]methyl}-3,9-diazabicyclo[4.2.1]non-9-yl](6-methoxypyridin-2-yl)methanone (enantiomer 2)<br><br>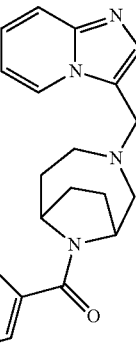<br><br>from 2-(5-chloropyridin-2-yl)imidazo[1,2-a]pyridine-3-carbaldehyde and 3,9-diazabicyclo[4.2.1]non-9-yl(6-methoxypyridin-2-yl)methanone (enantiomer 2)<br><br>$^1$H-NMR (400 MHz, DMSO-d$_6$): δ [ppm] = −0.008 (1.29), 0.008 (1.29), 1.234 (0.44), 1.271 (0.51), 1.296 (0.47), 1.340 (0.66), 1.469 (0.48), 1.617 (1.38), 1.646 (0.61), 1.760 (0.86), 1.776 (1.32), 1.796 (1.13), 1.826 (1.07), 1.852 (0.75), 1.978 (0.92), 1.999 (0.82), 2.045 (0.66), 2.074 (0.86), 2.367 (0.78), 2.413 (0.82), 2.577 (1.27), 2.609 (1.18), 2.659 (2.73), 2.711 (0.45), 2.827 (0.63), 2.862 (0.51), 2.951 (0.48), 2.972 (0.42), 3.751 (16.00), 3.780 (15.74), 4.421 (1.55), 4.437 (1.13), 4.455 (2.11), 4.503 (1.14), 4.537 (1.64), 4.566 (1.26), 4.586 (2.25), 4.607 (1.19), 4.633 (1.65), 4.660 (1.86), 4.667 (1.53), 4.695 (1.18), 6.882 (3.15), 6.903 (3.25), 6.955 (0.77), 6.972 (1.54), 6.989 (1.58), 7.005 (1.63), 7.023 (0.87), 7.225 (2.02), 7.243 (2.09), 7.254 (2.11), 7.271 (2.13), 7.320 (0.91), 7.329 (0.97), 7.343 (1.79), 7.357 (0.99), 7.365 (0.94), 7.606 (3.07), 7.629 (2.56), 7.765 (1.72), 7.772 (1.70), 7.785 (2.11), 7.793 (1.98), 7.804 (1.58), 7.812 (1.48), 7.977 (1.52), 7.985 (2.27), 7.992 (1.58), 7.999 (1.89), 8.006 (2.77), 8.013 (1.75), 8.188 (2.52), 8.206 (3.16), 8.227 (1.99), 8.560 (2.73), 8.578 (2.64), 8.623 (2.34), 8.628 (2.31), 8.666 (2.22), 8.671 (2.22).<br>LC-MS (method 2): R$_t$ = 1.17 min; m/z = 503/505 (M + H)$^+$. |
| 86 | [3-{[2-(4-chlorophenyl)imidazo[1,2-a]pyrimidin-3-yl]methyl}-3,9-diazabicyclo[4.2.1]non-9-yl](6-methoxypyridin-2-yl)methanone (enantiomer 1)<br><br>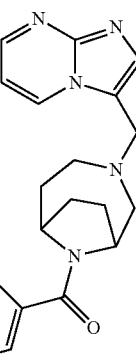<br><br>from 2-(4-chlorophenyl)imidazo[1,2-a]pyrimidine-3-carbaldehyde and 3,9-diazabicyclo[4.2.1]non-9-yl(6-methoxypyridin-2-yl)methanone (enantiomer 1)<br><br>$^1$H-NMR (400 MHz, DMSO-d$_6$): δ [ppm] = 1.234 (0.72), 1.336 (0.56), 1.363 (0.61), 1.393 (0.57), 1.500 (0.49), 1.620 (1.56), 1.638 (0.78), 1.669 (0.48), 1.715 (0.50), 1.863 (1.11), 1.881 (1.08), 1.984 (0.97), 2.006 (0.89), 2.022 (0.87), 2.053 (0.54), 2.085 (0.63), 2.329 (0.55), 2.366 (0.77), 2.403 (0.62), 2.428 (0.65), 2.455 (1.02), 2.564 (1.18), 2.583 (1.02), 2.612 (0.66), 2.666 (1.32), 2.689 (0.72), 2.710 (0.66), 2.722 (0.67), 2.755 (0.54), 2.809 (0.49), 3.748 (14.53), 3.791 (16.00), 3.854 (0.41), 3.862 (0.50), 4.113 (3.61), 4.156 (2.20), 4.173 (2.21), 4.209 (0.59), 4.431 (0.55), 4.452 (1.11), 4.471 (0.60), 4.603 (1.39), 4.628 (1.11), 4.661 (0.79), 4.680 (0.80), 6.892 (2.47), 6.913 (2.61), 7.096 (1.38), 7.107 (1.47), 7.114 (2.17), 7.125 (2.21), 7.132 (1.33), 7.142 (1.28), 7.226 (2.08), 7.244 (2.23), 7.290 (1.90), 7.308 (2.06), 7.536 (4.09), 7.541 (4.95), 7.557 (5.15), 7.562 (4.72), 7.766 (1.54), 7.780 (1.80), 7.784 (1.91), 7.800 (2.06), 7.805 (1.57), 7.819 (1.51), 7.942 (3.89), 7.964 (3.53), 7.983 (4.24), 8.004 (3.73), 8.581 (2.38), 8.586 (2.56), 8.591 (2.54), 8.595 (2.33), 9.014 (1.27), 9.019 (1.30), 9.032 (2.36), 9.037 (2.29), 9.050 (1.39), 9.055 (1.30).<br>LC-MS (method 2): R$_t$ = 1.76 min; m/z = 503/505 (M + H)$^+$. |
| 87 | [3-{[2-(4-chlorophenyl)imidazo[1,2-a]pyrimidin-3-yl]methyl}-3,9-diazabicyclo[4.2.1]non-9-yl](6-methoxypyridin-2-yl)methanone (enantiomer 2)<br><br>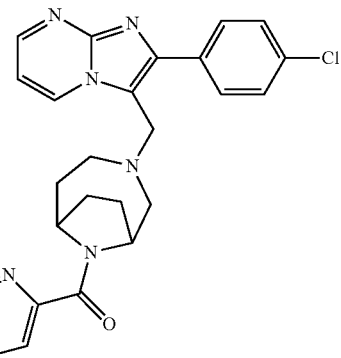<br><br>from 2-(4-chlorophenyl)imidazo[1,2-a]pyrimidine-3-carbaldehyde and 3,9-diazabicyclo[4.2.1]non-9-yl(6-methoxypyridin-2-yl)methanone (enantiomer 2)<br><br>$^1$H NMR (400 MHz, DMSO-d$_6$): δ [ppm] = 0.008 (1.21), 1.235 (1.01), 1.337 (0.70), 1.363 (0.73), 1.502 (0.54), 1.621 (1.60), 1.863 (1.23), 1.985 (1.06), 2.085 (0.64), 2.328 (0.65), 2.366 (0.95), 2.392 (0.75), 2.561 (1.25), 2.583 (0.99), 2.612 (0.65), 2.666 (1.30), 2.696 (0.77), 2.710 (0.78), 2.757 (0.57), 2.804 (0.52), 3.748 (14.57), 3.791 (16.00), 3.854 (0.62), 3.862 (0.55), 4.113 (3.54), 4.157 (2.20), 4.173 (2.13), 4.209 (0.60), 4.432 (0.58), 4.452 (1.12), 4.472 (0.61), 4.603 (1.51), 4.662 (0.82), 4.681 (0.79), 6.892 (2.57), 6.913 (2.71), 7.096 (1.43), 7.107 (1.50), 7.114 (2.15), 7.124 (2.14), 7.132 (1.39), 7.142 (1.27), 7.226 (2.02), 7.244 (2.18), 7.291 (1.90), 7.307 (1.99), 7.536 (4.35), 7.541 (5.05), 7.557 (5.23), 7.562 (4.71), 7.766 (1.70), 7.780 (1.92), 7.784 (1.92), 7.798 (2.08), 7.805 (1.61), 7.819 (1.55), 7.942 (3.93), 7.964 (3.51), 7.983 (4.28), 8.005 (3.68), 8.582 (2.49), 8.585 (2.67), 8.592 (2.57), 8.595 (2.36), 9.014 (1.32), 9.019 (1.31), 9.032 (2.35), 9.037 (2.22), 9.050 (1.40), 9.055 (1.26).<br>LC-MS (method 1): R$_t$ = 0.92 min; m/z =503/505 (M + H)$^+$. |

Example 88 and Example 89

[3-{[2-(4-Chlorophenyl)imidazo[1,2-a]pyridin-3-yl]methyl}-3,9-diazabicyclo[4.2.1]non-9-yl](2-fluorophenyl)methanone (Enantiomers 1 and 2)

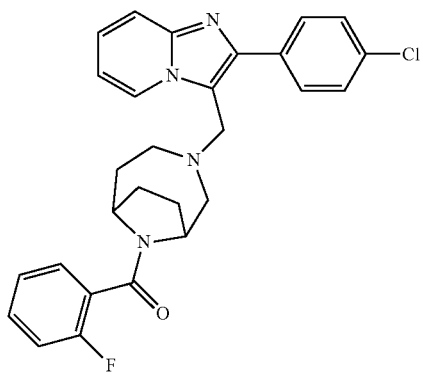 [SMILES: O=C(c1ccccc1F)N1C2CCC1CN(Cc1c(-c3ccc(Cl)cc3)nc3ccccn13)CC2]

117 mg (240 μmol) of racemic [3-{[2-(4-chlorophenyl)imidazo[1,2-a]pyridin-3-yl]methyl}-3,9-diazabicyclo[4.2.1]non-9-yl](2-fluorophenyl)methanone (Example 69) were separated into the enantiomers by preparative HPLC on a chiral phase [column: Daicel Chiralpak AD-H, 5 μm, 250 mm×20 mm; mobile phase: n-heptane/ethanol 70:30 (v/v)+0.2% diethylamine; flow rate: 15 ml/min; UV detection: 235 nm; temperature: 50° C.]:

Example 88 (Enantiomer 1)

Yield: 56 mg
$R_t$=5.70 min; chemical purity >99%; >99% ee
[column: Daicel Chiralpak IA, 5 μm, 250 mm×4.6 mm; mobile phase: isohexane/ethanol 70:30 (v/v)+0.2% diethylamine; flow rate: 1 ml/min; temperature: 50° C.; UV detection: 235 nm].
LC-MS (method 2): $R_t$=1.62 min; m/z=489/491 (M+H)$^+$.
$^1$H-NMR (400 MHz, DMSO-d$_6$): δ [ppm]=1.19-1.34 (m, 0.5H), 1.35-1.47 (m, 1.5H), 1.50-1.68 (m, 1H), 1.68-1.78 (m, 0.5H), 1.78-1.93 (m, 1H), 1.94-2.20 (m, 2H), 2.31-2.45 (m, 1.5H), 2.56-2.69 (m, 1H), 2.71-2.86 (m, 1H), 3.65-3.78 (m, 1H), 4.01-4.23 (m, 2H), 4.47-4.64 (m, 1H), 6.95-7.04 (m, 1H), 7.19-7.37 (m, 4H), 7.43-7.49 (m, 1H), 7.49-7.57 (m, 2H), 7.60 (dd, 1H), 7.87-8.02 (m, 2H), 8.49-8.70 (m, 1H).

Example 89 (Enantiomer 2)

Yield: 58 mg
$R_t$=6.60 min; chemical purity >99%; >99% ee
[column: Daicel Chiralpak IA, 5 μm, 250 mm×4.6 mm; mobile phase: isohexane/ethanol 70:30 (v/v)+0.2% diethylamine; flow rate: 1 ml/min; temperature: 50° C.; UV detection: 235 nm].
LC-MS (method 2): $R_t$=1.62 min; m/z=489/491 (M+H)$^+$.
$^1$H-NMR (400 MHz, DMSO-d$_6$): δ [ppm]=1.22-1.33 (m, 0.5H), 1.35-1.46 (m, 1.5H), 1.50-1.68 (m, 1H), 1.69-1.78 (m, 0.5H), 1.79-1.92 (m, 1H), 1.94-2.21 (m, 2H), 2.31-2.45 (m, 1.5H), 2.57-2.69 (m, 1H), 2.72-2.86 (m, 1H), 3.66-3.79 (m, 1H), 4.04-4.22 (m, 2H), 4.49-4.62 (m, 1H), 6.95-7.03 (m, 1H), 7.19-7.37 (m, 4H), 7.43-7.50 (m, 1H), 7.50-7.56 (m, 2H), 7.60 (dd, 1H), 7.77-8.07 (m, 2H), 8.45-8.71 (m, 1H).

Example 90 and Example 91

[3-{[2-(4-Chlorophenyl)imidazo[1,2-a]pyridin-3-yl]methyl}-3,9-diazabicyclo[4.2.1]non-9-yl](6-methoxypyridin-2-yl)methanone (Enantiomers 1 and 2)

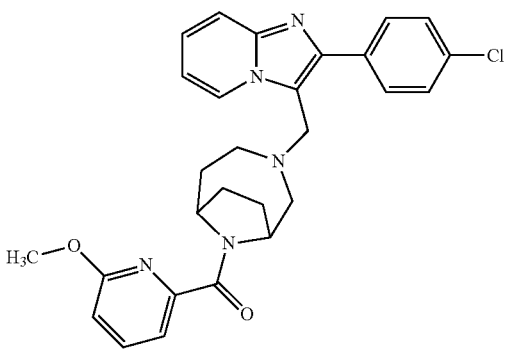 [SMILES: COc1cccc(C(=O)N2C3CCC2CN(Cc2c(-c4ccc(Cl)cc4)nc4ccccn24)CC3)n1]

195 mg (389 μmol) of racemic [3-{[2-(4-chlorophenyl)imidazo[1,2-a]pyridin-3-yl]methyl}-3,9-diazabicyclo[4.2.1]non-9-yl](6-methoxypyridin-2-yl)methanone (Example 70) were separated into the enantiomers by preparative HPLC on a chiral phase [column: Daicel Chiralpak IC, 5 μm, 250 mm×20 mm; mobile phase: n-heptane/ethanol 50:50 (v/v)+0.2% diethylamine; flow rate: 15 ml/min; UV detection: 235 nm; temperature: 40° C.]:

Example 90 (Enantiomer 1)

Yield: 92 mg
$R_t$=7.65 min; chemical purity >99%; >99% ee
[column: Daicel Chiralpak IA, 5 μm, 250 mm×4.6 mm; mobile phase: isohexane/ethanol 50:50 (v/v)+0.2% diethylamine; flow rate: 1 ml/min; temperature: 50° C.; UV detection: 235 nm].
LC-MS (method 2): $R_t$=1.63 min; m/z=502/504 (M+H)$^+$.
$^1$H-NMR (400 MHz, DMSO-d$_6$): δ [ppm]=1.26-1.44 (m, 1H), 1.44-1.54 (m, 0.5H), 1.56-1.68 (m, 1H), 1.69-1.92 (m, 2H), 1.95-2.13 (m, 1.5H), 2.31-2.88 (m, 4H), 4.05-4.21 (m, 2H), 4.45 (t, 0.5H), 4.55-4.70 (m, 1.5H), 6.90 (d, 1H), 6.97 (q, 1H), 7.20-7.34 (m, 2H), 7.52 (dd, 2H), 7.60 (dt, 1H), 7.73-7.84 (m, 1H), 7.94 (dd, 2H), 8.61 (t, 1H).

Example 91 (Enantiomer 2)

Yield: 94 mg
$R_t$=8.93 min; chemical purity >99%; >99% ee
[column: Daicel Chiralpak IA, 5 μm, 250 mm×4.6 mm; mobile phase: isohexane/ethanol 50:50 (v/v)+0.2% diethylamine; flow rate: 1 ml/min; temperature: 50° C.; UV detection: 235 nm].
LC-MS (method 2): $R_t$=1.64 min; m/z=502/504 (M+H)$^+$.
$^1$H-NMR (400 MHz, DMSO-d$_6$): δ [ppm]=1.27-1.44 (m, 1H), 1.43-1.54 (m, 0.5H), 1.56-1.69 (m, 1H), 1.69-1.79 (m, 0.5H), 1.79-1.91 (m, 1.5H), 1.95-2.14 (m, 1.5H), 2.31-2.88 (m, 4H), 4.04-4.22 (m, 2H), 4.45 (t, 0.5H), 4.55-4.70 (m, 1.5H), 6.90 (d, 1H), 6.97 (q, 1H), 7.19-7.35 (m, 2H), 7.52 (dd, 2H), 7.60 (dt, 1H), 7.75-7.83 (m, 1H), 7.94 (dd, 2H), 8.61 (t, 1H).

Analogously to Examples 13-16, the following compounds were prepared from the starting materials specified in each case:

| Example | Name/Structure/Starting materials | Analytical data |
|---|---|---|
| 92 | [3-{[2-(4-chlorophenyl)imidazo[1,2-a]pyridin-3-yl]methyl}-8-oxa-3,10-diazabicyclo[4.3.1]dec-10-yl](3-fluoro-6-methoxypyridin-2-yl)methanone (racemate)<br>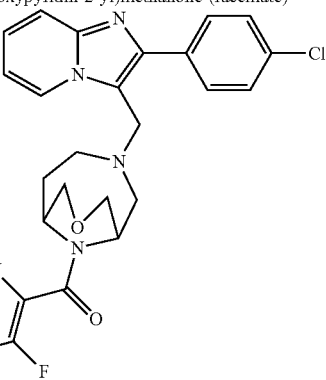<br>from 2-(4-chlorophenyl)imidazo[1,2-a]pyridine-3-carbaldehyde and (3-fluoro-6-methoxypyridin-2-yl)[8-oxa-3,10-diazabicyclo[4.3.1]dec-10-yl]methanone (racemate) | LC-MS (method 2):<br>$R_t$ = 1.47 min;<br>m/z = 536/538 (M + H)$^+$. |
| 93 | [3-{[2-(4-chlorophenyl)imidazo[1,2-a]pyrimidin-3-yl]methyl}-8-oxa-3,10-diazabicyclo[4.3.1]dec-10-yl](3-fluoro-6-methoxypyridin-2-yl)methanone (racemate)<br>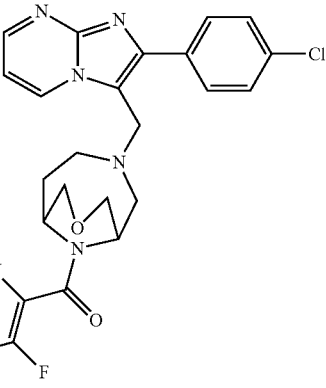<br>from 2-(4-chlorophenyl)imidazo[1,2-a]pyrimidine-3-carbaldehyde and (3-fluoro-6-methoxypyridin-2-yl)[8-oxa-3,10-diazabicyclo[4.3.1]dec-10-yl]methanone (racemate) | LC-MS (method 2):<br>$R_t$ = 1.67 min;<br>m/z = 537/539 (M + H)$^+$. |

Analogously to Example 17, the following compounds were prepared from the starting materials specified in each case:

| Example | Name/Structure/Starting materials | Analytical data |
|---|---|---|
| 94 | [3-{[2-(4-chlorophenyl)imidazo[1,2-a]pyridin-3-yl]methyl}-3,6-diazabicyclo[3.2.2]non-6-yl](3-fluoro-6-methoxypyridin-2-yl)methanone (enantiomer 1)<br>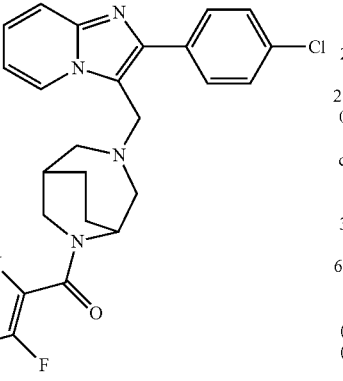<br>from 2-(4-chlorophenyl)imidazo[1,2-a]pyridine-3-carbaldehyde and 3,6-diazabicyclo[3.2.2]non-6-yl(3-fluoro-6-methoxypyridin-2-yl)methanone hydrochloride (enantiomer 1) | $^1$H-NMR (500 MHz, DMSO-$d_6$): δ [ppm] = 1.39-1.50 (m, 0.25H), 1.50-1.61 (m, 0.75H), 1.61-1.84 (m, 2.75H), 1.87-1.98 (m, 0.25H), 2.06 (br. s, 0.25H), 2.22-2.35 (m, 1H), 2.43-2.65 (m, 1.75H, partially covered by DMSO signal), 2.73-2.88 (m, 1H), 2.96 (br. dd, 0.75H), 3.00-3.09 (m, 0.25H), 3.17-3.35 (m, 0.5H, partially covered by H$_2$O signal), 3.39-3.50 (m, 0.75H), 3.60 (br. d, 0.75H), 3.63-3.71 (m, 3H), 3.83 (s, 0.75H), 4.00-4.14 (m, 2H), 4.54-4.62 (m, 0.25H), 6.88 (dd, 0.75H), 6.92-7.03 (m, 1.25H), 7.26-7.36 (m, 1H), 7.49-7.56 (m, 2H), 7.57-7.64 (m, 1H), 7.73 (t, 0.75H), 7.79 (t, 0.25H), 7.91-8.01 (m, 2H), 8.54-8.63 (m, 1H).<br>LC-MS (method 2):<br>R$_t$ = 1.56 min; m/z = 520/522 (M+H)$^+$. |
| 95 | [3-{[2-(4-chlorophenyl)imidazo[1,2-a]pyridin-3-yl]methyl}-3,6-diazabicyclo[3.2.2]non-6-yl](6-methoxypyridin-2-yl)methanone (enantiomer 1)<br>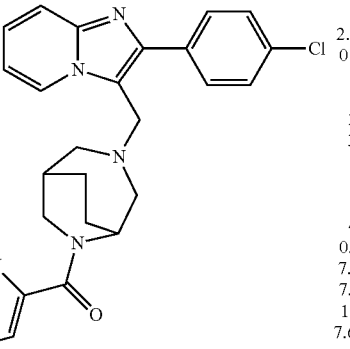<br>from 2-(4-chlorophenyl)imidazo[1,2-a]pyridine-3-carbaldehyde and 3,6-diazabicyclo[3.2.2]non-6-yl(6-methoxypyridin-2-yl)methanone hydrochloride (enantiomer 1) | $^1$H-NMR (500 MHz, DMSO-$d_6$): δ [ppm] = 1.42-1.59 (m, 1H), 1.60-1.85 (m, 2.75H), 1.86-1.98 (m, 0.25H), 2.03-2.11 (m, 0.25H), 2.23-2.31 (m, 0.75H), 2.31-2.38 (m, 0.25H), 2.45-2.63 (m, 1H, partially covered by DMSO signal), 2.72-2.88 (m, 1.75H), 2.93-3.04 (m, 1H), 3.37-3.49 (m, 1H), 3.53-3.67 (m, 3.25H), 3.85 (s, 0.75H), 3.98 (br. s, 0.75H), 4.04-4.14 (m, 2H), 4.55 (br. s, 0.25H), 6.82 (d, 0.75H), 6.88 (d, 0.25H), 6.92-7.01 (m, 1H), 7.09 (d, 0.75H), 7.21 (d, 0.25H), 7.26-7.35 (m, 1H), 7.49-7.57 (m, 2H), 7.57-7.64 (m, 1H), 7.75 (dd, 0.75H), 7.81 (dd, 0.25H), 7.92-8.02 (m, 2H), 8.59 (d, 1H).<br>LC-MS (method 2):<br>R$_t$ = 1.55 min; m/z = 502/504 (M + H)$^+$. |

| Example | Name/Structure/Starting materials | Analytical data |
|---|---|---|
| 96 | [3-{[2-(5-chloropyridin-2-yl)imidazo[1,2-a]pyridin-3-yl]methyl}-3,6-diazabicyclo[3.2.2]non-6-yl](3-fluoro-6-methoxypyridin-2-yl)methanone (enantiomer 1)<br><br>from 2-(5-chloropyridin-2-yl)imidazo[1,2-a]pyridine-3-carbaldehyde and 3,6-diazabicyclo[3.2.2]non-6-yl(3-fluoro-6-methoxypyridin-2-yl)methanone hydrochloride (enantiomer 1) | $^1$H-NMR (500 MHz, DMSO-$d_6$): δ [ppm] = 1.36-1.95 (m, 4.25H), 1.99-2.08 (m, 0.25H), 2.20-2.31 (m, 1H), 2.41-2.60 (m, 1H, partially covered by DMSO signal), 2.77 (br. dd, 0.75H), 2.89 (br. dd, 0.25H), 3.05 (br. dd, 1H), 3.14-3.29 (m, 0.5H), 3.41 (dd, 1H), 3.52-3.64 (m, 4H), 3.83 (s, 0.75H), 4.41-4.71 (m, 2.25H), 6.85 (dd, 0.75H), 6.91-7.06 (m, 1.25H), 7.28-7.39 (m, 1H), 7.57-7.65 (m, 1H), 7.70 (t, 0.75H), 7.80 (t, 0.25H), 7.96-8.03 (m, 1H), 8.17-8.25 (m, 1H), 8.48-8.59 (m, 1H), 8.67 (d, 1H).<br>LC-MS (method 2):<br>$R_t$ = 1.20 min; m/z = 521/523 (M + H)$^+$. |
| 97 | [3-{[2-(4-chlorophenyl)imidazo[1,2-a]pyrimidin-3-yl]methyl}-3,6-diazabicyclo[3.2.2]non-6-yl](3-fluoro-6-methoxypyridin-2-yl)methanone (enantiomer 1)<br><br>from 2-(4-chlorophenyl)imidazo[1,2-a]pyrimidine-3-carbaldehyde and 3,6-diazabicyclo[3.2.2]non-6-yl(3-fluoro-6-methoxypyridin-2-yl)methanone hydrochloride (enantiomer 1) | $^1$H-NMR (500 MHz, DMSO-$d_6$): δ [ppm] = 1.37-1.86 (m, 4H), 1.87-1.98 (m, 0.25H), 2.06 (br. s, 0.25H), 2.21-2.35 (m, 1H), 2.41-2.62 (m, 1.5H, partially covered by DMSO signal), 2.72-2.89 (m, 1H), 2.97 (br. dd, 0.75H), 3.05 (br. dd, 0.25H), 3.16-3.35 (m, 0.5H, partially covered by H$_2$O signal), 3.44 (dd, 0.75H), 3.55-3.70 (m, 3.75H), 3.82 (s, 0.75H), 4.01-4.17 (m, 2H), 4.58 (br. t, 0.25H), 6.88 (dd, 0.75H), 6.95 (dd, 0.25H), 7.07-7.19 (m, 1H), 7.52-7.62 (m, 2H), 7.69-7.84 (m, 1H), 7.93-8.04 (m, 2H), 8.54-8.63 (m, 1H), 8.96-9.07 (m, 1H).<br>LC-MS (method 2):<br>$R_t$ = 1.75 min; m/z = 521/523 (M + H)$^+$. |

| Example | Name/Structure/Starting materials | Analytical data |
|---|---|---|
| 98 | [3-{[2-(4-chlorophenyl)imidazo[1,2-a]pyrimidin-3-yl]methyl}-3,6-diazabicyclo[3.2.2]non-6-yl](6-methoxypyridin-2-yl)methanone (enantiomer 1)<br>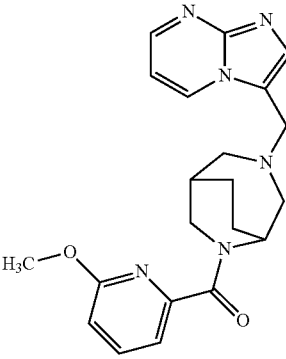<br>from 2-(4-chlorophenyl)imidazo[1,2-a]pyrimidine-3-carbaldehyde and 3,6-diazabicyclo[3.2.2]non-6-yl(6-methoxypyridin-2-yl)methanone hydrochloride (enantiomer 1) | $^1$H-NMR (500 MHz, DMSO-$d_6$): δ [ppm] = 1.42-1.86 (m, 4H), 1.86-1.98 (m, 0.25H), 2.07 (br. s, 0.25H), 2.26 (br. s, 0.75H), 2.34 (br. d, 0.25H), 2.57 (br. d, 0.75H), 2.70-2.88 (m, 1.75H), 2.94-3.05 (m, 1H), 3.37-3.48 (m, 1H), 3.53-3.66 (m, 3.25H), 3.85 (s, 0.75H), 3.97 (br.s, 0.75H), 4.02-4.16 (m, 2H), 4.54 (br. s, 0.25H), 6.82 (d, 0.75H), 6.89 (d, 0.25H), 7.06-7.22 (m, 2H), 7.51-7.61 (m, 2H), 7.71-7.85 (m, 1H), 7.94-8.02 (m, 2H), 8.54-8.62 (m, 1H), 8.98-9.06 (m, 1H).<br>LC-MS (method 2):<br>$R_t$ = 1.74 min; m/z = 503/505 (M + H)$^+$. |
| 99 | (3-chloro-6-methoxypyridin-2-yl)(3-{[2-(4-chlorophenyl)imidazo[1,2-a]pyrimidin-3-yl]methyl}-3,9-diazabicyclo[4.2.1]non-9-yl)methanone (racemate)<br>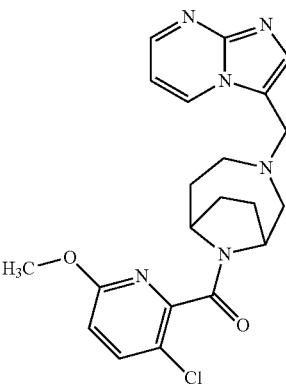<br>from 2-(4-chlorophenyl)imidazo[1,2-a]pyrimidine-3-carbaldehyde and (3-chloro-6-methoxypyridin-2-yl)(3,9-diazabicyclo[4.2.1]non-9-yl)methanone hydrochloride (racemate) | $^1$H-NMR (500 MHz, DMSO-$d_6$): δ [ppm] = 1.29-2.05 (m, 5.75H), 2.07-2.19 (m, 0.5H), 2.27-2.35 (m, 0.5H), 2.36-2.46 (m, 0.5H), 2.46-2.64 (m, 1.75H, partially covered by DMSO signal), 2.74-2.86 (m, 1H), 3.65-3.74 (m, 1H), 3.77 (s, 1.75H), 3.82 (s, 1.25H), 4.08-4.26 (m, 2H), 4.50-4.61 (m, 1H), 6.92 (dd, 1H), 7.10-7.18 (m, 1H), 7.51-7.61 (m, 2H), 7.87 (dd, 1H), 7.93 (d, 1H), 8.01 (d, 1H), 8.56-8.63 (m, 1H), 9.02-9.11 (m, 1H).<br>LC-MS (method 1):<br>$R_t$ = 0.92 min; m/z = 537/539 (M + H)$^+$ (Rotamer 1),<br>$R_t$ = 0.94 min; m/z = 537/539 (M + H)$^+$ (Rotamer 2). |

| Example | Name/Structure/Starting materials | Analytical data |
|---|---|---|
| 100 | (3-chloro-6-methoxypyridin-2-yl)(3-{[2-(5-chloropyridin-2-yl)imidazo[1,2-a]pyridin-3-yl]methyl}-3,9-diazabicyclo[4.2.1]non-9-yl)methanone (racemate)<br><br>[structure]<br><br>from 2-(5-chloropyridin-2-yl)imidazo[1,2-a]pyridine-3-carbaldehyde and (3-chloro-6-methoxypyridin-2-yl)(3,9-diazabicyclo[4.2.1]non-9-yl)methanone hydrochloride (racemate) | $^1$H-NMR (500 MHz, DMSO-$d_6$): δ [ppm] = 1.21-1.68 (m, 3.25H), 1.69-1.88 (m, 1.75H), 1.89-2.05 (m, 1H), 2.06-2.19 (m, 0.5H), 2.37 (br. d, 0.5H), 2.44-2.62 (m, 1.5H, partially covered by DMSO signal), 2.64-2.73 (m, 0.5H), 2.87-3.02 (m, 1H), 3.63-3.72 (m, 1H), 3.77 (s, 1.6H), 3.87 (s, 1.4H), 4.40-4.59 (m, 2H), 4.61-4.86 (m, 1H), 6.91 (dd, 1H), 6.98-7.05 (m, 1H), 7.31-7.40 (m, 1H), 7.62 (dd, 1H), 7.87 (dd, 1H), 8.00 (td, 1H), 8.21 (t, 1H), 8.55-8.65 (m, 1.5H), 8.69 (d, 0.5H).<br>LC-MS (method 1):<br>$R_t$ = 0.72 min; m/z = 537/539 (M + H)$^+$. |

Example 101

(3-Chloro-6-methoxypyridin-2-yl) [3-{[2-(4-isopropylphenyl)imidazo[1,2-a]pyrimidin-3-yl]methyl}-3,9-diazabicyclo[4.2.1]nonan-9-yl]methanone (Enantiomer 1)

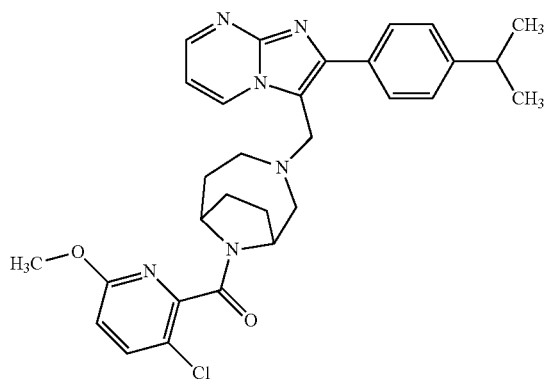 [SMILES: COc1ccc(Cl)c(C(=O)N2C3CCC2CN(Cc2c(-c4ccc(C(C)C)cc4)nc4ncccn24)CC3)n1]

Under argon, (3-chloro-6-methoxypyridin-2-yl)[(3,9-diazabicyclo[4.2.1]nonan-9-yl]methanone-hydrogen chloride (1/1) (Enantiomer 1) (90 mg, 270 µmol) was taken up in 2 ml of THF, and 98 µl (0.57 mmol) of N,N-diisopropylethylamine were added. The reaction solution was then stirred at room temperature for 2 hours. Subsequently, the reaction solution was concentrated to dryness and the residue obtained was then taken up in 2 ml of THF, and 2-[4-(propan-2-yl)phenyl]imidazo[1,2-a]pyrimidine-3-carbaldehyde (60.0 mg, 230 µmol), 0.25 ml of dichloromethane and acetic acid (32 µl, 570 µmol) were added. Sodium triacetoxyborohydride (72 mg, 340 µmol) was then added and the mixture was stirred at room temperature overnight. After the addition of saturated ammonium chloride solution, the reaction mixture was evaporated to dryness. The resulting residue was then taken up in ethyl acetate and washed with a saturated sodium carbonate solution, and the organic phase obtained was subsequently evaporated to dryness. The reaction mixture was then separated into its components directly by preparative HPLC (Method 9). The main component obtained was subsequently purified by column chromatography (silica gel; mobile phase ethyl acetate). This gave 56 mg (100% pure, 0.1 mmol, 46% of theory) of the title compound.

LC-MS (Method 2): $R_t$=1.95/1.98 min; m/z=545/547 (M+H)$^+$.

$^1$H NMR (500 MHz, DMSO-$d_6$) δ ppm 1.25 (d, 6H), 1.31-1.42 (m, 1H), 1.44-1.69 (m, 2H), 1.71-1.88 (m, 1.5H), 1.92-2.03 (m, 1H), 2.07-2.18 (m, 0.5H), 2.26-2.44 (m, 1H), 2.52-2.60 (m, 2H), 2.81 (br s, 1H), 2.95 (quin, 1H), 3.67-3.74 (m, 1H), 3.78 (s, 1.5H), 3.82 (s, 1.5H), 4.10-4.23 (m, 2H), 4.53-4.59 (m, 1H), 6.92 (dd, 1H), 7.12 (dd, 1H), 7.36 (br d, 1H), 7.38 (br d, 1H), 7.79 (d, 1H), 7.87 (d, 2H), 8.57 (s, 1H), 9.03 (t, 1H).

Analogously to Example 101, the following compounds were prepared from the starting materials stated in each case:

| Example | Name/Structure/Starting materials | Analytical data |
|---|---|---|
| 102 | (3-Fluoro-6-methoxypyridin-2-yl)[3-{[2-(4-isopropylphenyl)imidazo[1,2-a]pyrimidin-3-yl]methyl}-3,9-diazabicyclo[4.2.1]nonan-9-yl]methanone (Enantiomer 1) | $^1$H NMR (500 MHz, DMSO-$d_6$) δ ppm 1.25 (d, 6H), 1.30-1.41 (m, 1H), 1.44-2.17 (m, 5H), 2.33-2.47 (m, 2H), 2.52-2.64 |

| Example | Name/Structure/Starting materials | Analytical data |
|---|---|---|
| | 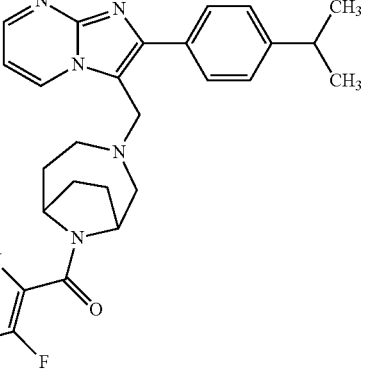<br><br>from 2-[4-(propan-2-yl)phenyl]imidazo[1,2-a]pyrimidine-3-carbaldehyde and [3,9-diazabicyclo[4.2.1]nonan-9-yl](3-fluoro-6-methoxypyridin-2-yl)methanone-hydrogen chloride (1/1) (Enantiomer 1) | (m, 1H), 2.76-2.86 (m, 1H), 2.95 (dt, 1H), 3.78 (d, 3H), 3.84-3.93 (m, 1H), 4.10-4.23 (m, 2H), 4.52-4.59 (m, 1H), 6.94 (ddd, 1H), 7.12 (ddd, 1H), 7.37 (dd, 2H), 7.74-7.82 (m, 2H), 7.87 (d, 1H), 8.57 (dd, 1H), 9.03 (ddd, 1H).<br>LC-MS (Method 2):<br>$R_t$ = 1.88 min; MS (ESIpos):<br>m/z = 529 (M + H)$^+$ |
| 103 | (3-Fluoro-6-methoxypyridin-2-yl)[3-{[2-(4-isopropylphenyl)imidazo[1,2-a]pyrimidin-3-yl]methyl}-3,9-diazabicyclo[4.2.1]nonan-9-yl]methanone (Enantiomer 2)<br><br>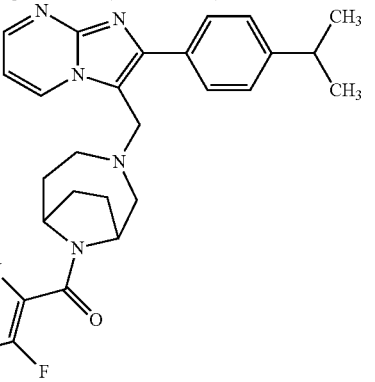<br><br>from 2-[4-(propan-2-yl)phenyl]imidazo[1,2-a]pyrimidine-3-carbaldehyde and [3,9-diazabicyclo[4.2.1]nonan-9-yl](3-fluoro-6-methoxypyridin-2-yl)methanone-hydrogen chloride (1/1) (Enantiomer 2) | $^1$H NMR (500 MHz, DMSO-d$_6$) δ ppm 1.25 (d, 6H), 1.31-1.40 (m, 1H), 1.43-2.19 (m, 5H), 2.30-2.47 (m, 2H), 2.55-2.64 (m, 1H), 2.76-2.86 (m, 1H), 2.95 (dt, 1H), 3.78 (d, 3H), 3.84-3.93 (m, 1H), 4.09-4.23 (m, 2H), 4.52-4.59 (m, 1H), 6.94 (ddd, 1H), 7.12 (ddd, 1H), 7.37 (dd, 2H), 7.74-7.82 (m, 2H), 7.87 (d, 1H), 8.57 (dd, 1H), 9.03 (ddd, 1H)<br>LC-MS (Method 2):<br>$R_t$ = 1.87 min; MS (ESIpos):<br>m/z = 529 (M + H)$^+$ |
| 104 | [3-{[2-(4-Isopropylphenyl)imidazo[1,2-a]pyrimidin-3-yl]methyl}-3,9-diazabicyclo[4.2.1]nonan-9-yl](6-methoxypyridin-2-yl)methanone (Enantiomer 1)<br><br>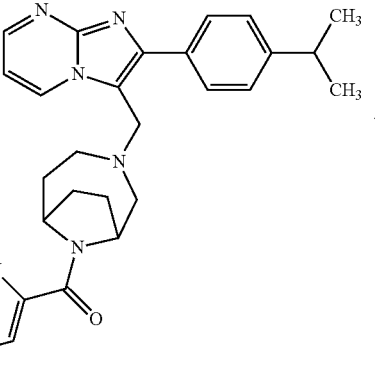<br><br>from 2-[4-(propan-2-yl)phenyl]imidazo[1,2-a]pyrimidine-3-carbaldehyde and [3,9- | $^1$H NMR (500 MHz, DMSO-d$_6$) δ ppm 1.25 (dd, 6H), 1.30-1.42 (m, 1H), 1.45-1.56 (m, 0.5H), 1.63 (br s, 1H), 1.70-1.93 (m, 2H), 1.96-2.13 (m, 1.5H), 2.33-2.47 (m, 1H), 2.52-2.68 (m, 2H), 2.70-2.87 (m, 1H), 2.91-2.99 (m, 1H), 3.74 (s, 1.5H), 3.79 (s, 1.5H), 4.08-4.20 (m, 2H), 4.46 (t, 0.5H), 4.55-4.72 (m, 1.5H), 6.88-6.92 (m, 1H), 7.07-7.12 (m, 1H), 7.22-7.31 (m, 1H), 7.36 (dd, 2H), 7.77-7.87 (m, 3H), 8.54-8.58 (m, 1H), 9.01 (t, 1H)<br>LC-MS (Method 2):<br>$R_t$ = 1.89 min; MS (ESIpos):<br>m/z = 511 (M + H)$^+$ |

| Example | Name/Structure/Starting materials | Analytical data |
|---|---|---|
| | diazabicyclo[4.2.1]nonan-9-yl](6-methoxypyridin-2-yl)methanone-hydrogen chloride (1/1) (Enantiomer 1) | |
| 105 | [(3-{[2-(4-Isopropylphenyl)imidazo[1,2-a]pyrimidin-3-yl]methyl}-3,9-diazabicyclo[4.2.1]nonan-9-yl](6-methoxypyridin-2-yl)methanone (Enantiomer 2)<br><br>from 2-[4-(propan-2-yl)phenyl]imidazo[1,2-a]pyrimidine-3-carbaldehyde and [3,9-diazabicyclo[4.2.1]nonan-9-yl](6-methoxypyridin-2-yl)methanone-hydrogen chloride (1/1) (Enantiomer 2) | $^1$H NMR (500 MHz, DMSO-$d_6$) δ ppm 1.25 (dd, 6H), 1.30-1.44 (m, 1H), 1.45-1.54 (m, 0.5H), 1.58-1.67 (m, 1H), 1.69-1.92 (m, 2H), 1.96-2.11 (m, 1.5H), 2.32-2.44 (m, 1H), 2.52-2.68 (m, 2H), 2.71-2.88 (m, 1H), 2.95 (quind, 1H), 3.74 (s, 1.5H), 3.79 (s, 1.5H), 4.09-4.20 (m, 2H), 4.46 (t, 0.5 H), 4.58-4.67 (m, 1.5H), 6.90 (ddd, 1H), 7.07-7.12 (m, 1H), 7.21-7.32 (m, 1H), 7.36 (dd, 2 H), 7.77-7.87 (m, 3H), 8.55-8.58 (m, 1H), 9.01 (t, 1H) LC-MS (Method 2): R$_t$ = 1.89 min; MS (ESIpos): m/z = 511 (M + H)$^+$ |
| 106 | (3-Chloro-6-methoxypyridin-2-yl)[3-{[2-(4-isopropylphenyl)imidazo[1,2-a]pyrimidin-3-yl]methyl}-3,9-diazabicyclo[4.2.1]nonan-9-yl]methanone (Enantiomer 2)<br><br>from 2-[4-(propan-2-yl)phenyl]imidazo[1,2-a]pyrimidine-3-carbaldehyde and (3-chloro-6-methoxypyridin-2-yl)[(3,9-diazabicyclo[4.2.1]nonan-9-yl]methanone-hydrogen chloride (1/1) (Enantiomer 2) | 1H NMR (500 MHz, DMSO-d6) δ ppm 1.25 (d, 6H), 1.30-1.42 (m, 1H), 1.44-1.69 (m, 2 H), 1.72-1.88 (m, 1.5H), 1.91-2.03 (m, 1H), 2.07-2.20 (m, 0.5H), 2.27-2.45 (m, 1H), 2.52-2.60 (m, 2H), 2.81 (br s, 1H), 2.95 (quin, 1H), 3.67-3.74 (m, 1H), 3.78 (s, 1.5H), 3.82 (s, 1.5H), 4.10-4.23 (m, 2 H), 4.53-4.59 (m, 1H), 6.92 (dd, 1H), 7.12 (dd, 1H), 7.36 (br d, 1H), 7.38 (br d, 1H), 7.79 (d, 1H), 7.87 (dt, 2H), 8.57 (s, 1H), 9.03 (ddd, 1H) LC-MS (Method 2): Rt = 1.94/1.98 min; MS (ESIpos): m/z = 545/547 (M + H)$^+$ |

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

B-1. In Vitro Electrophysiological Analysis of the Human TASK-1 and TASK-3 Channels Via Two-Electrode Voltage Clamp Technique in *Xenopus laevis* Oocytes

*Xenopus laevis* oocytes were selected as described elsewhere by way of illustration [Decher et al., *FEBS Lett.* 492, 84-89 (2001)]. Subsequently, the oocytes were injected with 0.5-5 ng of a cRNA solution coding for TASK-1 or TASK-3. For the electrophysiological analysis of the channel proteins expressed in the oocytes, the two-electrode voltage clamp technique [Stühmer, *Methods Enzymol.* 207, 319-339 (1992)] was used. The measurements were conducted as described [Decher et al., *FEBS Lett.* 492, 84-89 (2001)] at room temperature (21-22° C.) using a Turbo TEC 10CD amplifier (NPI), recorded at 2 kHz and filtered with 0.4 kHz. Substance administration was performed using a gravitation-driven perfusion system. Here, the oocyte is located in a measuring chamber and exposed to the solvent stream of 10 ml/min. The level in the measuring chamber is monitored and regulated by sucking off the solution using a peristaltic pump.

Table 1 below shows the half-maximum inhibition, determined in this test, of the human TASK-1 channel ($IC_{50}$) by representative working examples of the invention:

TABLE 1

| Example No. | TASK-1 $IC_{50}$ [nM] | TASK-3 $IC_{50}$ [nM] |
|---|---|---|
| 11 | 11.4 ± 2.2 | 4.8 ± 0.4 |
| 12 | 17.6 ± 2.2 | 13 ± 0.9 |
| 13 | 40.3 ± 3.4 | 23.5 ± 5.9 |
| 14 | 20.6 ± 3.1 | 17.3 ± 1.6 |
| 15 | 7.54 ± 1.4 | 15.5 ± 1.5 |
| 93 | 35.1 ± 3.5 | 41.8 ± 8.0 |

From the data in Table 1 it is evident that the human TASK-3 channel is blocked by compounds of the present invention.

B-2. Inhibition of Recombinant TASK-1 and TASK-3 In Vitro

The investigations on the inhibition of the recombinant TASK-1 and TASK-3 channels were conducted using stably transfected CHO cells. The compounds of the invention were tested here with administration of 40 mM of potassium chloride in the presence of a voltage-sensitive dye using the method described in detail in the following references [Whiteaker et al., Validation of FLIPR membrane potential dye for high-throughput screening of potassium channel modulators, *J. Biomol. Screen.* 6 (5), 305-312 (2001); Molecular Devices FLIPR Application Note: Measuring membrane potential using the FLIPR® membrane potential assay kit on Fluorometric Imaging Plate Reader (FLIPR®) systems, http://www.moleculardevices.com/reagents-supplies/assay-kits/ion-channels/flipr-membrane-potential-assay-kits]. The activity of the test substances was determined as their ability to inhibit a depolarization induced in the recombinant cells by 40 mM potassium chloride. The concentration which can block half of this depolarization is referred to as $IC_{50}$.

Table 2 below lists the $IC_{50}$ values from this assay determined for individual working examples of the invention (some as mean values from multiple independent individual determinations):

TABLE 2

| Example No. | TASK-1 $IC_{50}$ [nM] | TASK-3 $IC_{50}$ [nM] |
|---|---|---|
| 11 | 113 | 1.1 |
| 12 | 60.5 | 2.5 |
| 13 | 1000 | 2.2 |
| 14 | 760 | 4.5 |
| 15 | 250 | 7.3 |
| 16 | 1700 | 65 |
| 17 | 3300 | 15 |
| 18 | 1600 | 167 |
| 19 | 13500 | 580 |
| 20 | 3350 | 197 |
| 21 | 18000 | 140 |
| 22 | 27000 | 370 |
| 23 | 3000 | 24 |
| 24 | 3100 | 24 |
| 25 | 1100 | 11 |
| 26 | 830 | 6.9 |
| 27 | 150 | 3 |
| 28 | 280 | 5.6 |
| 29 | 660 | 4.4 |
| 30 | 2300 | 220 |
| 31 | 910 | 47 |
| 32 | 130 | 4.1 |
| 33 | 2600 | 110 |
| 34 | 4100 | 200 |
| 35 | 24000 | 500 |
| 36 | 30000 | 1000 |
| 37 | 30000 | 1000 |
| 38 | 250 | 4 |
| 39 | 370 | 13 |
| 40 | 3300 | 29 |
| 41 | 2200 | 160 |
| 43 | 2500 | 250 |
| 45 | 2900 | 170 |
| 46 | 16000 | 1000 |
| 47 | 3100 | 180 |
| 48 | 12000 | 430 |
| 49 | 5500 | 540 |
| 50 | 2500 | 440 |
| 51 | 1100 | 110 |
| 52 | 3800 | 140 |
| 53 | 1300 | 380 |
| 54 | 780 | 290 |
| 55 | 4000 | 1000 |
| 56 | 8500 | 1000 |
| 57 | 6200 | 2000 |
| 58 | 2900 | 920 |
| 59 | 1100 | 680 |
| 60 | 5200 | 1000 |
| 61 | 9400 | 1000 |
| 62 | 8400 | 1000 |
| 63 | 8400 | 800 |
| 64 | 7200 | 1800 |
| 65 | 1400 | 220 |
| 66 | 180 | 19 |
| 67 | 3400 | 370 |
| 68 | 230 | 31 |
| 69 | 1400 | 62 |
| 70 | 305 | 4.7 |
| 71 | 740 | 31 |
| 72 | 120 | 5.1 |
| 73 | 99 | 5 |
| 74 | 5000 | 200 |
| 75 | 2300 | 77 |
| 76 | 1400 | 66 |
| 77 | 3300 | 270 |
| 78 | 220 | 5, 3 |
| 79 | 290 | 11 |

TABLE 2-continued

| Example No. | TASK-1 IC$_{50}$ [nM] | TASK-3 IC$_{50}$ [nM] |
|---|---|---|
| 80 | 4500 | 93 |
| 81 | 590 | 9.2 |
| 82 | 30 | 1.4 |
| 83 | 410 | 17 |
| 84 | 350 | 25 |
| 85 | 6300 | 370 |
| 86 | 340 | 28 |
| 87 | 1600 | 210 |
| 88 | 91 | 1.6 |
| 89 | 310 | 19 |
| 90 | 43 | 2.8 |
| 91 | 290 | 5.5 |
| 92 | 85 | 2.5 |
| 93 | 340 | 12 |
| 94 | 3200 | 110 |
| 95 | 4900 | 710 |
| 99 | 290 | 34 |
| 100 | 370 | 42 |
| 101 | 400 | 16 |
| 102 | 170 | 36 |
| 103 | 1400 | 200 |
| 104 | 600 | 31 |
| 105 | 3700 | 370 |
| 106 | 1300 | 140 |

From the data in Table 2 it is evident that both TASK-1 and in particular TASK-3 are blocked. The results in Table 2 thus confirm the mechanism of action of the compounds according to the invention as dual TASK-1/3 inhibitors.

B-3. Animal Model of Obstructive Sleep Apnoea in the Pig

Using negative pressure, it is possible to induce collapse and thus obstruction of the upper respiratory tract in anaesthetized, spontaneously breathing pigs [Wirth et al., *Sleep* 36, 699-708 (2013)].

German Landrace pigs are used for the model. The pigs are anaesthetized and tracheotomized. One cannula each is inserted into the rostral and the caudal part of the trachea. Using a T connector, the rostral cannula is connected on the one hand to a device generating negative pressures and on the other hand to the caudal cannula. Using a T connector, the caudal cannula is connected to the rostral cannula and to a tube which allows spontaneous breathing circumventing the upper respiratory tract. By appropriate closing and opening of the tubes it is thus possible for the pig to change from normal nasal breathing to breathing via the caudal cannula during the time when the upper respiratory tract is isolated and connected to the device for generating negative pressures. The muscle activity of the Musculus genioglossus is recorded by electromyogram (EMG).

At certain points in time, the collapsibility of the upper respiratory tract is tested by having the pig breathe via the caudal cannula and applying negative pressures of −50, −100 and −150 cm water head (cm H$_2$O) to the upper respiratory tract. This causes the upper respiratory tract to collapse, which manifests itself in an interruption of the airflow and a pressure drop in the tube system. This test is conducted prior to the administration of the test substance and at certain intervals after the administration of the test substance. An appropriately effective test substance can prevent this collapse of the respiratory tract in the inspiratory phase.

After changeover from nasal breathing to breathing via the caudal cannula, it is not possible to measure any EMG activity of the Musculus genioglossus in the anaesthetized pig. As a further test, the negative pressure at which EMG activity restarts is then determined. This threshold value is, if a test substance is effective, shifted to more positive values. The test is likewise conducted prior to the administration of the test substance and at certain intervals after the administration of the test substance. Administration of the test substance can be intranasal, intravenous, subcutaneous, intraperitoneal or intragastral.

C. WORKING EXAMPLES OF PHARMACEUTICAL COMPOSITIONS

The compounds of the invention can be converted to pharmaceutical preparations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. Solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

Solution for Nasal Administration:

The compound of the invention is dissolved in a concentration below the saturation solubility in a physiologically acceptable solvent (e.g. purified water, phosphate buffer, citrate buffer). The solution may contain further additives for isotonization, for preservation, for adjusting the pH, for improvement in the solubility and/or for stabilization.

The invention claimed is:
1. A compound of formula (I)

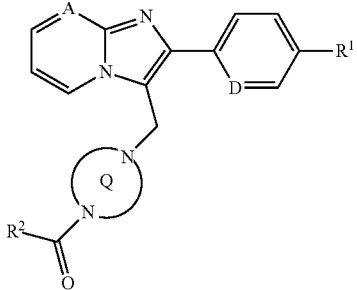

wherein the ring Q is a bridged 1,4-diazepane cycle of the formula

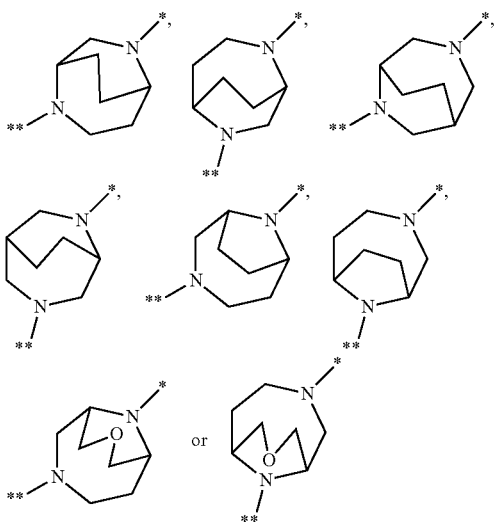

wherein * denotes the bond to the adjacent methylene group and ** the bond to the carbonyl group;
A is CH or N,
D is CH or N,
$R^1$ is halogen, cyano, ($C_1$-$C_4$)-alkyl, cyclopropyl or cyclobutyl,
 wherein ($C_1$-$C_4$)-alkyl is optionally up to trisubstituted by fluorine, and cyclopropyl and cyclobutyl are optionally up to disubstituted by fluorine;
and
$R^2$ is ($C_4$-$C_6$)-cycloalkyl wherein a ring $CH_2$ group is optionally replaced by —O—; or
$R^2$ is a phenyl group of the formula (a), a pyridyl group of the formula (b) or (c) or an azole group of the formula (d), (e), (f) or (g),

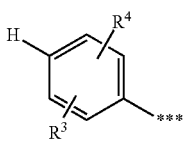

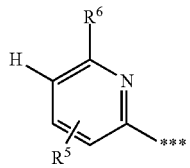

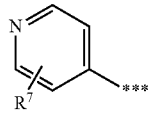

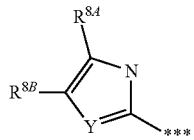

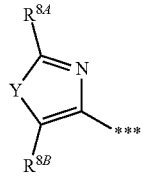

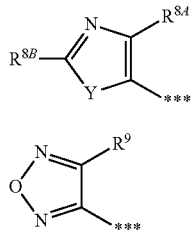

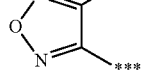

wherein *** marks the bond to the adjacent carbonyl group; and
$R^3$ is hydrogen, fluorine, chlorine, bromine or methyl;
$R^4$ is hydrogen, fluorine, chlorine, bromine, cyano, ($C_1$-$C_3$)-alkyl or ($C_1$-$C_3$)-alkoxy,
 wherein ($C_1$-$C_3$)-alkyl and ($C_1$-$C_3$)-alkoxy are optionally up to trisubstituted by fluorine;
$R^5$ is hydrogen, fluorine, chlorine, bromine or methyl,
$R^6$ is hydrogen, ($C_1$-$C_3$)-alkoxy, cyclobutyloxy, oxetan-3-yloxy, tetrahydrofuran-3-yloxy, tetrahydro-$_2$H-pyran-$_4$-yloxy, mono-($C_1$-$C_3$)-alkylamino, di-($C_1$-$C_3$)-alkylamino or ($C_1$-$C_3$)-alkylsulfanyl,
 wherein ($C_1$-$C_3$)-alkoxy is optionally up to trisubstituted by fluorine;
$R^7$ is hydrogen, fluorine, chlorine, bromine, ($C_1$-$C_3$)-alkyl or ($C_1$-$C_3$)-alkoxy;
$R^{8A}$ and $R^{8B}$ are identical or different and are independently hydrogen, fluorine, chlorine, bromine, ($C_1$-$C_3$)-alkyl, cyclopropyl or ($C_1$-$C_3$)-alkoxy,
 wherein ($C_1$-$C_3$)-alkyl and ($C_1$-$C_3$)-alkoxy are optionally up to trisubstituted by fluorine;
$R^9$ is hydrogen, ($C_1$-$C_3$)-alkyl or amino;
and
Y is O or S;
or
$R^2$ is an —$OR^{10}$ or —$NR^{11}R^{12}$ group wherein
$R^{10}$ is ($C_1$-$C_6$)-alkyl, ($C_4$-$C_6$)-cycloalkyl or [($C_3$-$C_6$)-cycloalkyl]methyl;

$R^{11}$ is hydrogen or $(C_1-C_3)$-alkyl; and $R^{12}$ is $(C_1-C_6)$-alkyl, $(C_3-C_6)$-cycloalkyl, phenyl or benzyl, wherein $(C_1-C_6)$-alkyl is optionally up to trisubstituted by fluorine, and where phenyl and the phenyl group in benzyl is optionally up to trisubstituted by identical or different radicals selected from the group consisting of fluorine, chlorine, methyl, ethyl, trifluoromethyl, methoxy, ethoxy and trifluoromethoxy;

or $R^{11}$ and $R^{12}$ are attached to one another and, together with the nitrogen atom to which they are bonded, form a pyrrolidine, piperidine, morpholine or thiomorpholine ring, or a salt, a solvate, or a solvate of the salt thereof.

2. The compound of formula (I) according to claim 1, wherein the ring Q is a bridged 1,4-diazepane cycle of the formula

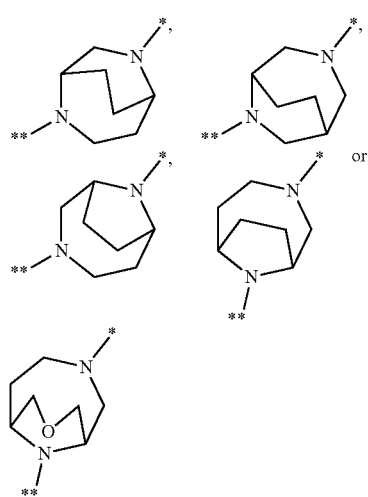

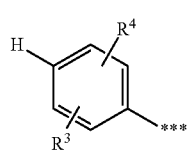

wherein * denotes the bond to the adjacent methylene group and ** the bond to the carbonyl group;

A is CH or N;

D is CH or N;

$R^1$ is fluorine, chlorine, bromine, methyl, isopropyl, tert-butyl, cyclopropyl or cyclobutyl;

and $R^2$ is cyclobutyl, cyclopentyl or cyclohexyl;

or $R^2$ is a phenyl group of the formula (a), a pyridyl group of the formula (b) or an azole group of the formula (d), (e), (f) or (g), (a)

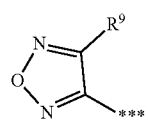

-continued (b)

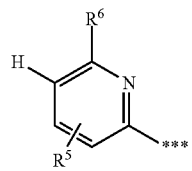

(d)

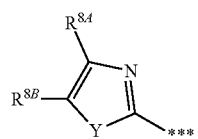

(e)

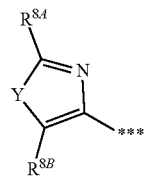

(f)

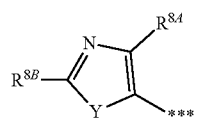

(g)

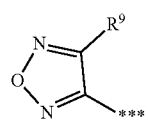

wherein *** marks the bond to the adjacent carbonyl group; and $R^3$ is hydrogen, fluorine or chlorine;

$R^4$ is fluorine, chlorine, cyano, $(C_1-C_3)$-alkyl, $(C_1-C_3)$-alkoxy or trifluoromethoxy;

$R^5$ is hydrogen, fluorine, chlorine, bromine or methyl;

$R^6$ is $(C_1-C_3)$-alkoxy, cyclobutyloxy or $(C_1-C_3)$-alkylsulfanyl, wherein $(C_1-C_3)$-alkoxy may be up to trisubstituted by fluorine;

$R^{8A}$ and $R^{8B}$ are identical or different and are independently hydrogen, chlorine, bromine, $(C_1-C_3)$-alkyl or cyclopropyl, wherein $(C_1-C_3)$-alkyl may be up to trisubstituted by fluorine;

$R^9$ is methyl or amino;

and

Y is O or S, or a salt, a solvate, or a solvate of the salt thereof.

3. The compound of formula (I) according to claim 1, wherein
the ring Q is a bridged 1,4-diazepane cycle of the formula

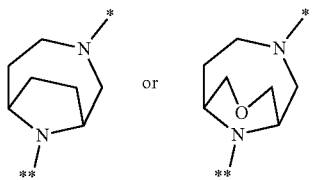

wherein * denotes the bond to the adjacent methylene group and ** the bond to the carbonyl group;
A is CH or N;
D is CH or N;
$R^1$ is chlorine, bromine, isopropyl or cyclopropyl; and
$R^2$ is cyclopentyl or cyclohexyl;
or
$R^2$ is a phenyl group of the formula (a), a pyridyl group of the formula (b) or an azole group of the formula (g),

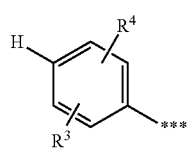

(a)

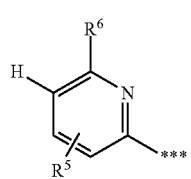

(b)

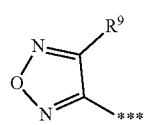

(g)

wherein *** marks the bond to the adjacent carbonyl group; and
$R^3$ is hydrogen, fluorine or chlorine;
$R^4$ is fluorine, chlorine, methyl, isopropyl, methoxy or ethoxy;
$R^5$ is hydrogen, fluorine, chlorine, bromine or methyl;
$R^6$ is methoxy, difluoromethoxy, trifluoromethoxy, isopropoxy, cyclobutyloxy or methylsulfanyl;
and
$R^9$ is methyl or amino,
or a salt, a solvate, or a solvate of the salt thereof.

4. A pharmaceutical composition comprising a compound according to claim 1 in combination with one or more inert, nontoxic, pharmaceutically suitable excipients.

5. A pharmaceutical combination comprising a compound according to claim 1 in combination with one or more further active compounds selected from the group consisting of respiratory stimulants, psychostimulating compounds, serotonin reuptake inhibitors, noradrenergic, serotonergic and tricyclic antidepressants, sGC stimulators, mineralocorticoid receptor antagonists, antiinflammatory drugs, immunomodulators, immunosuppressives and cytotoxic drugs.

6. A method for treatment of respiratory disorders, sleep-related respiratory disorders, obstructive sleep apnoeas, central sleep apnoeas, snoring, or cardiac arrhythmias, comprising administering to a human or animal in need thereof an effective amount of a compound of formula (I) according to claim 1.

7. The method of claim 6, wherein the method is a method for treatment of respiratory disorders.

8. The method of claim 6, wherein the method is a method for treatment of sleep-related respiratory disorders.

9. A method for treatment of respiratory disorders, sleep-related respiratory disorders, obstructive sleep apnoeas, central sleep apnoeas, snoring, or cardiac arrhythmias, in a human or animal in need thereof, comprising administering an effective amount of at least one compound according to claim 1 to the human or animal.

10. The method of claim 9, wherein the method is a method for treatment of respiratory disorders.

11. The method of claim 9, wherein the method is a method for treatment of sleep-related respiratory disorders.

12. A method for treatment of respiratory disorders, sleep-related respiratory disorders, obstructive sleep apnoea, central sleep apnoea, snoring, or cardiac arrhythmias, comprising administering to a human or animal in need thereof an effective amount of a pharmaceutical composition according to claim 4.

13. The method of claim 12, wherein the method is a method for treatment of respiratory disorders.

14. The method of claim 12, wherein the method is a method for treatment of sleep-related respiratory disorders.

15. A method for treatment of respiratory disorders, sleep-related respiratory disorders, obstructive sleep apnoeas, central sleep apnoeas, snoring, or cardiac arrhythmias, comprising administering to a human or animal in need thereof an effective amount of a pharmaceutical combination according to claim 5.

16. The method of claim 15, wherein the method is a method for treatment of respiratory disorders.

17. The method of claim 15, wherein the method is a method for treatment of sleep-related respiratory disorders.

18. A process for preparing a compound of formula (I) according to claim 1, comprising reacting a compound of formula (II)

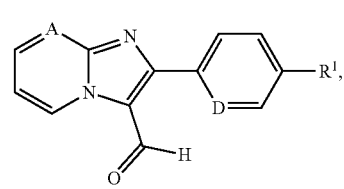

(II)

wherein A, D and $R^1$ are as defined in claim 1,
in the presence of a suitable reducing agent either
[A] with a compound of formula (III)

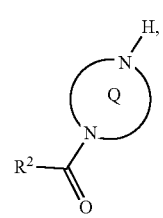

(III)

wherein R² and the ring Q are as defined in claim 1,
to give a compound of formula (I);
or

[B] with a protected diazabicyclic system of formula (IV)

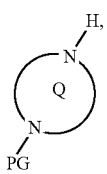
(IV)

wherein the ring Q is as defined in claim 1,
and
PG is a suitable amino protecting group,
at first to give a compound of formula (V)

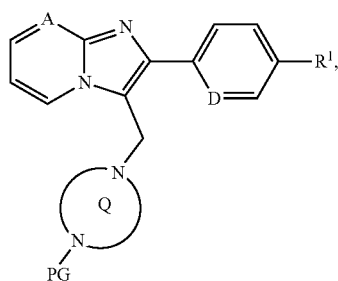
(V)

wherein A, D, PG, R¹ and the ring Q are as defined above,
then removing the protecting group PG to give a compound of formula (VI), and reacting the resulting compound of formula (VI)

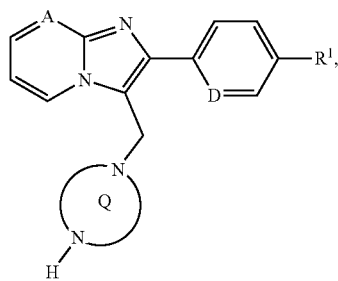
(VI)

wherein A, D, R¹ and the ring Q are as defined above,
depending on the specific meaning of the R² radical,
[B-1] with a carboxylic acid of the formula (VII)

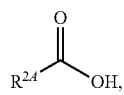
(VII)

wherein $R^{2A}$ is $(C_4-C_6)$-cycloalkyl wherein a ring $CH_2$ group is optionally replaced by —O—, or is a phenyl group of the formula (a), a pyridyl group of the formula (b) or (c) or an azole group of the formula (d), (e), (f) or (g), as defined in claim 1,
with activation of the carboxylic acid function in (VII), or with the corresponding acid chloride of the formula (VIII)

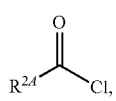
(VIII)

wherein $R^{2A}$ is as defined above,
to give a compound of the formula (I-A)

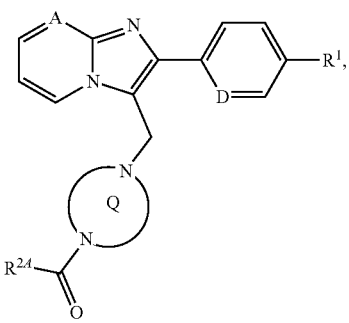
(I-A)

wherein A, D, R¹, $R^{2A}$ and the ring Q are as defined above;
or

[B-2] with a chloroformate or carbamoyl chloride of the formula (IX)

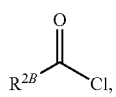
(IX)

wherein $R^{2B}$ is the —OR¹⁰ or —NR¹¹ᴬR¹² group
wherein
R¹⁰ and R¹² are as defined in claim 1,
and
R¹¹ᴬ has the definition of R¹¹ in claim 1, but is not hydrogen, to give a compound of the formula (I-B)

(I-B)

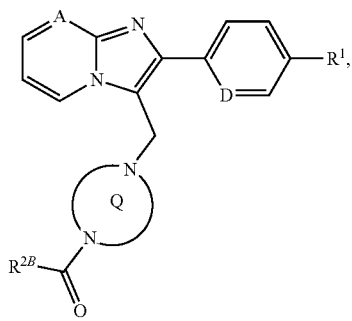

wherein A, D, $R^1$, $R^{2B}$ and the ring Q are as defined above;

or

[B-3] with an isocyanate of the formula (X)

$$R^{12}-N=C=O \quad (X),$$

wherein $R^{12}$ is as defined in claim 1, to give a compound of formula (I-C)

(I-C)

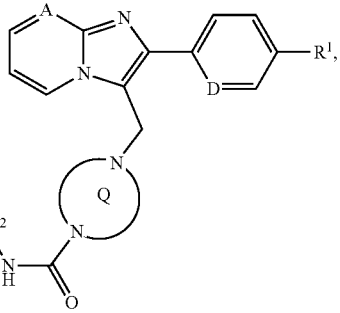

wherein A, D, $R^1$, $R^{12}$ and the ring Q are as defined above, and optionally separating the compound of formula (I), (I-A), (I-B) or (I-C) into its enantiomers and/or diastereomers and/or optionally converting the compound of formula (I), (I-A), (I-B) or (I-C) with the appropriate (i) solvents and/or (ii) acids to a salt, a solvate, or a solvate of the salt thereof.

19. The process of claim 18, wherein the suitable amino protecting group PG is tert-butoxycarbonyl, benzyloxycarbonyl or (9H-fluoren-9-ylmethoxy)carbonyl.

* * * * *